(12) United States Patent
Swidorski et al.

(10) Patent No.: US 8,906,889 B2
(45) Date of Patent: Dec. 9, 2014

(54) C-3 CYCLOALKENYL TRITERPENOIDS WITH HIV MATURATION INHIBITORY ACTIVITY

(71) Applicant: Bristol-Myers Squibb Company, Princeton, NJ (US)

(72) Inventors: Jacob Swidorski, Southington, CT (US); Nicholas A. Meanwell, East Hampton, CT (US); Alicia Regueiro-Ren, Middletown, CT (US); Sing-Yuen Sit, Meriden, CT (US); Jie Chen, Madison, CT (US); Yan Chen, Wallingford, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 44 days.

(21) Appl. No.: 13/760,726

(22) Filed: Feb. 6, 2013

(65) Prior Publication Data

US 2013/0210787 A1 Aug. 15, 2013

Related U.S. Application Data

(60) Provisional application No. 61/599,040, filed on Feb. 15, 2012.

(51) Int. Cl.
| | |
|---|---|
| A61K 31/56 | (2006.01) |
| A61K 31/58 | (2006.01) |
| C07J 53/00 | (2006.01) |
| C07J 63/00 | (2006.01) |
| A61K 45/06 | (2006.01) |

(52) U.S. Cl.
CPC .............. *C07J 53/002* (2013.01); *C07J 63/008* (2013.01); *A61K 45/06* (2013.01); *A61K 31/58* (2013.01)
USPC .............. 514/169; 514/176; 540/47; 552/510

(58) Field of Classification Search
CPC ........ C07J 63/008; A61K 31/56; A61K 31/58
USPC ...................... 552/510; 540/47; 514/169, 176
See application file for complete search history.

(56) References Cited

U.S. PATENT DOCUMENTS

| | | | |
|---|---|---|---|
| 5,679,828 | A | 10/1997 | Lee et al. |
| 7,354,924 | B2 | 4/2008 | Wang et al. |

(Continued)

FOREIGN PATENT DOCUMENTS

| | | |
|---|---|---|
| WO | WO 98/51293 | 11/1998 |
| WO | WO 98/51294 | 11/1998 |

(Continued)

OTHER PUBLICATIONS

Blair, W.S. et al., "HIV-1 entry—an expanding portal for drug discovery", Drug Discovery Today, vol. 5, No. 5, pp. 183-194 (2000).

(Continued)

*Primary Examiner* — Barbara P Badio
(74) *Attorney, Agent, or Firm* — John F. Levis

(57) ABSTRACT

Compounds having drug and bio-affecting properties, their pharmaceutical compositions and methods of use are set forth. In particular, C-3 cycloalkenyl triterpenoids that possess unique antiviral activity are provided as HIV maturation inhibitors, as represented by compounds of Formulas I, II, III and IV:

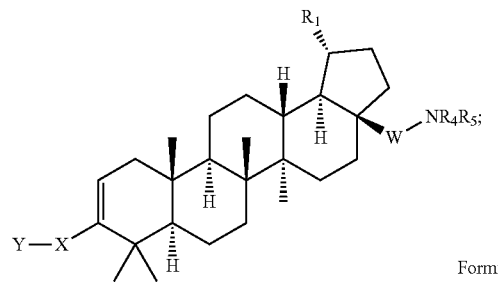

Formula I

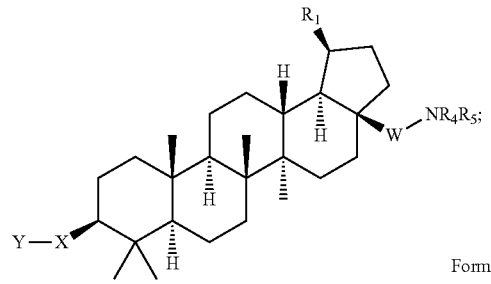

Formula II

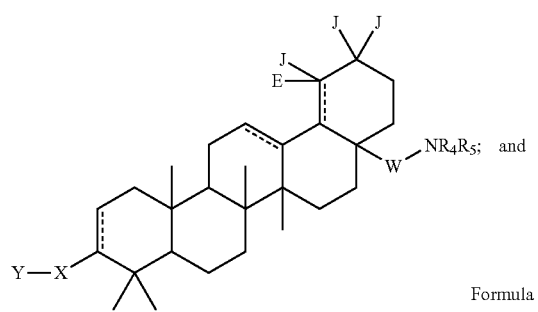

Formula III

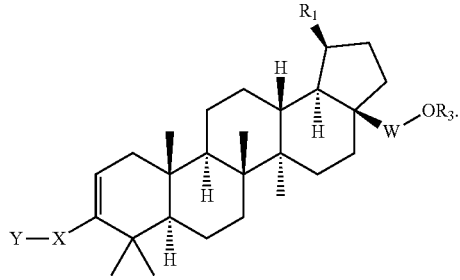

Formula IV wherein X can be a $C_{4-8}$ cycloalkyl, $C_{4-8}$ cycloalkenyl, $C_{4-9}$ spirocycloalkyl, $C_{4-9}$ spirocycloalkenyl, $C_{4-8}$ oxacycloalkyl, $C_{4-8}$ dioxacycloalkyl, $C_{6-8}$ oxacycloalkenyl, $C_{6-8}$ dioxacycloalkenyl, $C_{6-9}$ oxaspirocycloalkyl, or $C_{6-9}$ oxaspirocycloalkenyl ring. These compounds are useful for the treatment of HIV and AIDS.

19 Claims, No Drawings

(56) References Cited

U.S. PATENT DOCUMENTS

| | | |
|---|---|---|
| 7,365,221 B2 | 4/2008 | Allaway et al. |
| 7,745,625 B2 | 6/2010 | Ueda et al. |
| 8,748,415 B2 | 6/2014 | Regueiro-Ren et al. |
| 8,754,068 B2 | 6/2014 | Regueiro-Ren et al. |
| 8,754,069 B2 | 6/2014 | Liu et al. |
| 2005/0239748 A1 | 10/2005 | Power et al. |
| 2008/0207573 A1 | 8/2008 | Yager et al. |
| 2012/0142653 A1 | 6/2012 | Regueiro-Ren et al. |
| 2013/0035318 A1 | 2/2013 | Regueiro-Ren et al. |
| 2013/0296554 A1 | 11/2013 | Sin et al. |

FOREIGN PATENT DOCUMENTS

| | | | |
|---|---|---|---|
| WO | WO 2004/089357 | | 10/2004 |
| WO | WO 2006/053255 | | 5/2006 |
| WO | WO 2008/127364 | | 10/2008 |
| WO | WO 2009/020732 | | 2/2009 |
| WO | WO 2009/100532 | | 8/2009 |
| WO | WO 2011/007230 | | 1/2011 |
| WO | WO 2012106190 | * | 8/2012 |

OTHER PUBLICATIONS

Hotoda, H., "Small-molecule inhibitors of HIV-1 entry via chemokine receptors", Drugs of the Future, vol. 24, No. 12, pp. 1355-1362 (1999).

Kashiwada, Y. et al., "Betulinic Acid and Dihydrobetulinic Acid Derivatives as Potent Anti-HIV Agents", Journal of Medicinal Chemistry, vol. 39, No. 5, pp. 1016-1017 (1996).

Meanwell, N.A. et al., "Inhibitors of the entry of HIV into host cells", Current Opinion in Drug Discovery & Development, vol. 6, No. 4, pp. 451-461 (2003).

Pokrovskii, A.G. et al., "Synthesis of derivatives of plant triterpenes and study of their antiviral and immunostimulating activity", Khimiya y Interesakh Ustoichivogo Razvitiya, vol. 9, No. 3, pp. 485-491 (2001) (English abstract).

Sodroski, J.G., "HIV-1 Entry Inhibitors in the Side Pocket: Minireview", Cell, vol. 99, pp. 243-246 (1999).

Zhu, Y.-M. et al., "Synthesis and Anti-HIV Activity of Oleanolic Acid Derivatives," Bioorganic & Medicinal Chemistry Letters, 11, pp. 3115-3118 (2001).

Swidorski et al., U.S. Appl. No. 14/172,389 filed Feb. 4, 2014.

Swidorski et al., U.S. Appl. No. 14/186,533 filed Feb. 21, 2014.

\* cited by examiner

C-3 CYCLOALKENYL TRITERPENOIDS WITH HIV MATURATION INHIBITORY ACTIVITY

CROSS REFERENCE TO RELATED APPLICATION

This non-provisional application claims the benefit of U.S. Provisional Application Ser. No. 61/599,040 filed Feb. 15, 2012.

FIELD OF THE INVENTION

The present invention relates to novel compounds useful against HIV and, more particularly, to compounds derived from betulinic acid and other structurally-related compounds which are useful as HIV maturation inhibitors, and to pharmaceutical compositions containing same, as well as to methods for their preparation.

BACKGROUND OF THE INVENTION

HIV-1 (human immunodeficiency virus-1) infection remains a major medical problem, with an estimated 45-50 million people infected worldwide at the end of 2010. The number of cases of HIV and AIDS (acquired immunodeficiency syndrome) has risen rapidly. In 2005, approximately 5.0 million new infections were reported, and 3.1 million people died from AIDS. Currently available drugs for the treatment of HIV include nucleoside reverse transcriptase (RT) inhibitors or approved single pill combinations: zidovudine (or AZT or RETROVIR®), didanosine (or VIDEX®), stavudine (or ZERIT®), lamivudine (or 3TC or EPIVIR®), zalcitabine (or DDC or HIVID®), abacavir succinate (or ZIAGEN®), Tenofovir disoproxil fumarate salt (or VIREAD®), emtricitabine (or FTC-EMTRIVA®), COMBIVIR® (contains -3TC plus AZT), TRIZIVIR® (contains abacavir, lamivudine, and zidovudine), EPZICOM® (contains abacavir and lamivudine), TRUVADA® (contains VIREAD® and EMTRIVA®); non-nucleoside reverse transcriptase inhibitors: nevirapine (or VIRAMUNE®), delavirdine (or RESCRIPTOR®) and efavirenz (or SUSTIVA®), ATRIPLA® (TRUVADA®+SUSTIVA®), and etravirine, and peptidomimetic protease inhibitors or approved formulations: saquinavir, indinavir, ritonavir, nelfinavir, amprenavir, lopinavir, KALETRA® (lopinavir and Ritonavir), darunavir, atazanavir (REYATAZ®) and tipranavir (APTIVUS®) and cobicistat, and integrase inhibitors such as raltegravir (ISENTRESS®), and entry inhibitors such as enfuvirtide (T-20) (FUZEON®) and maraviroc (SELZENTRY®).

Each of these drugs can only transiently restrain viral replication if used alone. However, when used in combination, these drugs have a profound effect on viremia and disease progression. In fact, significant reductions in death rates among AIDS patients have been recently documented as a consequence of the widespread application of combination therapy. However, despite these impressive results, 30 to 50% of patients may ultimately fail combination drug therapies. Insufficient drug potency, non-compliance, restricted tissue penetration and drug-specific limitations within certain cell types (e.g. most nucleoside analogs cannot be phosphorylated in resting cells) may account for the incomplete suppression of sensitive viruses. Furthermore, the high replication rate and rapid turnover of HIV-1 combined with the frequent incorporation of mutations, leads to the appearance of drug-resistant variants and treatment failures when sub-optimal drug concentrations are present. Therefore, novel anti-HIV agents exhibiting distinct resistance patterns, and favorable pharmacokinetic as well as safety profiles are needed to provide more treatment options. Improved HIV fusion inhibitors and HIV entry coreceptor antagonists are two examples of new classes of anti-HIV agents further being studied by a number of investigators.

HIV attachment inhibitors are a further subclass of antiviral compounds that bind to the HIV surface glycoprotein gp120, and interfere with the interaction between the surface protein gp120 and the host cell receptor CD4. Thus, they prevent HIV from attaching to the human CD4 T-cell, and block HIV replication in the first stage of the HIV life cycle. The properties of HIV attachment inhibitors have been improved in an effort to obtain compounds with maximized utility and efficacy as antiviral agents. In particular, U.S. Pat. Nos. 7,354,924 and 7,745,625 are illustrative of HIV attachment inhibitors.

Another emerging class of compounds for the treatment of HIV are called HIV maturation inhibitors. Maturation is the last of as many as 10 or more steps in HIV replication or the HIV life cycle, in which HIV becomes infectious as a consequence of several HIV protease-mediated cleavage events in the gag protein that ultimately results in release of the capsid (CA) protein. Maturation inhibitors prevent the HIV capsid from properly assembling and maturing, from forming a protective outer coat, or from emerging from human cells. Instead, non-infectious viruses are produced, preventing subsequent cycles of HIV infection.

Certain derivatives of betulinic acid have now been shown to exhibit potent anti-HIV activity as HIV maturation inhibitors. For example, U.S. Pat. No. 7,365,221 discloses monoacylated betulin and dihydrobetuline derivatives, and their use as anti-HIV agents. As discussed in the '221 reference, esterification of betulinic acid (1) with certain substituted acyl groups, such as 3',3'-dimethylglutaryl and 3',3'-dimethylsuccinyl groups produced derivatives having enhanced activity (Kashiwada, Y., et al., J. Med. Chem. 39:1016-1017 (1996)). Acylated betulinic acid and dihydrobetulinic acid derivatives that are potent anti-HIV agents are also described in U.S. Pat. No. 5,679,828. Esterification of the hydroxyl in the 3 carbon of betulin with succinic acid also produced a compound capable of inhibiting HIV-1 activity (Pokrovskii, A. G., et al., Gos. Nauchnyi Tsentr Virusol. Biotekhnol. "Vector", Koltsovo, Russia. Khimiya v Interesakh Ustoichivogo Razvitiya, 9:485-491 (2001)).

Other references to the use of treating HIV infection with compounds derived from betulinic acid include US 2005/0239748 and US 2008/0207573, as well as WO2006/053255, WO2009/100532 and WO2011/007230.

One HIV maturation compound that has been in development has been identified as Bevirimat or PA-457, with the chemical formula of $C_{36}H_{56}O_6$ and the IUPAC name of 3β-(3-carboxy-3-methyl-butanoyloxy) lup-20(29)-en-28-oic acid.

Reference is also made herein to the applications by Bristol-Myers Squibb entitled "MODIFIED C-3 BETULINIC ACID DERIVATIVES AS HIV MATURATION INHIBITORS" U.S. Ser. No. 13/151,706 filed on Jun. 2, 2011 (US 2012-0142707) and "C-28 AMIDES OF MODIFIED C-3 BETULINIC ACID DERIVATIVES AS HIV MATURATION INHIBITORS" U.S. Ser. No. 13/151,722, filed on Jun. 2, 2011 (US 2012-0142653). Reference is also made to the application entitled "C-28 AMINES OF C-3 MODIFIED BETULINIC ACID DERIVATIVES AS HIV MATURATION INHIBITORS" U.S. Ser. No. 13/359,680, filed on Jan. 27, 2012. In addition, reference is made to the application entitled "C-17 AND C-3 MODIFIED TRITERPENOIDS WITH HIV MATURATION INHIBITORY ACTIVITY" U.S. Ser. No. 13/359,727 filed on Jan. 27, 2012.

What is now needed in the art are new compounds which are useful as HIV maturation inhibitors, as well as new pharmaceutical compositions containing these compounds.

SUMMARY OF THE INVENTION

The present invention provides compounds of Formulas I, II, III and IV below, including pharmaceutically acceptable salts thereof, their pharmaceutical formulations, and their use in patients suffering from or susceptible to a virus such as HIV. The compounds of Formulas I-IV are effective antiviral agents, particularly as inhibitors of HIV. They are useful for the treatment of HIV and AIDS.

One embodiment of the present invention is directed to a compound, including pharmaceutically acceptable salts thereof, which is selected from the group of:
a compound of formula I

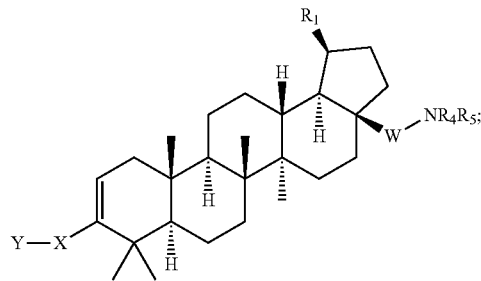

Formula I a compound of formula II

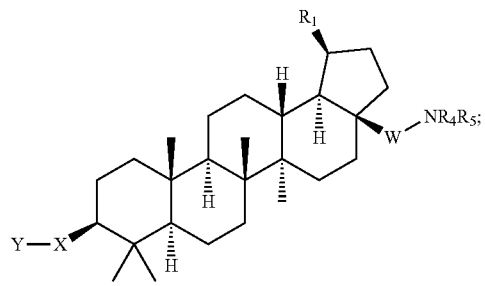

Formula II a compound of formula III

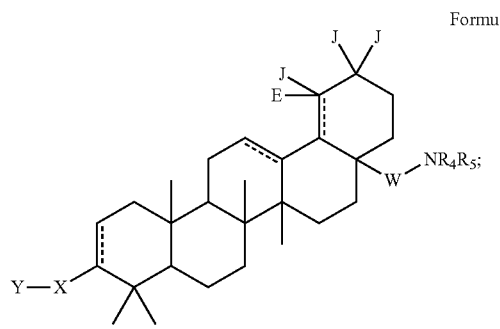

Formula III and
a compound of formula IV

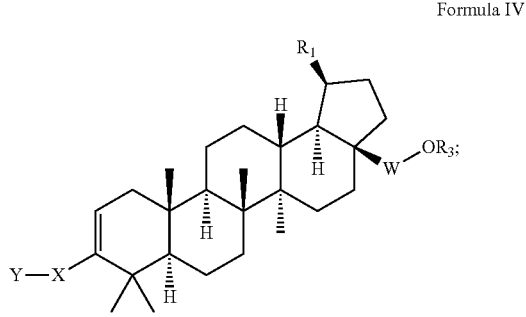

Formula IV wherein $R_1$ is isopropenyl or isopropyl;

J and E are independently —H or —$CH_3$, and E is absent when the double bond is present;

X is selected from the group of $C_{4-8}$ cycloalkyl, $C_{4-8}$ cycloalkenyl, $C_{4-9}$ spirocycloalkyl, $C_{4-9}$ spirocycloalkenyl, $C_{4-8}$ oxacycloalkyl, $C_{4-8}$ dioxacycloalkyl, $C_{6-8}$ oxacycloalkenyl, $C_{6-8}$ dioxacycloalkenyl, $C_6$ cyclodialkenyl, $C_6$ oxacyclodialkenyl, $C_{6-9}$ oxaspirocycloalkyl and $C_{6-9}$ oxaspirocycloalkenyl ring, wherein X is substituted with A, wherein A is at least one member selected from the group of —H, -halo, -hydroxyl, —$C_{1-6}$alkyl, —$C_{1-6}$ alkoxy, —$C_{1-6}$ alkyl-Q, -alkylsubstituted $C_{1-6}$ alkyl-Q, —CN, —$CF_2$Q, —$NR_8R_9$, —$COOR_2$ and —$CONR_2R_2$;

X can also be selected from the group of:

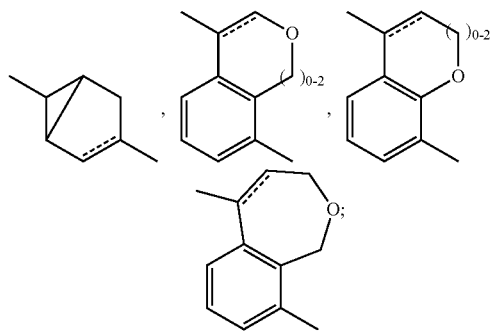

wherein Q is selected from the group of aryl, heteroaryl, substituted heteroaryl, —$OR_2$, —$COOR_3$, —$NR_2R_2$, —$SO_2R_7$, —$CONHSO_2R_3$, and —$CONHSO_2NR_2R_2$;

$R_2$ is —H, —$C_{1-6}$ alkyl, -alkylsubstituted $C_{1-6}$ alkyl or -arylsubstituted $C_{1-6}$ alkyl;

Y is selected from the group of —$COOR_2$, —C(O)$NR_2SO_2R_3$, —C(O)$NHSO_2NR_2R_2$, —$NR_2SO_2R_2$, —$SO_2NR_2R_2$, —$C_{3-6}$ cycloalkyl-$COOR_2$, —$C_{2-6}$ alkenyl-$COOR_2$, —$C_{2-6}$ alkynyl-$COOR_2$, —$C_{1-6}$alkyl-$COOR_2$, -alkylsubstituted $C_{1-6}$ alkyl, —$COOR_2$, $CF_2$—$COOR_2$, —NHC(O)$(CH_2)_n$—$COOR_2$, —$SO_2NR_2C(O)R_2$, _tetrazole, and —CONHOH, wherein n=1-6;

W is absent, $CH_2$ or CO;

$R_3$ is —$C_{1-6}$ alkyl or -alkylsubstituted $C_{1-6}$ alkyl;

$R_4$ is selected from the group of —H, —$C_{1-6}$ alkyl, —$C_{1-6}$ alkyl-C(OR$_3$)$_2$—$C_{3-6}$cycloalkyl, —$C_{1-6}$ substituted alkyl, —$C_{1-6}$ alkyl-$C_{3-6}$cycloalkyl, —$C_{1-6}$ alkyl-$Q_1$, —$C_{1-6}$ alkyl-$C_{3-6}$cycloalkyl-$Q_1$, aryl, heteroaryl, substituted heteroaryl, —COR$_6$, —COCOR$_6$, —SO$_2$R$_7$, —SO$_2$NR$_2$R$_2$,

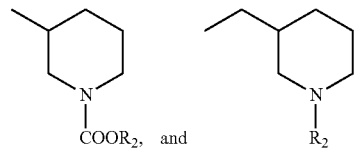

with the proviso that $R_4$ or $R_5$ cannot be COR$_6$ or COCOR$_6$ when W is CO;

wherein $Q_1$ is selected from the group of heteroaryl, substituted heteroaryl, halogen, —CF$_3$, —OR$_2$, —COOR$_2$, —NR$_8$R$_9$, —CONR$_{10}$R$_{11}$ and —SO$_2$R$_7$;

$R_5$ is selected from the group of —H, —$C_{1-6}$ alkyl, —$C_{3-6}$ cycloalkyl, —$C_{1-6}$ alkylsubstituted alkyl, —$C_{1-6}$alkyl-NR$_8$R$_9$, —COR$_{10}$, —COR$_6$, —COCOR$_6$, —SO$_2$R$_7$ and —SO$_2$NR$_2$R$_2$;

with the proviso that only one of $R_4$ or $R_5$ can be selected from the group of —COR$_6$, —COCOR$_6$, —SO$_2$R$_7$ and —SO$_2$NR$_2$R$_2$;

or when W is absent or is CH$_2$, then $R_4$ and $R_5$ can be taken together with the adjacent N to form

$R_6$ is selected from the group of —H, —$C_{1-6}$ alkyl, —$C_{1-6}$ alkyl-substitutedalkyl, —$C_{3-6}$ cycloalkyl, —$C_{3-6}$ substitutedcycloalkyl-$Q_2$, —$C_{1-6}$ alkyl-$Q_2$, —$C_{1-6}$ alkyl-substitutedalkyl-$Q_2$, —$C_{3-6}$ cycloalkyl-$Q_2$, aryl-$Q_2$, —NR$_{13}$R$_{14}$, and —OR$_{15}$;

wherein $Q_2$ is selected from the group of aryl, heteroaryl, substituted heteroaryl, —OR$_2$, —COOR$_2$, —NR$_8$R$_9$, SO$_2$R$_7$, —CONHSO$_2$R$_3$, and —CONHSO$_2$NR$_2$R$_2$;

$R_7$ is selected from the group of —$C_{1-6}$ alkyl, —$C_{1-6}$ substituted alkyl, —$C_{3-6}$ cycloalkyl, —CF$_3$, aryl, and heteroaryl;

$R_8$ and $R_9$ are independently selected from the group of —H, —$C_{1-6}$ alkyl, —$C_{1-6}$ substituted alkyl, aryl, heteroaryl, substituted aryl, substituted heteroaryl, —$C_{1-6}$ alkyl-$Q_2$, and —COOR$_3$, and $R_8$ and $R_9$ can also be independently selected from the group of

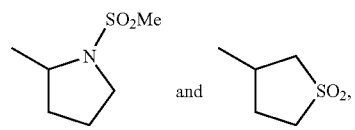

or $R_8$ and $R_9$ are taken together with the adjacent N to form a cycle selected from the group of:

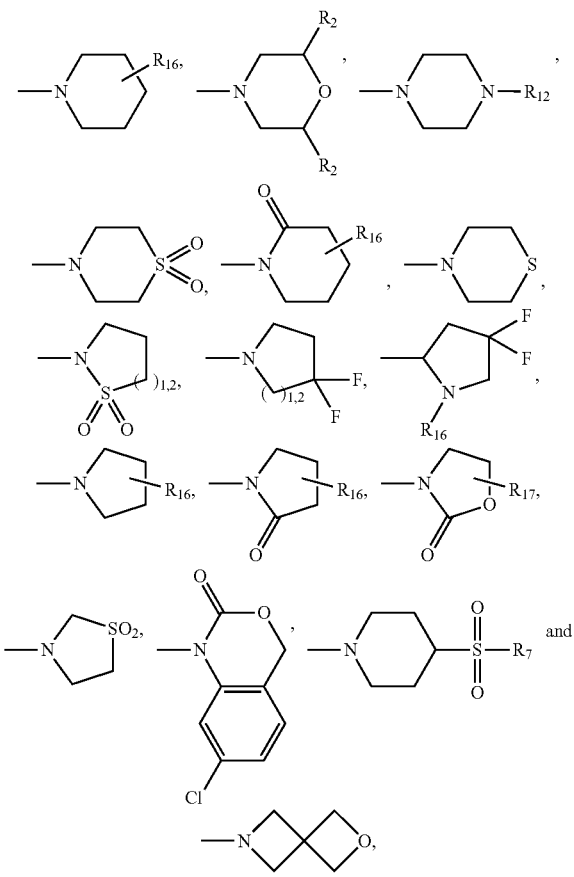

with the proviso that only one of $R_8$ or $R_9$ can be —COOR$_3$;

$R_{10}$ and $R_{11}$ are independently selected from the group of —H, —$C_{1-6}$ alkyl, —$C_{1-6}$ substituted alkyl and —$C_{3-6}$ cycloalkyl, or $R_{10}$ and $R_{11}$ are taken together with the adjacent N to form a cycle such as

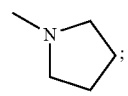

$R_{12}$ is selected from the group of —$C_{1-6}$ alkyl, —$C_{1-6}$ alkyl-OH; —$C_{1-6}$ alkyl, —$C_{1-6}$ substituted alkyl, —$C_{3-6}$ cycloalkyl, —COR$_7$, —COONR$_{22}$R$_{23}$, —SOR$_7$, and —SONR$_{24}$R$_{25}$;

$R_{13}$ and $R_{14}$ are independently selected from the group of —H, —$C_{1-6}$ alkyl, —$C_{3-6}$ cycloalkyl, —$C_{1-6}$ substituted alkyl, —$C_{1-6}$ alkyl-$Q_3$, —$C_{1-6}$ alkyl-$C_{3-6}$ cycloalkyl-$Q_3$, $C_{1-6}$ substituted alkyl-$Q_3$ and

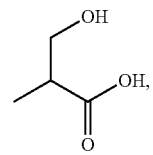

or $R_{13}$ and $R_{14}$ are taken together with the adjacent N to form a cycle selected from the group of:

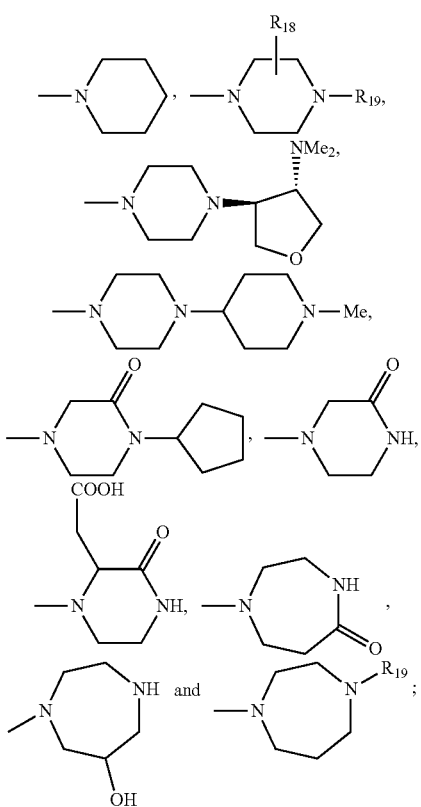

$Q_3$ is selected from the group of heteroaryl, substituted heteroaryl, $-NR_{20}R_{21}$, $-CONR_2R_2$, $-COOR_2$, $-OR_2$, and $-SO_2R_3$;

$R_{15}$ is selected from the group of $-C_{1-6}$ alkyl, $-C_{3-6}$ cycloalkyl, $-C_{1-6}$ substituted alkyl, $-C_{1-6}$ alkyl-$Q_3$, $-C_{1-6}$ alkyl-$C_{3-6}$ cycloalkyl-$Q_3$ and $-C_{1-6}$ substituted alkyl-$Q_3$, $R_{16}$ is selected from the group of $-H$, $-C_{1-6}$ alkyl, $-NR_2R_2$, and $-COOR_3$;

$R_{17}$ is selected from the group of $-H$, $-C_{1-6}$ alkyl, $-COOR_3$, and aryl;

$R_{18}$ is selected from the group of $-COOR_2$ and $-C_{1-6}$ alkyl-$COOR_2$;

$R_{19}$ is selected from the group of $-H$, $-C_{1-6}$ alkyl, $-C_{1-6}$ alkyl-$Q_4$, $-COR_3$, $-COOR_3$, wherein $Q_4$ is selected from the group of $-NR_2R_2$ and $-OR_2$;

$R_{20}$ and $R_{21}$ are independently selected from the group of $-H$, $-C_{1-6}$ alkyl, $-C_{1-6}$ substituted alkyl, $-C_{1-6}$ substituted alkyl-$OR_2$, and $-COR_3$, or $R_{20}$ and $R_{21}$ are taken together with the adjacent N to form a cycle selected from the group of

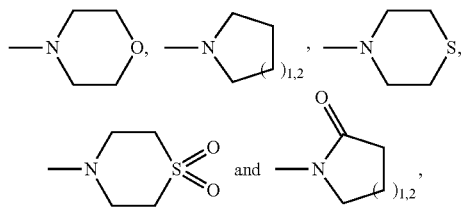

with the proviso that only one of $R_{20}$ or $R_{21}$ can be $-COR_3$, $R_{22}$ and $R_{23}$ are independently selected from the group of H, $-C_{1-6}$ alkyl, $-C_{1-6}$ substituted alkyl, and $-C_{1-6}$ cycloalkyl, or $R_{22}$ and $R_{23}$ are taken together with the adjacent N to form a cycle selected from the group of

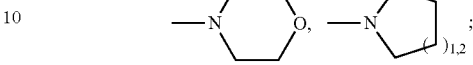

$R_{24}$ and $R_{25}$ are independently from the group of H, $-C_{1-6}$ alkyl, $-C_{1-6}$ substituted alkyl, $-C_{1-6}$ alkyl-$Q_5$, $-C_{1-6}$ cycloalkyl, aryl, substituted aryl, heteroaryl, and substituted heteroaryl, and $Q_5$ is selected from the group of halogen and $SO_2R_3$.

In a further embodiment, there is provided a method for treating mammals infected with a virus, especially wherein said virus is HIV, comprising administering to said mammal an antiviral effective amount of a compound which is selected from the group of compounds of Formulas I, II, III and IV above, and one or more pharmaceutically acceptable carriers, excipients or diluents. Optionally, the compound of Formulas I, II, III, and/or IV can be administered in combination with an antiviral effective amount of another—AIDS treatment agent selected from the group consisting of: (a) an AIDS antiviral agent; (b) an anti-infective agent; (c) an immunomodulator; and (d) other HIV entry inhibitors.

Another embodiment of the present invention is a pharmaceutical composition comprising an antiviral effective amount of a compound which is selected from the group of compounds of Formulas I, II, III, and IV, and one or more pharmaceutically acceptable carriers, excipients, and diluents; and optionally in combination with an antiviral effective amount of another AIDS treatment agent selected from the group consisting of: (a) an AIDS antiviral agent; (b) an anti-infective agent; (c) an immunomodulator; and (d) other HIV entry inhibitors.

In another embodiment of the invention there is provided one or more methods for making the compounds of Formulas I, II, III and IV herein.

Also provided herein are intermediate compounds useful in making the compounds of Formulas I, II, III and IV herein.

The present invention is directed to these, as well as other important ends, hereinafter described.

DETAILED DESCRIPTION OF THE EMBODIMENTS

Since the compounds of the present invention may possess asymmetric centers and therefore occur as mixtures of diastereomers and enantiomers, the present disclosure includes the individual diastereoisomeric and enantiomeric forms of the compounds of Formulas I, II and III in addition to the mixtures thereof.

Definitions

Unless otherwise specifically set forth elsewhere in the application, one or more of the following terms may be used herein, and shall have the following meanings:

"H" refers to hydrogen, including its isotopes, such as deuterium.

The term "$C_{1-6}$ alkyl" as used herein and in the claims (unless specified otherwise) mean straight or branched chain alkyl groups such as methyl, ethyl, propyl, isopropyl, butyl, isobutyl, t-butyl, amyl, hexyl and the like.

"$C_1$-$C_4$-fluoroalkyl" refers to F-substituted $C_1$-$C_4$ alkyl wherein at least one H atom is substituted with F atom, and each H atom can be independently substituted by F atom;

"Halogen" refers to chlorine, bromine, iodine or fluorine.

An "aryl" or "Ar" group refers to an all carbon monocyclic or fused-ring polycyclic (i.e., rings which share adjacent pairs of carbon atoms) groups having a completely conjugated pi-electron system. Examples, without limitation, of aryl groups are phenyl, napthalenyl and anthracenyl. The aryl group may be substituted or unsubstituted. When substituted the substituted group(s) is preferably one or more selected from alkyl, cycloalkyl, aryl, heteroaryl, heteroalicyclic, hydroxy, alkoxy, aryloxy, heteroaryloxy, heteroalicycloxy, thiohydroxy, thioaryloxy, thioheteroaryloxy, thioheteroalicycloxy, cyano, halogen, nitro, carbonyl, O-carbamyl, N-carbamyl, C-amido, N-amido, C-carboxy, O-carboxy, sulfinyl, sulfonyl, sulfonamido, trihalomethyl, ureido, amino and —NR$^x$R$^y$, wherein R$^x$ and R$^y$ are independently selected from the group consisting of hydrogen, alkyl, cycloalkyl, aryl, carbonyl, C-carboxy, sulfonyl, trihalomethyl, and, combined, a five- or six-member heteroalicyclic ring.

As used herein, a "heteroaryl" group refers to a monocyclic or fused ring (i.e., rings which share an adjacent pair of atoms) group having in the ring(s) one or more atoms selected from the group consisting of nitrogen, oxygen and sulfur and, in addition, having a completely conjugated pi-electron system. Unless otherwise indicated, the heteroaryl group may be attached at either a carbon or nitrogen atom within the heteroaryl group. It should be noted that the term heteroaryl is intended to encompass an N-oxide of the parent heteroaryl if such an N-oxide is chemically feasible as is known in the art. Examples, without limitation, of heteroaryl groups are furyl, thienyl, benzothienyl, thiazolyl, imidazolyl, oxazolyl, oxadiazolyl, thiadiazolyl, benzothiazolyl, triazolyl, tetrazolyl, isoxazolyl, isothiazolyl, pyrrolyl, pyranyl, tetrahydropyranyl, pyrazolyl, pyridyl, pyrimidinyl, quinolinyl, isoquinolinyl, purinyl, carbazolyl, benzoxazolyl, benzimidazolyl, indolyl, isoindolyl, pyrazinyl. diazinyl, pyrazine, triazinyl, tetrazinyl, and tetrazolyl. When substituted the substituted group(s) is preferably one or more selected from alkyl, cycloalkyl, aryl, heteroaryl, heteroalicyclic, hydroxy, alkoxy, aryloxy, heteroaryloxy, heteroalicycloxy, thioalkoxy, thiohydroxy, thioaryloxy, thioheteroaryloxy, thioheteroalicycloxy, cyano, halogen, nitro, carbonyl, O-carbamyl, N-carbamyl, C-amido, N-amido, C-carboxy, O-carboxy, sulfinyl, sulfonyl, sulfonamido, trihalomethyl, ureido, amino, and —NR$^x$R$^y$, wherein R$^x$ and R$^y$ are as defined above.

As used herein, a "heteroalicyclic" group refers to a monocyclic or fused ring group having in the ring(s) one or more atoms selected from the group consisting of nitrogen, oxygen and sulfur. Rings are selected from those which provide stable arrangements of bonds and are not intended to encompass systems which would not exist. The rings may also have one or more double bonds. However, the rings do not have a completely conjugated pi-electron system. Examples, without limitation, of heteroalicyclic groups are azetidinyl, piperidyl, piperazinyl, imidazolinyl, thiazolidinyl, 3-pyrrolidin-1-yl, morpholinyl, thiomorpholinyl and tetrahydropyranyl. When substituted the substituted group(s) is preferably one or more selected from alkyl, cycloalkyl, aryl, heteroaryl, heteroalicyclic, hydroxy, alkoxy, aryloxy, heteroaryloxy, heteroalicycloxy, thiohydroxy, thioalkoxy, thioaryloxy, thioheteroaryloxy, thioheteroalicycloxy, cyano, halogen, nitro, carbonyl, thiocarbonyl, O-carbamyl, N-carbamyl, O-thiocarbamyl, N-thiocarbamyl, C-amido, C-thioamido, N-amido, C-carboxy, O-carboxy, sulfinyl, sulfonyl, sulfonamido, trihalomethanesulfonamido, trihalomethanesulfonyl, silyl, guanyl, guanidino, ureido, phosphonyl, amino and —NR$^x$R$^y$, wherein R$^x$ and R$^y$ are as defined above.

An "alkyl" group refers to a saturated aliphatic hydrocarbon including straight chain and branched chain groups. Preferably, the alkyl group has 1 to 20 carbon atoms (whenever a numerical range; e.g., "1-20", is stated herein, it means that the group, in this case the alkyl group may contain 1 carbon atom, 2 carbon atoms, 3 carbon atoms, etc. up to and including 20 carbon atoms). More preferably, it is a medium size alkyl having 1 to 10 carbon atoms. Most preferably, it is a lower alkyl having 1 to 4 carbon atoms. The alkyl group may be substituted or unsubstituted. When substituted, the substituent group(s) is preferably one or more individually selected from trihaloalkyl, cycloalkyl, aryl, heteroaryl, heteroalicyclic, hydroxy, alkoxy, aryloxy, heteroaryloxy, heteroalicycloxy, thiohydroxy, thioalkoxy, thioaryloxy, thioheteroaryloxy, thioheteroalicycloxy, cyano, halo, nitro, carbonyl, thiocarbonyl, O-carbamyl, N-carbamyl, O-thiocarbamyl, N-thiocarbamyl, C-amido, C-thioamido, N-amido, C-carboxy, O-carboxy, sulfinyl, sulfonyl, sulfonamido, trihalomethanesulfonamido, trihalomethanesulfonyl, and combined, a five- or six-member heteroalicyclic ring.

A "cycloalkyl" group refers to an all-carbon monocyclic or fused ring (i.e., rings which share and adjacent pair of carbon atoms) group wherein one or more rings does not have a completely conjugated pi-electron system. Examples, without limitation, of cycloalkyl groups are cyclopropane, cyclobutane, cyclopentane, cyclopentene, cyclohexane, cyclohexene, cycloheptane, cycloheptene and adamantane. A cycloalkyl group may be substituted or unsubstituted. When substituted, the substituent group(s) is preferably one or more individually selected from alkyl, aryl, heteroaryl, heteroalicyclic, hydroxy, alkoxy, aryloxy, heteroaryloxy, heteroalicycloxy, thiohydroxy, thioalkoxy, thioaryloxy, thioheteroaryloxy, thioheteroalicycloxy, cyano, halo, nitro, carbonyl, thiocarbonyl, O-carbamyl, N-carbamyl, O-thiocarbamyl, N-thiocarbamyl, C-amido, C-thioamido, N-amido, C-carboxy, O-carboxy, sulfinyl, sulfonyl, sulfonamido, trihalomethanesulfonamido, trihalomethanesulfonyl, silyl, amidino, guanidino, ureido, phosphonyl, amino and —NR$^x$R$^y$ with R$^x$ and R$^y$ as defined above.

An "alkenyl" group refers to an alkyl group, as defined herein, having at least two carbon atoms and at least one carbon-carbon double bond.

An "alkynyl" group refers to an alkyl group, as defined herein, having at least two carbon atoms and at least one carbon-carbon triple bond.

A "hydroxy" group refers to an —OH group.

An "alkoxy" group refers to both an —O-alkyl and an —O-cycloalkyl group as defined herein.

An "aryloxy" group refers to both an —O-aryl and an —O-heteroaryl group, as defined herein.

A "heteroaryloxy" group refers to a heteroaryl-O— group with heteroaryl as defined herein.

A "heteroalicycloxy" group refers to a heteroalicyclic-O— group with heteroalicyclic as defined herein.

A "thiohydroxy" group refers to an —SH group.

A "thioalkoxy" group refers to both an S-alkyl and an —S-cycloalkyl group, as defined herein.

A "thioaryloxy" group refers to both an —S-aryl and an —S-heteroaryl group, as defined herein.

A "thioheteroaryloxy" group refers to a heteroaryl-S— group with heteroaryl as defined herein.

A "thioheteroalicycloxy" group refers to a heteroalicyclic-S— group with heteroalicyclic as defined herein.

A "carbonyl" group refers to a —C(=O)—R" group, where R" is selected from the group consisting of hydrogen, alkyl, alkenyl, alkynyl, cycloalkyl, aryl, heteroaryl (bonded through a ring carbon) and heteroalicyclic (bonded through a ring carbon), as each is defined herein.

An "aldehyde" group refers to a carbonyl group where R" is hydrogen.

A "thiocarbonyl" group refers to a —C(=S)—R" group, with R" as defined herein.

A "Keto" group refers to a —CC(=O)C— group wherein the carbon on either or both sides of the C=O may be alkyl, cycloalkyl, aryl or a carbon of a heteroaryl or heteroalicyclic group.

A "trihalomethanecarbonyl" group refers to a $Z_3CC(=O)$— group with said Z being a halogen.

A "C-carboxy" group refers to a —C(=O)O—R" groups, with R" as defined herein.

An "O-carboxy" group refers to a R"C(=O)O— group, with R" as defined herein.

A "carboxylic acid" group refers to a C-carboxy group in which R" is hydrogen.

A "trihalomethyl" group refers to a —$CZ_3$, group wherein Z is a halogen group as defined herein.

A "trihalomethanesulfonyl" group refers to an $Z_3CS(=O)_2$— groups with Z as defined above.

A "trihalomethanesulfonamido" group refers to a $Z_3CS(=O)_2NR^x$— group with Z as defined above and $R^x$ being H or $(C_{1-6})$alkyl.

A "sulfinyl" group refers to a —S(=O)—R" group, with R" being $(C_{1-6})$alkyl.

A "sulfonyl" group refers to a —$S(=O)_2R$" group with R" being $(C_{1-6})$alkyl.

A "S-sulfonamido" group refers to a —$S(=O)_2NR^XR^Y$, with $R^X$ and $R^Y$ independently being H or $(C_{1-6})$alkyl.

A "N-Sulfonamido" group refers to a R"$S(=O)_2NR_X$— group, with Rx being H or $(C_{1-6})$alkyl.

A "O-carbamyl" group refers to a —OC(=O)$NR^xR^y$ group, with $R^X$ and $R^Y$ independently being H or $(C_{1-6})$alkyl.

A "N-carbamyl" group refers to a $R^xOC(=O)NR^y$ group, with $R^x$ and $R^y$ independently being H or $(C_{1-6})$alkyl.

A "O-thiocarbamyl" group refers to a —OC(=S)$NR^xR^y$ group, with $R^x$ and $R^y$ independently being H or $(C_{1-6})$alkyl.

A "N-thiocarbamyl" group refers to a $R^xOC(=S)NR^y$— group, with $R^x$ and $R^y$ independently being H or $(C_{1-6})$alkyl.

An "amino" group refers to an —$NH_2$ group.

A "C-amido" group refers to a —C(=O)$NR^xR^y$ group, with Rx and $R^y$ independently being H or $(C_{1-6})$alkyl.

A "C-thioamido" group refers to a —C(=S)$NR^xR^y$ group, with $R^x$ and $R^y$ independently being H or $(C_{1-6})$alkyl.

A "N-amido" group refers to a $R^xC(=O)NR^y$— group, with $R^x$ and $R^y$ independently being H or $(C_{1-6})$alkyl.

An "ureido" group refers to a —$NR^xC(=O)NR^yR^{y2}$ group, with $R^x$, $R^y$, and $R^{y2}$ independently being H or $(C_{1-6})$alkyl.

A "guanidino" group refers to a —$R^xNC(=N)NR^yR^{y2}$ group, with $R^x$, $R^y$, and $R^{y2}$ independently being H or $(C_{1-6})$alkyl.

A "amidino" group refers to a $R^xR^yNC(=N)$— group, with $R^x$ and $R^y$ independently being H or $(C_{1-6})$alkyl.

A "cyano" group refers to a —CN group.

A "silyl" group refers to a —$Si(R")_3$, with R" being $(C_{1-6})$alkyl or phenyl.

A "phosphonyl" group refers to a $P(=O)(OR^x)_2$ with Rx being $(C_{1-6})$alkyl.

A "hydrazino" group refers to a —$NR^xNR^yR^{y2}$ group, with $R^x$, $R^y$, and $R^{y2}$ independently being H or $(C_{1-6})$alkyl.

A "4, 5, or 6 membered ring cyclic N-lactam" group refers to

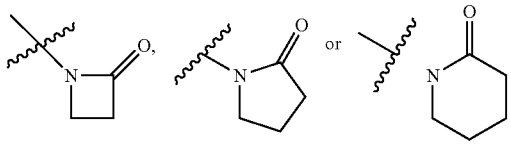

A "spiro" group is a bicyclic organic group with rings connected through just one atom. The rings can be different in nature or identical. The connecting atom is also called the spiroatom, most often a quaternary carbon ("spiro carbon").

An "oxospiro" or "oxaspiro" group is a spiro group having an oxygen contained within the bicyclic ring structure. A "dioxospiro" or "dioxaspiro" group has two oxygens within the bicyclic ring structure.

Any two adjacent R groups may combine to form an additional aryl, cycloalkyl, heteroaryl or heterocyclic ring fused to the ring initially bearing those R groups.

It is known in the art that nitrogen atoms in heteroaryl systems can be "participating in a heteroaryl ring double bond", and this refers to the form of double bonds in the two tautomeric structures which comprise five-member ring heteroaryl groups. This dictates whether nitrogens can be substituted as well understood by chemists in the art. The disclosure and claims of the present disclosure are based on the known general principles of chemical bonding. It is understood that the claims do not encompass structures known to be unstable or not able to exist based on the literature.

Pharmaceutically acceptable salts and prodrugs of compounds disclosed herein are within the scope of the invention. The term "pharmaceutically acceptable salt" as used herein and in the claims is intended to include nontoxic base addition salts. Suitable salts include those derived from organic and inorganic acids such as, without limitation, hydrochloric acid, hydrobromic acid, phosphoric acid, sulfuric acid, methanesulfonic acid, acetic acid, tartaric acid, lactic acid, sulfinic acid, citric acid, maleic acid, fumaric acid, sorbic acid, aconitic acid, salicylic acid, phthalic acid, and the like. The term "pharmaceutically acceptable salt" as used herein is also intended to include salts of acidic groups, such as a carboxylate, with such counterions as ammonium, alkali metal salts, particularly sodium or potassium, alkaline earth metal salts, particularly calcium or magnesium, and salts with suitable organic bases such as lower alkylamines (methylamine, ethylamine, cyclohexylamine, and the like) or with substituted lower alkylamines (e.g. hydroxyl-substituted alkylamines such as diethanolamine, triethanolamine or tris(hydroxymethyl)-aminomethane), or with bases such as piperidine or morpholine.

As stated above, the compounds of the invention also include "prodrugs". The term "prodrug" as used herein encompasses both the term "prodrug esters" and the term "prodrug ethers".

As set forth above, the invention is directed to a compound, including pharmaceutically acceptable salts thereof, which is selected from the group of:

a compound of formula I

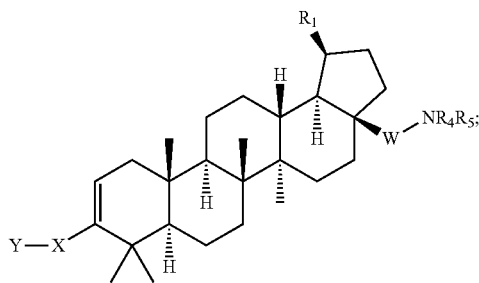

Formula I a compound of formula II

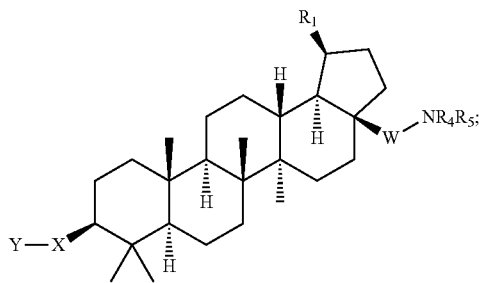

Formula II a compound of formula III

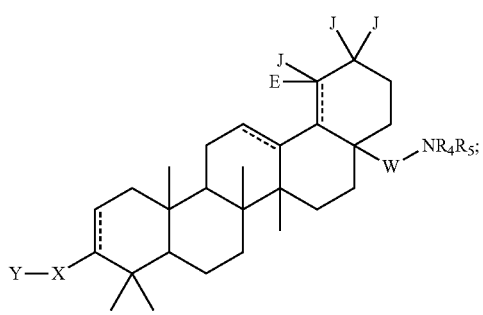

Formula III and a compound of formula IV

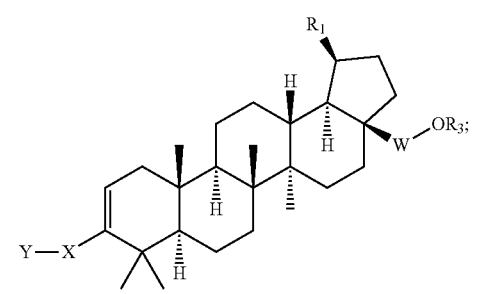

Formula IV wherein $R_1$ is isopropenyl or isopropyl;
J and E are independently —H or —$CH_3$, and E is absent when the double bond is present;
X is selected from the group of $C_{4-8}$ cycloalkyl, $C_{4-8}$ cycloalkenyl, $C_{4-9}$ spirocycloalkyl, $C_{4-9}$ spirocycloalkenyl, $C_{4-8}$ oxacycloalkyl, $C_{4-8}$ dioxacycloalkyl, $C_{6-8}$ oxacycloalkenyl, $C_{6-8}$ dioxacycloalkenyl, $C_6$ cyclodialkenyl, $C_6$ oxacyclodialkenyl, $C_{6-9}$ oxaspirocycloalkyl and $C_{6-9}$ oxaspirocycloalkenyl ring, wherein X is substituted with A, wherein A is at least one member selected from the group of —H, -halo, -hydroxyl, —$C_{1-6}$alkyl, —$C_{1-6}$ alkoxy, —$C_{1-6}$ alkyl-Q, -alkylsubstituted $C_{1-6}$ alkyl-Q, —CN, —$CF_2$Q, —$NR_8R_9$, —$COOR_2$ and —$CONR_2R_2$,
X can also be selected from the group of:

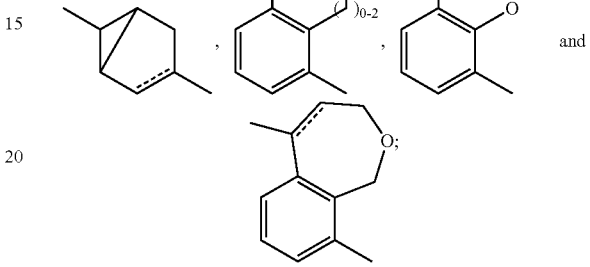

wherein Q is selected from the group of aryl, heteroaryl, substituted heteroaryl, —$OR_2$, —$COOR_3$, —$NR_2R_2$, —$SO_2R_7$, —$CONHSO_2R_3$, and —$CONHSO_2NR_2R_2$;
$R_2$ is —H, —$C_{1-6}$ alkyl, -alkylsubstituted $C_{1-6}$ alkyl or -arylsubstituted $C_{1-6}$ alkyl;
Y is selected from the group of —$COOR_2$, —C(O)$NR_2SO_2R_3$, —C(O)$NHSO_2NR_2R_2$, —$NR_2SO_2R_2$, —$SO_2NR_2R_2$, —$C_{3-6}$ cycloalkyl-$COOR_2$, —$C_{2-6}$ alkenyl-$COOR_2$, —$C_{2-6}$ alkynyl-$COOR_2$, —$C_{1-6}$ alkyl-$COOR_2$, -alkylsubstituted $C_{1-6}$ alkyl, —$COOR_2$, $CF_2$—$COOR_2$, —NHC(O)($CH_2$)$_n$—$COOR_2$, —$SO_2NR_2C(O)R_2$, _tetrazole, and —CONHOH,
wherein n=1-6;
W is absent, $CH_2$ or CO;
$R_3$ is —$C_{1-6}$ alkyl or -alkylsubstituted $C_{1-6}$ alkyl;
$R_4$ is selected from the group of —H, —$C_{1-6}$ alkyl, —$C_{1-6}$ alkyl-C($OR_3$)$_2$—$C_{3-6}$cycloalkyl, —$C_{1-6}$ substituted alkyl, —$C_{1-6}$ alkyl-$C_{3-6}$ cycloalkyl, —$C_{1-6}$ alkyl-$Q_1$, —$C_{1-6}$ alkyl-$C_{3-6}$ cycloalkyl-$Q_1$, aryl, heteroaryl, substituted heteroaryl, —$COR_6$, —$COCOR_6$, —$SO_2R_7$, —$SO_2NR_2R_2$,

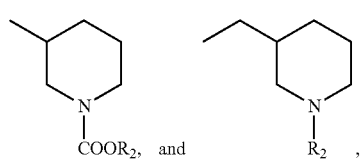

with the proviso that $R_4$ or $R_5$ cannot be $COR_6$ or $COCOR_6$ when W is CO;
wherein $Q_1$ is selected from the group of heteroaryl, substituted heteroaryl, halogen, —$CF_3$, —$OR_2$, —$COOR_2$, —$NR_8R_9$, —$CONR_{10}R_{11}$ and —$SO_2R_7$;
$R_5$ is selected from the group of —H, —$C_{1-6}$ alkyl, —$C_{3-6}$ cycloalkyl, —$C_{1-6}$ alkylsubstituted alkyl, —$C_{1-6}$alkyl-$NR_8R_9$, —$COR_{10}$, —$COR_6$, —$COCOR_6$, —$SO_2R_7$ and —$SO_2NR_2R_2$;
with the proviso that only one of $R_4$ or $R_5$ can be selected from the group of —$COR_6$, —$COCOR_6$, —$SO_2R_7$ and —$SO_2NR_2R_2$;

or when W is absent or is CH$_2$, then R$_4$ and R$_5$ can be taken together with the adjacent N to form

;

R$_6$ is selected from the group of —H, —C$_{1-6}$ alkyl, —C$_{1-6}$ alkyl-substitutedalkyl, —C$_{3-6}$ cycloalkyl, —C$_{3-6}$ substitutedcycloalkyl-Q$_2$, —C$_{1-6}$ alkyl-Q$_2$, —C$_{1-6}$ alkyl-substitutedalkyl-Q$_2$, —C$_{3-6}$ cycloalkyl-Q$_2$, aryl-Q$_2$, —NR$_{13}$R$_{14}$, and —OR$_{15}$;

wherein Q$_2$ is selected from the group of aryl, heteroaryl, substituted heteroaryl, —OR$_2$, —COOR$_2$, —NR$_8$R$_9$, SO$_2$R$_7$, —CONHSO$_2$R$_3$, and —CONHSO$_2$NR$_2$R$_2$;

R$_7$ is selected from the group of —C$_{1-6}$ alkyl, —C$_{1-6}$ substituted alkyl, —C$_{3-6}$ cycloalkyl, —CF$_3$, aryl, and heteroaryl;

R$_8$ and R$_9$ are independently selected from the group of —H, —C$_{1-6}$ alkyl, —C$_{1-6}$ substituted alkyl, aryl, heteroaryl, substituted aryl, substituted heteroaryl, —C$_{1-6}$ alkyl-Q$_2$, and —COOR$_3$, and R$_8$ and R$_9$ can also be independently selected from the group of

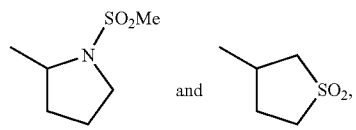

or R$_8$ and R$_9$ are taken together with the adjacent N to form a cycle selected from the group of:

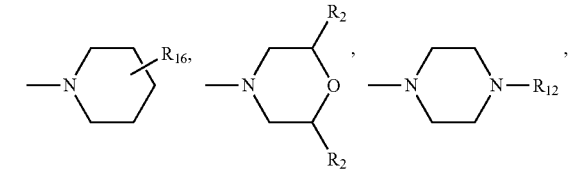

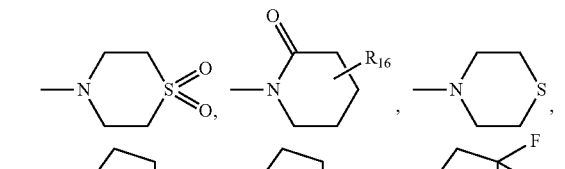

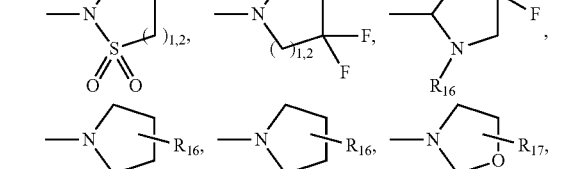

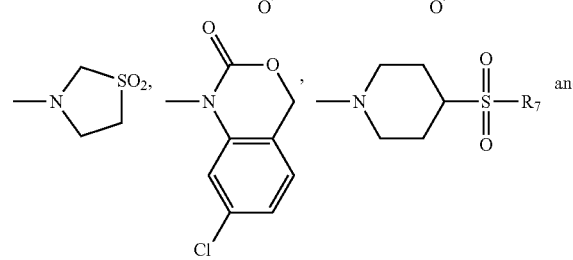

-continued

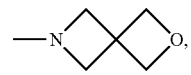

with the proviso that only one of R$_8$ or R$_9$ can be —COOR$_3$;

R$_{10}$ and R$_{11}$ are independently selected from the group of —H, —C$_{1-6}$ alkyl, —C$_{1-6}$ substituted alkyl and —C$_{3-6}$ cycloalkyl, or R$_{10}$ and R$_{11}$ are taken together with the adjacent N to form a cycle such as

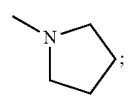

R$_{12}$ is selected from the group of —C$_{1-6}$ alkyl, —C$_{1-6}$ alkyl-OH; —C$_{1-6}$ alkyl, —C$_{1-6}$ substituted alkyl, —C$_{3-6}$ cycloalkyl, —COR$_7$, —COONR$_{22}$R$_{23}$, —SOR$_7$, and —SONR$_{24}$R$_{25}$;

R$_{13}$ and R$_{14}$ are independently selected from the group of —H, —C$_{1-6}$ alkyl, —C$_{3-6}$ cycloalkyl, —C$_{1-6}$ substituted alkyl, —C$_{1-6}$ alkyl-Q$_3$, —C$_{1-6}$ alkyl-C$_{3-6}$ cycloalkyl-Q$_3$, C$_{1-6}$ substituted alkyl-Q$_3$ and

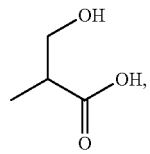

or R$_{13}$ and R$_{14}$ are taken together with the adjacent N to form a cycle selected from the group of:

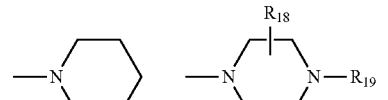

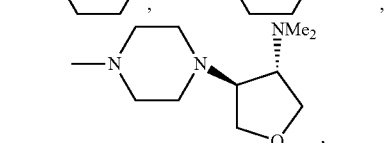

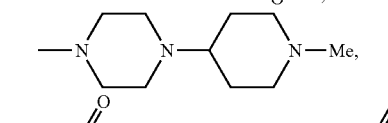

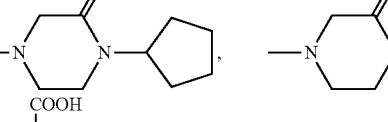

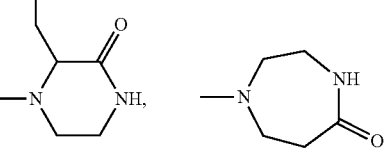

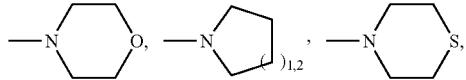

$Q_3$ is selected from the group of heteroaryl, substituted heteroaryl, —$NR_{20}R_{21}$, —$CONR_2R_2$, —$COOR_2$, —$OR_2$, and —$SO_2R_3$;

$R_{15}$ is selected from the group of —$C_{1-6}$ alkyl, —$C_{3-6}$ cycloalkyl, —$C_{1-6}$ substituted alkyl, —$C_{1-6}$ alkyl-$Q_3$, —$C_{1-6}$alkyl-$C_{3-6}$cycloalkyl-$Q_3$ and —$C_{1-6}$ substituted alkyl-$Q_3$, $R_{16}$ is selected from the group of —H, —$C_{1-6}$ alkyl, —$NR_2R_2$, and —$COOR_3$;

$R_{17}$ is selected from the group of —H, —$C_{1-6}$ alkyl, —$COOR_3$, and aryl;

$R_{18}$ is selected from the group of —$COOR_2$ and —$C_{1-6}$ alkyl-$COOR_2$;

$R_{19}$ is selected from the group of —H, —$C_{1-6}$ alkyl, —$C_{1-6}$ alkyl-$Q_4$, —$COR_3$, —$COOR_3$, wherein $Q_4$ is selected from the group of —$NR_2R_2$ and —$OR_2$;

$R_{20}$ and $R_{21}$ are independently selected from the group of —H, —$C_{1-6}$ alkyl, —$C_{1-6}$ substituted alkyl, —$C_{1-6}$ substituted alkyl-$OR_2$, and —$COR_3$, or $R_{20}$ and $R_{21}$ are taken together with the adjacent N to form a cycle selected from the group of

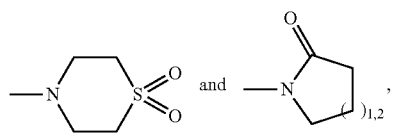

with the proviso that only one of $R_{20}$ or $R_{21}$ can be —$COR_3$;

$R_{22}$ and $R_{23}$ are independently selected from the group of H, —$C_{1-6}$ alkyl, —$C_{1-6}$ substituted alkyl, and —$C_{1-6}$ cycloalkyl, or $R_{22}$ and $R_{23}$ are taken together with the adjacent N to form a cycle selected from the group of

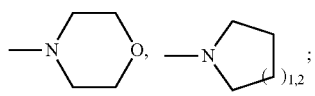

$R_{24}$ and $R_{25}$ are independently from the group of H, —$C_{1-6}$ alkyl, —$C_{1-6}$ substituted alkyl, —$C_{1-6}$ alkyl-$Q_5$, —$C_{1-6}$ cycloalkyl, aryl, substituted aryl, heteroaryl, and substituted heteroaryl, and $Q_5$ is selected from the group of halogen and $SO_2R_3$.

Even more preferred compounds include those wherein $R_1$ is isopropenyl.

Also preferred are compounds wherein W is absent.

Also preferred compounds include those which are encompassed by Formula I. Of these, those wherein X is a $C_{4-8}$ cycloalkenyl, $C_{4-9}$ spirocycloalkyl or $C_{4-9}$ spirocycloalkenyl group are even more preferred.

Also preferred are compounds of Formula I wherein Y is in the para position.

Also preferred are compounds of Formula I wherein A is at least one member selected from the group of —H, —OH, -halo, —$C_{1-3}$ alkyl, and —$C_{1-3}$ alkoxy, wherein -halo is selected from the group of —Cl, —F and —Br, with —F being more preferred. It is even more preferred that A is —H.

Also preferred are compounds of Formula I wherein Y is —$COOR_2$, and more preferably —COOH.

A preferred class of compounds, including pharmaceutically acceptable salts thereof, includes the following structures:

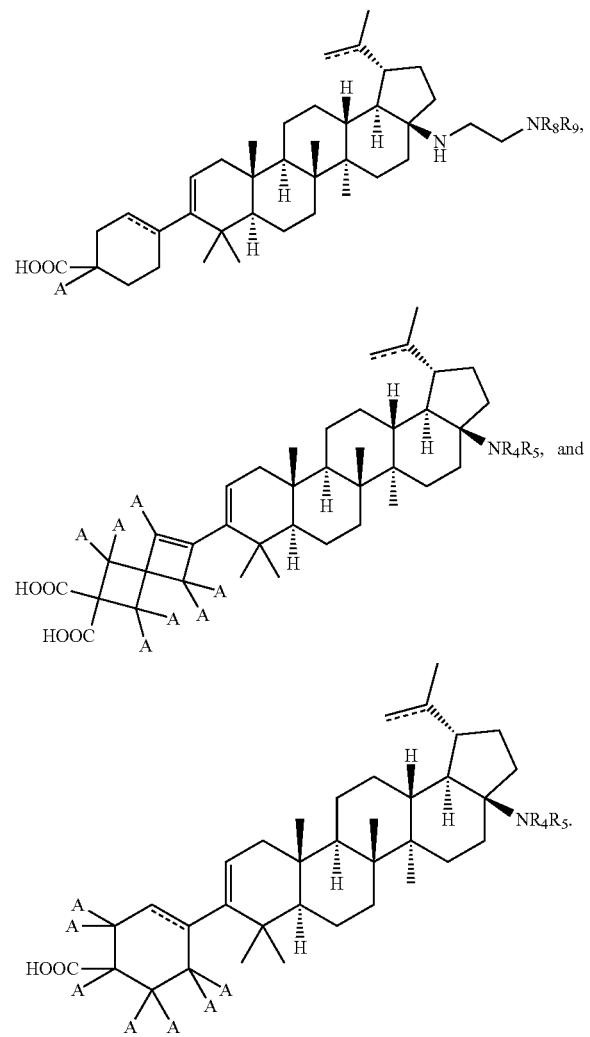

Other compounds, including pharmaceutically acceptable salts thereof, which are preferred as part of the invention include the following:

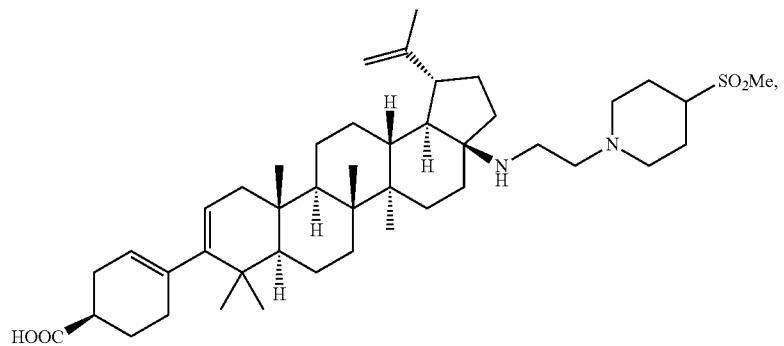
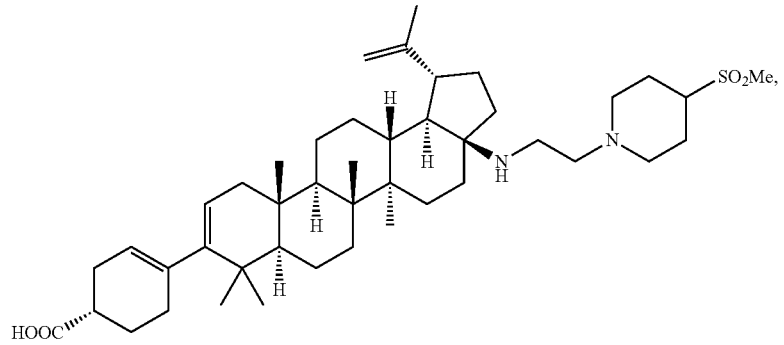
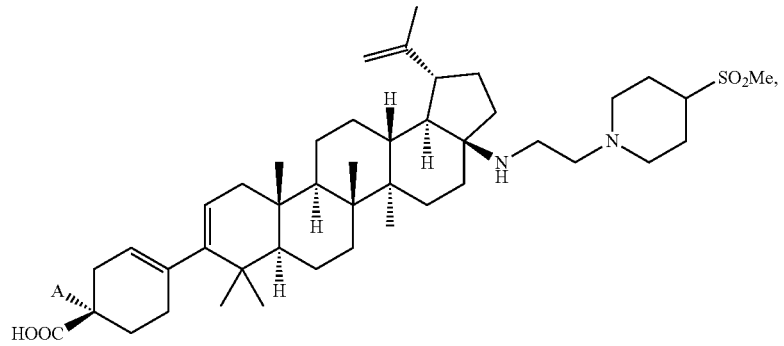
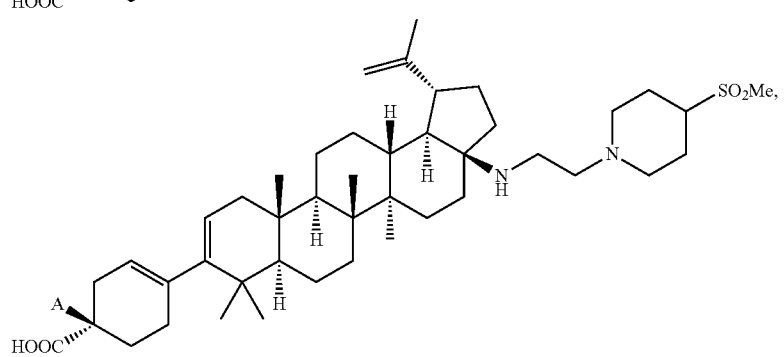
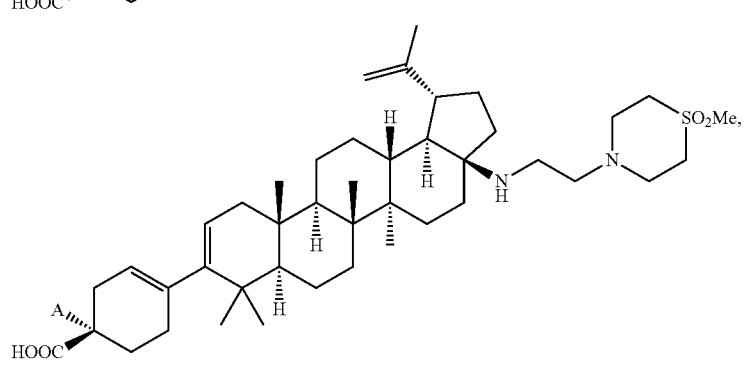

-continued
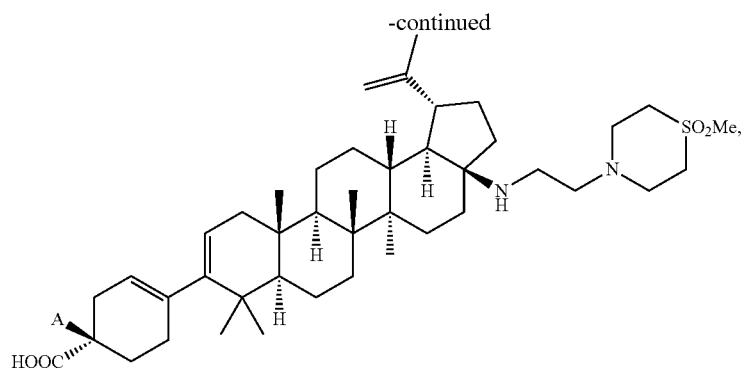
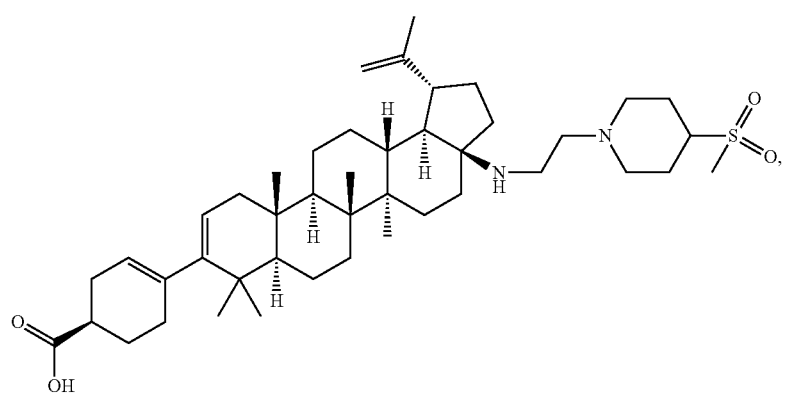
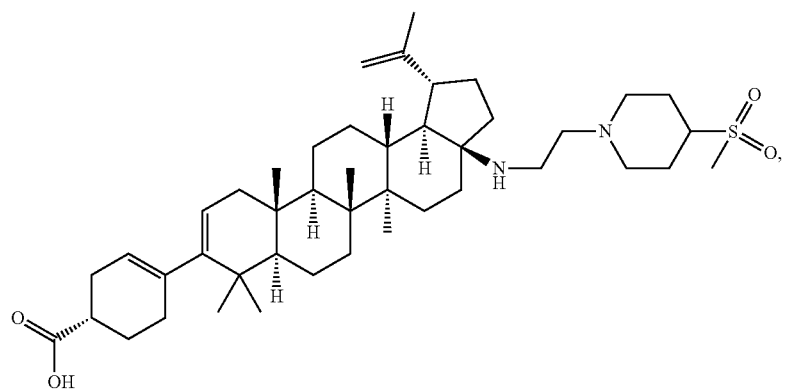
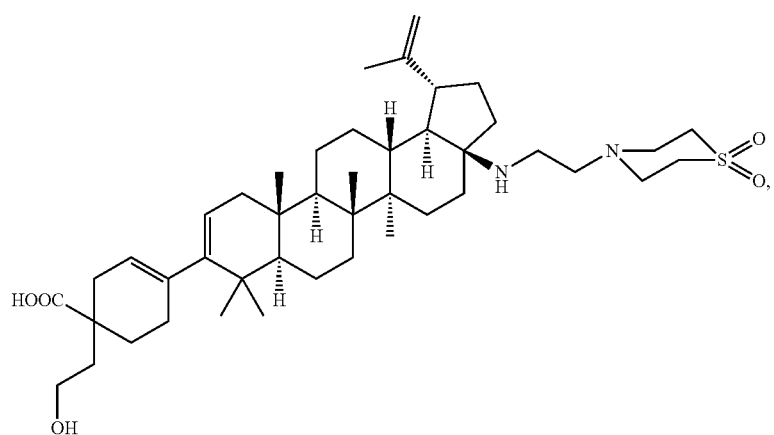

-continued

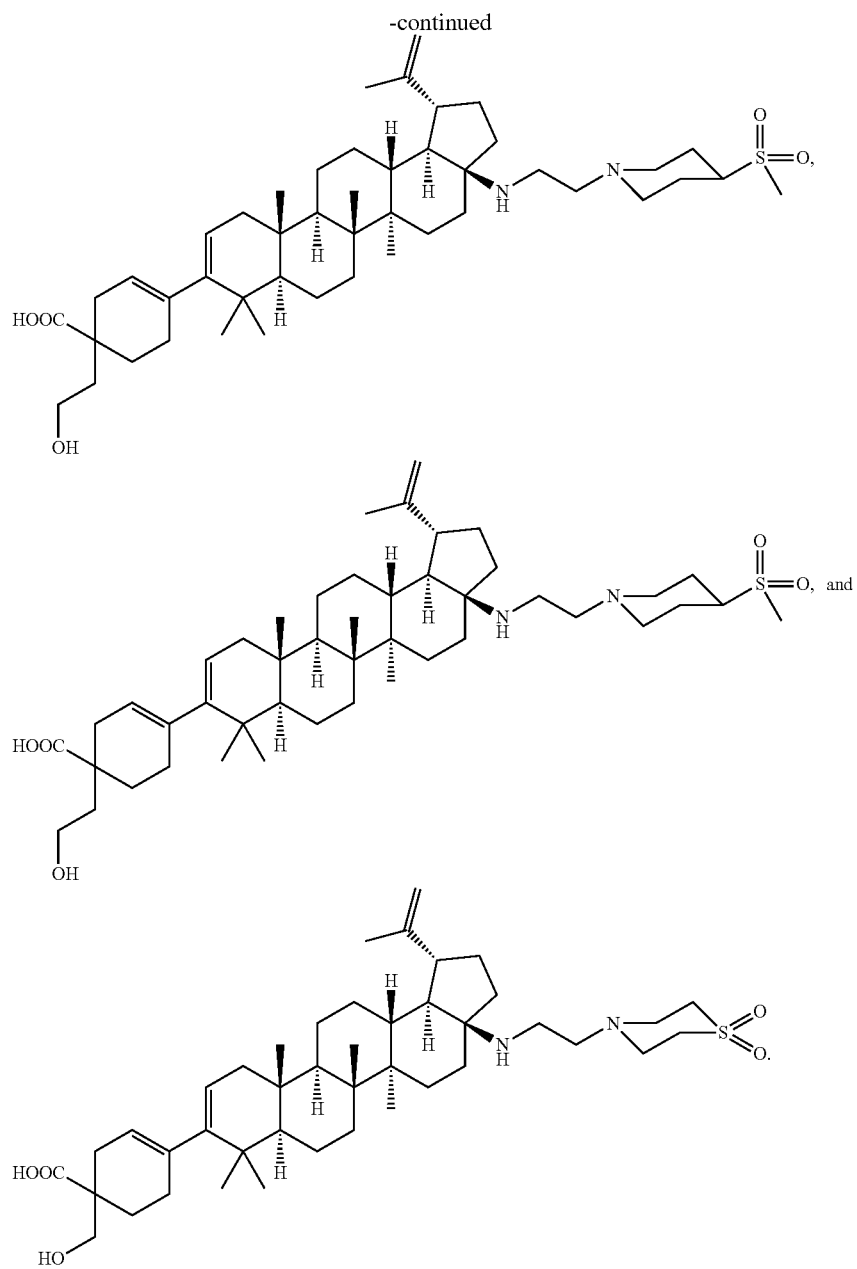

The compounds of the present invention, according to all the various embodiments described above, may be administered orally, parenterally (including subcutaneous injections, intravenous, intramuscular, intrasternal injection or infusion techniques), by inhalation spray, or rectally, and by other means, in dosage unit formulations containing non-toxic pharmaceutically acceptable carriers, excipients and diluents available to the skilled artisan. One or more adjuvants may also be included.

Thus, in accordance with the present invention, there is further provided a method of treatment, and a pharmaceutical composition, for treating viral infections such as HIV infection and AIDS. The treatment involves administering to a patient in need of such treatment a pharmaceutical composition which contains an antiviral effective amount of one or more of the compounds of Formulas I, II, and/or III, together with one or more pharmaceutically acceptable carriers, excipients or diluents. As used herein, the term "antiviral effective amount" means the total amount of each active component of the composition and method that is sufficient to show a meaningful patient benefit, i.e., inhibiting, ameliorating, or healing of acute conditions characterized by inhibition of the HIV infection. When applied to an individual active ingredient, administered alone, the term refers to that ingredient alone. When applied to a combination, the term refers to combined amounts of the active ingredients that result in the therapeutic effect, whether administered in combination, serially or simultaneously. The terms "treat, treating, treatment" as used herein and in the claims means preventing, ameliorating or healing diseases associated with HIV infection.

The pharmaceutical compositions of the invention may be in the form of orally administrable suspensions or tablets; as well as nasal sprays, sterile injectable preparations, for example, as sterile injectable aqueous or oleaginous suspensions or suppositories. Pharmaceutically acceptable carriers, excipients or diluents may be utilized in the pharmaceutical compositions, and are those utilized in the art of pharmaceutical preparations.

When administered orally as a suspension, these compositions are prepared according to techniques typically known in the art of pharmaceutical formulation and may contain microcrystalline cellulose for imparting bulk, alginic acid or sodium alginate as a suspending agent, methylcellulose as a viscosity enhancer, and sweeteners/flavoring agents known in the art. As immediate release tablets, these compositions may contain microcrystalline cellulose, dicalcium phosphate, starch, magnesium stearate and lactose and/or other excipients, binders, extenders, disintegrants, diluents, and lubricants known in the art.

The injectable solutions or suspensions may be formulated according to known art, using suitable non-toxic, parenterally acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

The compounds herein set forth can be administered orally to humans in a dosage range of about 1 to 100 mg/kg body weight in divided doses, usually over an extended period, such as days, weeks, months, or even years. One preferred dosage range is about 1 to 10 mg/kg body weight orally in divided doses. Another preferred dosage range is about 1 to 20 mg/kg body weight in divided doses. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Also contemplated herein are combinations of the compounds of Formulas I, II, III and/or IV herein set forth, together with one or more other agents useful in the treatment of AIDS. For example, the compounds of this disclosure may be effectively administered, whether at periods of pre-exposure and/or post-exposure, in combination with effective amounts of the AIDS antivirals, immunomodulators, antiinfectives, or vaccines, such as those in the following non-limiting table:

| Drug Name | Manufacturer | Indication |
| --- | --- | --- |
| ANTIVIRALS | | |
| 097 | Hoechst/Bayer | HIV infection, AIDS, ARC (non-nucleoside reverse transcriptase (RT) inhibitor) |
| Amprenavir 141 W94 GW 141 | Glaxo Wellcome | HIV infection, AIDS, ARC (protease inhibitor) |
| Abacavir (1592U89) GW 1592 | Glaxo Wellcome | HIV infection, AIDS, ARC (RT inhibitor) |
| Acemannan | Carrington Labs (Irving, TX) | ARC |
| Acyclovir | Burroughs Wellcome | HIV infection, AIDS, ARC |
| AD-439 | Tanox Biosystems | HIV infection, AIDS, ARC |
| AD-519 | Tanox Biosystems | HIV infection, AIDS, ARC |
| Adefovir dipivoxil | Gilead Sciences | HIV infection |
| AL-721 | Ethigen (Los Angeles, CA) | ARC, PGL HIV positive, AIDS |
| Alpha Interferon | Glaxo Wellcome | Kaposi's sarcoma, HIV in combination w/Retrovir |
| Ansamycin LM 427 | Adria Laboratories (Dublin, OH) Erbamont (Stamford, CT) | ARC |
| Antibody which Neutralizes pH Labile alpha aberrant Interferon | Advanced Biotherapy Concepts (Rockville, MD) | AIDS, ARC |
| AR177 | Aronex Pharm | HIV infection, AIDS, ARC |
| Beta-fluoro-ddA | Nat'l Cancer Institute | AIDS-associated diseases |
| BMS-234475 (CGP-61755) | Bristol-Myers Squibb/ Novartis | HIV infection, AIDS, ARC (protease inhibitor) |
| CI-1012 | Warner-Lambert | HIV-1 infection |
| Cidofovir | Gilead Science | CMV retinitis, herpes, papillomavirus |
| Curdlan sulfate | AJI Pharma USA | HIV infection |
| Cytomegalovirus Immune globin | MedImmune | CMV retinitis |

-continued

| Drug Name | Manufacturer | Indication |
|---|---|---|
| Cytovene<br>Ganciclovir | Syntex | Sight threatening<br>CMV<br>peripheral CMV<br>retinitis |
| Darunavir | Tibotec- J & J | HIV infection, AIDS, ARC<br>(protease inhibitor) |
| Delaviridine | Pharmacia-Upjohn | HIV infection,<br>AIDS, ARC<br>(RT inhibitor) |
| Dextran Sulfate | Ueno Fine Chem.<br>Ind. Ltd. (Osaka,<br>Japan) | AIDS, ARC, HIV<br>positive<br>asymptomatic |
| ddC<br>Dideoxycytidine | Hoffman-La Roche | HIV infection, AIDS,<br>ARC |
| ddI<br>Dideoxyinosine | Bristol-Myers Squibb | HIV infection, AIDS,<br>ARC; combination<br>with AZT/d4T |
| DMP-450 | AVID<br>(Camden, NJ) | HIV infection,<br>AIDS, ARC<br>(protease inhibitor) |
| Efavirenz<br>(DMP 266, SUSTIVA ®)<br>(−)6-Chloro-4-(S)-<br>cyclopropylethynyl-<br>4(S)-trifluoro-<br>methyl-1,4-dihydro-<br>2H-3,1-benzoxazin-<br>2-one, STOCRINE | Bristol Myers Squibb | HIV infection,<br>AIDS, ARC<br>(non-nucleoside RT<br>inhibitor) |
| EL10 | Elan Corp, PLC<br>(Gainesville, GA) | HIV infection |
| Etravirine | Tibotec/J & J | HIV infection, AIDS, ARC<br>(non-nucleoside<br>reverse transcriptase<br>inhibitor) |
| Famciclovir | Smith Kline | herpes zoster,<br>herpes simplex |
| GS 840 | Gilead | HIV infection,<br>AIDS, ARC<br>(reverse transcriptase<br>inhibitor) |
| HBY097 | Hoechst Marion<br>Roussel | HIV infection,<br>AIDS, ARC<br>(non-nucleoside<br>reverse transcriptase<br>inhibitor) |
| Hypericin | VIMRx Pharm. | HIV infection, AIDS,<br>ARC |
| Recombinant Human<br>Interferon Beta | Triton Biosciences<br>(Almeda, CA) | AIDS, Kaposi's<br>sarcoma, ARC |
| Interferon alfa-n3 | Interferon Sciences | ARC, AIDS |
| Indinavir | Merck | HIV infection, AIDS,<br>ARC, asymptomatic<br>HIV positive, also in<br>combination with<br>AZT/ddI/ddC |
| ISIS 2922 | ISIS Pharmaceuticals | CMV retinitis |
| KNI-272 | Nat'l Cancer Institute | HIV-assoc. diseases |
| Lamivudine, 3TC | Glaxo Wellcome | HIV infection,<br>AIDS, ARC<br>(reverse<br>transcriptase<br>inhibitor); also<br>with AZT |
| Lobucavir | Bristol-Myers Squibb | CMV infection |
| Nelfinavir | Agouron<br>Pharmaceuticals | HIV infection,<br>AIDS, ARC<br>(protease inhibitor) |
| Nevirapine | Boeheringer<br>Ingleheim | HIV infection,<br>AIDS, ARC<br>(RT inhibitor) |
| Novapren | Novaferon Labs, Inc.<br>(Akron, OH) | HIV inhibitor |
| Peptide T<br>Octapeptide<br>Sequence | Peninsula Labs<br>(Belmont, CA) | AIDS |

| Drug Name | Manufacturer | Indication |
|---|---|---|
| Trisodium Phosphonoformate | Astra Pharm. Products, Inc. | CMV retinitis, HIV infection, other CMV infections |
| PNU-140690 | Pharmacia Upjohn | HIV infection, AIDS, ARC (protease inhibitor) |
| Probucol | Vyrex | HIV infection, AIDS |
| RBC-CD4 | Sheffield Med. Tech (Houston, TX) | HIV infection, AIDS, ARC |
| Ritonavir | Abbott | HIV infection, AIDS, ARC (protease inhibitor) |
| Saquinavir | Hoffmann-LaRoche | HIV infection, AIDS, ARC (protease inhibitor) |
| Stavudine; d4T Didehydrodeoxy-Thymidine | Bristol-Myers Squibb | HIV infection, AIDS, ARC |
| Tipranavir | Boehringer Ingelheim | HIV infection, AIDS, ARC (protease inhibitor) |
| Valaciclovir | Glaxo Wellcome | Genital HSV & CMV infections |
| Virazole Ribavirin | Viratek/ICN (Costa Mesa, CA) | asymptomatic HIV positive, LAS, ARC |
| VX-478 | Vertex | HIV infection, AIDS, ARC |
| Zalcitabine | Hoffmann-LaRoche | HIV infection, AIDS, ARC, with AZT |
| Zidovudine; AZT | Glaxo Wellcome | HIV infection, AIDS, ARC, Kaposi's sarcoma, in combination with other therapies |
| Tenofovir disoproxil, fumarate salt (VIREAD ®) | Gilead | HIV infection, AIDS, (reverse transcriptase inhibitor) |
| EMTRIVA ® (Emtricitabine) (FTC) | Gilead | HIV infection, AIDS, (reverse transcriptase inhibitor) |
| COMBIVIR ® | GSK | HIV infection, AIDS, (reverse transcriptase inhibitor) |
| Abacavir succinate (or ZIAGEN ®) | GSK | HIV infection, AIDS, (reverse transcriptase inhibitor) |
| REYATAZ ® (or atazanavir) | Bristol-Myers Squibb | HIV infection AIDs, protease inhibitor |
| FUZEON ® (Enfuvirtide or T-20) | Roche/Trimeris | HIV infection AIDs, viral Fusion inhibitor |
| LEXIVA ® (or Fosamprenavir calcium) | GSK/Vertex | HIV infection AIDs, viral protease inhibitor |
| SELZENTRY ® Maraviroc; (UK 427857) | Pfizer | HIV infection AIDs, (CCR5 antagonist, in development) |
| TRIZIVIR ® | GSK | HIV infection AIDs, (three drug combination) |
| Sch-417690 (vicriviroc) | Schering-Plough | HIV infection AIDs, (CCR5 antagonist, in development) |
| TAK-652 | Takeda | HIV infection AIDs, (CCR5 antagonist, in development) |
| GSK 873140 (ONO-4128) | GSK/ONO | HIV infection AIDs, (CCR5 antagonist, in development) |
| Integrase Inhibitor MK-0518 Raltegravir | Merck | HIV infection AIDs |

| Drug Name | Manufacturer | Indication |
|---|---|---|
| TRUVADA ® | Gilead | Combination of Tenofovir disoproxil fumarate salt (VIREAD ®) and EMTRIVA ® (Emtricitabine) |
| Integrase Inhibitor GS917/JTK-303 Elvitegravir | Gilead/Japan Tobacco | HIV Infection AIDs in development |
| Triple drug combination ATRIPLA ® | Gilead/Bristol-Myers Squibb | Combination of Tenofovir disoproxil fumarate salt (VIREAD ®), EMTRIVA ® (Emtricitabine), and SUSTIVA ® (Efavirenz) |
| FESTINAVIR ® 4'-ethynyl-d4T | Oncolys BioPharma BMS | HIV infection AIDs in development |
| CMX-157 Lipid conjugate of nucleotide tenofovir | Chimerix | HIV infection AIDs |
| GSK1349572 Integrase inhibitor | GSK | HIV infection AIDs |
| IMMUNOMODULATORS | | |
| AS-101 | Wyeth-Ayerst | AIDS |
| Bropirimine | Pharmacia Upjohn | Advanced AIDS |
| Acemannan | Carrington Labs, Inc. (Irving, TX) | AIDS, ARC |
| CL246,738 | Wyeth Lederle Labs | AIDS, Kaposi's sarcoma |
| FP-21399 | Fuki ImmunoPharm | Blocks HIV fusion with CD4+ cells |
| Gamma Interferon | Genentech | ARC, in combination w/TNF (tumor necrosis factor) |
| Granulocyte Macrophage Colony Stimulating Factor | Genetics Institute Sandoz | AIDS |
| Granulocyte Macrophage Colony Stimulating Factor | Hoechst-Roussel Immunex | AIDS |
| Granulocyte Macrophage Colony Stimulating Factor | Schering-Plough | AIDS, combination w/AZT |
| HIV Core Particle Immunostimulant | Rorer | Seropositive HIV |
| IL-2 Interleukin-2 | Cetus | AIDS, in combination w/AZT |
| IL-2 Interleukin-2 | Hoffman-LaRoche Immunex | AIDS, ARC, HIV, in combination w/AZT |
| IL-2 Interleukin-2 (aldeslukin) | Chiron | AIDS, increase in CD4 cell counts |
| Immune Globulin Intravenous (human) | Cutter Biological (Berkeley, CA) | Pediatric AIDS, in combination w/AZT |
| IMREG-1 | Imreg (New Orleans, LA) | AIDS, Kaposi's sarcoma, ARC, PGL |
| IMREG-2 | Imreg (New Orleans, LA) | AIDS, Kaposi's sarcoma, ARC, PGL |
| Imuthiol Diethyl Dithio Carbamate | Merieux Institute | AIDS, ARC |
| Alpha-2 Interferon | Schering Plough | Kaposi's sarcoma w/AZT, AIDS |
| Methionine-Enkephalin | TNI Pharmaceutical (Chicago, IL) | AIDS, ARC |
| MTP-PE Muramyl-Tripeptide | Ciba-Geigy Corp. | Kaposi's sarcoma |
| Granulocyte Colony Stimulating Factor | Amgen | AIDS, in combination w/AZT |
| Remune | Immune Response Corp. | Immunotherapeutic |
| rCD4 Recombinant Soluble Human CD4 | Genentech | AIDS, ARC |
| rCD4-IgG hybrids | | AIDS, ARC |

-continued

| Drug Name | Manufacturer | Indication |
|---|---|---|
| Recombinant Soluble Human CD4 | Biogen | AIDS, ARC |
| Interferon Alfa 2a | Hoffman-La Roche | Kaposi's sarcoma AIDS, ARC, in combination w/AZT |
| SK&F106528 Soluble T4 | Smith Kline | HIV infection |
| Thymopentin | Immunobiology Research Institute (Annandale, NJ) | HIV infection |
| Tumor Necrosis Factor; TNF | Genentech | ARC, in combination w/gamma Interferon |
| ANTI-INFECTIVES | | |
| Clindamycin with Primaquine | Pharmacia Upjohn | PCP |
| Fluconazole | Pfizer | Cryptococcal meningitis, candidiasis |
| Pastille Nystatin Pastille | Squibb Corp. | Prevention of oral candidiasis |
| Ornidyl Eflornithine | Merrell Dow | PCP |
| Pentamidine Isethionate (IM & IV) | LyphoMed (Rosemont, IL) | PCP treatment |
| Trimethoprim | | Antibacterial |
| Trimethoprim/sulfa | | Antibacterial |
| Piritrexim | Burroughs Wellcome | PCP treatment |
| Pentamidine Isethionate for Inhalation | Fisons Corporation | PCP prophylaxis |
| Spiramycin | Rhone-Poulenc | Cryptosporidial diarrhea |
| Intraconazole-R51211 | Janssen-Pharm. | Histoplasmosis; cryptococcal meningitis |
| Trimetrexate | Warner-Lambert | PCP |
| Daunorubicin | NeXstar, Sequus | Kaposi's sarcoma |
| Recombinant Human Erythropoietin | Ortho Pharm. Corp. | Severe anemia assoc. with AZT therapy |
| Recombinant Human Growth Hormone | Serono | AIDS-related wasting, cachexia |
| Megestrol Acetate | Bristol-Myers Squibb | Treatment of anorexia assoc. W/AIDS |
| Testosterone | Alza, Smith Kline | AIDS-related wasting |
| Total Enteral Nutrition | Norwich Eaton Pharmaceuticals | Diarrhea and malabsorption related to AIDS |

Additionally, the compounds of the disclosure herein set forth may be used in combination with HIV entry inhibitors. Examples of such HIV entry inhibitors are discussed in DRUGS OF THE FUTURE 1999, 24(12), pp. 1355-1362; CELL, Vol. 9, pp. 243-246, Oct. 29, 1999; and DRUG DISCOVERY TODAY, Vol. 5, No. 5, May 2000, pp. 183-194 and *Inhibitors of the entry of HIV into host cells.* Meanwell, Nicholas A.; Kadow, John F., Current Opinion in Drug Discovery & Development (2003), 6(4), 451-461. Specifically the compounds can be utilized in combination with attachment inhibitors, fusion inhibitors, and chemokine receptor antagonists aimed at either the CCR5 or CXCR4 coreceptor. HIV attachment inhibitors are also set forth in U.S. Pat. Nos. 7,354,924 and 7,745,625.

It will be understood that the scope of combinations of the compounds of this application with AIDS antivirals, immunomodulators, anti-infectives, HIV entry inhibitors or vaccines is not limited to the list in the above Table but includes, in principle, any combination with any pharmaceutical composition useful for the treatment of AIDS.

Preferred combinations are simultaneous or alternating treatments with a compound of the present disclosure and an inhibitor of HIV protease and/or a non-nucleoside inhibitor of HIV reverse transcriptase. An optional fourth component in the combination is a nucleoside inhibitor of HIV reverse transcriptase, such as AZT, 3TC, ddC or ddI. A preferred inhibitor of HIV protease is REYATAZ® (active ingredient Atazanavir). Typically a dose of 300 to 600 mg is administered once a day. This may be co-administered with a low dose of Ritonavir (50 to 500 mgs). Another preferred inhibitor of HIV protease is KALETRA®. Another useful inhibitor of HIV protease is indinavir, which is the sulfate salt of N-(2 (R)-hydroxy-1-(S)-indanyl)-2(R)-phenylmethyl-4-(S)-hydroxy-5-(1-(4-(3-pyridyl-methyl)-2(S)-N'-(t-butylcarboxamido)-piperazinyl))-pentaneamide ethanolate, and is synthesized according to U.S. Pat. No. 5,413,999. Indinavir is generally administered at a dosage of 800 mg three times a day. Other preferred protease inhibitors are nelfinavir and ritonavir. Another preferred inhibitor of HIV protease is saquinavir which is administered in a dosage of 600 or 1200 mg tid. Preferred non-nucleoside inhibitors of HIV reverse transcriptase include efavirenz. These combinations may have unexpected effects on limiting the spread and degree of infection of HIV. Preferred combinations include those with the following (1) indinavir with efavirenz, and, optionally, AZT and/or 3TC and/or ddI and/or ddC; (2) indinavir, and any of AZT and/or ddI and/or ddC and/or 3TC, in particular, indinavir and AZT and 3TC; (3) stavudine and 3TC and/or zidovudine; (4) tenofovir disoproxil fumarate salt and emtricitabine.

In such combinations the compound of the present invention and other active agents may be administered separately or in conjunction. In addition, the administration of one element may be prior to, concurrent to, or subsequent to the administration of other agent(s).

GENERAL CHEMISTRY (METHODS OF SYNTHESIS)

The present invention comprises compounds of Formulas I, II, III, and IV their pharmaceutical formulations, and their use in patients suffering from or susceptible to HIV infection. The compounds of Formulas I, II, III, and IV also include pharmaceutically acceptable salts thereof. General procedures to construct compounds of Formulas I, II, III and IV and intermediates useful for their synthesis are described in the following Schemes (after the Abbreviations).

Abbreviations

One or more of the following abbreviations, most of which are conventional abbreviations well known to those skilled in the art, may be used throughout the description of the disclosure and the examples:
Bz$_2$O=benzoic anhydride
TBTU=O-(benzotriazol-1-yl)-N,N,N',N'-tetramethyluronium tetrafluoroborate
HATU=2-(1H-7-azabenzotriazol-1-yl)-1,1,3,3-tetramethyluronium hexafluorophosphate methanaminium
DCE=dichloroethane
DCM=dichloromethane
CDI=carbonyl diimidazole
prep. HPLC=preparative high performance liquid chromatography
rt=room temperature
DIPEA=diisopropylethylamine
DMAP=4-dimethylaminopyridine
DMSO=dimethylsulfoxide
THF=tetrahydrofuran
KHMDS=potassium bis(trimethylsilyl)amide
min=minute(s)
h=hour(s)
sat.=saturated
TEA=triethylamine
EtOAc=ethyl acetate
TFA=trifluoroacetic acid
PCC=pyridinium chlorochromate
TLC=thin layer chromatography
Tf$_2$NPh=(trifluoromethylsulfonyl)methanesulfonamide
dioxane=1,4-dioxane
PG=protective group
atm=atmosphere(s)
mol=mole(s)
mmol=milimole(s)
mg=milligram(s)
μg=microgram(s)
μl=microliter(s)
μm=micrometer(s)
mm=millimeter(s)
HOAc=acetic acid
MeOH=methanol
DMF=N,N-dimethylformamide
TBAF=tetrabutylammonium fluoride
TBDMSCl=tert-butyldimethylsilyl chloride
RBF=round bottom flask
DI=deionized The terms "C-3" and "C-28" refer to certain positions of a triterpene core as numbered in accordance with IUPAC rules (positions depicted below with respect to an illustrative triterpene: betulin):

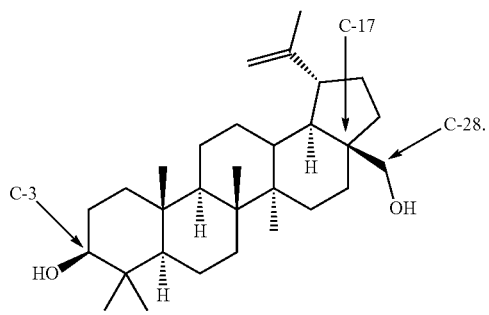

The same numbering is maintained when referring to the compound series in schemes and general descriptions of methods.

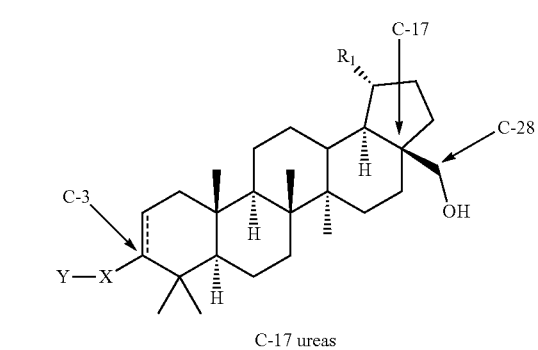

C-17 ureas

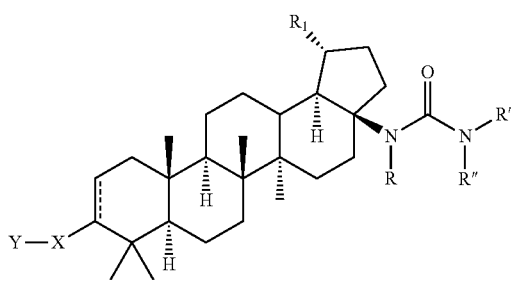

C-17 amides

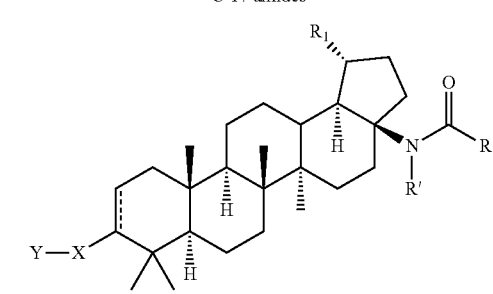

C-17 amines

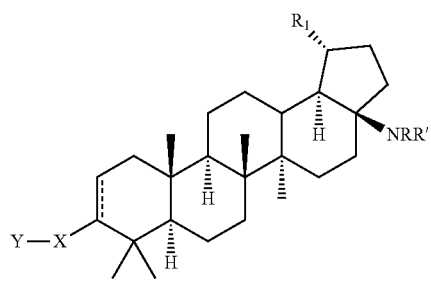

C-17 carbamates

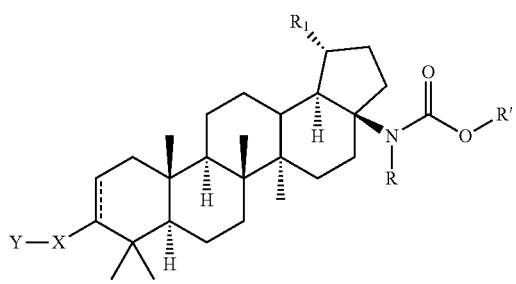

[C-28 amines

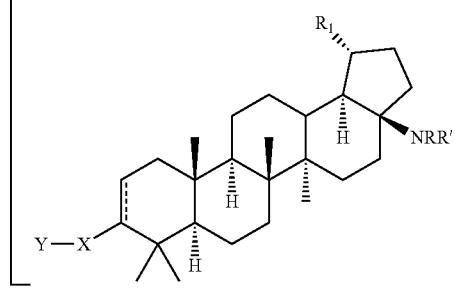
]

Preparation of Compounds of Formulas I, II, III and IV General Chemistry Schemes Compounds of Formula I can be prepared from commercially available (Aldrich, others) betulinic acid by chemistry described in the following schemes. Compounds of Formula II, III and IV are described thereafter.

General reaction schemes are set forth as follows:

Scheme 1

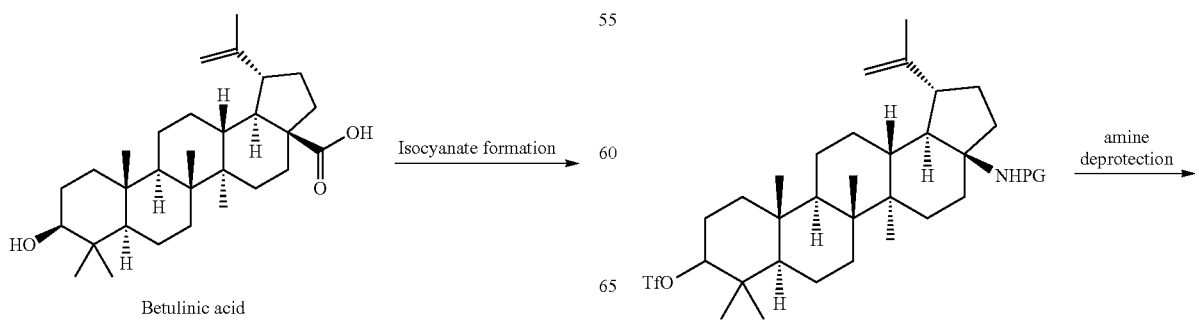

Betulinic acid

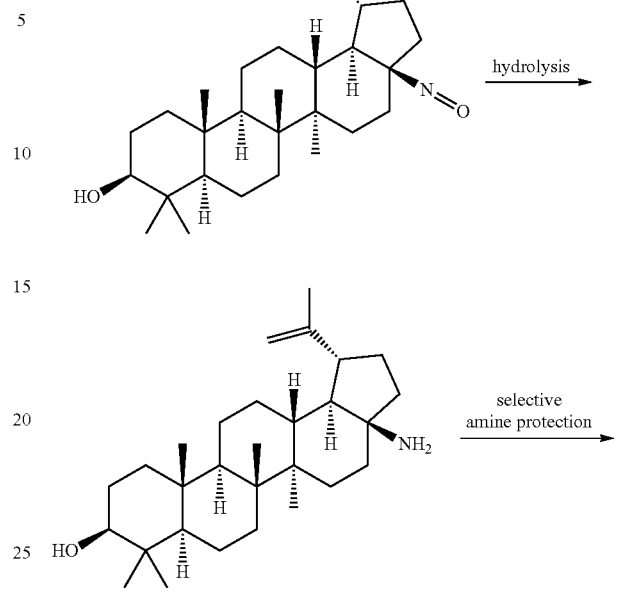

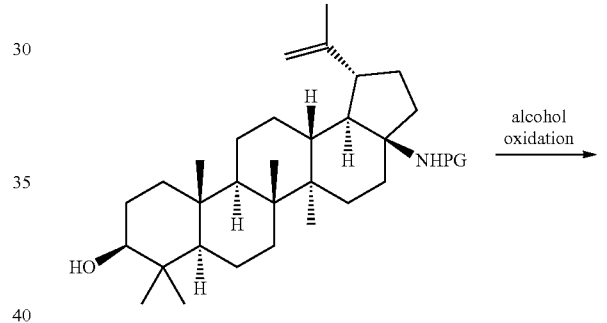

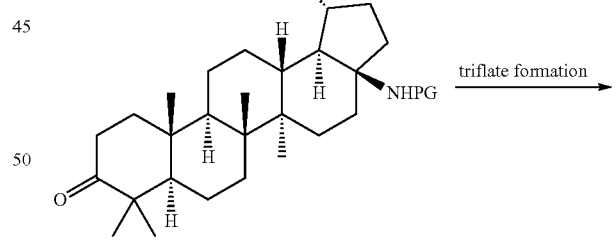

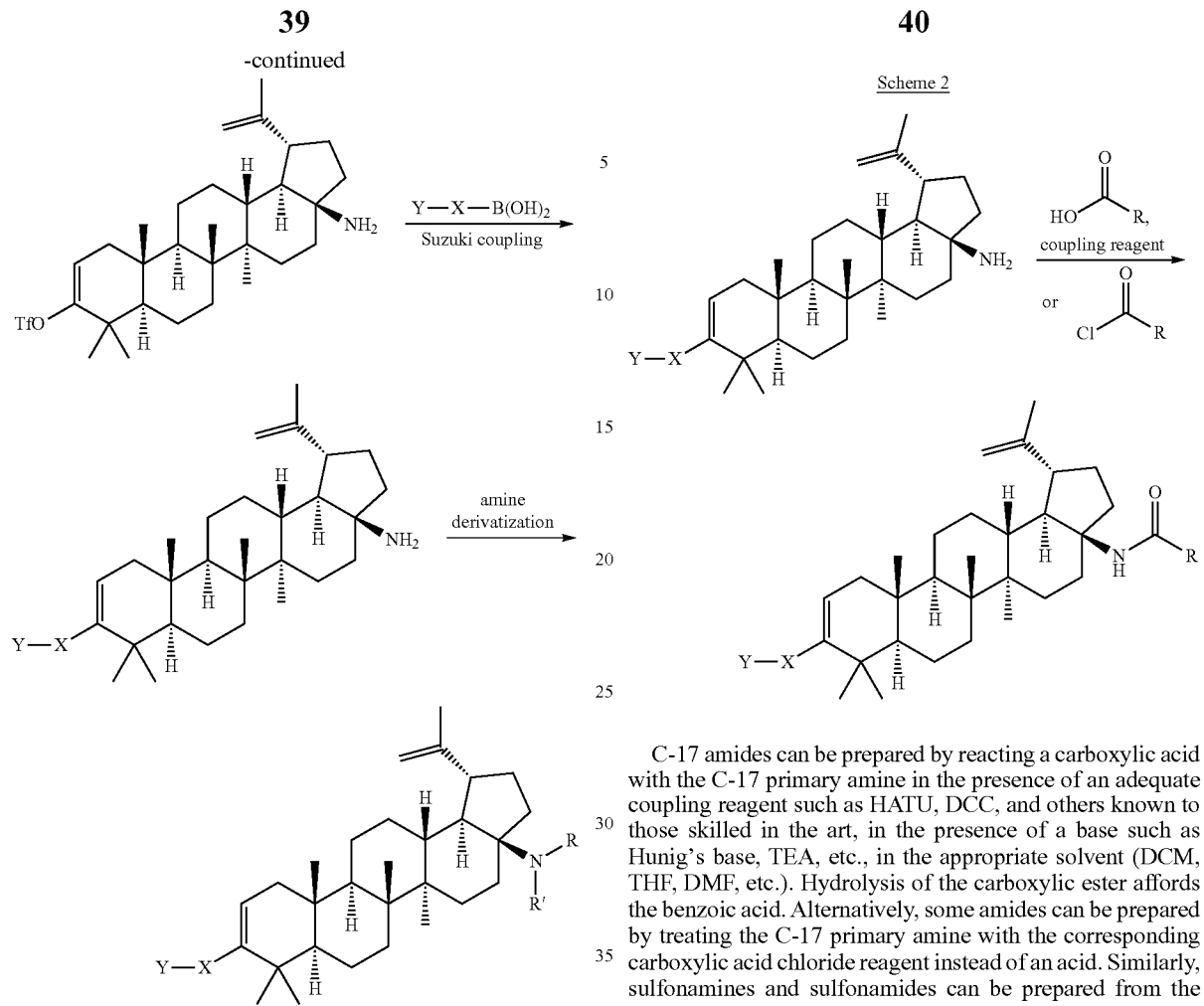

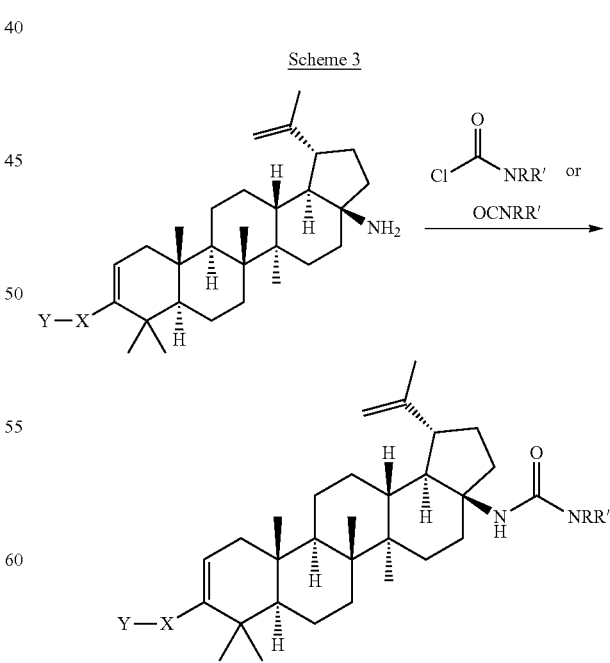

Compounds of formula I can be prepared from betulinic acid as described in Scheme 1. Curtis rearrangement of betulinic acid can be accomplished without protection of the C-3 hydroxyl group to render the C-17 isocyanate which upon acid hydrolysis affords the C-17 amine The C-17 amine is then selectively protected with an amine protective group (i.e F-moc, Boc) to then perform the oxidation of the C-3 hydroxy group to a ketone under standard conditions (i.e. PCC, Dess-Martin reagent, etc). Conversion of the ketone into its triflate can be accomplished by methods known to those skilled in the art. The protective group in the amino group is then taken off to produce the C-17 unsubstituted amine Installation of the C-3 moiety is accomplished via Suzuki coupling of the triflate with the corresponding boronic acid as described above. Alternatively, the triflate coupling with the corresponding boronic acid can be performed before the deprotection of the C-17 amine Once deprotected, the C-17 amino group can then be further derivatized by methods know to those skilled in the art such as alkylation, reductive amination, acylation, etc. Several of these methods are described in the Schemes below (Scheme 2-7). In some cases, an additional step is needed to unmask any functional group that may be functionalized with a protective group (i.e. when Y is COOH, is always masked as the corresponding ester COOR until this last step).

The C-17 primary amine can be further modified using standard methods, known to those skill in the art. Some examples are shown in the following schemes.

C-17 amides can be prepared by reacting a carboxylic acid with the C-17 primary amine in the presence of an adequate coupling reagent such as HATU, DCC, and others known to those skilled in the art, in the presence of a base such as Hunig's base, TEA, etc., in the appropriate solvent (DCM, THF, DMF, etc.). Hydrolysis of the carboxylic ester affords the benzoic acid. Alternatively, some amides can be prepared by treating the C-17 primary amine with the corresponding carboxylic acid chloride reagent instead of an acid. Similarly, sulfonamines and sulfonamides can be prepared from the C-17 primary amine by using a sulfonyl chloride as the sulfonylating agent.

C-17 ureas can be prepared by reacting the corresponding carbamoyl chloride or isocyanate in the presence of a base such as Hunig's base, TEA, etc., in the appropriate solvent (DCM, THF, DMF, etc.). C-17 carbamates can be prepared in a similar manner using a chloroformate instead of the carbamoyl chloride.

mesylate, tosylate or triflate in the presence of a base. Heating may be needed in some cases. Hydrolysis of the carboxylic ester renders the benzoic acid product.

Scheme 4

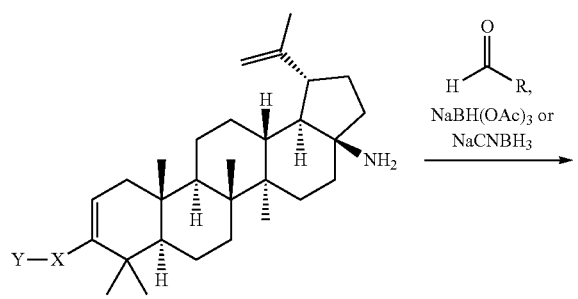

The C-17 primary amine can be treated with an aldehyde under reductive amination conditions (e.g. NaBH(OAc)$_3$) in the presence of AcOH/NaOAc or Ti(OPr)$_4$ in a solvent such as THF, 1,4-dioxane, DCE or DCM) to afford C-17 secondary amines Scheme 6

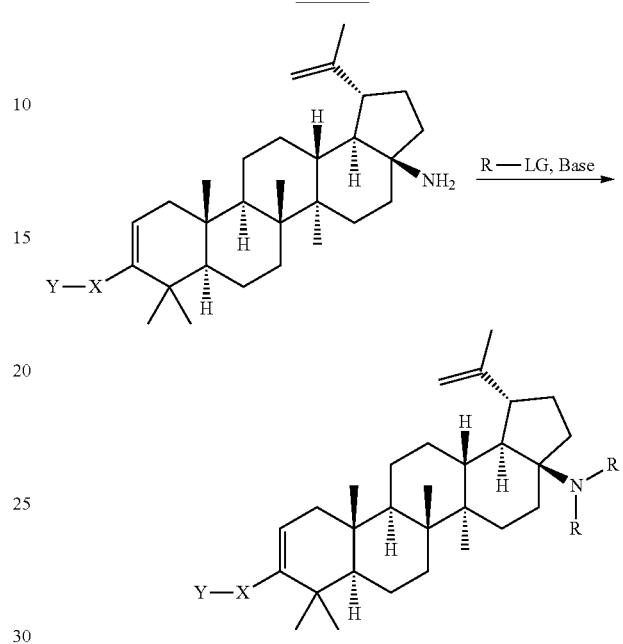

In some cases, by prolonging the reaction times and heating the reaction mixture, the dialkylated product can also be formed.

Scheme 5

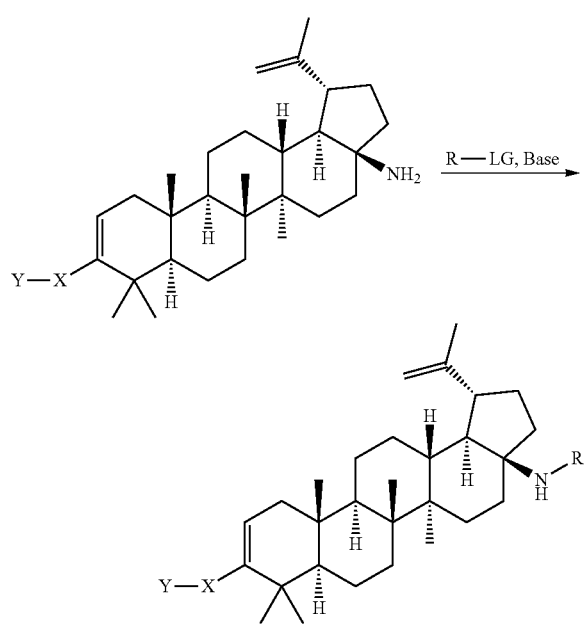

Some C-17 amines can be prepared by alkylation of the C-17 primary amine with an alkylating agent (R-LG), where LG is a leaving group such as, but not limited to Br, Cl, I, Scheme 7

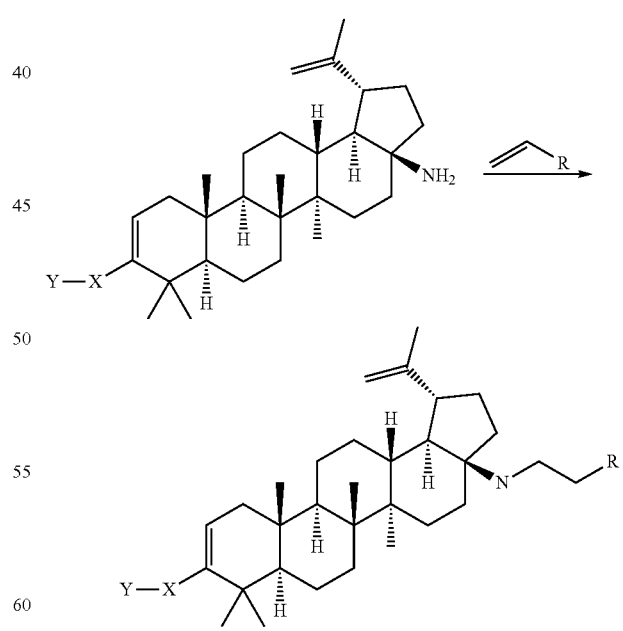

Alternatively, some C-17 amines can be prepared by 1,4-addition to Michael acceptors.

Substituents R, R' and R" may contain functional groups (i.e. COOH, COOR, OH, NHR) that can be further modified by methods know to those skilled in the art. The modification can be carried out before or after the final deprotection of the carboxylic acid is performed depending on the nature of the functional group.

Alternatively, the C-17 secondary amine can be further modified (i.e. alkylated, acylated, sulfonylated, etc.) using some of the methods described above or other standard methods known to those skilled in the art.

Compounds of formula II can be prepared using the chemistry methods described above for compounds of formula I, with one extra step which consists of saturation of the double bonds as shown in scheme 8.

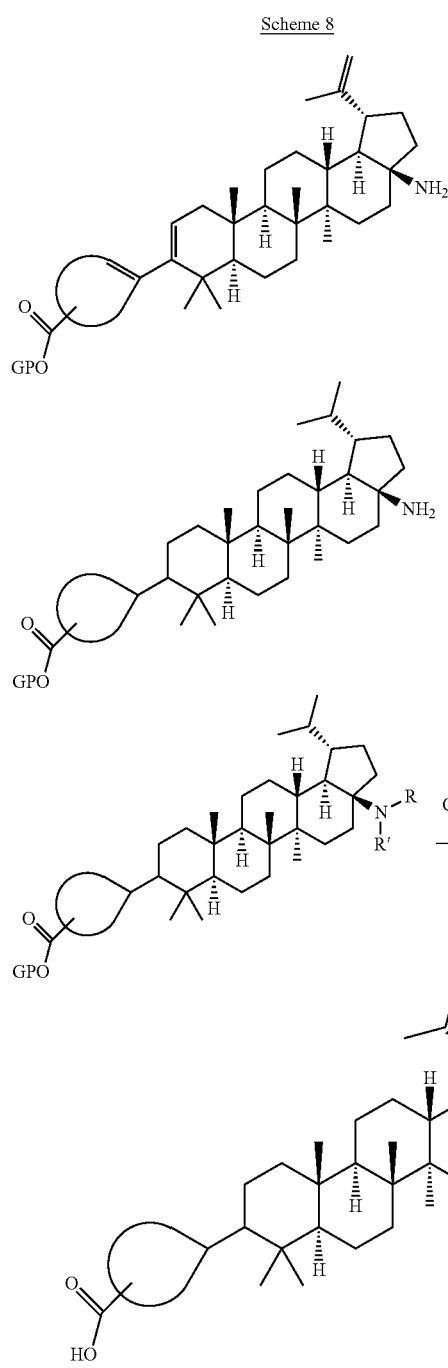

Alternatively, the hydrogenation of the olefins can be controlled to preserve the A-ring unsaturation as shown in scheme 9.

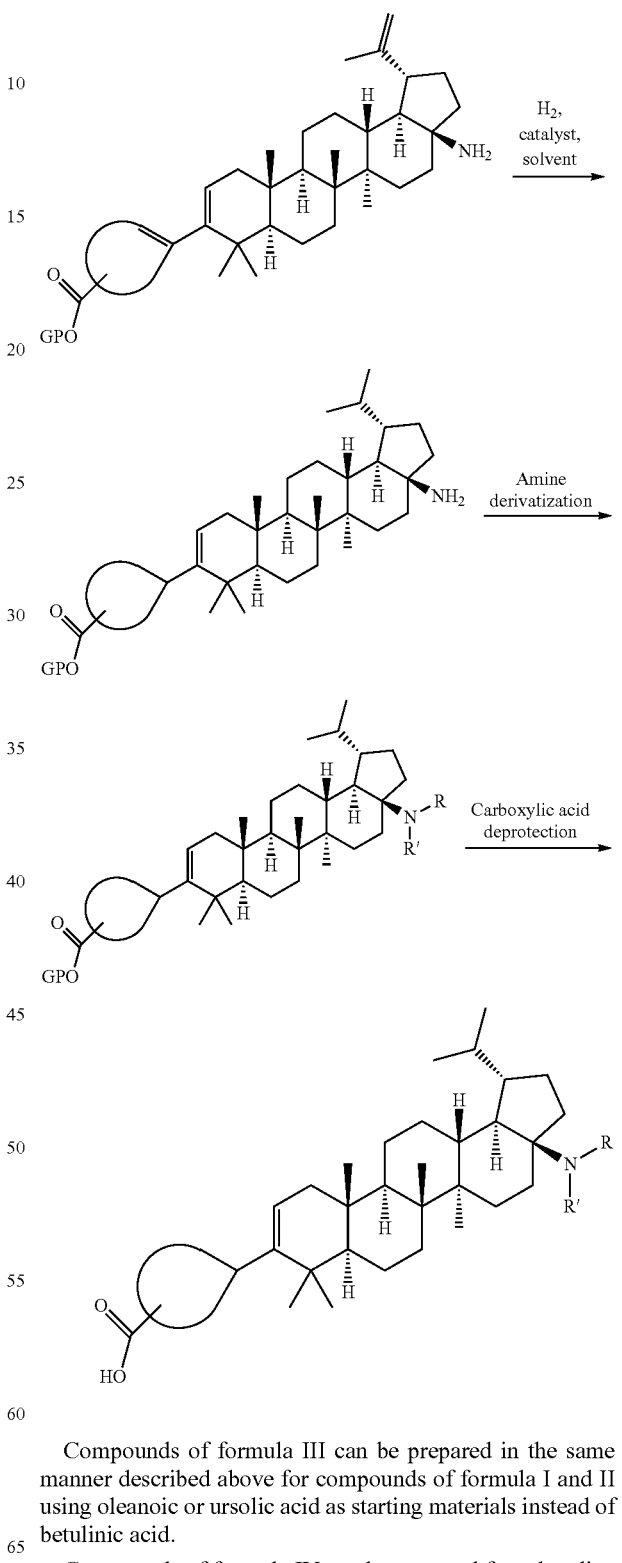

Compounds of formula III can be prepared in the same manner described above for compounds of formula I and II using oleanoic or ursolic acid as starting materials instead of betulinic acid.

Compounds of formula IV can be prepared from betuline or betulinic acid as described in the scheme below:

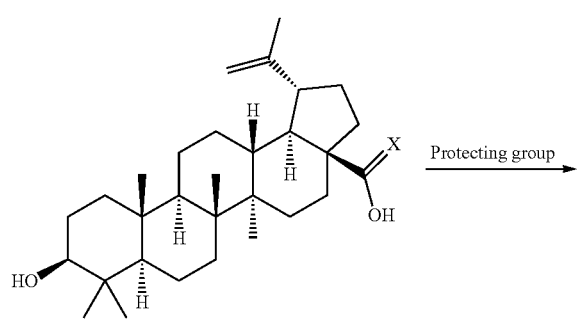

Betulinic acid X = O
Betuline X = HH

Protecting group →

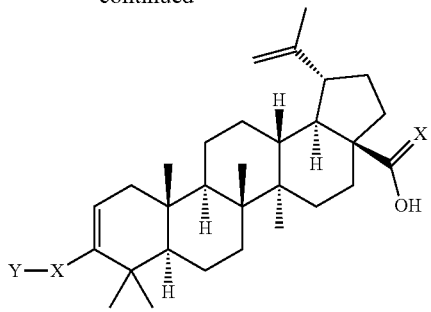

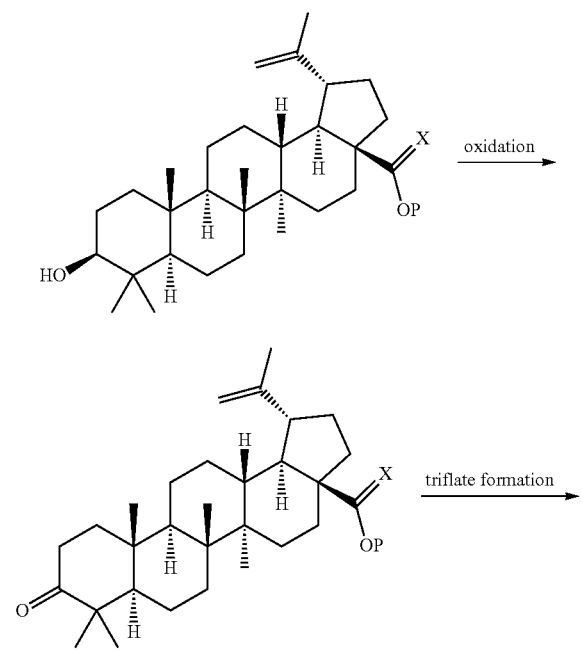

oxidation → triflate formation →

Suzuki coupling
(HO)₂BX—Y →

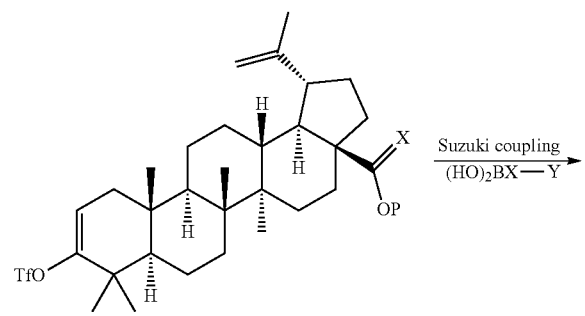

Deprotection →

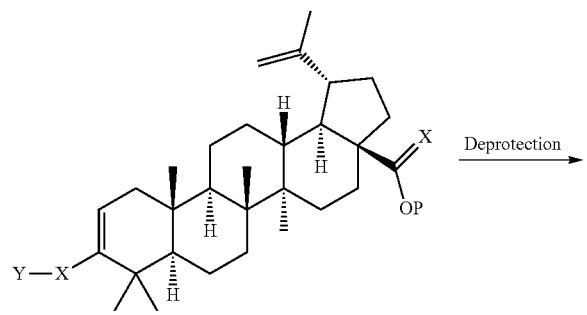

EXAMPLES

The following examples illustrate typical syntheses of the compounds of Formulas I, II, III and IV as described generally above. These examples are illustrative only and are not intended to limit the disclosure in any way. The reagents and starting materials are readily available to one of ordinary skill in the art.

Chemistry

Typical Procedures and Characterization of Selected Examples:

Unless otherwise stated, solvents and reagents were used directly as obtained from commercial sources, and reactions were performed under a nitrogen atmosphere. Flash chromatography was conducted on Silica gel 60 (0.040-0.063 particle size; EM Science supply). $^1$H NMR spectra were recorded on Bruker DRX-500f at 500 MHz (or Bruker AV 400 MHz, Bruker DPX-300B or Varian Gemini 300 at 300 MHz as stated). The chemical shifts were reported in ppm on the δ scale relative to δTMS=0. The following internal references were used for the residual protons in the following solvents: CDCl$_3$ $\delta_H$ 7.26), CD$_3$OD ($\delta_H$ 3.30), Acetic-d4 (Acetic Acid d$_4$) $\delta_H$ 11.6, 2.07), DMSO mix or DMSO-D6_CDCl$_3$ (($_H$ 2.50 and 8.25) (ratio 75%:25%), and DMSO-D6 ($\delta_H$ 2.50). Standard acronyms were employed to describe the multiplicity patterns: s (singlet), br. s (broad singlet), d (doublet), t (triplet), q (quartet), m (multiplet), b (broad), app (apparent). The coupling constant (J) is in Hertz. All Liquid Chromatography (LC) data were recorded on a Shimadzu LC-10AS liquid chromatograph using a SPD-10AV UV-Vis detector with Mass Spectrometry (MS) data determined using a Micromass Platform for LC in electrospray mode.

LC/MS methods:

Method 1

Start % B=0, Final % B=100 over 2 minute gradient, hold at 100% B

Flow Rate=1 mL/min

Wavelength=220 nm

Solvent A=90% water, 10% acetonitrile, 0.1% TFA

Solvent B=10% water, 90% acetonitrile, 0.1% TFA

Column=Phenomenex Luna C18, 3 μm, 2.0×30 mm

Method 2

Start % B=0, Final % B=100 over 2 minute gradient, hold at 100% B

Flow Rate=1 mL/Min

Wavelength=220 nm

Solvent A=90% Water, 10% methanol/0.1% TFA

Solvent B=10% Water, 90% methanol/0.1% TFA

Column=Phenomenex Luna C18, 3 μm, 2.0×30 mm

Method 3

Start % B=0, Final % B=100 over 2 minute gradient, hold at 100% B

Flow Rate=1 mL/Min
Wavelength=220 nm
Solvent A=95% Water, 5% methanol/10 Mm ammonium acetate
Solvent B=5% Water, 95% methanol/10 Mm ammonium acetate
Column=Phenomenex Luna C18, 3 μm, 2.0×30 mm
Method 4:
Start % B=30, Final % B=100, gradient Time=2 min
Flow Rate=0.8 mL/min
Wavelength=220
Solvent A=10% MeOH-90% $H_2O$(0.1% TFA)
Solvent B=90% MeOH-10% $H_2O$(0.1% TFA)
Column=Xbridge Phenyl 2.1×50 mm 2.5 μm
Method 5:
Start % B=30, Final % B=100, gradient Time=2 min
Flow Rate=1 mL/min
Wavelength=220
Solvent A=5% MeOH-95% $H_2O$-10 mM $NH_4OAc$
Solvent B=95% MeOH-5% $H_2O$-10 mM $NH_4OAc$
Column=Phenomenex LUNA $C_{18}$ 2.0×30 mm 3 μm
Method 6:
Start % B=0, Final % B=100, gradient Time=4 min
Flow Rate=0.8 mL/min
Wavelength=220
Solvent Pair=MeOH:$H_2O$:(0.1% TFA)
Solvent A=10% MeOH-90% $H_2O$(0.1% TFA)
Solvent B=90% MeOH-10% $H_2O$(0.1% TFA)
Column=Xbridge Phenyl 2.1×50 mm 2.5 μm
Method 7:
Start % B=10, Final % B=100, gradient Time=3 min
Flow Rate=0.8 mL/min
Wavelength=220
Solvent A=5% MeOH-95% $H_2O$-10 mM $NH_4OAc$
Solvent B=95% MeOH-5% $H_2O$-10 mM $NH_4OAc$
Column=Phenomenex LUNA $C_{18}$ 2.0×50 mm 3 μm
Method 8:
Start % B=20, Final % B=100, gradient Time=2 min
Flow Rate=0.8 mL/min
Wavelength=220
Solvent A=10% MeOH-90% $H_2O$(0.1% TFA)
Solvent B=90% MeOH-10% $H_2O$(0.1% TFA)
Column=Xbridge Phenyl 2.1×50 mm 2.5 μm
Method 9:
Start % B=50, Final % B=100, gradient Time=6 min
Flow Rate=0.8 mL/min
Wavelength=220
Solvent A=10% MeOH-90% $H_2O$(0.1% TFA)
Solvent B=90% MeOH-10% $H_2O$(0.1% TFA)
Column=PHENOMENEX-LUNA 2.0×50 mm 3 μm
Method 10:
Start % B=30, Final % B=100, gradient Time=3 min
Flow Rate=0.8 mL/min
Wavelength=220
Solvent A=10% MeOH-90% $H_2O$(0.1% TFA)
Solvent B=90% MeOH-10% $H_2O$(0.1% TFA)
Column=PHENOMENEX-$C_{18}$ 2.0×50 mm 3 μm
Method 11:
Start % B=0, Final % B=100, gradient Time=4 min
Flow Rate=0.8 mL/min
Wavelength=220
Solvent A=10% MeOH-90% $H_2O$(0.1% TFA)
Solvent B=90% MeOH-10% $H_2O$(0.1% TFA)
Column=PHENOMENEX-$C_{18}$ 2.0×50 mm 3 μm
Method 12:
Start % B=40, Final % B=100, gradient Time=4 min
Flow Rate=0.8 mL/min
Wavelength=220
Solvent A=10% MeOH-90% $H_2O$(0.1% TFA)
Solvent B=90% MeOH-10% $H_2O$(0.1% TFA)
Column=PHENOMENEX-$C_{18}$ 2.0×50 mm 3 μm
Method 13:
Start % B=50, Final % B=100, gradient Time=4 min
Flow Rate=0.8 mL/min
Wavelength=220
Solvent A=10% MeOH-90% $H_2O$(0.1% TFA)
Solvent B=90% MeOH-10% $H_2O$(0.1% TFA)
Column=PHENOMENEX-$C_{18}$ 2.0×50 mm 3 μm
Method 14:
Start % B=75, Final % B=100, gradient Time=2 min
Flow Rate=1.0 mL/min
Wavelength=220
Solvent A=10% MeOH-90% $H_2O$(0.1% TFA)
Solvent B=90% MeOH-10% $H_2O$(0.1% TFA)
Column=PHENOMENEX-$C_{18}$ 2.0×30 mm 3 μm
Method 15:
Start % B=50, Final % B=90, gradient Time=4 min
Flow Rate=0.8 mL/min
Wavelength=220
Solvent A=10% MeOH-90% $H_2O$(0.1% TFA)
Solvent B=90% MeOH-10% $H_2O$(0.1% TFA)
Column=PHENOMENEX-$C_{18}$ 2.0×50 mm 3 μm
Method 16:
Start % B=50, Final % B=100, gradient Time=3 min
Flow Rate=0.8 mL/min
Wavelength=220
Solvent A=10% MeOH-90% $H_2O$(0.1% TFA)
Solvent B=90% MeOH-10% $H_2O$(0.1% TFA)
Column=PHENOMENEX-$C_{18}$ 2.0×50 mm 3 μm
Method 17:
Start % B=25, Final % B=100, gradient Time=2 min
Flow Rate=1.0 mL/min
Wavelength=220
Solvent A=10% MeOH-90% $H_2O$(0.1% TFA)
Solvent B=90% MeOH-10% $H_2O$(0.1% TFA)
Column=PHENOMENEX-$C_{18}$ 2.0×30 mm 3 μm
Method 18:
Start % B=50, Final % B=100, gradient Time=4 min
Flow Rate=0.8 mL/min
Wavelength=220
Solvent A=10% MeOH-90% $H_2O$(0.1% TFA)
Solvent B=90% MeOH-10% $H_2O$(0.1% TFA)
Column=PHENOMENEX-$C_{18}$ 2.0×30 mm 3 μm
Method 19:
Start % B=50, Final % B=100, gradient Time=4 min
Flow Rate=0.8 mL/min
Wavelength=220
Solvent A=10% MeOH-90% $H_2O$(0.1% TFA)
Solvent B=90% MeOH-10% $H_2O$(0.1% TFA)
Column=PHENOMENEX-$C_{18}$ 2.0×50 mm 3 μm
Method 20:
Start % B=0, Final % B=80, gradient Time=4 min
Flow Rate=0.8 mL/min
Wavelength=220
Solvent A=10% MeOH-90% $H_2O$(0.1% TFA)
Solvent B=90% MeOH-10% $H_2O$(0.1% TFA)
Column=PHENOMENEX-$C_{18}$ 2.0×50 mm 3 μm
Method 21:
Start % B=0, Final % B=100, gradient Time=3 min
Flow Rate=0.8 mL/min
Wavelength=220
Solvent A=10% MeOH-90% $H_2O$(0.1% TFA)
Solvent B=90% MeOH-10% $H_2O$(0.1% TFA)
Column=PHENOMENEX-$C_{18}$ 2.0×50 mm 3 μm Prep HPLC
Method 1
Start % B=25 Final % B=100 over 10 minute gradient, hold at 100% B
Flow Rate=25 mL/min
Solvent A=10% ACN-90% $H_2O$-0.1% TFA
Solvent B=90% ACN-10% $H_2O$-0.1% TFA
Column=X-bridge Phenyl 19×100 mm 3 μm
Method 2
Start % B=25 Final % B=100 over 12 minute gradient, hold at 100% B
Flow Rate=25 mL/min
Solvent A=10% ACN-90% $H_2O$-0.1% TFA
Solvent B=90% ACN-10% $H_2O$-0.1% TFA
Column=X-bridge Phenyl 19×100 mm 5 μm
Method 3
Start % B=30 Final % B=100 over 12 minute gradient, hold at 100% B
Flow Rate=25 mL/min
Solvent A=10% ACN-90% $H_2O$-0.1% TFA
Solvent B=90% ACN-10% $H_2O$-0.1% TFA
Column=X-bridge Phenyl 19×100 mm 5 μm
Method 4
Start % B=15 Final % B=100 over 20 minute gradient, hold at 100% B
Flow Rate=40 mL/min
Solvent A=10% ACN-90% $H_2O$-0.1% TFA
Solvent B=90% ACN-10% $H_2O$-0.1% TFA
Column=Waters Sunfire 30×100 mm 5 μm
Method 5
Start % B=15 Final % B=100 over 15 minute gradient, hold at 100% B
Flow Rate=40 mL/min
Solvent A=10% ACN-90% $H_2O$-0.1% TFA
Solvent B=90% ACN-10% $H_2O$-0.1% TFA
Column=Waters Sunfire 30×100 mm 5 μm
Method 6
Start % B=20 Final % B=80 over 20 minute gradient
Flow Rate=40 mL/min
Solvent A=10% ACN-90% $H_2O$-0.1% TFA
Solvent B=90% ACN-10% $H_2O$-0.1% TFA
Column=Waters Sunfire 30×100 mm 5 μm
Method 7
Start % B=20 Final % B=75 over 25 minute gradient
Flow Rate=40 mL/min
Solvent A=10% ACN-90% $H_2O$-0.1% TFA
Solvent B=90% ACN-10% $H_2O$-0.1% TFA
Column=Waters Sunfire 30×100 mm 5 μm
Method 8
Start % B=25 Final % B=90 over 15 minute gradient
Flow Rate=40 mL/min
Solvent A=10% ACN-90% $H_2O$-0.1% TFA
Solvent B=90% ACN-10% $H_2O$-0.1% TFA
Column=Waters Sunfire 30×100 mm 5 μm
Method 9
Start % B=25 Final % B=80 over 20 minute gradient
Flow Rate=40 mL/min
Solvent A=10% ACN-90% $H_2O$-0.1% TFA
Solvent B=90% ACN-10% $H_2O$-0.1% TFA
Column=Waters Sunfire 30×100 mm 5 μm
Method 10
Start % B=20 Final % B=100 over 15 minute gradient
Flow Rate=40 mL/min
Solvent A=10% ACN-90% $H_2O$-0.1% TFA
Solvent B=90% ACN-10% $H_2O$-0.1% TFA
Column=Waters Sunfire 30×100 mm 5 μm
Method 11
Start % B=10 Final % B=85 over 12 minute gradient
Flow Rate=40 mL/min
Solvent A=10% ACN-90% $H_2O$-0.1% TFA
Solvent B=90% ACN-10% $H_2O$-0.1% TFA
Column=Waters Sunfire 30×100 mm 5 μm
Method 12
Start % B=40 Final % B=100 over 12 minute gradient, hold at 100% B
Flow Rate=25 mL/min
Solvent A=5% MeOH-95% $H_2O$-10 mM ammonium acetate
Solvent B=95% MeOH-5% $H_2O$-10 mM ammonium acetate
Column=X-bridge Phenyl 19×100 mm 5 μm
Method 13:
Start % B=10, Final % B=100, gradient Time=10 min
Flow Rate=25 mL/min
Wavelength=220
Solvent A=5% MeCN-95% $H_2O$-10 mM $NH_4OAc$
Solvent B=95% MeCN-5% $H_2O$-10 mM $NH_4OAc$
Column=Xbridge OBD Prep Shield RP-18 19×100 mm 5 μm
Method 14:
Start % B=10, Final % B=100, gradient Time=10 min
Flow Rate=25 mL/min
Wavelength=220
Solvent A=5% MeCN-95% $H_2O$-10 mM $NH_4OAc$
Solvent B=95% MeCN-5% $H_2O$-10 mM $NH_4OAc$
Column=Xbridge Prep $C_{18}$ 19×100 mm 5 μm
Method 15:
Start % B=10, Final % B=100, gradient Time=10 min
Flow Rate=40 mL/min
Wavelength=220
Solvent A=10% MeCN-90% $H_2O$(0.1% TFA)
Solvent B=90% MeCN-10% $H_2O$(0.1% TFA)
Column=WATERS-Sunfire 30×100 mm S5
Method 16:
Start % B=10, Final % B=90, gradient Time=15 min
Flow Rate=40 mL/min
Wavelength=220
Solvent A=10% MeCN-90% $H_2O$(0.1% TFA)
Solvent B=90% MeCN-10% $H_2O$(0.1% TFA)
Column=Waters-Sunfire 30×100 mm S5
Chiral SFC Method 1
Column: ChiralCel OJ-H, 30×250 mm, 5 μm
Mobile Phase: 10% EtOH (w/15 mM $NH_3$)/90% $CO_2$
Pressure: 120 bar
Temperature: 35° C.
Flow Rate: 70 mL/min
UV: 205 nm
Injection: 0.5 mL (~10 mg/mL in $CH_3Cl$:EtOH (9:1)) stacked @ 6.5' intervals
Fraction Collection: Peak 1:14.25°-15.50'
  Peak 2:15.70°-17.80'
Chiral SFC Method 2
Column: ChiralCel OJ-H, 30×250 mm, 5 μm
Mobile Phase: 30% MeOH/70% $CO_2$
Pressure: 100 bar
Temperature: 35° C.
Flow Rate: 70 mL/min
UV: 210 nm
Injection: 0.4 mL (~500 mg/mL in MeOH) @ 7.70' intervals
Fraction Collection: Peak 1:4.45°-5.65'
  Peak 2:5.90°-9.40'

Key intermediate 1 was prepared by the following methods:

Method 1

Intermediate 1

Preparation of (1R,3aS,5aR,5bR,7aR,11aR,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl trifluoromethanesulfonate

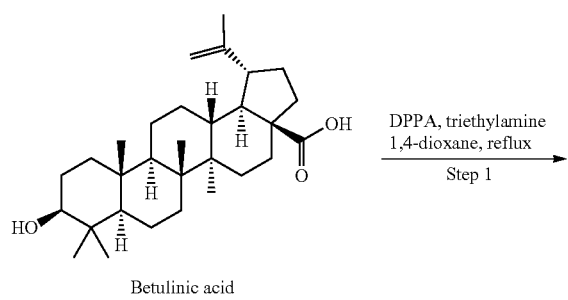
Betulinic acid

DPPA, triethylamine
1,4-dioxane, reflux
Step 1

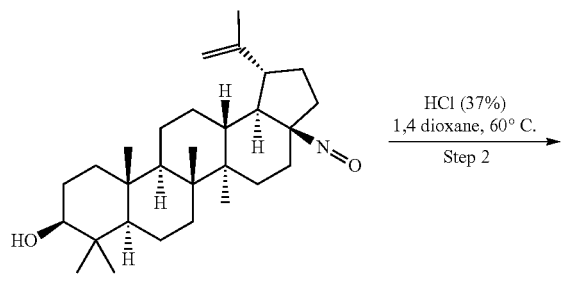

HCl (37%)
1,4 dioxane, 60° C.
Step 2

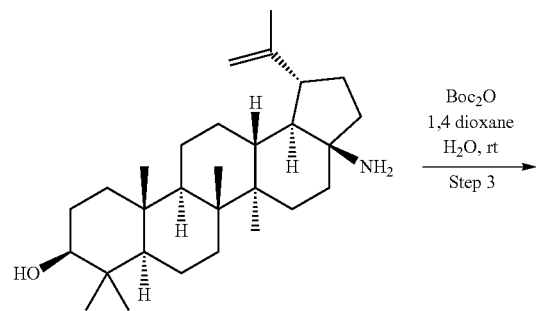

Boc₂O
1,4 dioxane
H₂O, rt
Step 3

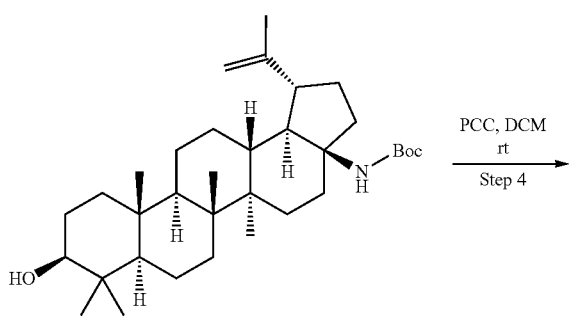

PCC, DCM
rt
Step 4

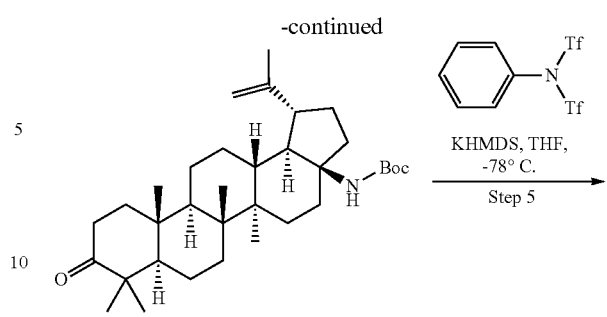

KHMDS, THF,
−78° C.
Step 5

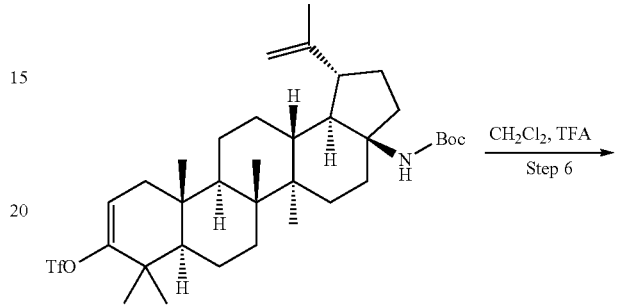

CH₂Cl₂, TFA
Step 6

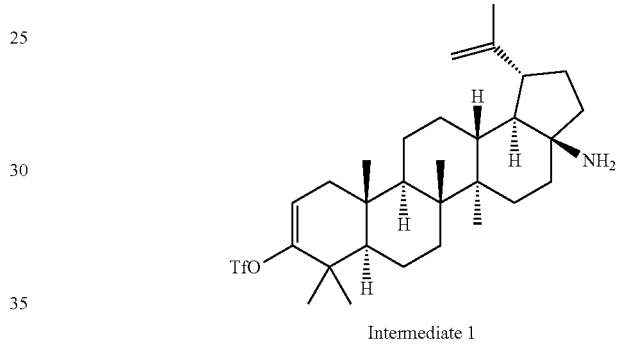

Intermediate 1

Step 1: Preparation of (1R,3aS,5aR,5bR,7aR,9S,11aR,11bR,13aR,13bR)-3a-isocyanato-5a,5b,8,8,11a-pentamethyl-1-(prop-1-en-2-yl)icosahydro-1H-cyclopenta[a]chrysen-9-ol

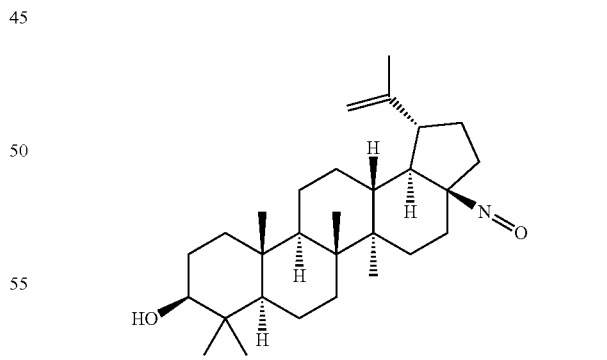

To a suspension of betulinic acid (10 g, 21.90 mmol) in 1,4-dioxane (100 mL) was added triethylamine (9.16 mL, 65.7 mmol) and diphenyl phosphorazidate (7.08 mL, 32.8 mmol). The mixture was heated to reflux. Upon heating, all solids dissolved. After heating the mixture for 26 h, the mixture was cooled to rt and was concentrated under reduced pressure. The residue was diluted with 100 mL of water and was extracted with dichloromethane (3×100 mL). The combined organic layers were dried with sodium sulfate. The drying agent was removed by filtration and the filtrate was concentrated under reduced pressure. The residue was purified by flash chromatography using a 0-15% EtOAc in hexanes gradient and a Thomson 240 g silica gel column. The fractions containing the expected product were combined and concentrated under reduced pressure. A second batch of less-pure product was concentrated and was repurified using a Thomson 240 g column and the same gradient. The fractions containing the expected product were combined with the first-batch to give the title compound as a white solid (7.76 g, 17.10 mmol, 78% yield). $^1$H NMR (400 MHz, chloroform-d) δ=4.75 (s, 1H), 4.67-4.62 (m, 1H), 3.20 (dt, J=11.3, 5.6 Hz, 1H), 2.55 (td, J=10.9, 5.9 Hz, 1H), 2.17-2.03 (m, 1H), 1.92-1.76 (m, 4H), 1.69 (s, 3H), 1.06 (s, 3H), 0.98 (s, 3H), 0.95 (s, 3H), 0.85 (s, 3H), 0.78 (s, 3H), 1.74-0.66 (m, 20H).

Step 2: Preparation of (1R,3aS,5aR,5bR,7aR,9S,11aR,11bR,13aR,13bR)-3a-amino-5a,5b,8,8,11a-pentamethyl-1-(prop-1-en-2-yl)icosahydro-1H-cyclopenta[a]chrysen-9-ol, HCl

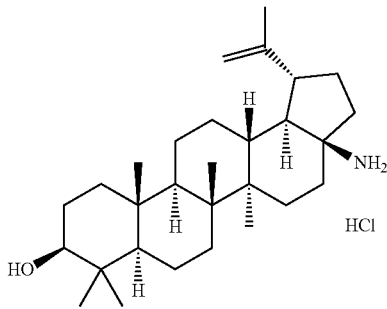

To a solution of (1R,3aS,5aR,5bR,7aR,9S,11aR,11bR,13aR,13bR)-3a-isocyanato-5a,5b,8,8,11a-pentamethyl-1-(prop-1-en-2-yl)icosahydro-1H-cyclopenta[a]chrysen-9-ol (7.76 g, 17.10 mmol) in 1,4-dioxane (100 mL) was added HCl (37%) (21.07 mL, 257 mmol). The mixture was heated to 60° C. for 15 h, then was cooled to rt and concentrated under reduced pressure. The residue was dissolved in dichloromethane and methanol and was concentrated two additional times to give (1R,3aS,5aR,5bR,7aR,9S,11aR,11bR,13aR,13bR)-3a-amino-5a,5b,8,8,11a-pentamethyl-1-(prop-1-en-2-yl)icosahydro-1H-cyclopenta[a]chrysen-9-ol, HCl (7.75 g, 16.7 mmol, 98% yield) as an off-white foam. The crude product was used in the next step with no purification.

Step 3: Preparation of tert-butyl((1R,3aS,5aR,5bR,7aR,9S,11aR,11bR,13aR,13bR)-9-hydroxy-5a,5b,8,8,11a-pentamethyl-1-(prop-1-en-2-yl)icosahydro-1H-cyclopenta[a]chrysen-3a-yl)carbamate

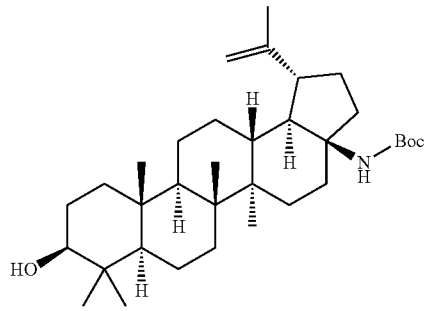

To a solution of (1R,3aS,5aR,5bR,7aR,9S,11aR,11bR,13aR,13bR)-3a-amino-5a,5b,8,8,11a-pentamethyl-1-(prop-1-en-2-yl)icosahydro-1H-cyclopenta[a]chrysen-9-ol, HCl (7.75 g, 16.7 mmol) in 1,4-dioxane (100 mL) was added water (25 mL), sodium bicarbonate (4.21 g, 50.2 mmol) and Boc anhydride (5.82 mL, 25.08 mmol). The mixture was stirred at rt for 16 h then the mixture was diluted with 100 mL of water and was extracted with ethyl acetate (3×100 mL). The combined organic layers were washed with brine, dried over magnesium sulfate, filtered and concentrated under reduced pressure to give tert-butyl((1R,3aS,5aR,5bR,7aR,9S,11aR,11bR,13aR,13bR)-9-hydroxy-5a,5b,8,8,11a-pentamethyl-1-(prop-1-en-2-yl)icosahydro-1H-cyclopenta[a]chrysen-3a-yl)carbamate as an off-white foam. $^1$H NMR (500 MHz, chloroform-d) δ=4.74 (d, J=1.6 Hz, 1H), 4.64-4.62 (m, 1H), 4.34 (br. s., 1H), 3.24-3.18 (m, 1H), 2.63-2.35 (m, 3H), 2.06-1.93 (m, 1H), 1.71 (s, 3H), 1.46 (s, 9H), 1.04 (s, 3H), 0.99 (s, 3H), 0.98 (s, 3H), 0.86 (s, 3H), 0.79 (s, 3H), 1.77-0.68 (m, 22H).

Step 4: Preparation of tert-butyl((1R,3aS,5aR,5bR,7aR,11aR,11bR,13aR,13bR)-5a,5b,8,8,11a-pentamethyl-9-oxo-1-(prop-1-en-2-yl)icosahydro-11'-cyclopenta[a]chrysen-3a-yl)carbamate

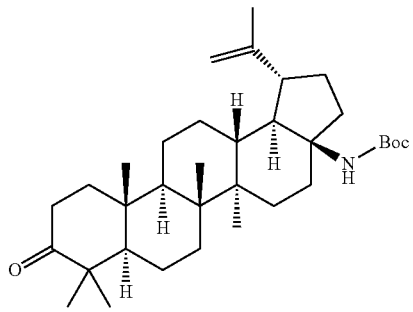

To a solution of the resulting tert-butyl ((1R,3aS,5aR,5bR,7aR,9S,11aR,11bR,13aR,13bR)-9-hydroxy-5a,5b,8,8,11a-pentamethyl-1-(prop-1-en-2-yl)icosahydro-1H-cyclopenta[a]chrysen-3a-yl)carbamate in dichloromethane (100 mL) was added pyridinium chlorochromate (4.69 g, 21.74 mmol). The mixture was stirred at rt for 5 h then an additional 1.0 g of PCC was added and the mixture was stirred at rt for 1 h. The mixture was filtered through a plug of silica gel and celite which was washed with a solution of 25% ethyl acetate in hexanes. The filtrate was concentrated under reduced pressure to give tert-butyl ((1R,3aS,5aR,5bR,7aR,11aR,11bR,13aR,13bR)-5a,5b,8,8,11a-pentamethyl-9-oxo-1-(prop-1-en-2-yl)icosahydro-1H-cyclopenta[a]chrysen-3a-yl) carbamate as a light-yellow foam. $^1$H NMR (500 MHz, chloroform-d) δ=4.74 (d, J=1.7 Hz, 1H), 4.63 (t, J=1.7 Hz, 1H), 4.34 (br. s., 1H), 2.65-2.34 (m, 5H), 2.05-1.88 (m, 2H), 1.71 (s, 3H), 1.47 (s, 9H), 1.10 (s, 3H), 1.08 (s, 3H), 1.05 (s, 3H), 0.99 (s, 3H), 0.96 (s, 3H), 1.76-0.93 (m, 18H).

Step 5: Preparation of (1R,3aS,5aR,5bR,7aR,11aR, 11bR,13aR,13bR)-3a-((tert-butoxycarbonyl)amino)-5a,5b,8,8,11a-pentamethyl-1-(prop-1-en-2-yl)-2,3, 3a,4,5,5a,5b,6,7,7a,8,11,11a,11b,12,13,13a,13b-octadecahydro-1H-cyclopenta[a]chrysen-9-yl trifluoromethanesulfonate

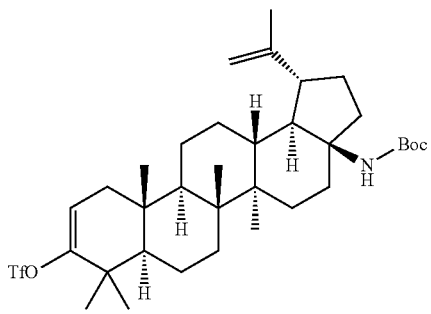

A solution of the resulting tert-butyl((1R,3aS,5aR,5bR, 7aR,11aR,11bR,13aR,13bR)-5a,5b,8,8,11a-pentamethyl-9-oxo-1-(prop-1-en-2-yl)icosahydro-1H-cyclopenta[a]chrysen-3a-yl)carbamate in THF (100 mL) was cooled to −78° C. To the solution was added KHMDS (0.91M in THF) (40.4 mL, 36.8 mmol). The mixture was stirred for 20 minutes at −78° C. then a solution of 1,1,1-trifluoro-N-phenyl-N-(trifluoromethyl)sulfonyl methanesulfonamide (7.47 g, 20.90 mmol) in THF (100 mL) was added via canula. The mixture was stirred at −78° C. for 5 h, then was quenched with 100 mL of water and was extracted with ethyl acetate (3×75 mL). The combined organic layers were dried with magnesium sulfate. The drying agent was removed by filtration and the filtrate was concentrated under reduced pressure. The residue was taken up in a small amount of DCM and methanol and the yellow solids that formed were removed by filtration. The filtrate was again concentrated and treated with methanol and the solids that formed were again removed by filtration. The filtrate was concentrated and was adsorbed to silica gel and was then purified by flash chromatography using a 0-50% ethyl acetate in hexanes gradient and a Thomson 240 g silica gel column. The fractions containing the deprotected product were combined and were concentrated under reduced pressure to give a mixture of products. This mixture was repurified by flash chromatography using a 0-10% EtOAc in hexanes gradient and a 240 g Thomson silica gel column. The fractions containing the expected product were combined and concentrated under reduced pressure to give (1R,3aS,5aR, 5bR,7aR,11aR,11bR,13aR,13bR)-3a-((tert-butoxycarbonyl) amino)-5a,5b,8,8,11a-pentamethyl-1-(prop-1-en-2-yl)-2,3, 3a,4,5,5a,5b,6,7,7a,8,11,11a,11b,12,13,13a,13b-octadecahydro-1H-cyclopenta[a]chrysen-9-yl trifluoromethanesulfonate (1.31 g, 1.99 mmol, 11.9% over 3 steps). $^1$H NMR (500 MHz, CHLOROFORM-d) δ=5.57 (dd, J=6.7, 1.8 Hz, 1H), 4.73 (s, 1H), 4.62 (s, 1H), 4.32 (br. s., 1H), 2.64-2.31 (m, 3H), 2.16 (dd, J=17.0, 6.8 Hz, 1H), 2.04-1.94 (m, 1H), 1.70 (s, 3H), 1.45 (s, 9H), 1.13 (s, 3H), 1.06 (s, 3H), 1.03 (s, 3H), 0.97 (s, 3H), 0.93 (s, 3H), 1.82-0.86 (m, 18H).

Step 6: Preparation of (1R,3aS,5aR,5bR,7aR,11aR, 11bR,13aR,13bR)-3a-amino-5a,5b,8,8,11a-pentamethyl-1-(prop-1-en-2-yl)-2,3,3a,4,5,5a,5b,6,7,7a,8, 11,11a,11b,12,13,13a,13b-octadecahydro-1H-cyclopenta[a]chrysen-9-yl trifluoromethanesulfonate

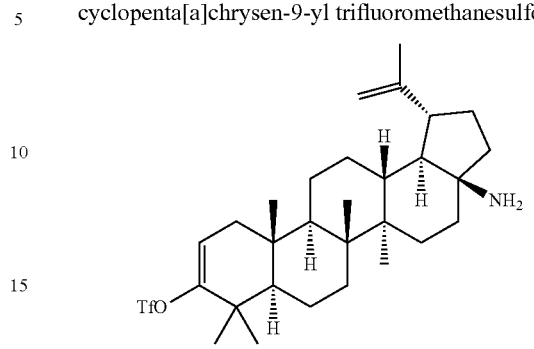

To a solution of (1R,3aS,5aR,5bR,7aR,11aR,11bR,13aR, 13bR)-3a-((tert-butoxycarbonyl)amino)-5a,5b,8,8,11a-pentamethyl-1-(prop-1-en-2-yl)-2,3,3a,4,5,5a,5b,6,7,7a,8,11, 11a,11b,12,13,13a,13b-octadecahydro-1H-cyclopenta[a] chrysen-9-yl trifluoromethanesulfonate (0.2 g, 0.304 mmol) in dichloromethane (2 mL) was added trifluoroacetic acid (0.5 mL, 6.49 mmol). The mixture was stirred at rt for 1.5 h then was concentrated under reduced pressure. The residue was diluted with saturated aqueous sodium bicarbonate (20 mL) and extracted with dichloromethane (3×20 mL). The combined organic layers were dried with sodium sulfate. The drying agent was removed by filtration. The filtrate was concentrated and adsorbed to silica gel and purified using a 12-100% ethyl acetate in hexanes gradient and a 12 g Thomson silica gel column. The fractions containing the expected product were combined and were concentrated under reduced pressure to give (1R,3aS,5aR,5bR,7aR,11aR,11bR,13 aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a, 13b-octadecahydro-1H-cyclopenta[a]chrysen-9-yl trifluoromethanesulfonate (0.109 g, 0.195 mmol, 64.3% yield) as an off-white solid. $^1$H NMR (500 MHz, chloroform-d) δ=5.57 (dd, J=6.8, 1.9 Hz, 1H), 4.73 (d, J=1.6 Hz, 1H), 4.63-4.60 (m, 1H), 2.54 (td, J=10.9, 5.3 Hz, 1H), 2.17 (dd, J=17.1, 6.9 Hz, 1H), 2.08-1.99 (m, 1H), 1.70 (s, 3H), 1.13 (s, 3H), 1.08 (s, 3H), 1.03 (s, 3H), 0.97 (s, 3H), 0.93 (s, 3H), 1.82-0.91 (m, 20H).

Method 2

Intermediate 1

Preparation of (1R,3aS,5aR,5bR,7aR,11aR,11bR, 13aR,13bR)-3a-amino-5a,5b,8,8,11a-pentamethyl-1-(prop-1-en-2-yl)-2,3,3a,4,5,5a,5b,6,7,7a,8,11,11a, 11b,12,13,13a,13b-octadecahydro-1H-cyclopenta[a] chrysen-9-yl trifluoromethanesulfonate

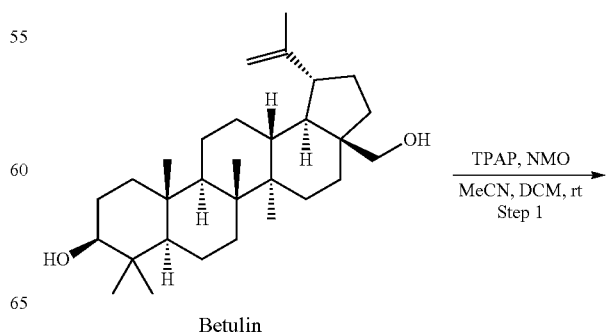

Betulin

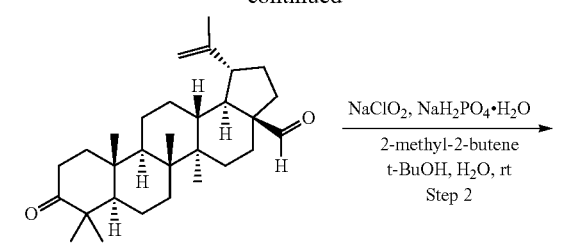

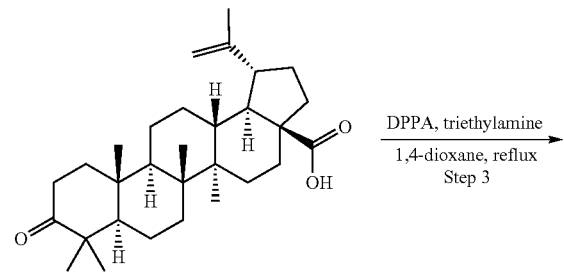

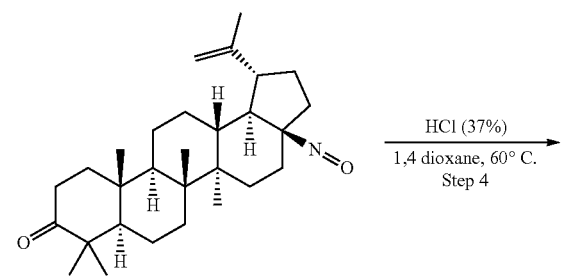

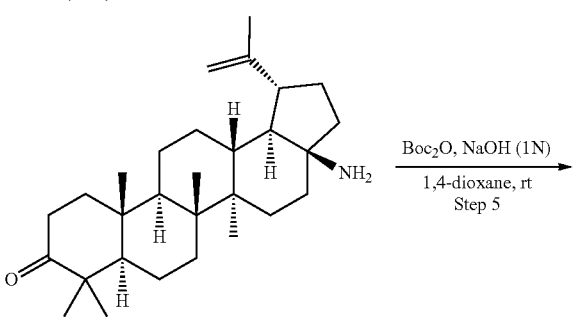

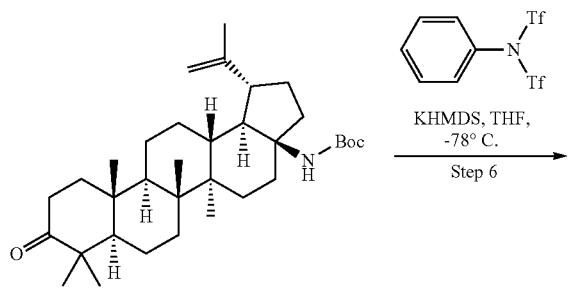

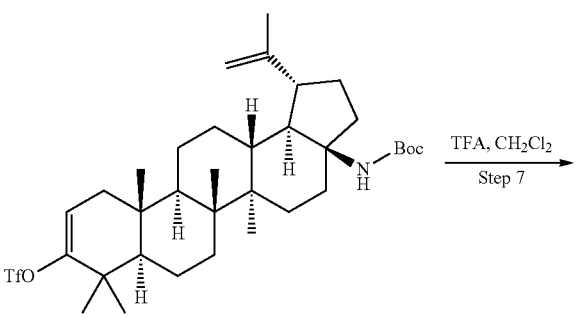

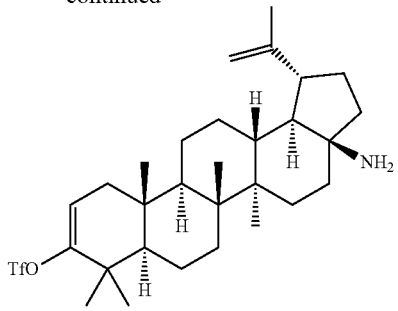

Intermediate 1

Step 1: Preparation of (1R,3aS,5aR,5bR,7aR,11aR,11bR,13aR,13bR)-5a,5b,8,8,11a-pentamethyl-9-oxo-1-(prop-1-en-2-yl)icosahydro-1H-cyclopenta[a]chrysene-3a-carbaldehyde To suspension of (1R,3aS,5aR,5bR,7aR,9S,11aR,11bR,13aR,13bR)-3a-(hydroxymethyl)-5a,5b,8,8,11a-pentamethyl-1-(prop-1-en-2-yl)icosahydro-1H-cyclopenta[a]chrysen-9-ol (20 g, 45.2 mmol) in acetonitrile (200 mL) and DCM (300 mL) was added 4 angstrom molecular sieves (5 g) and the mixture was stirred for 10 minutes at rt. To the mixture was then added NMO (15.88 g, 136 mmol) and TPAP (0.794 g, 2.259 mmol). The dark green mixture was stirred under nitrogen overnight. Additional NMO (2.0 g) and TPAP (0.08 g) were added and the mixture was stirred at rt for 7 h. The mixture was filtered through a pad of silica gel and celite which was washed with dichloromethane then 25% EtOAc in hexanes. The filtrate was concentrated under reduced pressure and purified using a Thomson 240 g silica gel column and a 15-20% ethyl acetate in hexanes gradient. The title product was isolated as a white foam (17.6 g, 40.1 mmol, 89%). $^1$H NMR (400 MHz, chloroform-d) δ=9.68 (d, J=1.5 Hz, 1H), 4.77 (d, J=2.0 Hz, 1H), 4.66-4.63 (m, 1H), 2.89 (td, J=11.2, 5.8 Hz, 1H), 2.56-2.36 (m, 2H), 2.16-2.03 (m, 2H), 1.97-1.84 (m, 2H), 1.71 (s, 3H), 1.08 (s, 3H), 1.03 (s, 3H), 1.00 (s, 3H), 0.97 (s, 3H), 0.94 (s, 3H), 1.83-0.87 (m, 18H).

Step 2: Preparation of (1R,3aS,5aR,5bR,7aR,11aR, 11bR,13aR,13bR)-5a,5b,8,8,11a-pentamethyl-9-oxo-1-(prop-1-en-2-yl)icosahydro-1H-cyclopenta[a]chrysene-3a-carboxylic acid

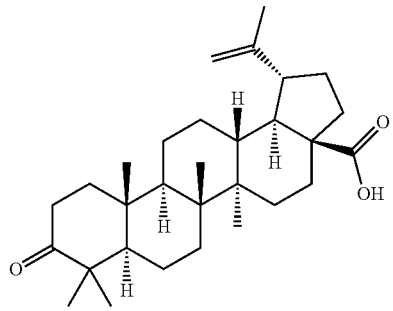

To a solution of (1R,3aS,5aR,5bR,7aR,11aR,11bR,13aR, 13bR)-5a,5b,8,8,11a-pentamethyl-9-oxo-1-(prop-1-en-2-yl)icosahydro-1H-cyclopenta[a]chrysene-3a-carbaldehyde (17.6 g, 36.1 mmol) in t-BuOH (100 mL) was added 2-methyl-2-butene (40 mL, 476 mmol). A solution of sodium chlorite (15 g, 133 mmol) and sodium phosphate monobasic monohydrate (25 g, 181 mmol) in water (200 mL) was added drop wise over 1.25 h and the mixture was stirred at rt for an additional 45 minutes. The mixture was diluted with saturated aqueous ammonium chloride (100 mL) and extracted with ethyl acetate (3×125 mL). The combined organic layers were washed with brine and dried over sodium sulfate. The drying agent was removed by filtration and the filtrate was concentrated under reduced pressure. The residue was purified by using a 300 g Thomson silica gel column and a 10-50% ethyl acetate in hexanes gradient. The fractions containing the expected product were combined and concentrated under reduced pressure to give (1R,3aS,5aR,5bR,7aR,11aR,11bR, 13aR,13bR)-5a,5b,8,8,11a-pentamethyl-9-oxo-1-(prop-1-en-2-yl)icosahydro-1H-cyclopenta[a]chrysene-3a-carboxylic acid as a white foam (16.4 g, 36.1 mmol, 100%). LCMS: m/e 453.2 (M−H)$^-$, 2.61 min (method 3). $^1$H NMR (400 MHz, chloroform-d) δ=10.02 (br. s., 1H), 4.75 (d, J=1.8 Hz, 1H), 4.64-4.61 (m, 1H), 3.02 (td, J=10.8, 4.8 Hz, 1H), 2.55-2.36 (m, 3H), 2.33-2.19 (m, 2H), 2.08-1.86 (m, 4H), 1.70 (s, 3H), 1.08 (s, 3H), 1.02 (s, 3H), 1.00 (s, 3H), 0.98 (s, 3H), 0.93 (s, 3H), 1.82-0.90 (m, 15H).

Step 3: Preparation of (1R,3aS,5aR,5bR,7aR,11aR, 11bR,13aR,13bR)-3a-isocyanato-5a,5b,8,8,11a-pentamethyl-1-(prop-1-en-2-yl)octadecahydro-1H-cyclopenta[a]chrysen-9(5bH)-one

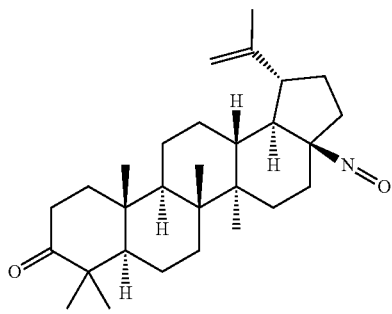

To a solution of (1R,3aS,5aR,5bR,7aR,11aR,11bR,13aR, 13bR)-5a,5b,8,8,11a-pentamethyl-9-oxo-1-(prop-1-en-2-yl)icosahydro-1H-cyclopenta[a]chrysene-3a-carboxylic acid (16.41 g, 36.1 mmol) in 1,4-dioxane (200 mL) was added triethylamine (15.09 mL, 108 mmol) and diphenyl phosphorazidate (11.67 mL, 54.2 mmol). The mixture was heated to reflux for 18.5 h, then was cooled to rt and concentrated under reduced pressure. The residue was split into two portions and was purified using a 0-15% ethyl acetate in hexanes gradient and a Thomson 240 g silica gel column to purify each portion. The fractions containing the expected product were combined and concentrated under reduced pressure to give (1R, 3aS,5aR,5bR,7aR,11aR,11bR,13aR,13bR)-3a-isocyanato-5a,5b,8,8,11a-pentamethyl-1-(prop-1-en-2-yl) octadecahydro-1H-cyclopenta[a]chrysen-9(5bH)-one (10.3 g, 22.80 mmol, 63.2% yield) as an off-white foam. $^1$H NMR (400 MHz, chloroform-d) δ=4.75 (d, J=2.0 Hz, 1H), 4.66-4.63 (m, 1H), 2.60-2.36 (m, 4H), 2.17-2.04 (m, 1H), 1.69 (s, 3H), 1.10 (s, 3H), 1.08 (s, 3H), 1.04 (s, 3H), 0.95 (s, 6H), 2.01-0.71 (m, 20H).

Step 4: Preparation of (1R,3aS,5aR,5bR,7aR,11aR, 11bR,13aR,13bR)-3a-amino-5a,5b,8,8,11a-pentamethyl-1-(prop-1-en-2-yl)octadecahydro-1H-cyclopenta[a]chrysen-9(5bH)-one, HCl

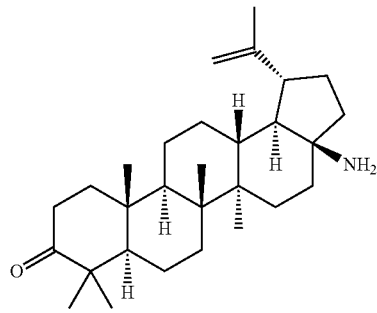

To a solution of (1R,3aS,5aR,5bR,7aR,11aR,11bR,13aR, 13bR)-3a-isocyanato-5a,5b,8,8,11a-pentamethyl-1-(prop-1-en-2-yl)octadecahydro-1H-cyclopenta[a]chrysen-9(5bH)-one (10.3 g, 22.80 mmol) in 1,4-dioxane (100 mL) was added HCl (37%) (28.1 mL, 342 mmol). The mixture was heated to 60° C. for 15.5 h then was cooled to rt and was concentrated under reduced pressure. The residue was diluted with saturated aqueous sodium bicarbonate (150 mL) and was extracted with dichloromethane (3×100 mL). The combined organic layers were dried with sodium sulfate, filtered and concentrated under reduced pressure. The residue was purified by flash chromatography using a 20-60% ethyl acetate in hexanes gradient with 0.1% triethyl amine added to the mixture. The fractions containing the expected product were combined and concentrated under reduced pressure to give (1R,3aS,5aR,5bR,7aR,11aR,11bR,13aR,13bR)-3a-amino-5a,5b,8,8,11a-pentamethyl-1-(prop-1-en-2-yl)octadecahydro-1H-cyclopenta[a]chrysen-9(5bH)-one, HCl (5.4 g, 11.68 mmol, 51.2% yield) as a yellow foam. LCMS: m/e 426.5 (M+H)$^+$, 1.59 min (method 1). $^1$H NMR (400 MHz, CHLOROFORM-d) δ=4.73 (d, J=2.3 Hz, 1H), 4.60 (dd, J=2.4, 1.4 Hz, 1H), 2.58-2.37 (m, 3H), 2.11-1.98 (m, 1H), 1.94-1.87 (m, 1H), 1.69 (d, J=0.5 Hz, 3H), 1.09 (s, 3H), 1.08 (s, 3H), 1.03 (s, 3H), 0.97 (s, 3H), 0.94 (s, 3H), 1.79-0.91 (m, 20H).

Step 5: Preparation of tert-butyl((1R,3aS,5aR,5bR, 7aR,11aR,11bR,13aR,13bR)-5a,5b,8,8,11a-pentamethyl-9-oxo-1-(prop-1-en-2-yl)icosahydro-1H-cyclopenta[a]chrysen-3a-yl)carbamate

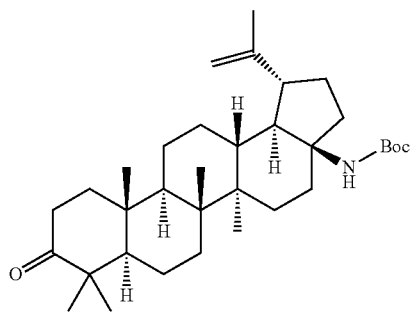

To a solution of (1R,3aS,5aR,5bR,7aR,11aR,11bR,13aR, 13bR)-3a-amino-5a,5b,8,8,11a-pentamethyl-1-(prop-1-en-2-yl)octadecahydro-1H-cyclopenta[a]chrysen-9(5bH)-one (5.25 g, 12.33 mmol) in 1,4-dioxane (50 mL) was added sodium hydroxide (1N) (24.67 mL, 24.67 mmol) followed by di-tert-butyl dicarbonate (3.15 mL, 13.57 mmol). The mixture was stirred at rt for 2 h then 30 mL of methanol, 50 mL of dichloromethane and 20 mL of water were added to help solubilize the mixture. After stirring for 1.5 h at rt, the reaction was not complete, so di-tert-butyl dicarbonate (0.3 g) was added and the mixture stirred at rt for 3 h. Again di-tert-butyl dicarbonate (0.3 g) was added and the mixture was stirred at rt for 16 h. Since traces of starting material were still present, di-tert-butyl dicarbonate (1 g) was added to the mixture and the stirring was continued for 6 h at which point TLC showed no starting material remaining. The mixture was diluted with water (75 mL) and extracted with dichloromethane (3×100 mL). The combined organic layers were washed with water (100 mL) then were dried with sodium sulfate, filtered and concentrated under reduced pressure. The residue was purified using a 0-10% ethyl acetate in hexanes gradient and a 240 g silica gel column. The fractions containing the expected product were combined and concentrated under reduced pressure to give tert-butyl((1R,3aS,5aR,5bR,7aR,11aR,11bR, 13aR,13bR)-5a,5b,8,8,11a-pentamethyl-9-oxo-1-(prop-1-en-2-yl)icosahydro-1H-cyclopenta[a]chrysen-3a-yl) carbamate (5.85 g, 11.13 mmol, 90% yield) as a white foam. $^1$H NMR (400 MHz, chloroform-d) δ=4.72 (s, 1H), 4.62 (s, 1H), 4.33 (br. s., 1H), 2.64-2.32 (m, 5H), 2.06-1.84 (m, 2H), 1.69 (s, 3H), 1.45 (s, 9H), 1.08 (s, 3H), 1.06 (s, 3H), 1.03 (s, 3H), 0.97 (s, 3H), 0.94 (s, 3H), 1.74-0.86 (m, 18H).

Step 6: Preparation of (1R,3aS,5aR,5bR,7aR,11aR, 11bR,13aR,13bR)-3a-((tert-butoxycarbonyl)amino)-5a,5b,8,8,11a-pentamethyl-1-(prop-1-en-2-yl)-2,3, 3a,4,5,5a,5b,6,7,7a,8,11,11a,11b,12,13,13a,13b-octadecahydro-1H-cyclopenta[a]chrysen-9-yl trifluoromethanesulfonate

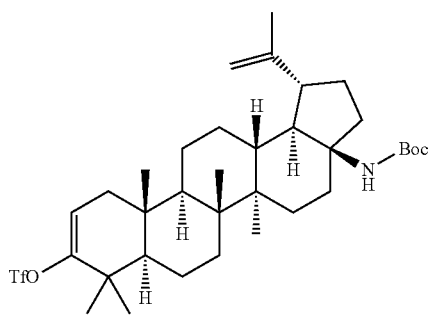

A flask containing a solution of tert-butyl ((1R,3 aS,5aR, 5bR,7aR,11aR,11bR,13aR,13bR)-5a,5b,8,8,11a-pentamethyl-9-oxo-1-(prop-1-en-2-yl)icosahydro-1H-cyclopenta [a]chrysen-3a-yl)carbamate (1.2 g, 2.282 mmol) and 1,1,1-trifluoro-N-phenyl-N-(trifluoromethyl)sulfonyl methanesulfonamide (1.019 g, 2.85 mmol) in THF (20 mL) was cooled to −78° C. To the solution was added KHMDS (0.91 M in THF) (5.52 mL, 5.02 mmol). The mixture was stirred at −78° C. for 1 h then warmed to rt and stirred for 1 h. The reaction was then quenched with saturated aqueous ammonium chloride (30 mL) and extracted with ethyl acetate (3×30 mL). The combined organic layers were dried over magnesium sulfate. The drying agent was removed by filtration and the filtrate was concentrated under reduced pressure. The crude material was purified using a 0-12% ethyl acetate in hexanes gradient and a Thomson 80 g silica gel column. The fractions containing the expected product were combined and concentrated under reduced pressure to give (1R, 3aS,5aR,5bR,7aR,11aR,11bR,13aR,13bR)-3a-((tert-butoxycarbonyl)amino)-5a,5b,8,8,11a-pentamethyl-1-(prop-1-en-2-yl)-2,3,3a,4,5,5a,5b,6,7,7a,8,11,11a,11b,12,13,13a, 13b-octadecahydro-1H-cyclopenta[a]chrysen-9-yl trifluoromethanesulfonate (0.9 g, 1.368 mmol, 59.9% yield) as a white foam. $^1$H NMR (500 MHz, chloroform-d) δ=5.57 (dd, J=6.7, 1.8 Hz, 1H), 4.73 (s, 1H), 4.62 (s, 1H), 4.32 (br. s., 1H), 2.64-2.31 (m, 3H), 2.16 (dd, J=17.0, 6.8 Hz, 1H), 2.04-1.94 (m, 1H), 1.70 (s, 3H), 1.45 (s, 9H), 1.13 (s, 3H), 1.06 (s, 3H), 1.03 (s, 3H), 0.97 (s, 3H), 0.93 (s, 3H), 1.82-0.86 (m, 18H).

Step 7: Same experimental procedure described for Step 6 in method 1 above.

Alternatively, the intermediate (1R,3aS,5aR,5bR,7aR, 11aR,11bR,13aR,13bR)-3a-isocyanato-5a,5b,8,8,11a-pentamethyl-1-(prop-1-en-2-yl)octadecahydro-1H-cyclopenta [a]chrysen-9(5bH)-one can be prepared from betulinic acid following the scheme shown below:

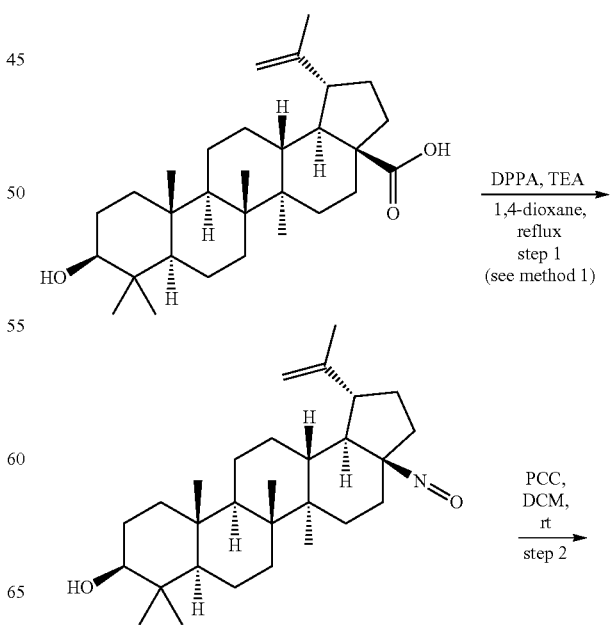

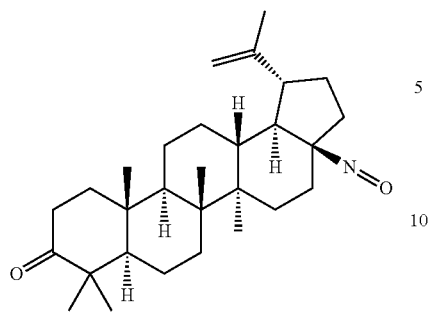

Step 1: Preparation of (1R,3aS,5aR,5bR,7aR,9S, 11aR,11bR,13aR,13bR)-3a-isocyanato-5a,5b,8,8, 11a-pentamethyl-1-(prop-1-en-2-yl)icosahydro-1H-cyclopenta[a]chrysen-9-ol The title compound was prepared using the same conditions described above in Step 1, method 1 using betulinic acid as starting material.

Step 2

To a solution of 24 g of crude (1R,3aS,5aR,5bR,7aR,9S, 11aR,11bR,13aR,13bR)-3a-isocyanato-5a,5b,8,8,11a-pentamethyl-1-(prop-1-en-2-yl)icosahydro-1H-cyclopenta[a]chrysen-9-ol in dichloromethane (200 mL) was added PCC (11.80 g, 54.8 mmol) in three portions over 45 minutes. The mixture was stirred at rt for 4 h, then an additional 1 g of PCC was added and the mixture was further stirred at rt for 2 h. The mixture was filtered through a plug of silica gel and celite and the plug was washed with a 1:1 solution of ethyl acetate: hexanes. The filtrate was concentrated under reduced pressure to give the crude product which was used in the next step with no additional purification. $^1$H NMR (500 MHz, Chloroform-d) δ=4.76-4.74 (m, 1H), 4.65-4.63 (m, 1H), 2.62-2.36 (m, 3H), 2.16-2.03 (m, 1H), 1.69 (s, 3H), 1.10 (s, 3H), 1.08 (s, 3H), 1.04 (s, 3H), 0.96 (s, 6H), 1.95-0.91 (m, 21H).

Preparation of diisopropyl 6-(4,4,5,5-tetramethyl-1, 3,2-dioxaborolan-2-yl)spiro[3.3]hept-5-ene-2,2-dicarboxylate

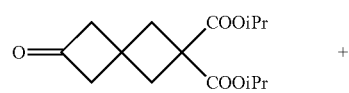

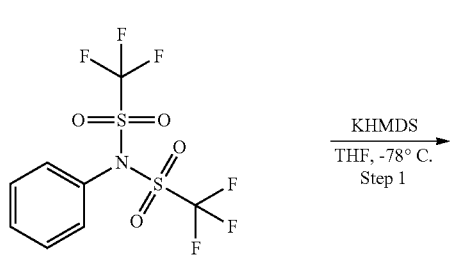

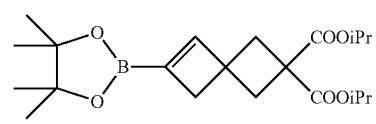

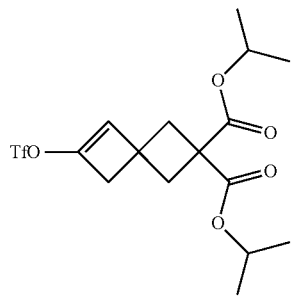 [SMILES: CC(C)OC(=O)C1(C(=O)OC(C)C)CC2(C=C(OS(=O)(=O)C(F)(F)F)C2)C1]

Step 1: Preparation of diisopropyl 6-(((trifluoromethyl)sulfonyl)oxy)spiro[3.3]hept-5-ene-2,2-dicarboxylate A solution of diisopropyl 6-oxospiro[3.3]heptane-2,2-dicarboxylate (prepared as described in *Tetrahedron: Asymmetry.* 2008, 19, 2924-293) (5.36 g, 18.98 mmol) in THF (40 mL) was cooled to −78° C. To the solution was added KHMDS (0.91M in THF) (31.3 mL, 28.5 mmol). The mixture was stirred for 30 minutes at −78° C. then a solution of 1,1,1-trifluoro-N-phenyl-N-((trifluoromethyl)sulfonyl) methanesulfonamide (8.48 g, 23.73 mmol) in THF (40 mL) was added via cannula. After 4.5 h of stirring at −78° C., an additional 2.0 g of 1,1,1-trifluoro-N-phenyl-N-((trifluoromethyl)sulfonyl)methanesulfonamide was added to the mixture and it was further stirred at −78° C. After 1 h of stirring, the mixture was diluted with water (100 mL), was warmed to rt and was extracted with ethyl acetate (3×75 mL). The combined organic layers were washed with brine, dried over magnesium sulfate, filtered and concentrated under reduced pressure. The residue was adsorbed to silica gel and was purified by flash chromatography using a Thomson 240 g silica gel column and a 0-12% ethyl acetate in hexanes gradient. The fractions containing the product were combined and were concentrated under reduced pressure to give diisopropyl 6-(((trifluoromethyl)sulfonyl)oxy)spiro[3.3]hept-5-ene-2,2-dicarboxylate (1.16 g, 2.80 mmol, 14.74% yield) as a clear, colorless oil that partially solidified under vacuum at rt. $^1$H NMR (500 MHz, CHLOROFORM-d) δ=5.53 (s, 1H), 5.14-5.03 (m, 2H), 2.95 (s, 2H), 2.77 (s, 4H), 1.27 (d, J=6.3 Hz, 6H), 1.26 (d, J=6.3 Hz, 6H). Note: A small amount of impurity was also present in the sample and was visible in the aromatic region of the spectra. The product was used in the next step of the reaction sequence with the impurity present.

Step 2: Preparation of diisopropyl 6-(4,4,5,5-tetramethyl-1,3,2-dioxaborolan-2-yl)spiro[3.3]hept-5-ene-2,2-dicarboxylate

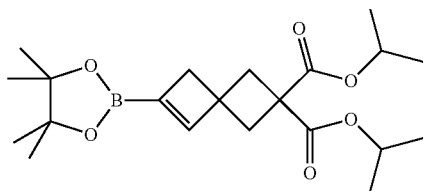 [SMILES: CC(C)OC(=O)C1(C(=O)OC(C)C)CC2(C=C(B3OC(C)(C)C(C)(C)O3)C2)C1]

To a rbf containing diisopropyl 6-(((trifluoromethyl)sulfonyl)oxy)spiro[3.3]hept-5-ene-2,2-dicarboxylate (1.16 g, 2.80 mmol) was added bis(binacolato)diboron (0.782 g, 3.08 mmol), potassium acetate (0.687 g, 7.00 mmol), and PdCl$_2$(dppf)-CH$_2$Cl$_2$ adduct (0.069 g, 0.084 mmol). The mixture was diluted with dioxane (10 mL), flushed with N$_2$, and heated to 70° C. for 22 h. The mixture was cooled to rt, diluted with water (30 mL) and extracted with dichloromethane (3×30 mL). The combined organic layers were dried over sodium sulfate, filtered and concentrated under reduced pressure. The residue was purified by flash chromatography using a 0-10% ethyl acetate in hexanes gradient and a Thomson 40 g silica gel column. The fractions containing the expected product were combined and concentrated under reduced pressure to give diisopropyl 6-(4,4,5,5-tetramethyl-1,3,2-dioxaborolan-2-yl)spiro[3.3]hept-5-ene-2,2-dicarboxylate (1.044 g, 2.66 mmol, 95% yield) as a yellow oil. $^1$H NMR (400 MHz, Chloroform-d) δ=6.86 (s, 1H), 5.05 (dd, J=11.8, 6.3 Hz, 2H), 2.70 (s, 4H), 2.61 (s, 2H), 1.26 (s, 12H), 1.23 (d, J=6.3 Hz, 1H), 1.23 (d, J=6.3 Hz, 1H).

Preparation of methyl 6-(4,4,5,5-tetramethyl-1,3,2-dioxaborolan-2-yl)spiro[3.3]hept-5-ene-2-carboxylate

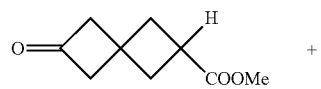 +

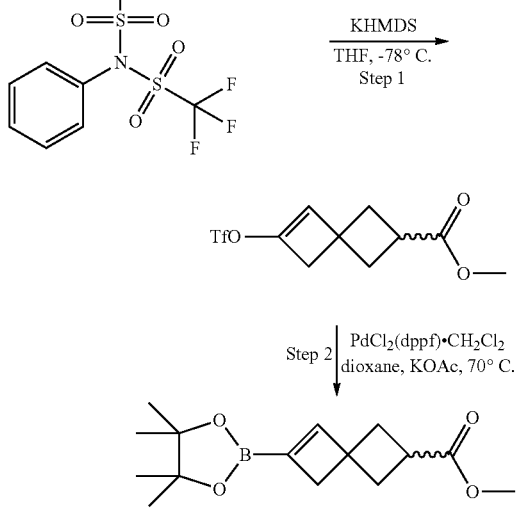

Step 1: Preparation of methyl 6-(((trifluoromethyl)sulfonyl)oxy)spiro[3.3]hept-5-ene-2-carboxylate

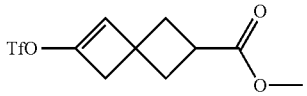 [SMILES: COC(=O)C1CC2(C=C(OS(=O)(=O)C(F)(F)F)C2)C1]

A solution of methyl 6-oxospiro[3.3]heptane-2-carboxylate (prepared as described in *Tetrahedron: Asymmetry.* 2008, 19, 2924-2930) (0.599 g, 3.56 mmol) in THF (6 mL) was cooled to −78° C. To the solution was added KHMDS (0.91 M in THF) (4.89 mL, 4.45 mmol). The mixture was stirred for 30 minutes at −78° C. then a solution of 1,1,1-trifluoro-N-phenyl-N-(((trifluoromethyl)sulfonyl)methanesulfonamide (1.527 g, 4.27 mmol) in THF (6 mL) was added via cannula. After 4 h of stirring at −78° C., the reaction was diluted with water (20 mL), warmed to rt and extracted with ethyl acetate (3×30 mL). The combined organic layers were washed with brine, dried over MgSO$_4$, filtered and concentrated under reduced pressure. The residue was purified by flash chromatography using a 0-10% EtOAc in hexanes gradient and a Thomson 40 g silica gel column. The fractions containing the expected product were combined and concentrated under reduced pressure to give methyl 6-(((trifluoromethyl)sulfonyl)oxy)spiro[3.3]hept-5-ene-2-carboxylate (0.242 g, 0.806 mmol, 22.6% yield) as a clear, light-yellow oil. $^1$H NMR showed a mixture of the two diastereomers (0.4:1 ratio) which were not separated and were used in the next step with no additional purification. Isomer 1 (minor): $^1$H NMR (500 MHz, CHLOROFORM-d) δ=5.58 (s, 1H), 3.71 (s, 3H), 3.14-3.05 (m, 1H), 2.90 (s, 2H), 2.60-2.52 (m, 2H), 2.47-2.40 (m, 2H). Isomer 2 (major): $^1$H NMR (500 MHz, chloroform-d) δ=5.48 (s, 1H), 3.70 (s, 3H), 3.14-3.05 (m, 1H), 2.94 (s, 2H), 2.60-2.52 (m, 2H), 2.47-2.40 (m, 2H).

Step 2: Preparation of methyl 6-(4,4,5,5-tetramethyl-1,3,2-dioxaborolan-2-yl)spiro[3.3]hept-5-ene-2-carboxylate

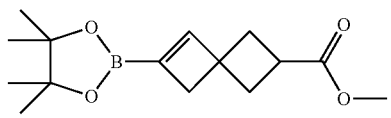

To a vial containing methyl 6-(((trifluoromethyl)sulfonyl)oxy)spiro[3.3]hept-5-ene-2-carboxylate (0.242 g, 0.806 mmol) (0.4:1 mixture of diastereomers) was added bis(binacolato)diboron (0.225 g, 0.887 mmol), potassium acetate (0.198 g, 2.015 mmol), and PdCl$_2$(dppf)-CH$_2$Cl$_2$ Adduct (0.020 g, 0.024 mmol). The mixture was diluted with 1,4-dioxane (5 mL), flushed with nitrogen and the vial was sealed and heated to 70° C. for 23 h. The mixture was cooled to rt and filtered through a plug of silica gel and celite (washed with 25% EtOAc in hexanes). The filtrate was concentrated under reduced pressure to give methyl 6-(4,4,5,5-tetramethyl-1,3,2-dioxaborolan-2-yl)spiro[3.3]hept-5-ene-2-carboxylate (0.224 g, 0.806 mmol, 100% yield) as a brown oil. $^1$H NMR showed a mixture of the two diastereomers (0.8:1 ratio) which were not separated, but were used in the next step with no additional purification. Isomer 1 (minor): $^1$H NMR (500 MHz, CHLOROFORM-d) δ=7.02 (s, 1H), 3.68 (s, 3H), 3.05 (dq, J=17.6, 8.7 Hz, 1H), 2.55 (s, 2H), 2.53-2.46 (m, 2H), 2.41-2.32 (m, 2H), 1.29-1.26 (m, 12H). Isomer 2 (major): $^1$H NMR (500 MHz, CHLOROFORM-d) δ=6.81 (s, 1H), 3.68 (s, 3H), 3.05 (dq, J=17.6, 8.7 Hz, 1H), 2.66 (s, 2H), 2.53-2.46 (m, 2H), 2.41-2.32 (m, 2H), 1.28-1.26 (m, 12H). (Note: excess bis(binacolato)diboron is also seen in the multiplet at 1.29-1.26 ppm and will be removed after the subsequent step).

Example 1

Preparation of 6-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)spiro[3.3]hept-5-ene-2,2-dicarboxylic acid, HCl

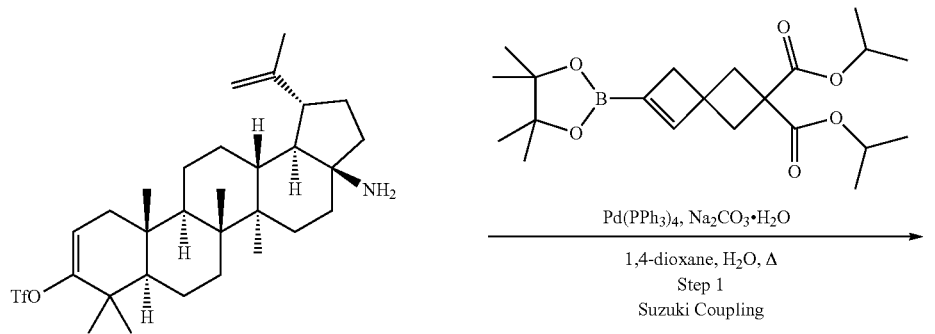

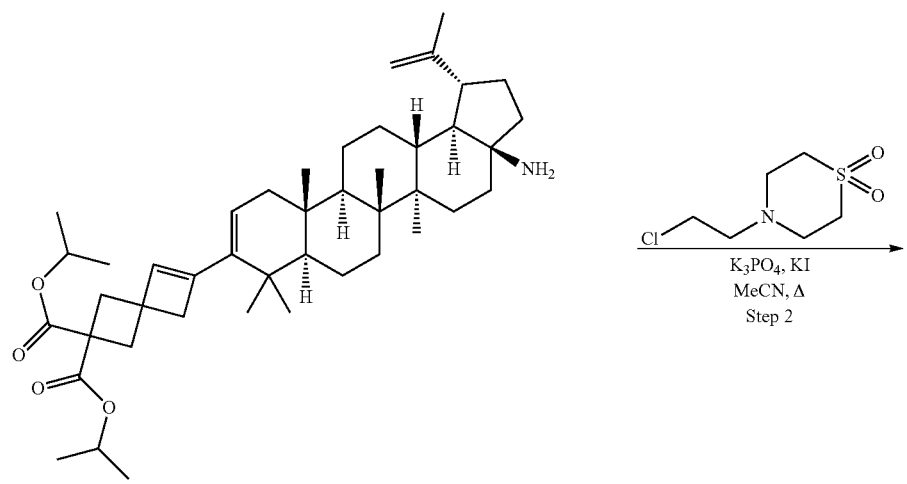

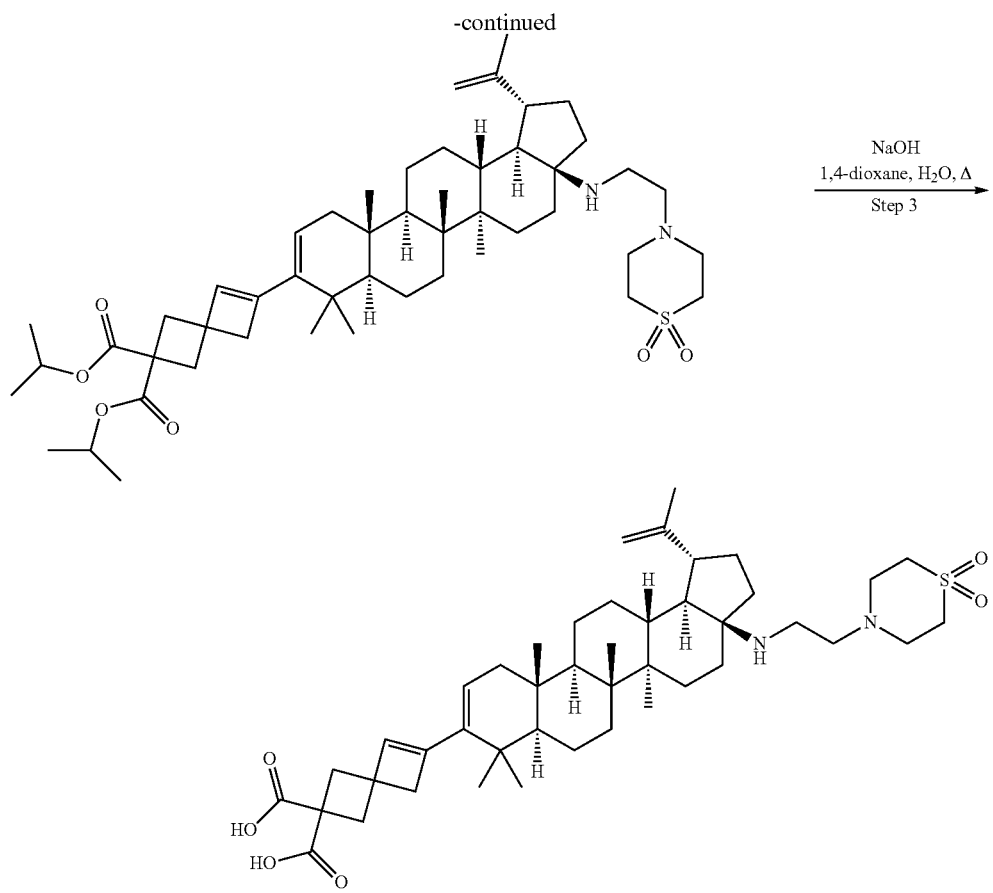

Example 1

Step 1: Suzuki coupling—Preparation of diisopropyl 6-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)spiro[3.3]hept-5-ene-2,2-dicarboxylate

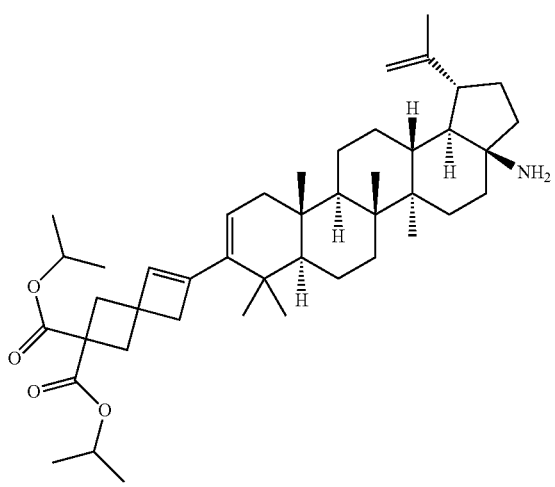

To a vial containing (1R,3aS,5aR,5bR,7aR,11aR,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl trifluoromethanesulfonate (1.54 g, 2.76 mmol) was added diisopropyl 6-(4,4,5,5-tetramethyl-1,3,2-dioxaborolan-2-yl)spiro[3.3]hept-5-ene-2,2-dicarboxylate (1.044 g, 2.66 mmol), sodium carbonate monohydrate (0.856 g, 6.90 mmol) and tetrakis(triphenylphosphine)palladium(0) (0.096 g, 0.083 mmol). The mixture was diluted with 1,4-dioxane (12 mL) and water (3 mL), then was flushed with nitrogen and the vial was sealed and heated to 85° C. After 5.5 h of heating, the mixture was cooled to rt. The mixture was diluted with water (40 mL) and extracted with dichloromethane (3×40 mL). The combined organic layers were dried over sodium sulfate. The drying agent was removed by filtration and the filtrate was concentrated under reduced pressure. The residue was purified by flash chromatography using a 0-50% ethyl acetate in hexanes gradient and a Thomson 80 g silica gel column. The fractions containing the expected product were combined and concentrated under reduced pressure to give diisopropyl 6-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)spiro[3.3]hept-5-ene-2,2-dicarboxylate (1.19 g, 1.766 mmol, 63.9% yield) as an off-white solid. LCMS: m/e 674.7 (M+H)$^+$, 2.30 min (method 1). $^1$H NMR (500 MHz, chloroform-d) δ=5.87 (s, 1H), 5.52 (dd, J=6.4, 1.8 Hz, 1H), 5.13-5.01 (m, 2H), 4.73

(br. s., 1H), 4.61 (br. s., 1H), 2.74-2.66 (m, 4H), 2.63-2.51 (m, 3H), 2.14-1.99 (m, 2H), 1.70 (s, 3H), 1.27-1.23 (m, 12H), 1.15 (s, 3H), 1.07 (br. s., 3H), 1.06 (s, 3H), 0.97 (s, 3H), 0.83 (s, 3H), 1.76-0.80 (m, 20H).

Step 2: Preparation of diisopropyl 6-((1R,3aS,5aR, 5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a, 8,11,11a,11b,12,13,13a,13b-octadecahydro-1H-cyclopenta[a]chrysen-9-yl)spiro[3.3]hept-5-ene-2,2-dicarboxylate and diisopropyl 6-((1R,3aS,5aR,5bR, 7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,6,7,7a, 8,11b,12,13,13a-tetradecahydro-1H-cyclopenta[a]chrysen-9(5bH,11aH,13bH)-ylidene)spiro[3.3]heptane-2,2-dicarboxylate g, 0.074 mmol), 4-(2-chloroethyl)thiomorpholine 1,1-dioxide, HCl (0.052 g, 0.223 mmol), potassium iodide (0.032 g, 0.193 mmol) and phosphoric acid, potassium salt (0.079 g, 0.371 mmol). The mixture was diluted with acetonitrile (1 mL), flushed with nitrogen, sealed and heated to 120° C. for 18.5 h. The mixture was cooled to rt, concentrated under reduced pressure and purified using a 0-50% ethyl acetate in hexanes gradient and a Thomson 12 g silica gel column. The fractions containing the products were combined and concentrated under reduced pressure to give 24 mg of a mixture of two compounds as an off-white foam. The two compounds were separated by supercritical fluid chromatography to give two regioisomeric products: The diisopropyl 6-((1R,3aS, 5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12, 13,13a,13b-octadecahydro-1H-cyclopenta[a]chrysen-9-yl) spiro[3.3]hept-5-ene-2,2-dicarboxylate (6.6 mg, 0.0079 mmol, 10.7% yield) and diisopropyl 6-((1R,3aS,5aR,5bR,

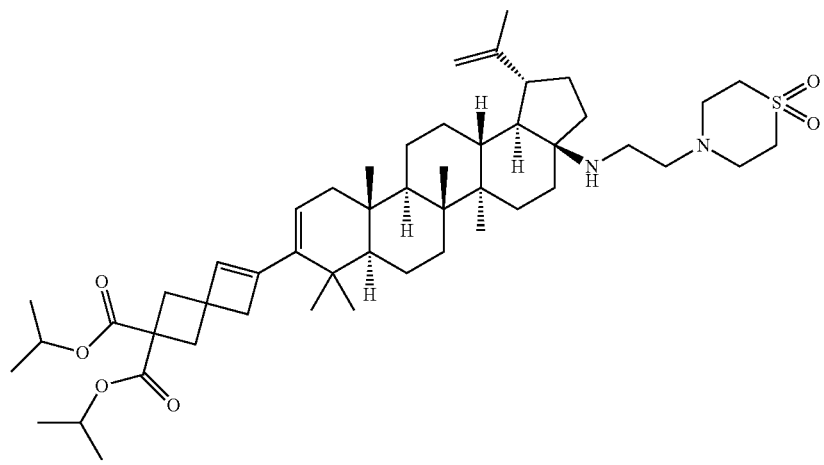

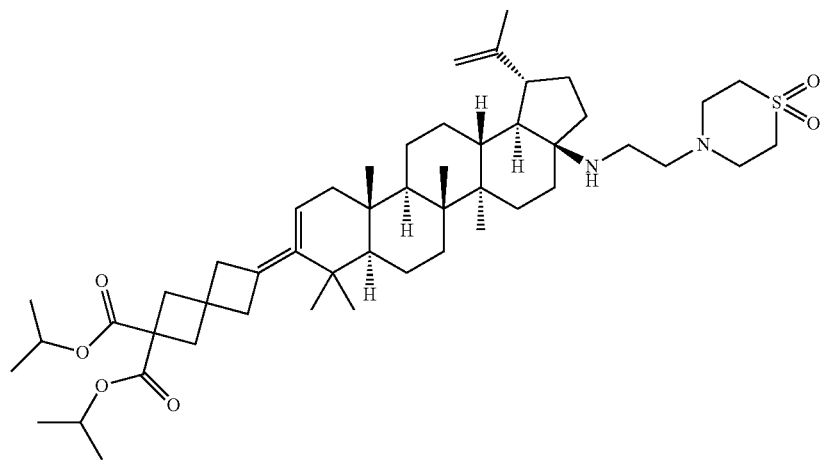

To a sealable flask was added diisopropyl 6-((1R,3 aS,5aR, 5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8, 11,11a,11b,12,13,13a,13b-octadecahydro-1H-cyclopenta[a] chrysen-9-yl)spiro[3.3]hept-5-ene-2,2-dicarboxylate (0.05

7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,6,7,7a,8,11b,12,13,13a-tetradecahydro-1H-cyclopenta[a]chrysen-9(5bH,11aH, 13bH)-ylidene)spiro[3.3]heptane-2,2-dicarboxylate (9.1 mg, 0.0109 mmol, 14.7% yield). For diisopropyl 6-((1R,3aS,5aR,5bR,7aR,11aS,11bR,13 aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)spiro[3.3]hept-5-ene-2,2-dicarboxylate LCMS: m/e 835.7 (M+H)$^+$, 2.24 min (method 1). $^1$H NMR (500 MHz, chloroform-d) δ=5.87 (s, 1H), 5.54-5.49 (m, 1H), 5.13-5.01 (m, 2H), 4.72 (s, 1H), 4.60 (s, 1H), 3.12-2.99 (m, 9H), 2.75-2.43 (m, 12H), 2.10 (dd, J=17.9, 6.5 Hz, 1H), 1.69 (s, 3H), 1.25 (t, J=6.1 Hz, 12H), 1.15 (s, 3H), 1.07 (s, 6H), 0.97 (s, 3H), 0.82 (s, 3H), 2.02-0.77 (m, 20H).

For diisopropyl 6-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,6,7,7a,8,11b,12,13,13a-tetradecahydro-1H-cyclopenta[a]chrysen-9(5bH,11aH,13bH)-ylidene)spiro[3.3]heptane-2,2-dicarboxylate LCMS: m/e 835.7 (M+H)$^+$, 2.23 min (method 1). $^1$H NMR (500 MHz, chloroform-d) δ=5.87 (d, J=10.1 Hz, 1H), 5.73 (d, J=9.9 Hz, 1H), 5.10-5.01 (m, 2H), 4.72 (s, 1H), 4.61 (s, 1H), 3.13-2.94 (m, 10H), 2.87-2.73 (m, 2H), 2.71-2.43 (m, 9H), 1.69 (s, 3H), 1.24 (dd, J=6.2, 2.4 Hz, 12H), 1.10 (s, 3H), 1.08 (s, 3H), 1.04 (s, 3H), 0.94 (s, 3H), 0.93 (s, 3H), 2.01-0.80 (m, 21H).

Step 3

To a solution of diisopropyl 6-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)spiro[3.3]hept-5-ene-2,2-dicarboxylate (6.6 mg, 7.90 mmol) in 1,4-dioxane (1 mL) was added NaOH (10N) (0.05 mL, 0.500 mmol) and the mixture was heated to 85° C. for 23.25 h. The mixture was cooled to rt then was diluted with 1,4-dioxane (0.5 mL) and methanol (1 mL). The mixture was then acidified by adding 1N HCl and further diluted with water (2 mL). The solids formed were collected by filtration to give 6-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)spiro[3.3]hept-5-ene-2,2-dicarboxylic acid, HCl (4.0 mg, 5.0 mmol, 63% yield) as a white solid. LCMS: m/e 751.6 (M+H)$^+$, 1.62 min (method 1). $^1$H NMR (500 MHz, acetic acid-d$_4$) δ=5.98 (s, 1H), 5.61 (d, J=4.4 Hz, 1H), 4.83 (s, 1H), 4.73 (s, 1H), 3.45 (d, J=11.8 Hz, 1H), 3.34-3.01 (m, 12H), 2.98-2.91 (m, 1H), 2.84 (s, 4H), 2.71-2.63 (m, 2H), 1.77-1.74 (m, 3H), 1.27-1.25 (m, 3H), 1.21 (s, 3H), 1.14 (s, 3H), 1.11 (s, 3H), 0.93 (s, 3H), 2.32-0.87 (m, 21H).

Example 2

Preparation of 6-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,6,7,7a,8,11b,12,13,13a-tetradecahydro-1H-cyclopenta[a]chrysen-9(5bH,11aH,13bH)-ylidene)spiro[3.3]heptane-2,2-dicarboxylic acid, HCl

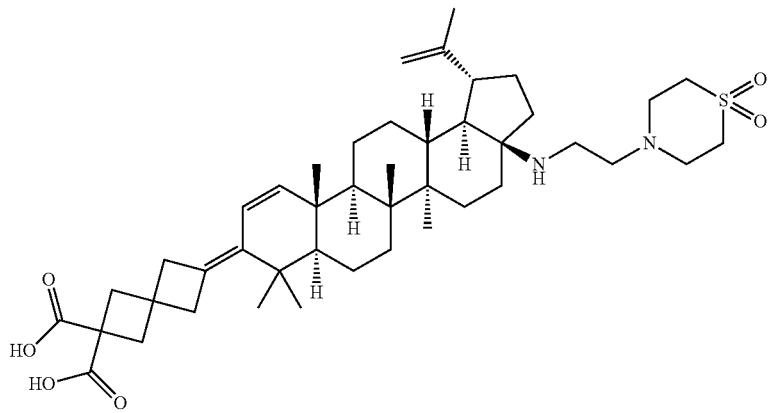

To a solution of diisopropyl 6-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,6,7,7a,8,11b,12,13,13a-tetradecahydro-1H-cyclopenta[a]chrysen-9(5bH,11aH,13bH)-ylidene)spiro[3.3]heptane-2,2-dicarboxylate (9.1 mg, 10.90 μmol) in 1,4-dioxane (1 mL) was added NaOH (10N) (0.05 mL, 0.500 mmol) and the mixture was heated to 85° C. After 23.25 h of heating, the mixture was cooled to rt then diluted with 1,4-dioxane (0.5 mL) and methanol (1 mL). The mixture was acidified by adding 1N HCl and further diluted with water (2 mL). The solids formed were collected by filtration to give 6-((1R,3 aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,6,7,7a,8,11b,12,13,13a-tetradecahydro-1H-cyclopenta[a]chrysen-9(5bH,11aH,13bH)-ylidene)spiro[3.3]heptane-2,2-dicarboxylic acid, HCl (6 mg, 7.6 μmol, 70% yield) as a white solid. LCMS: m/e 751.6 (M+H)$^+$, 1.98 min (method 1). $^1$H NMR (500 MHz, acetic acid-d$_4$) δ=5.92 (d, J=9.9 Hz, 1H), 5.81 (d, J=9.8 Hz, 1H), 4.84 (br. s., 1H), 4.74 (s, 1H), 3.45 (br. s., 1H), 3.36-3.00 (m, 13H), 2.98-2.79 (m, 3H), 2.74 (d, J=7.7 Hz, 4H), 1.76 (s, 3H), 1.26 (s, 3H), 1.17 (s, 3H), 1.12 (s, 3H), 1.09 (s, 3H), 1.02 (s, 3H), 2.32-0.87 (m, 20H).

Example 3
Preparation of 6-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)spiro[3.3]hept-5-ene-2-carboxylic acid, HCl
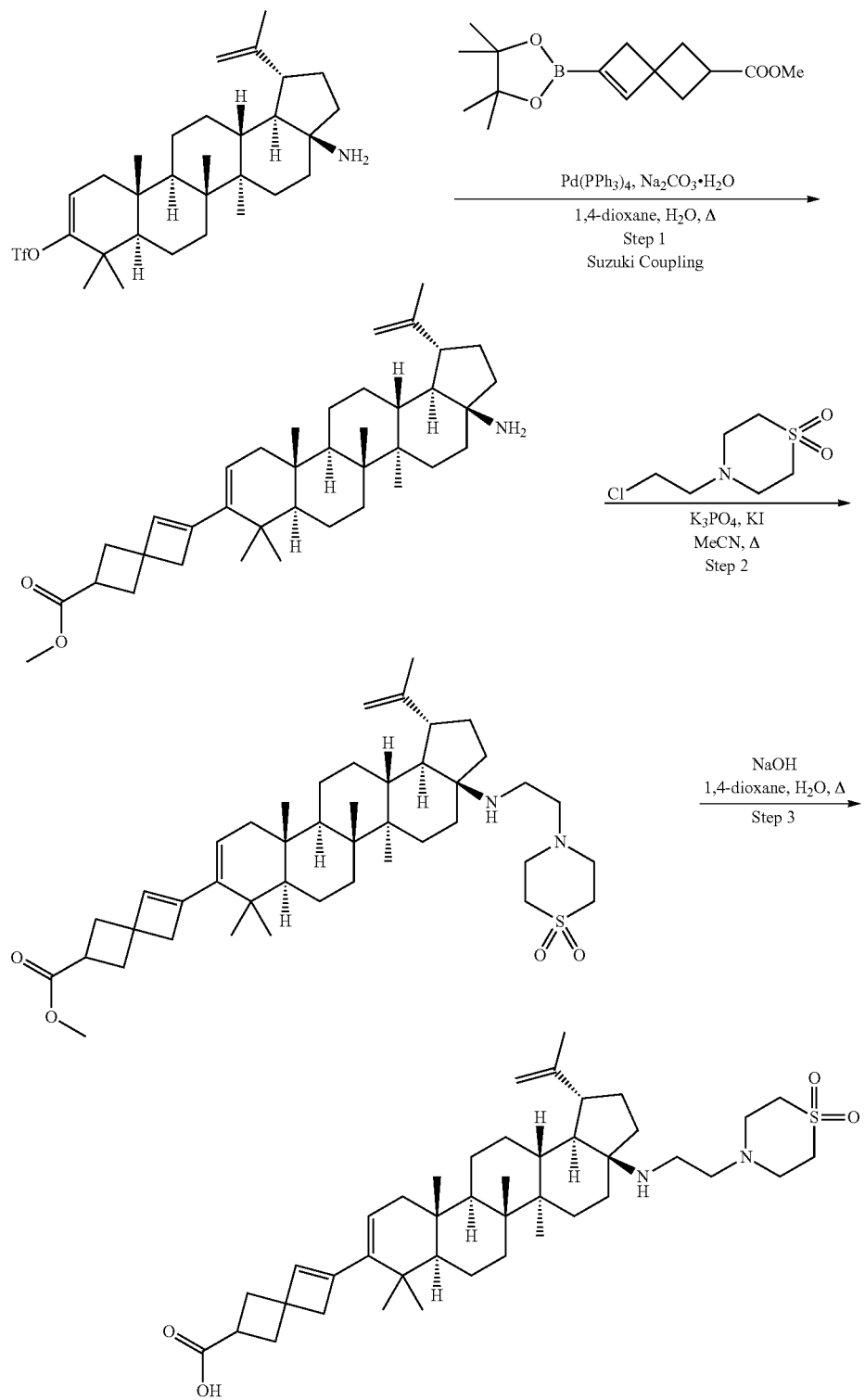
Example 3

Step 1: Suzuki coupling —Preparation of methyl 6-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)spiro[3.3]hept-5-ene-2-carboxylate Step 2: Preparation of methyl 6-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)spiro[3.3]hept-5-ene-2-carboxylate

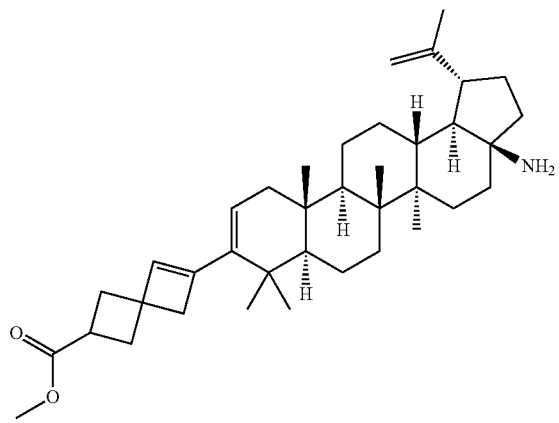

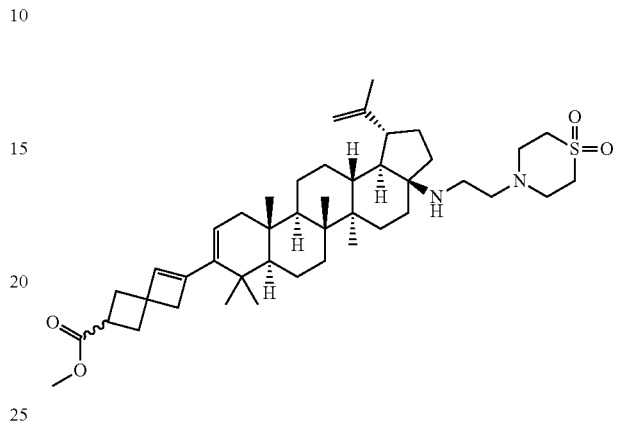

To a vial containing (1R,3aS,5aR,5bR,7aR,11aR,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl trifluoromethanesulfonate (0.418 g, 0.749 mmol) was added methyl 6-(4,4,5,5-tetramethyl-1,3,2-dioxaborolan-2-yl)spiro[3.3]hept-5-ene-2-carboxylate (0.250 g, 0.899 mmol), sodium carbonate monohydrate (0.232 g, 1.874 mmol) and tetrakis(triphenylphosphine)palladium(0) (0.026 g, 0.022 mmol). The mixture was diluted with 1,4-dioxane (4 mL) and water (1 mL), then was flushed with nitrogen and the vial was sealed and heated to 85° C. After 5.5 h of heating, the mixture was cooled to rt, concentrated under reduced pressure, adsorbed to silica gel, and purified by chromatography using a 0-45% ethyl acetate in hexanes gradient and a 40 g Thomson silica gel column. The fractions containing the expected product were combined and concentrated under reduced pressure to give methyl 6-((1R,3 aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)spiro[3.3]hept-5-ene-2-carboxylate (0.31 g, 0.554 mmol, 73.9% yield) as an off-white solid. $^1$H NMR showed a mixture of the two diastereomers (0.8:1 ratio) which were not separated and were used in the next step with no additional purification. LCMS: m/e 560.47 (M+H)$^+$, 2.46 min (method 2). Mixture of diastereomers: $^1$H NMR (500 MHz, chloroform-d) δ=6.00 (s, 0.45H, minor diastereomer), 5.84 (s, 0.55H, major diastereomer), 5.54 (td, J=6.1, 2.2 Hz, 1H), 4.75 (d, J=2.0 Hz, 1H), 4.62 (dd, J=2.3, 1.3 Hz, 1H), 3.71 (m, 3H), 3.13-2.99 (m, 1H), 2.70-2.31 (m, 7H), 2.18-1.84 (m, 4H), 1.72 (s, 3H), 1.18 (d, J=3.5 Hz, 3H), 1.10-1.08 (m, 6H), 0.99 (s, 3H), 0.85 (s, 3H), 1.68-0.83 (m, 19H).

To a sealable vial was added methyl 6-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)spiro[3.3]hept-5-ene-2-carboxylate (0.25 g, 0.447 mmol), 4-(2-chloroethyl)thiomorpholine 1,1-dioxide, HCl (0.25 g, 1.068 mmol), potassium iodide (0.222 g, 1.340 mmol) and phosphoric acid, potassium salt (0.474 g, 2.233 mmol). The mixture was diluted with acetonitrile (4 mL), was flushed with nitrogen, then was sealed and heated to 100° C. for 15.5 h. The mixture was cooled to rt, diluted with water (30 mL) and extracted with dichloromethane (3×40 mL). The combined organic layers were dried with sodium sulfate, filtered and concentrated under reduced pressure. The residue was purified by chromatography using a 40 g Thomson silica gel column and a 6-50% ethyl acetate in hexanes gradient. The fractions containing the expected product were combined and were concentrated under reduced pressure to give methyl 6-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)spiro[3.3]hept-5-ene-2-carboxylate (0.20 g, 0.277 mmol, 62.1% yield) as an off-white foam. $^1$H NMR showed a mixture of the two diastereomers (0.8:1 ratio) which were not separated and were used in the next step with no additional purification. LCMS: m/e 721.7 (M+H)$^+$, 2.04 min (method 1).

Step 3

To a solution of methyl 6-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)spiro[3.3]hept-5-ene-2-carboxylate (0.025 g, 0.035 mmol) in 1,4- dioxane (2 mL) was added NaOH (10N) (0.2 mL, 2.000 mmol). The mixture was warmed to 65° C. for 15 h then cooled to rt. The mixture was acidified adding a solution of HCl (0.2 mL of conc. HCl in 2 mL of water). Water was slowly added to this solution until it turned cloudy. Then the mixture was set aside and solids precipitated out of the solution. The solids were collected by filtration and washed with water first and then with diethyl ether to give 6-((1R,3aS,5aR, 5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12, 13,13a,13b-octadecahydro-1H-cyclopenta[a]chrysen-9-yl) spiro[3.3]hept-5-ene-2-carboxylic acid, HCl (22.8 mg, 0.031 mmol, 89% yield) as an off-white solid. $^1$H NMR showed a mixture of diastereomers in a 0.8:1 ratio. LCMS: m/e 707.7 (M+H)$^+$, 1.90 min (method 1). Mixture of diastereomers: $^1$H NMR (500 MHz, acetic acid-d$_4$) δ=6.08 (s, 0.45H), 5.90 (s, 0.55H), 5.63-5.56 (m, 1H), 4.89 (s, 1H), 4.74 (s, 1H), 3.53-3.08 (m, 16H), 2.72-2.34 (m, 7H), 1.76 (s, 3H), 1.28 (s, 3H), 1.22 (d, J=4.6 Hz, 3H), 1.14 (s, 3H), 1.12 (s, 3H), 0.92 (s, 3H), 2.24-0.87 (m, 17H).

Example 4

Preparation of 4-((1R,3aS,5aR,5bR,7aR,11aS,11bR, 13aR,13bR)-3a-((2-(1,1-dioxidothiomorpholino) ethyl)amino)-5a,5b,8,8,11a-pentamethyl-1-(prop-1-en-2-yl)-2,3,3a,4,5,5a,5b,6,7,7a,8,11,11a,11b,12,13, 13a,13b-octadecahydro-1H-cyclopenta[a]chrysen-9-yl)cyclohex-3-enecarboxylic acid, TFA

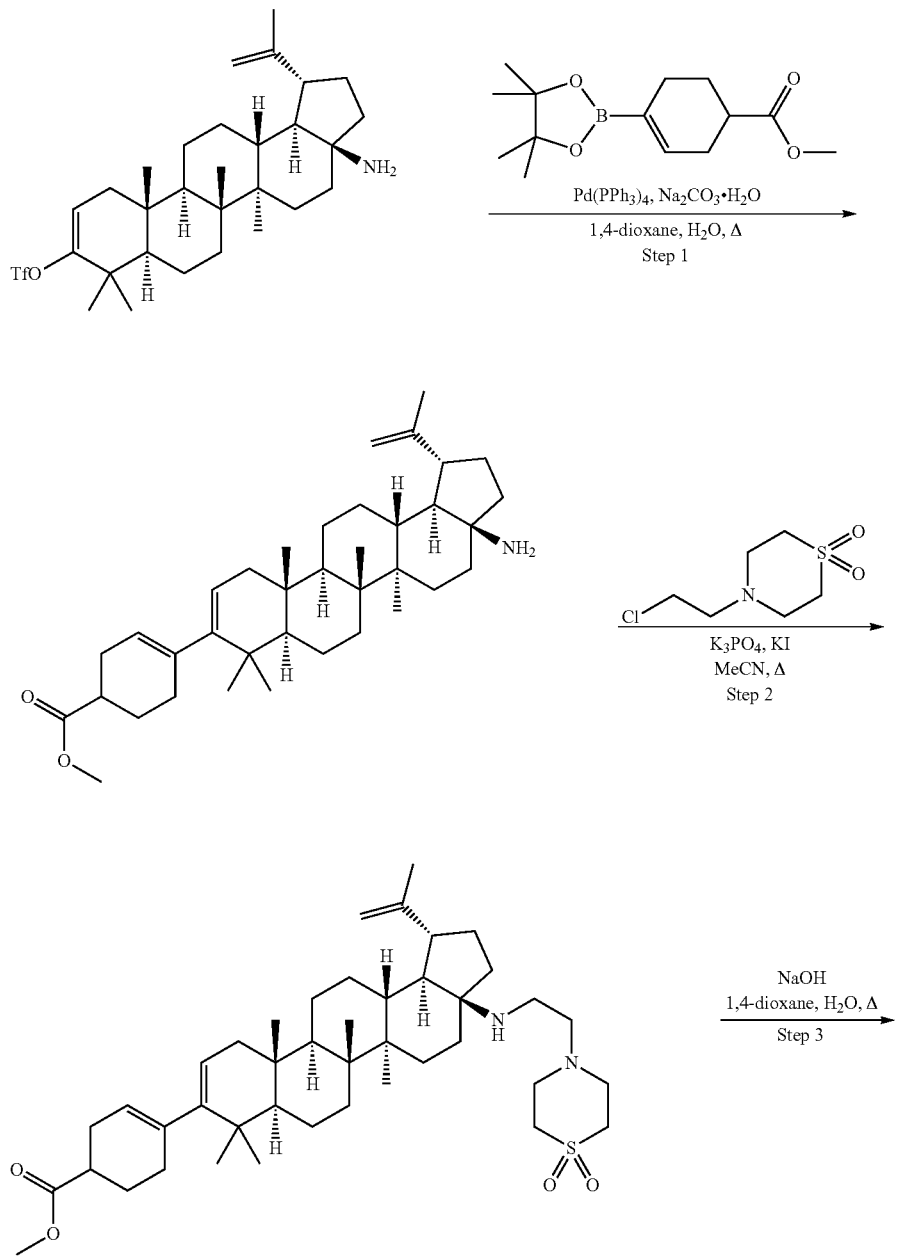

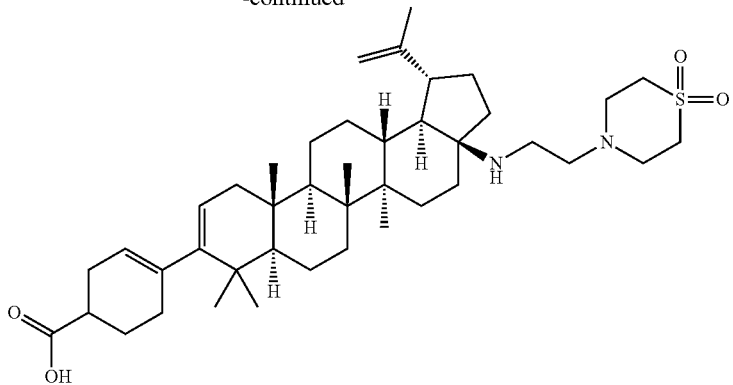

Example 4

Step 1. Preparation of methyl 4-((1R,3aS,5aR,5bR, 7aR,11aS,11bR,13aR,13bR)-3a-amino-5a,5b,8,8, 11a-pentamethyl-1-(prop-1-en-2-yl)-2,3,3a,4,5,5a, 5b,6,7,7a,8,11,11a,11b,12,13,13a,13b-octadecahydro-1H-cyclopenta[a]chrysen-9-yl) cyclohex-3-enecarboxylate

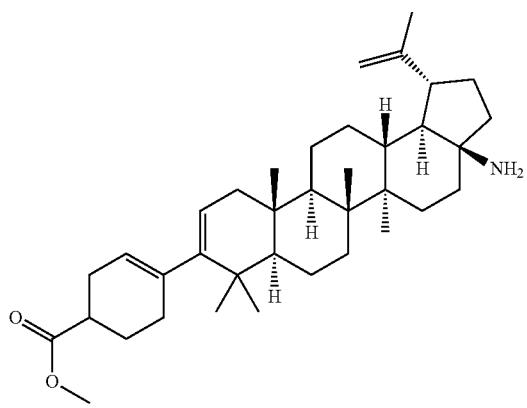

To a sealable vial containing (1R,3aS,5aR,5bR,7aR,11aR, 11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12, 13,13a,13b-octadecahydro-1H-cyclopenta[a]chrysen-9-yl trifluoromethanesulfonate (0.109 g, 0.195 mmol) was added methyl 4-(4,4,5,5-tetramethyl-1,3,2-dioxaborolan-2-yl)cyclohex-3-enecarboxylate (0.078 g, 0.293 mmol), sodium carbonate hydrate (0.073 g, 0.586 mmol), and tetrakis(triphenylphosphine)palladium(0) (6.77 mg, 5.86 mmol). The mixture was diluted with 1,4-dioxane (2 mL) and water (0.5 mL) then was flushed with nitrogen, sealed and heated to 85° C. in an oil bath. After 20.5 h, the mixture was cooled to rt, diluted with water (10 mL) and extracted with dichloromethane (3×10 mL). The combined organic layers were dried with sodium sulfate. The drying agent was removed by filtration and the filtrate was concentrated under reduced pressure. The residue was adsorbed to silica gel and purified by chromatography using a 12 g Thomson silica gel column and a 10%-80% ethyl acetate in hexanes gradient. The fractions containing the expected product were combined and concentrated under reduced pressure to give methyl 4-((1R,3 aS,5aR,5bR,7aR,11aS,11bR,13aR,13bR)-3a-amino-5a,5b, 8,8,11a-pentamethyl-1-(prop-1-en-2-yl)-2,3,3a,4,5,5a,5b,6, 7,7a,8,11,11a,11b,12,13,13a,13b-octadecahydro-1H-cyclopenta[a]chrysen-9-yl)cyclohex-3-enecarboxylate (0.035 g, 0.064 mmol, 32.7% yield) as an off-white solid. $^1$H NMR (400 MHz, chloroform-d) δ=5.35 (br. s., 1H), 5.19 (d, J=5.8 Hz, 1H), 4.73 (s, 1H), 4.60 (br. s., 1H), 3.69 (s, 3H), 2.55 (td, J=10.7, 5.1 Hz, 2H), 2.31 (d, J=2.3 Hz, 2H), 2.22-1.94 (m, 6H), 1.70 (s, 3H), 1.07 (s, 3H), 1.79-0.81 (m, 34H).

Step 2. Preparation of methyl 4-((1R,3aS,5aR,5bR, 7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8, 11,11a,11b,12,13,13a,13b-octadecahydro-1H-cyclopenta[a]chrysen-9-yl)cyclohex-3-enecarboxylate To a sealable vial was added methyl 4-((1R,3aS,5aR,5bR, 7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11, 11a,11b,12,13,13a,13b-octadecahydro-1H-cyclopenta[a] chrysen-9-yl)cyclohex-3-enecarboxylate (0.035 g, 0.064 mmol), 4-(2-chloroethyl)thiomorpholine 1,1-dioxide, HCl (0.045 g, 0.192 mmol), potassium iodide (0.032 g, 0.192 mmol) and phosphoric acid, potassium salt (0.068 g, 0.319 mmol). The mixture was diluted with acetonitrile (1 mL), flushed with nitrogen, sealed and heated to 110° C. After 21.75 h of heating, the mixture was cooled to rt. The crude mixture was diluted with water (10 mL) and extracted with dichloromethane (3×10 mL). The combined organic layers were dried with sodium sulfate. The drying agent was removed by filtration and the filtrate was concentrated under reduced pressure. The residue was adsorbed to silica gel and purified by chromatography using 12 g Thomson silica gel column and a 10-80% EtOAc in hexanes gradient. The fractions containing the expected product were combined and concentrated under reduced pressure to give methyl 4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylate (0.0295 g, 0.042 mmol, 65.1% yield) as a clear film. LCMS: m/e 709.7 (M+H)$^+$, 1.90 min (method 1).

Step 3

To a solution of methyl 4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylate (0.029 g, 0.041 mmol) in 1,4-dioxane (2 mL) was added sodium hydroxide (1N) (0.204 mL, 0.204 mmol). The mixture was warmed to 70° C. After heating the mixture for 16 h, it was cooled to rt and was acidified by adding 1 mL of 1N HCl. Then water was added until solids formed. The solids were collected by filtration, dissolved in 1,4-dioxane and methanol and purified by prep HPLC (method 2, retention time: 6.6 minutes). The fractions containing the expected product were combined and concentrated under reduced pressure to give 4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylic acid, TFA (0.014 g, 0.02 mmol, 41% yield) as a white solid. LCMS: m/e 695.6 (M+H)$^+$, 1.75 min (method 1). $^1$H NMR (400 MHz, acetic acid, d$_4$) δ=5.37 (br. s., 1H), 5.22 (d, J=6.0 Hz, 1H), 4.80 (s, 1H), 4.70 (s, 1H), 3.50-3.42 (m, 1H), 3.32-3.03 (m, 11H), 2.93-2.84 (m, 1H), 2.63-2.54 (m, 1H), 1.72 (s, 3H), 1.22 (s, 3H), 1.08 (s, 3H), 1.02-0.92 (m, 9H), 2.37-0.79 (m, 28H).

Example 5

Preparation of 6-((1S,3aS,5aR,5bR,7aR,11aS,11bR,13aR,13bR)-3a-((2-(1,1-dioxidothiomorpholino)ethyl)amino)-1-isopropyl-5a,5b,8,8,11a-pentamethyl-2,3,3a,4,5,5a,5b,6,7,7a,8,11,11a,11b,12,13,13a,13b-octadecahydro-1H-cyclopenta[a]chrysen-9-yl)spiro[3.3]heptane-2,2-dicarboxylic acid, TFA

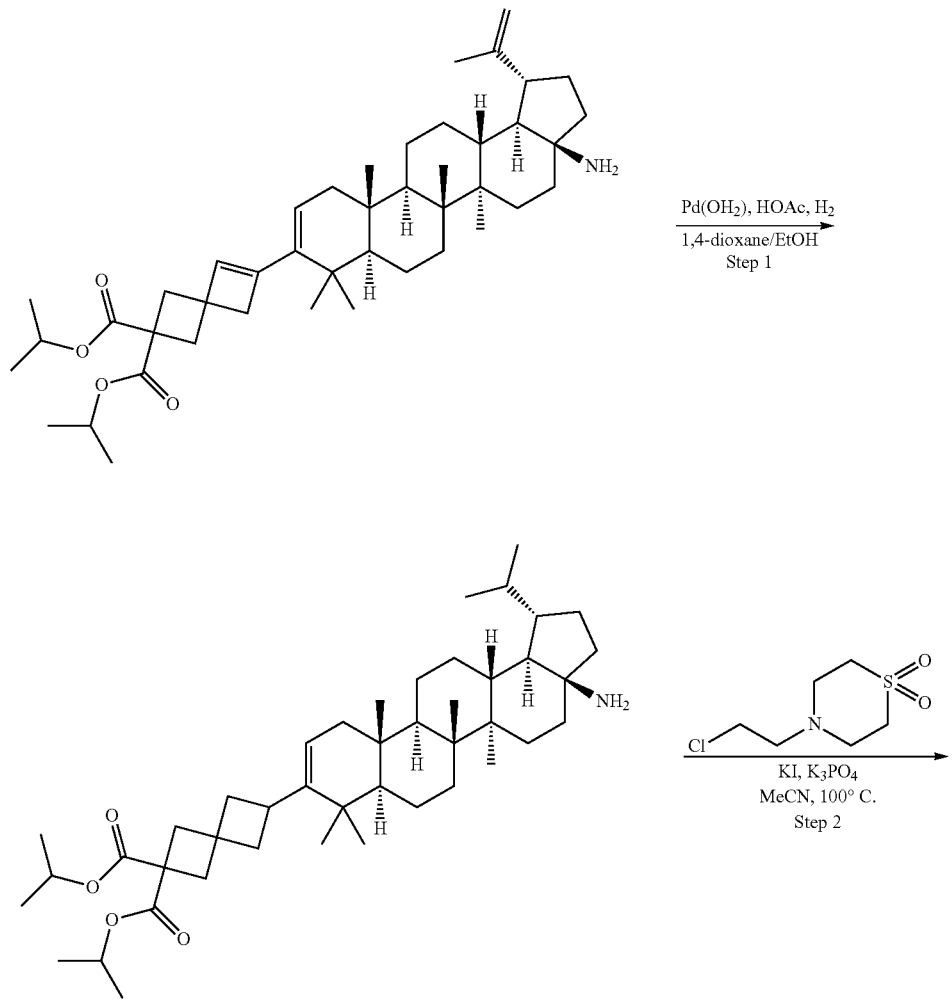

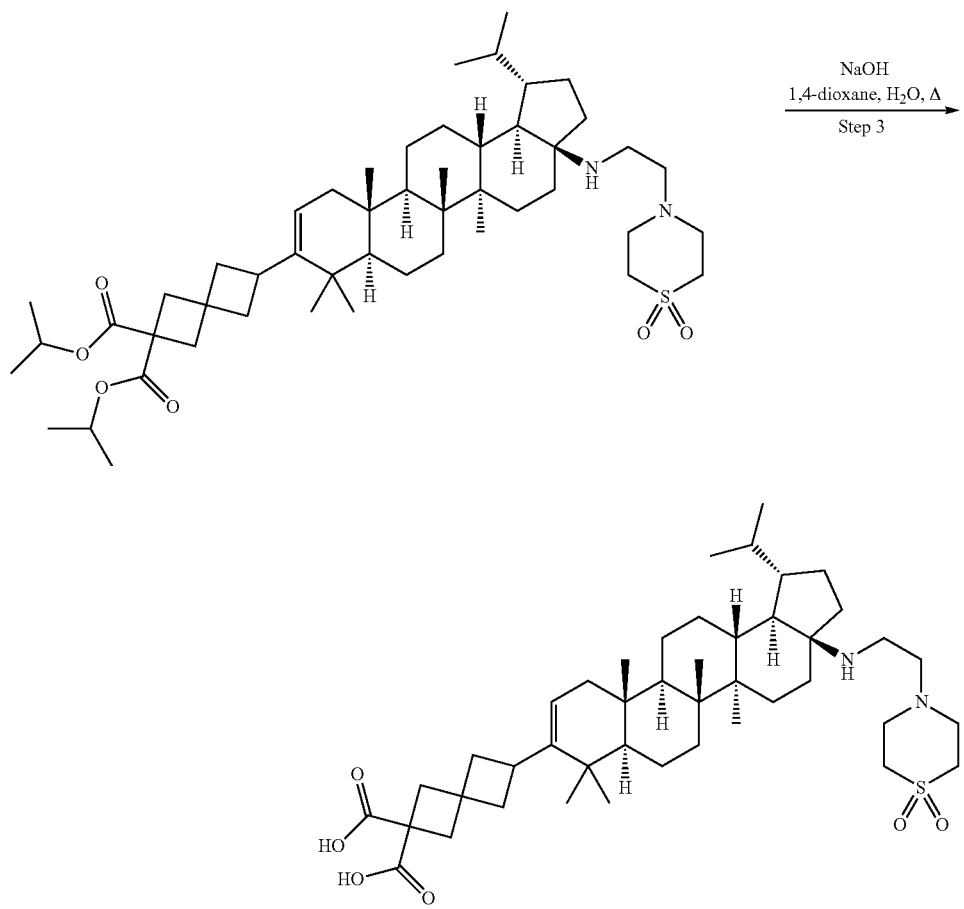

Example 5

Step 1. Preparation of diisopropyl 6-((1S,3aS,5aR, 5bR,7aR,11aS,11bR,13aR,13bR)-3a-((2-(1,1-dioxidothiomorpholino)ethyl)amino)-1-isopropyl-5a,5b,8, 8,11a-pentamethyl-2,3,3a,4,5,5a,5b,6,7,7a,8,11,11a, 11b,12,13,13a,13b-octadecahydro-1H-cyclopenta[a] chrysen-9-yl)spiro[3.3]heptane-2,2-dicarboxylate

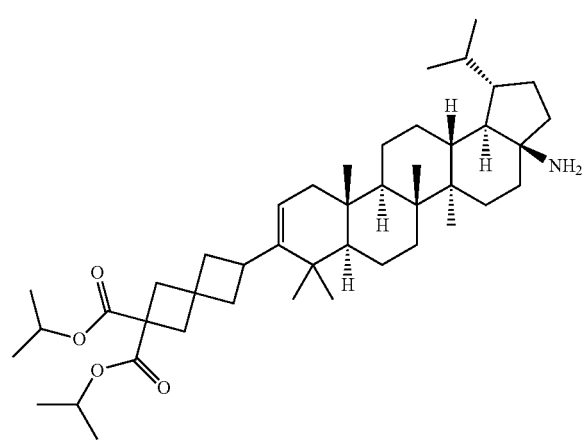

To a solution of diisopropyl 6-((1R,3aS,5aR,5bR,7aR, 11aS,11bR,13aR,13bR)-3a-amino-5a,5b,8,8,11a-pentamethyl-1-(prop-1-en-2-yl)-2,3,3a,4,5,5a,5b,6,7,7a,8,11,11a, 11b,12,13,13a,13b-octadecahydro-1H-cyclopenta[a] chrysen-9-yl)spiro[3.3]hept-5-ene-2,2-dicarboxylate (0.057 g, 0.085 mmol) in ethanol (2 mL), 1,4-dioxane (2 mL) and acetic acid (0.02 mL, 0.349 mmol) was added palladium hydroxide (20% on carbon) (0.072 g, 0.103 mmol). The mixture as stirred under 1 atm of hydrogen overnight. After stirring the mixture for 15 h, it was filtered through a plug of celite (washed with MeOH) then the filtrate was concentrated under reduced pressure. The residue was diluted with 15 mL of sat. aq. NaHCO₃ and extracted with dichloromethane (3×15 mL). The combined organic layers were dried with sodium sulfate. The drying agent was removed by filtration and the filtrate was concentrated under reduced pressure to give diisopropyl 6-((1S,3aS,5aR,5bR,7aR,11aS,11bR,13aR, 13bR)-3a-amino-1-isopropyl-5a,5b,8,8,11a-pentamethyl-2, 3,3a,4,5,5a,5b,6,7,7a,8,11,11a,11b,12,13,13a,13b-octadecahydro-1H-cyclopenta[a]chrysen-9-yl)spiro[3.3] heptane-2,2-dicarboxylate (0.057 g, 0.085 mmol, 100% yield) as an off-white solid. $^1$H NMR (500 MHz, chloroform-d) δ=5.33 (d, J=5.7 Hz, 1H), 5.11-5.02 (m, 2H), 3.80-3.72 (m, 1H), 3.68-3.60 (m, 1H), 2.66 (s, 2H), 2.44 (s, 2H), 2.99-0.64 (m, 62H).

Step 2. Preparation of diisopropyl 6-((1S,3aS,5aR, 5bR,7aR,11aS,11bR,13aR,13bR)-3a-((2-(1,1-dioxidothiomorpholino)ethyl)amino)-1-isopropyl-5a,5b,8, 8,11a-pentamethyl-2,3,3a,4,5,5a,5b,6,7,7a,8,11,11a, 11b,12,13,13a,13b-octadecahydro-1H-cyclopenta[a] chrysen-9-yl)spiro[3.3]heptane-2,2-dicarboxylate To a sealable vial was added diisopropyl 6-((1S,3 aS,5aR, 5bR,7aR,11aS,11bR,13 aR,13bR)-3a-amino-1-isopropyl-5a,5b,8,8,11a-pentamethyl-2,3,3a,4,5,5a,5b,6,7,7a,8,11, 11a,11b,12,13,13a,13b-octadecahydro-1H-cyclopenta[a] chrysen-9-yl)spiro[3.3]heptane-2,2-dicarboxylate (0.057 g, 0.085 mmol), 4-(2-chloroethyl)thiomorpholine 1,1-dioxide, HCl (0.060 g, 0.255 mmol), potassium iodide (0.028 g, 0.170 mmol) and phosphoric acid, potassium salt (0.090 g, 0.425 mmol). The mixture was diluted with acetonitrile (1.5 mL), flushed with nitrogen, sealed and heated to 100° C. After 15 h of heating, the mixture was adsorbed to silica gel and purified by flash chromatography using a Thomson 12 g silica gel column and a 12-100% ethyl acetate in hexanes gradient. The fractions containing the expected product were combined and concentrated under reduced pressure to give diisopropyl 6-((1S,3aS,5aR,5bR,7aR,11aS,11bR,13aR,13bR)-3a-((2-(1, 1-dioxidothiomorpholino)ethyl)amino)-1-isopropyl-5a,5b, 8,8,11a-pentamethyl-2,3,3a,4,5,5a,5b,6,7,7a,8,11,11a,11b, 12,13,13a,13b-octadecahydro-1H-cyclopenta[a]chrysen-9-yl)spiro[3.3]heptane-2,2-dicarboxylate (0.04 g, 0.048 mmol, 56.1% yield) as an off-white foam. LCMS: m/e 839.8 (M+H)+, 2.33 min (method 1).

Step 3

To a solution of diisopropyl 6-((1S,3aS,5aR,5bR,7aR, 11aS,11bR,13aR,13bR)-3a-((2-(1,1-dioxidothiomorpholino)ethyl)amino)-1-isopropyl-5a,5b,8,8,11a-pentamethyl-2,3,3a,4,5,5a,5b,6,7,7a,8,11,11a,11b,12,13,13a,13b-octadecahydro-1H-cyclopenta[a]chrysen-9-yl)spiro[3.3] heptane-2,2-dicarboxylate (0.04 g, 0.048 mmol) in 1,4-dioxane (2 mL) was added sodium hydroxide (10N) (0.095 mL, 0.953 mmol) and the mixture was heated to 85° C. After heating the mixture for 15 h, it was cooled to rt and was made acidic by adding 1N HCl. The mixture was then diluted with methanol and dioxane, filtered through a plug of glass wool and was purified by prep HPLC (method 1, retention time: 5.1 minutes). The fractions containing the expected product were combined and concentrated under reduced pressure to give 6-((1S,3aS,5aR,5bR,7aR,11aS,11bR,13aR,13bR)-3a-((2-(1, 1-dioxidothiomorpholino)ethyl)amino)-1-isopropyl-5a,5b, 8,8,11a-pentamethyl-2,3,3a,4,5,5a,5b,6,7,7a,8,11,11a,11b, 12,13,13a,13b-octadecahydro-1H-cyclopenta[a]chrysen-9-yl)spiro[3.3]heptane-2,2-dicarboxylic acid, TFA (0.025 g, 0.029 mmol, 60% yield) as an off-white solid. LCMS: m/e 755.6 (M+H)+, 1.67 min (method 1). $^1$H NMR (400 MHz, acetic acid-$d_4$) δ=5.38 (d, J=5.8 Hz, 1H), 2.76 (s, 2H), 2.53 (s, 2H), 1.21 (s, 3H), 1.05 (s, 3H), 0.96 (s, 3H), 0.89 (d, J=6.0 Hz, 6H), 0.81 (d, J=6.5 Hz, 3H), 3.47-0.67 (m, 44H).

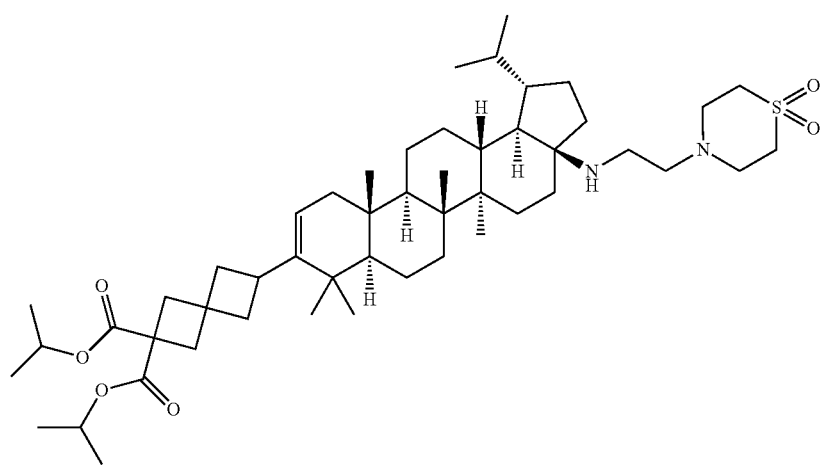

Example 6
Preparation of 6-((1R,3aS,5aR,5bR,7aR,11aS,11bR, 13aR,13bR)-3a-carboxy-5a,5b,8,8,11a-pentamethyl-1-(prop-1-en-2-yl)-2,3,3a,4,5,5a,5b,6,7,7a,8,11,11a, 11b,12,13,13a,13b-octadecahydro-1H-cyclopenta[a] chrysen-9-yl)spiro[3.3]hept-5-ene-2,2-dicarboxylic acid
5
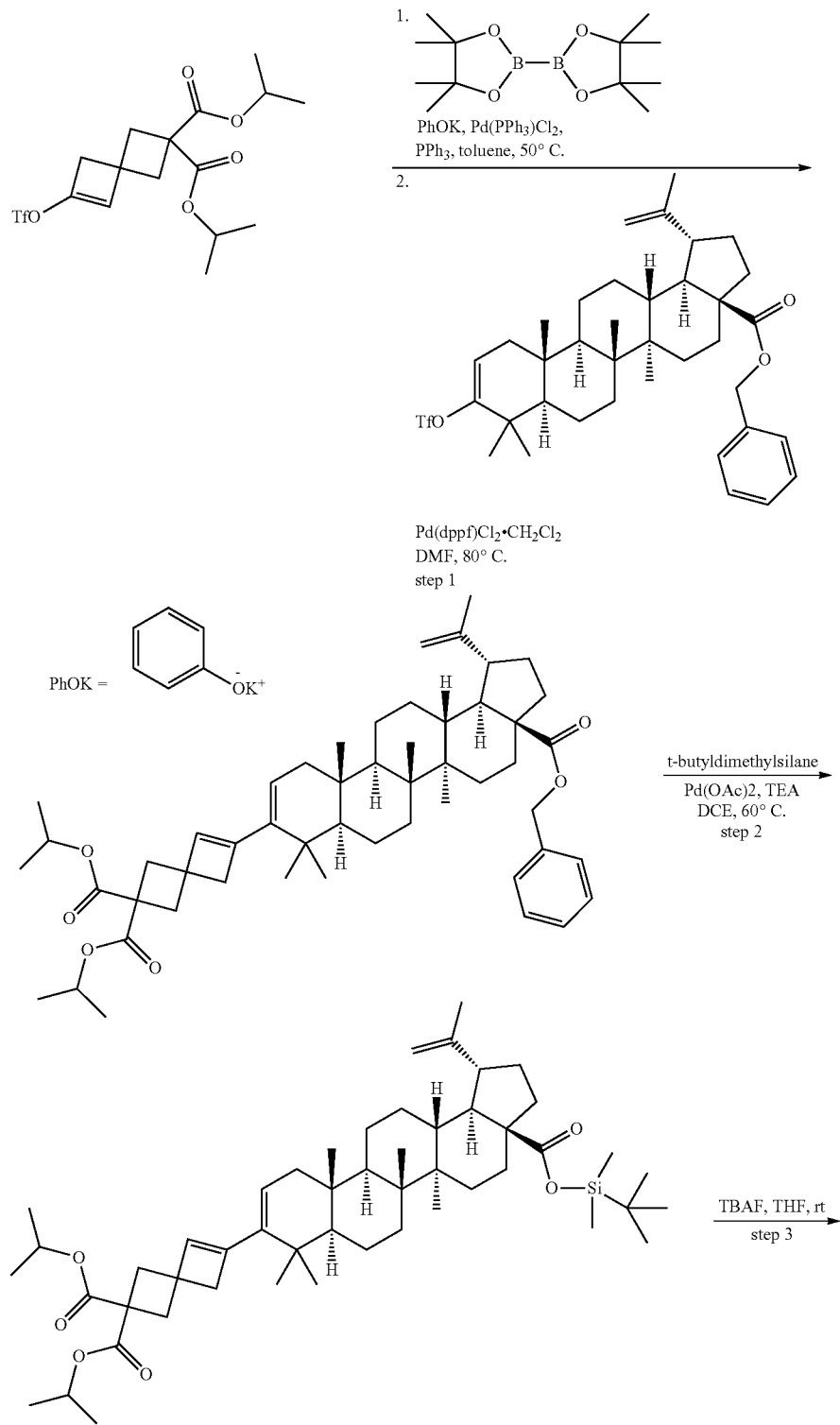

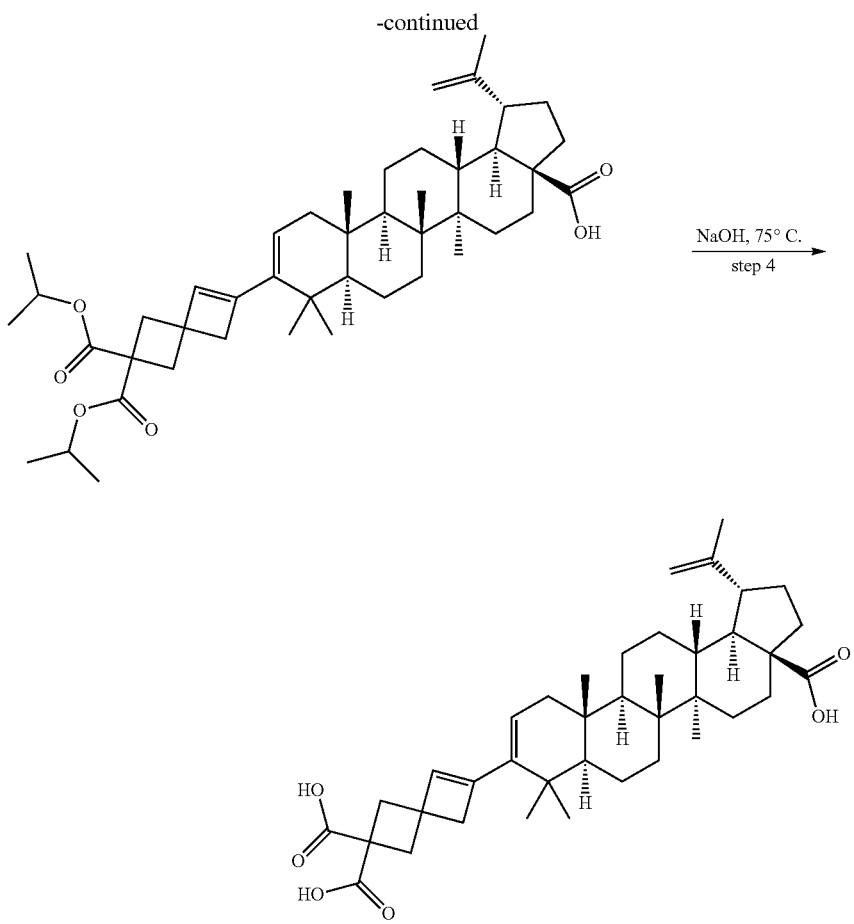

Example 6

Step 1: Preparation of diisopropyl 6-((1R,3aS,5aR, 5bR,7aR,11aS,11bR,13aR,13bR)-3a-((benzyloxy) carbonyl)-5a,5b,8,8,11a-pentamethyl-1-(prop-1-en-2-yl)-2,3,3a,4,5,5a,5b,6,7,7a,8,11,11a,11b,12,13,13a, 13b-octadecahydro-1H-cyclopenta[a]chrysen-9-yl) spiro[3.3]hept-5-ene-2,2-dicarboxylate The following procedure was modified from *J. Am. Chem. Soc.* 2002, 124, 8001-8006. To a rbf containing diisopropyl 6-(((trifluoromethyl)sulfonyl)oxy)spiro[3.3]hept-5-ene-2,2-dicarboxylate (0.095 g, 0.229 mmol) was added bis(pinacolato)dibororon (0.064 g, 0.252 mmol), phenolate, K+(0.045 g, 0.344 mmol), triphenylphospine (3.61 mg, 0.014 mmol), and bis(triphenylphosphine)palladium(II) chloride (4.83 mg, 6.88 mmol). The mixture was diluted with toluene (2 mL), flushed with nitrogen, then was heated to 50° C. for 3 h. The mixture was cooled to rt and TLC showed all starting material had been consumed. To the mixture was added (1R,3aS,5aR, 5bR,7aR,11aR,11bR,13aR,13bR)-benzyl 5a,5b,8,8,11a-pentamethyl-1-(prop-1-en-2-yl)-9-(((trifluoromethyl)sulfonyl)oxy)-2,3,3a,4,5,5a,5b,6,7,7a,8,11,11a,11b,12,13,13a, 13b-octadecahydro-1H-cyclopenta[a]chrysene-3a-carboxylate (0.149 g, 0.220 mmol), phosphoric acid, potassium salt (0.146 g, 0.688 mmol) and PdCl₂(dppf)-CH₂Cl₂ adduct (5.62 mg, 6.88 μmol). The mixture was diluted with DMF (2.000 mL), flushed with nitrogen, then was heated to 80° C. After heating the mixture for an additional 90 h, it was cooled to rt and was concentrated under reduced pressure, then was dissolved in DCM and MeOH and was filtered through a plug of silica gel and celite. The filtrate was concentrated under reduced pressure, and was purified by flash chromatography using a 0-25% ethyl acetate in hexanes gradient and a 12 g silica gel column. The major isolate from the purification contained a mixture of products, so it was further purified by flash chromatography using a slower, 0-5, 5-5, 5-10% ethyl acetate/hexanes gradient and a 12 g silica gel column. The fractions containing the expected product were combined and concentrated under reduced pressure to give diisopropyl 6-((1R,3aS,5aR,5bR,7aR,11aS,11bR,13aR, 13bR)-3a-((benzyloxy)carbonyl)-5a,5b,8,8,11a-pentamethyl-1-(prop-1-en-2-yl)-2,3,3a,4,5,5a,5b,6,7,7a,8,11,11a, 11b,12,13,13a,13b-octadecahydro-1H-cyclopenta[a] chrysen-9-yl)spiro[3.3]hept-5-ene-2,2-dicarboxylate (0.053 g, 0.047 mmol (based on 70% purity), 20.4% yield) as a colorless foam. $^1$H NMR (500 MHz, chloroform-d) δ=7.40-7.30 (m, 5H), 5.86 (s, 1H), 5.51 (dd, J=6.4, 1.8 Hz, 1H), 5.19-5.02 (m, 4H), 4.73 (d, J=1.5 Hz, 1H), 4.60 (s, 1H), 3.08-2.98 (m, 1H), 2.73-2.66 (m, 4H), 2.62-2.54 (m, 2H), 1.69 (s, 3H), 2.53-0.74 (m, 49H). The material was used in the next step with no additional purification.

Step 2: Preparation of diisopropyl 6-((1R,3aS,5aR, 5bR,7aR,11aS,11bR,13aR,13bR)-3a-(((tert-butyldimethylsilyl)oxy)carbonyl)-5a,5b,8,8,11a-pentamethyl-1-(prop-1-en-2-yl)-2,3,3a,4,5,5a,5b,6,7,7a, 8,11,11a,11b,12,13,13a,13b-octadecahydro-1H-cyclopenta[a]chrysen-9-yl)spiro[3.3]hept-5-ene-2,2-dicarboxylate To a rbf containing a solution of diisopropyl 6-((1R,3 aS,5aR,5bR,7aR,11aS,11bR,13aR,13bR)-3a-((benzyloxy) carbonyl)-5a,5b,8,8,11a-pentamethyl-1-(prop-1-en-2-yl)-2, 3,3a,4,5,5a,5b,6,7,7a,8,11,11a,11b,12,13,13a,13b-octadecahydro-1H-cyclopenta[a]chrysen-9-yl)spiro[3.3]hept-5-ene-2,2-dicarboxylate (0.053 g, 0.047 mmol (based on 70% purity)) in DCE (2 mL) was added triethylamine (10.43 µl, 0.075 mmol), t-butyldimethylsilane (0.016 mL, 0.094 mmol), and palladium(II) acetate (2.63 mg, 0.012 mmol). The mixture was flushed with nitrogen, then was heated to 60° C. for 4.5 h. An additional 3 mg of palladium (II) acetate were added along with 16 µL of t-butyldimethylsilane. The mixture was flushed with nitrogen, then was heated to 60° C. for an additional 2.5 h. The mixture was cooled to rt and was filtered through a plug of celite and sicla gel which was then washed with 25% EtOAc in hexanes. The filtrate was concentrated under reduced pressure to give diisopropyl 6-((1R,3 aS,5aR, 5bR,7aR,11aS,11bR,13 aR,13bR)-3a-(((tert-butyldimethylsilyl)oxy)carbonyl)-5a,5b,8,8,11a-pentamethyl-1-(prop-1-en-2-yl)-2,3,3a,4,5,5a,5b,6,7,7a,8,11,11a,11b,12,13,13a, 13b-octadecahydro-1H-cyclopenta[a]chrysen-9-yl)spiro [3.3]hept-5-ene-2,2-dicarboxylate (0.026 g, 0.021 mmol (based on 65% purity), 44.2% yield) as a clear, colorless foam. $^1$H NMR (500 MHz, chloroform-d) δ=5.86 (s, 1H), 5.51 (dd, J=6.3, 1.7 Hz, 1H), 5.13-5.01 (m, 2H), 4.73 (s, 1H), 4.60 (s, 1H), 3.06 (td, J=10.8, 4.1 Hz, 1H), 2.73-2.66 (m, 4H), 2.62-2.55 (m, 2H), 1.69 (s, 3H), 0.96 (s, 9H), 2.54-0.76 (m, 49H), 0.30-0.28 (m, 6H). The material was used in the next step with no additional purification.

Step 3: Preparation of (1R,3aS,5aR,5bR,7aR,11aS, 11bR,13aR,13bR)-9-(6,6-bis(isopropoxycarbonyl) spiro[3.3]hept-1-en-2-yl)-5a,5b,8,8,11a-pentamethyl-1-(prop-1-en-2-yl)-2,3,3a,4,5,5a,5b,6,7,7a,8, 11,11a,11b,12,13,13a,13b-octadecahydro-1H-cyclopenta[a]chrysene-3a-carboxylic acid To a solution of diisopropyl 6-((1R,3aS,5aR,5bR,7aR, 11aS,11bR,13aR,13bR)-3a-(((tert-butyldimethylsilyl)oxy) carbonyl)-5a,5b,8,8,11a-pentamethyl-1-(prop-1-en-2-yl)-2, 3,3a,4,5,5a,5b,6,7,7a,8,11,11a,11b,12,13,13a,13b-octadecahydro-1H-cyclopenta[a]chrysen-9-yl)spiro[3.3] hept-5-ene-2,2-dicarboxylate (0.026 g, 0.021 mmol (based on 65% purity)) in THF (2 mL) was added TBAF (75% in water) (10.81 mg, 0.031 mmol). The mixture was stirred at rt for 30 minutes, then was diluted with 15 mL of 1N HCl and was extracted with ethyl acetate (3×20 mL). The combined organic layers were washed with brine, dried over magnesium sulfate, filtered, and concentrated under reduced pressure to give (1R,3aS,5aR,5bR,7aR,11aS,11bR,13aR,13bR)-9-(6,6-bis(isopropoxycarbonyl)spiro[3.3]hept-1-en-2-yl)-5a,5b,8, 8,11a-pentamethyl-1-(prop-1-en-2-yl)-2,3,3a,4,5,5a,5b,6,7, 7a,8,11,11a,11b,12,13,13a,13b-octadecahydro-1H-cyclopenta[a]chrysene-3a-carboxylic acid (0.024 g, 0.021 mmol (based on 60% purity), 100% yield). The material was used in the next step with no additional purification. LCMS: m/e 701.5 (M-H)$^-$, 3.35 min (method 3). $^1$H NMR (400 MHz, chloroform-d) δ=10.58 (br. s., 1H), 5.87 (s, 1H), 5.52 (d, J=4.8 Hz, 1H), 5.13-5.02 (m, 2H), 4.75 (s, 1H), 4.62 (br. s., 1H), 3.07-2.97 (m, 1H), 2.70 (s, 4H), 2.63-2.55 (m, 2H), 1.70 (s, 3H), 2.54-0.77 (m, 49H). The material was used in the next step with no additional purification.

Step 4

To a solution of (1R,3aS,5aR,5bR,7aR,11aS,11bR,13aR, 13bR)-9-(6,6-bis(isopropoxycarbonyl)spiro[3.3]hept-1-en-2-yl)-5a,5b,8,8,11a-pentamethyl-1-(prop-1-en-2-yl)-2,3,3a, 4,5,5a,5b,6,7,7a,8,11,11a,11b,12,13,13a,13b-octadecahydro-1H-cyclopenta[a]chrysene-3a-carboxylic acid (0.025 g, 0.021 mmol (based on 60% purity)) in 1,4-dioxane (2 mL) was added NaOH (1N) (0.25 ml, 0.250 mmol). The mixture was heated to 75° C. for 66 h, then was cooled to rt. LC/MS was inconclusive. To the mixture was added 5 mL of 1N HCl, then the mixture was extracted with dichloromethane (3×15 mL) and dried with sodium sulfate. The drying agent was removed by filtration and the filtrate was concentrated under reduced pressure. The residue was again dissolved in 1,4 dioxane (3 mL) and 0.1 mL of 10N NaOH was added. The mixture was heated to 75° C. for 16.5 h, then was cooled to rt. To the mixture was added 10 mL of 1N HCl then the mixture was further diluted with 10 mL of water and it was extracted with dichloromethane (3×20 mL). The combined organic layers were dried with sodium sulfate, filtered, and concentrated under reduced pressure. The residue was dissolved in DMSO and was purified by prep HPLC (method 12, retention time: 10.2 minutes). The fractions containing the expected product were combined and concentrated under reduced pressure to give 6-((1R,3aS,5aR,5bR, 7aR,11aS,11bR,13aR,13bR)-3a-carboxy-5a,5b,8,8,11a-pentamethyl-1-(prop-1-en-2-yl)-2,3,3a,4,5,5a,5b,6,7,7a,8, 11,11a,11b,12,13,13a,13b-octadecahydro-1H-cyclopenta[a] chrysen-9-yl)spiro[3.3]hept-5-ene-2,2-dicarboxylic acid (0.015 g, 0.021 mmol (based on 86% purity), 99% yield) as a white solid. LCMS: m/e 617.4 (M-H)$^-$, 2.42 min (method 3). $^1$H NMR (500 MHz, acetic acid-d$_4$) δ=5.93 (s, 1H), 5.58 (d, J=4.6 Hz, 1H), 4.76 (br. s., 1H), 4.62 (br. s., 1H), 3.08-2.99 (m, 1H), 2.81 (s, 4H), 2.69-2.59 (m, 2H), 1.71 (s, 3H), 2.40-0.80 (m, 37H).

Preparation of diethyl 4-(4,4,5,5-tetramethyl-1,3,2-dioxaborolan-2-yl)cyclohex-3-ene-1,1-dicarboxylate

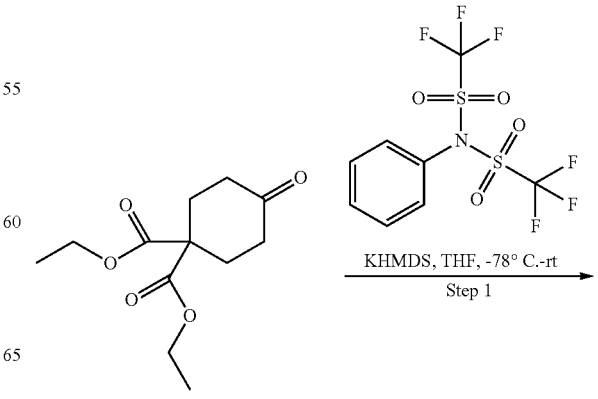

Step 1: Preparation of diethyl 4-(((trifluoromethyl)sulfonyl)oxy)cyclohex-3-ene-1,1-dicarboxylate

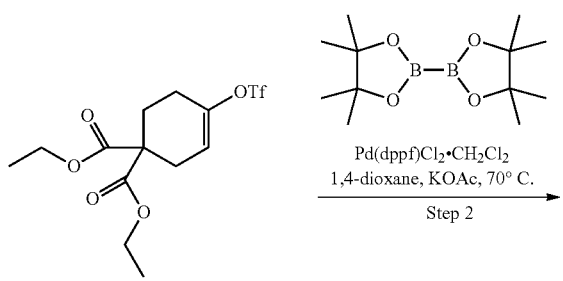

A flask containing a solution of diethyl 4-oxocyclohexane-1,1-dicarboxylate (0.505 g, 2.084 mmol) and 1,1,1-Trifluoro-N-phenyl-N-(trifluoromethyl)sulfonyl methanesulfonamide (0.819 g, 2.293 mmol) in THF (10 mL) was cooled to −78° C. To the solution was added KHMDS (0.5M in toluene) (6.25 mL, 3.13 mmol). The mixture was stirred at −78° C. for 1.5 h then was warmed to rt and was stirred for 1 h. The reaction was quenched with sat. aq ammonium chloride (30 mL) and was extracted with ethyl acetate (3×30 mL). The combined organic layers were dried over magnesium sulfate, filtered, and concentrated under reduced pressure. The residue was purified by flash chromatography using a 0-20% ethyl acetate in hexanes gradient. The fractions containing the expected product were combined and concentrated under reduced pressure to give the product which still contained impurities. The residue was repurified using a 0-50% toluene in hexanes gradient followed by a 0-10% ethyl acetate in hexanes. The fractions containing the expected product were combined and concentrated under reduced pressure to give the expected product as a clear, colorless oil (0.417 g, 1.114 mmol, 53.4% yield). $^1$H NMR (500 MHz, chloroform-d) δ=5.82-5.75 (m, 1H), 4.29-4.18 (m, 4H), 2.84-2.75 (m, 2H), 2.50-2.41 (m, 2H), 2.35-2.30 (m, 2H), 1.31-1.26 (m, 6H).

Step 2. Preparation of diethyl 4-(4,4,5,5-tetramethyl-1,3,2-dioxaborolan-2-yl)cyclohex-3-ene-1,1-dicarboxylate To a flask containing diethyl 4-(((trifluoromethyl)sulfonyl)oxy)cyclohex-3-ene-1,1-dicarboxylate (0.4 g, 1.069 mmol) was added bis(pinacolato)diboron (0.285 g, 1.122 mmol), potassium acetate (0.262 g, 2.67 mmol), and 1,1'-Bis(diphenylphosphino)ferrocenepalladium(II) dichloride (0.026 g, 0.032 mmol). The mixture was diluted with 1,4-dioxane (10 mL), flushed with nitrogen, and was heated to 70° C. for 5 h. The mixture was cooled to rt, diluted with water (25 mL), and extracted with ethyl acetate (3×25 mL). The combined organic layers were washed with brine, dried over magnesium sulfate, filtered, and concentrated under reduced pressure. The residue was purified by flash chromatography using a 40 g silica gel column and a 0-20% ethyl acetate in hexanes gradient. The fractions containing the expected product were combined and concentrated under reduced pressure to give the title compound as a clear, colorless oil. The product was used in the next step with no additional purification.

Example 7

Preparation of 4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-ene-1,1-dicarboxylic acid, TFA

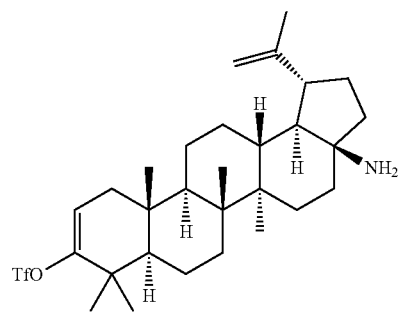
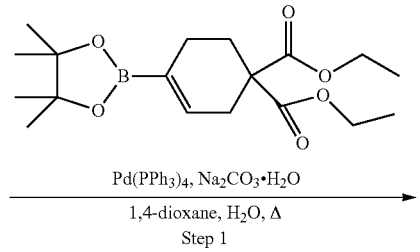

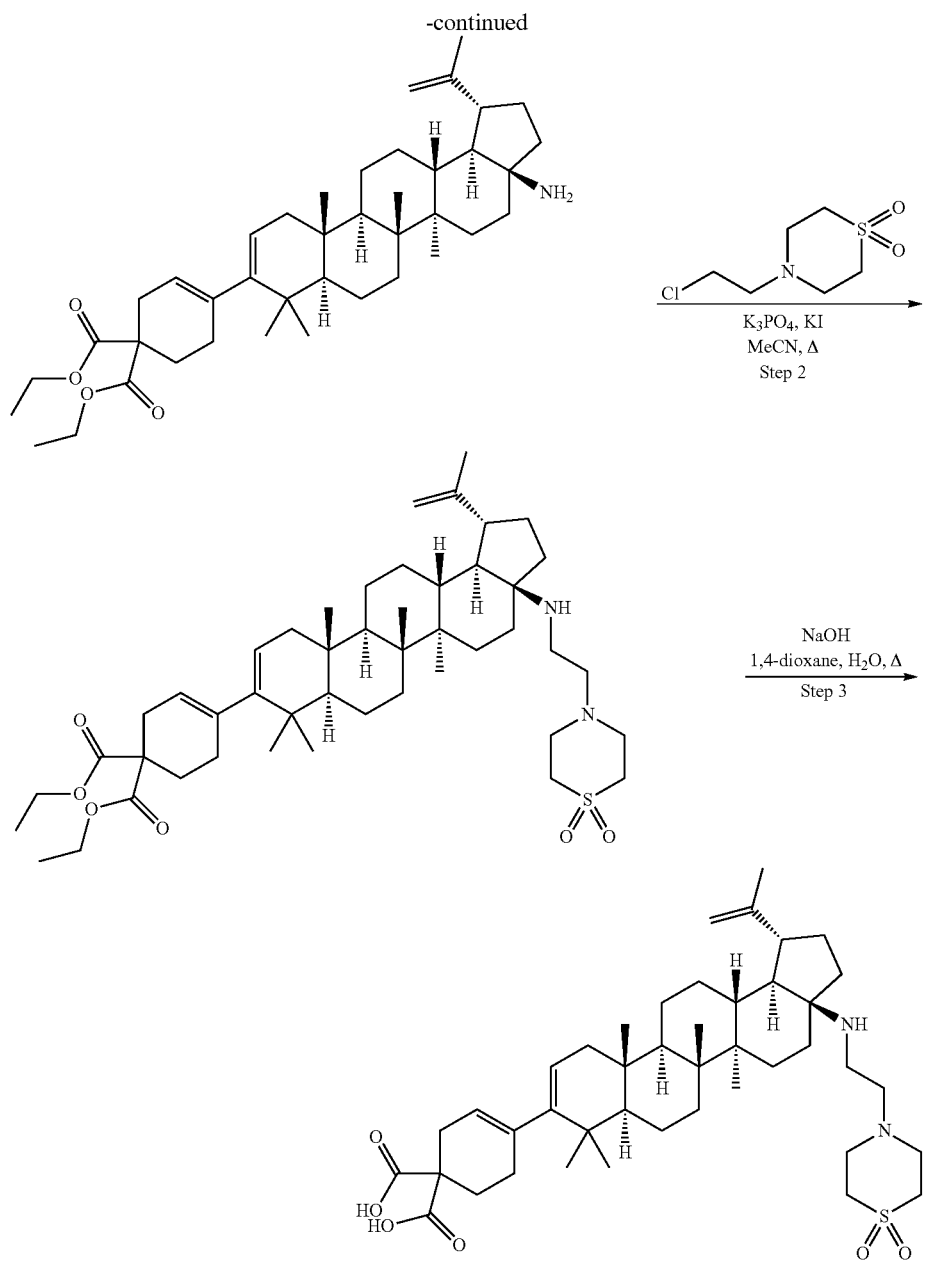

Example 7

Step 1: Preparation of diethyl 4-((1R,3aS,5aR,5bR, 7aR,11aS,11bR,13aR,13bR)-3a-amino-5a,5b,8,8, 11a-pentamethyl-1-(prop-1-en-2-yl)-2,3,3a,4,5,5a, 5b,6,7,7a,8,11,11a,11b,12,13,13a,13b-octadecahydro-1H-cyclopenta[a]chrysen-9-yl) cyclohex-3-ene-1,1-dicarboxylate To a sealable vial containing (1R,3aS,5aR,5bR,7aR,11aR, 11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12, 13,13a,13b-octadecahydro-1H-cyclopenta[a]chrysen-9-yl trifluoromethanesulfonate (0.25 g, 0.448 mmol) was added diethyl 4-(4,4,5,5-tetramethyl-1,3,2-dioxaborolan-2-yl)cyclohex-3-ene-1,1-dicarboxylate (0.374 g, 0.531 mmol), sodium carbonate hydrate (0.167 g, 1.345 mmol), and palladium tetrakis (0.016 g, 0.013 mmol). The mixture was diluted with 1,4-dioxane (4 mL) and water (1 mL) then was flushed with nitrogen and was sealed and heated to 85° C. in an oil bath. After 5 h of heating, the mixture was cooled to rt, was diluted with water (20 mL), and was extracted with ethyl acetate (3×20 mL). The combined organic layers were washed with brine, dried over magnesium sulfate, filtered, and concentrated under reduced pressure. The residue was purified by flash chromatography using a 10-50% ethyl acetate in hexanes gradient. diethyl 4-((1R,3aS,5aR,5bR, 7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11, 11a,11b,12,13,13a,13b-octadecahydro-1H-cyclopenta[a] chrysen-9-yl)cyclohex-3-ene-1,1-dicarboxylate, a white solid, was recovered as the minor isolate (0.032 g, 0.05 mmol, 11.3% yield). LCMS: m/e 634.6 (M+H)+, 2.10 min (method 1).

Step 2: Preparation of diethyl 4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-ene-1,1-dicarboxylate To a sealable vial was added diethyl 4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-ene-1,1-dicarboxylate (0.032 g, 0.050 mmol), 4-(2-chloroethyl)thiomorpholine 1,1-dioxide, HCl (0.035 g, 0.151 mmol), potassium iodide (0.025 g, 0.151 mmol), and phosphoric acid, potassium salt (0.078 g, 0.367 mmol). The mixture was diluted with acetonitrile (1 mL), flushed with nitrogen, and was sealed and heated to 100° C. After 15.5 h of heating, the mixture was cooled to rt the mixture was diluted with water (10 mL) and was extracted with dichloromethane (3×10 mL). The combined organic layers were dried with sodium sulfate, filtered, and concentrated under reduced pressure. The residue was purified by flash chromatography using a 10-85% ethyl acetate in hexanes gradient. The fractions containing the expected product were combined and concentrated under reduced pressure to give diethyl 4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-ene-1,1-dicarboxylate (0.031 g, 0.039 mmol, 77% yield) as a clear, colorless film. LCMS: m/e 795.7 (M+H)$^+$, 2.21 min (method 1).

Step 3

To a solution of diethyl 4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-ene-1,1-dicarboxylate (0.031 g, 0.039 mmol) in 1,4-dioxane (2 mL) was added NaOH (1N) (0.312 mL, 0.312 mmol). The mixture was heated to 70° C. for 23 h, then was cooled to rt. LC/MS showed mono-hydrolyzed product present so NaOH (10N) (0.05 mL, 0.500 mmol) was added and the mixture was heated to 70° C. for an additional 18.5 h. The mixture was cooled to rt, diluted with methanol, dioxane, and water, then was purified by prep HPLC (method 3, retention time: 4.8 minutes). The fractions containing the expected product were combined and were concentrated under reduced pressure to give 4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-ene-1,1-dicarboxylic acid, TFA (12.4 mg, 0.014 mmol, 35% yield) as a white solid. LCMS: m/e 739.6 (M+H)$^+$, 1.50 min (method 1). $^1$H NMR (400 MHz, acetic acid, d$_4$) δ=5.37 (br. s., 1H), 5.20 (d, J=5.3 Hz, 1H), 4.79 (s, 1H), 4.69 (s, 1H), 3.47 (d, J=12.3 Hz, 1H), 3.32-3.01 (m, 11H), 2.86 (br. s., 1H), 2.64 (br. s., 2H), 1.71 (s, 3H), 1.21 (s, 3H), 1.08 (s, 3H), 0.96 (s, 3H), 0.93 (s, 3H), 0.93 (br. s., 3H), 2.29-0.87 (m, 26H).

Example 8

Preparation of 4-((1S,3aS,5aR,5bR,7aR,11aS,11bR,13aR,13bR)-3a-((2-(1,1-dioxidothiomorpholino)ethyl)amino)-1-isopropyl-5a,5b,8,8,11a-pentamethyl-2,3,3a,4,5,5a,5b,6,7,7a,8,11,11a,11b,12,13,13a,13b-octadecahydro-1H-cyclopenta[a]chrysen-9-yl)cyclohex-3-enecarboxylic acid, TFA

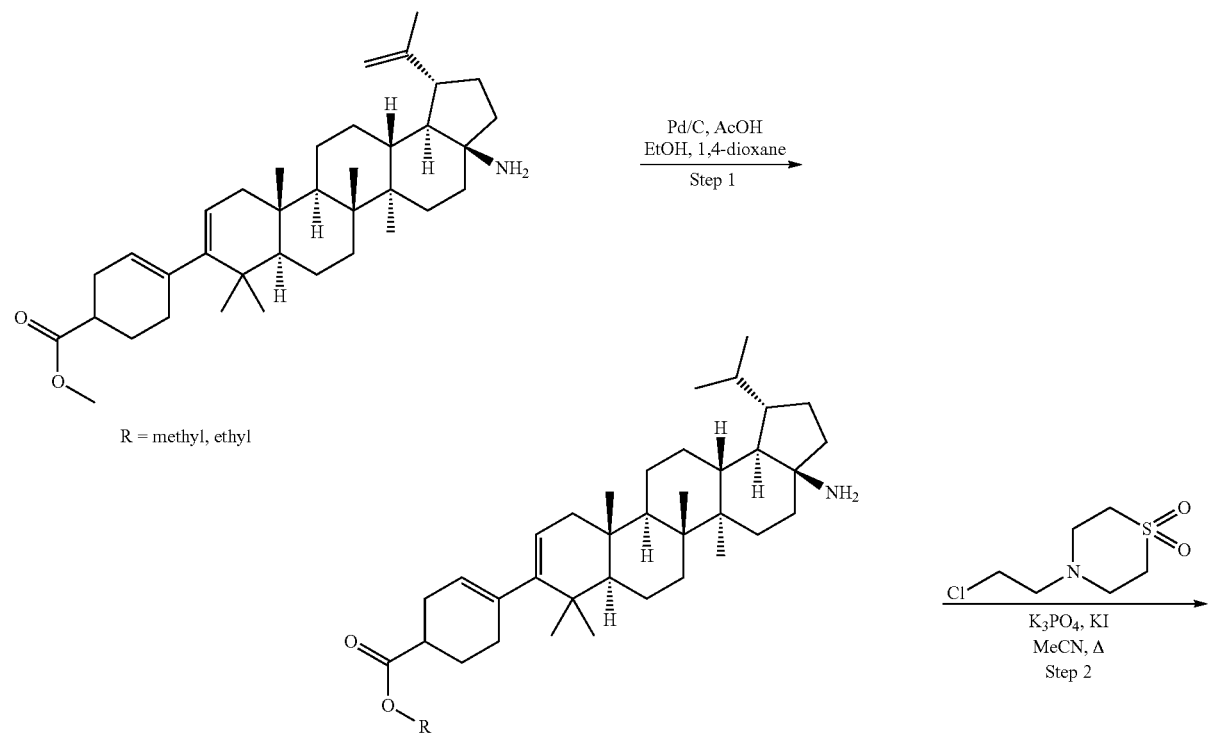

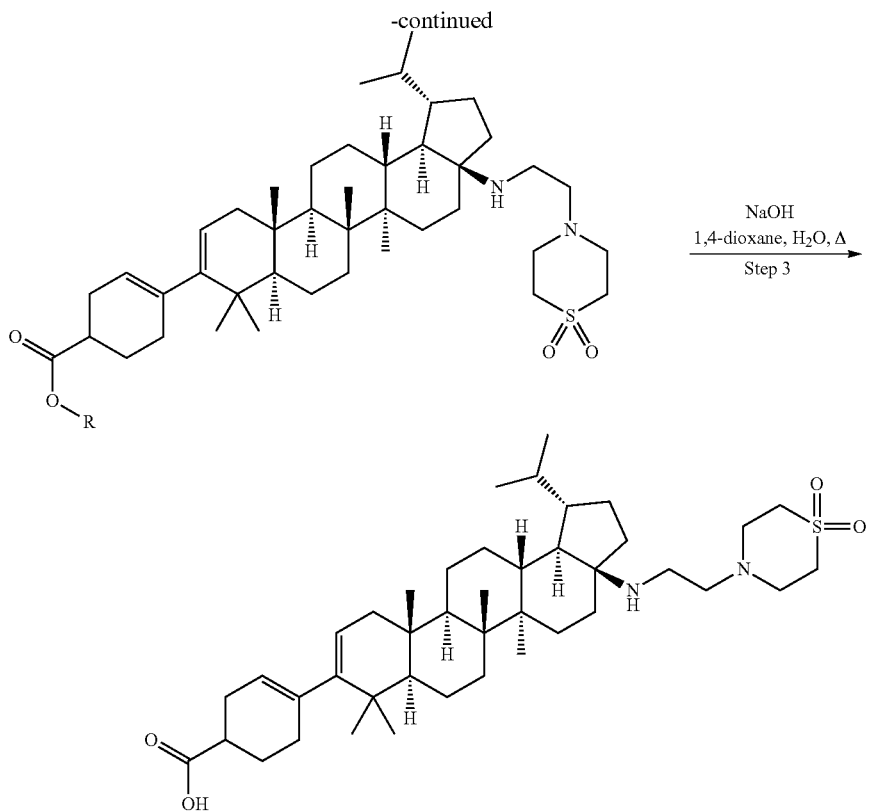

Example 8

Step 1: Preparation of ethyl 4-((1S,3aS,5aR,5bR, 7aR,11aS,11bR,13aR,13bR)-3a-amino-1-isopropyl-5a,5b,8,8,11a-pentamethyl-2,3,3a,4,5,5a,5b,6,7,7a,8,11,11a,11b,12,13,13a,13b-octadecahydro-1H-cyclopenta[a]chrysen-9-yl)cyclohex-3-enecarboxylate To a solution of ethyl 4-((1R,3aS,5aR,5bR,7aR,11aS,11bR,13aR,13bR)-3a-amino-5a,5b,8,8,11a-(prop-1-en-2-yl)-2,3,3a,4,5,5a,5b,6,7,7a,8,11,11a,11b,12,13,13a,13b-octadecahydro-1H-cyclopenta[a]chrysen-9-yl) cyclohex-3-enecarboxylate (0.1 g, 0.178 mmol) in ethanol (5 mL), 1,4-dioxane (2 mL) and acetic acid (0.051 mL, 0.890 mmol) was added 10% palladium on carbon (0.095 g, 0.089 mmol). The mixture was evacuated and refilled with nitrogen three times then was stirred under 1 atmosphere of hydrogen gas for 16 h. The mixture was evacuated and flushed with nitrogen, then was filtered through celite and was concentrated under reduced pressure to give the expected product (0.100 g, 0.178 mmol, 100% yield) as an off-white solid. $^1$H NMR (400 MHz, chloroform-d) δ=5.36 (br. s., 1H), 5.19 (d, J=5.8 Hz, 1H), 4.19-4.11 (m, 2H), 2.57-2.47 (m, 1H), 2.31 (dd, J=2.9, 2.1 Hz, 2H), 2.17 (dd, J=4.6, 2.6 Hz, 2H), 2.12-0.70 (m, 52H).

Step 2: Preparation of ethyl 4-((1S,3aS,5aR,5bR, 7aR,11aS,11bR,13aR,13bR)-3a-((2-(1,1-dioxidothiomorpholino)ethyl)amino)-1-isopropyl-5a,5b,8,8,11a-pentamethyl-2,3,3a,4,5,5a,5b,6,7,7a,8,11,11a,11b,12,13,13a,13b-octadecahydro-1H-cyclopenta[a]chrysen-9-yl)cyclohex-3-enecarboxylate To a sealable vial was added ethyl 4-((1S,3aS,5aR,5bR,7aR,11aS,11bR,13aR,13bR)-3a-amino-1-isopropyl-5a,5b,8,8,11a-pentamethyl-2,3,3a,4,5,5a,5b,6,7,7a,8,11,11a,11b,12,13,13a,13b-octadecahydro-1H-cyclopenta[a]chrysen-9-yl) cyclohex-3-enecarboxylate (0.1 g, 0.177 mmol), 4-(2-chloroethyl)thiomorpholine 1,1-dioxide, HCl (0.125 g, 0.532 mmol), potassium iodide (0.088 g, 0.532 mmol) and phosphoric acid, potassium salt (0.188 g, 0.887 mmol). The mixture was diluted with acetonitrile (2 mL) and flushed with nitrogen, then the vial was sealed and heated to 100° C. for 15.5 h. The mixture was cooled to rt and was diluted with water (20 mL) then was extracted with dichloromethane (3×20 mL). The combined organic layers were dried with sodium sulfate, filtered, and concentrated under reduced pressure. The residue was adsorbed to silica gel, then was purified by flash chromatography using a 20-50% ethyl acetate in hexanes gradient and a 25 g silica gel column. The fractions containing the expected product were combined and were concentrated under reduced pressure to give ethyl 4-((1S,3aS,5aR,5bR,7aR,11aS,11bR,13aR,13bR)-3a-((2-(1,1-dioxidothiomorpholino)ethyl)amino)-1-isopropyl-5a,5b,8,8,11a-pentamethyl-2,3,3a,4,5,5a,5b,6,7,7a,8,11,11a,11b,12,13,13a,13b-octadecahydro-1H-cyclopenta[a]chrysen-9-yl) cyclohex-3-enecarboxylate (0.059 g, 0.081 mmol, 45.9% yield) as an off-white foam. LCMS: m/e 725.6 (M+H)$^+$, 2.24 min (method 1).

Step 3

To a solution of ethyl 4-((1S,3aS,5aR,5bR,7aR,11aS,11bR,13aR,13bR)-3a-((2-(1,1-dioxidothiomorpholino) ethyl)amino)-1-isopropyl-5a,5b,8,8,11a-pentamethyl-2,3,3a,4,5,5a,5b,6,7,7a,8,11,11a,11b,12,13,13a,13b-octadecahydro-1H-cyclopenta[a]chrysen-9-yl)cyclohex-3- enecarboxylate (0.059 g, 0.081 mmol) in 1,4-dioxane (2 mL) was added sodium hydroxide (1N) (0.407 mL, 0.407 mmol). The mixture was heated to 70° C. for 16 h then was cooled to rt. The mixture was purified by prep HPLC (method 3, retention time: 5.7 minutes). The fractions containing the expected product were combined and concentrated under reduced pressure to give the expected product. Minor impurities remained, so a second purification by prep HPLC followed (method 4, retention time: 12.7 minutes). The fractions containing the expected product were combined and concentrated under reduced pressure to give 4-((1S,3aS,5aR,5bR,7aR,11aS,11bR,13aR,13bR)-3a-((2-(1,1-dioxidothiomorpholino)ethyl)amino)-1-isopropyl-5a,5b,8,8,11a-pentamethyl-2,3,3a,4,5,5a,5b,6,7,7a,8,11,11a,11b,12,13,13a,13b-octadecahydro-1H-cyclopenta[a]chrysen-9-yl)cyclohex-3-enecarboxylic acid, TFA (0.012 g, 0.015 mmol, 18.5% yield) as a white solid. LCMS: m/e 697.6 (M+H)$^+$, 1.92 min (method 1). $^1$H NMR (400 MHz, acetic acid-d$_4$) δ=5.37 (br. s., 1H), 5.23 (d, J=6.0 Hz, 1H), 3.41 (d, J=12.3 Hz, 1H), 3.35-3.02 (m, 11H), 2.63-2.54 (m, 1H), 1.22 (s, 3H), 1.06 (s, 3H), 0.89 (d, J=6.8 Hz, 3H), 0.81 (d, J=6.5 Hz, 3H), 2.40-0.76 (m, 39H).

Example 9 and Example 10

Preparation of (R)-4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylic acid, TFA and (S)-4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylic acid, TFA

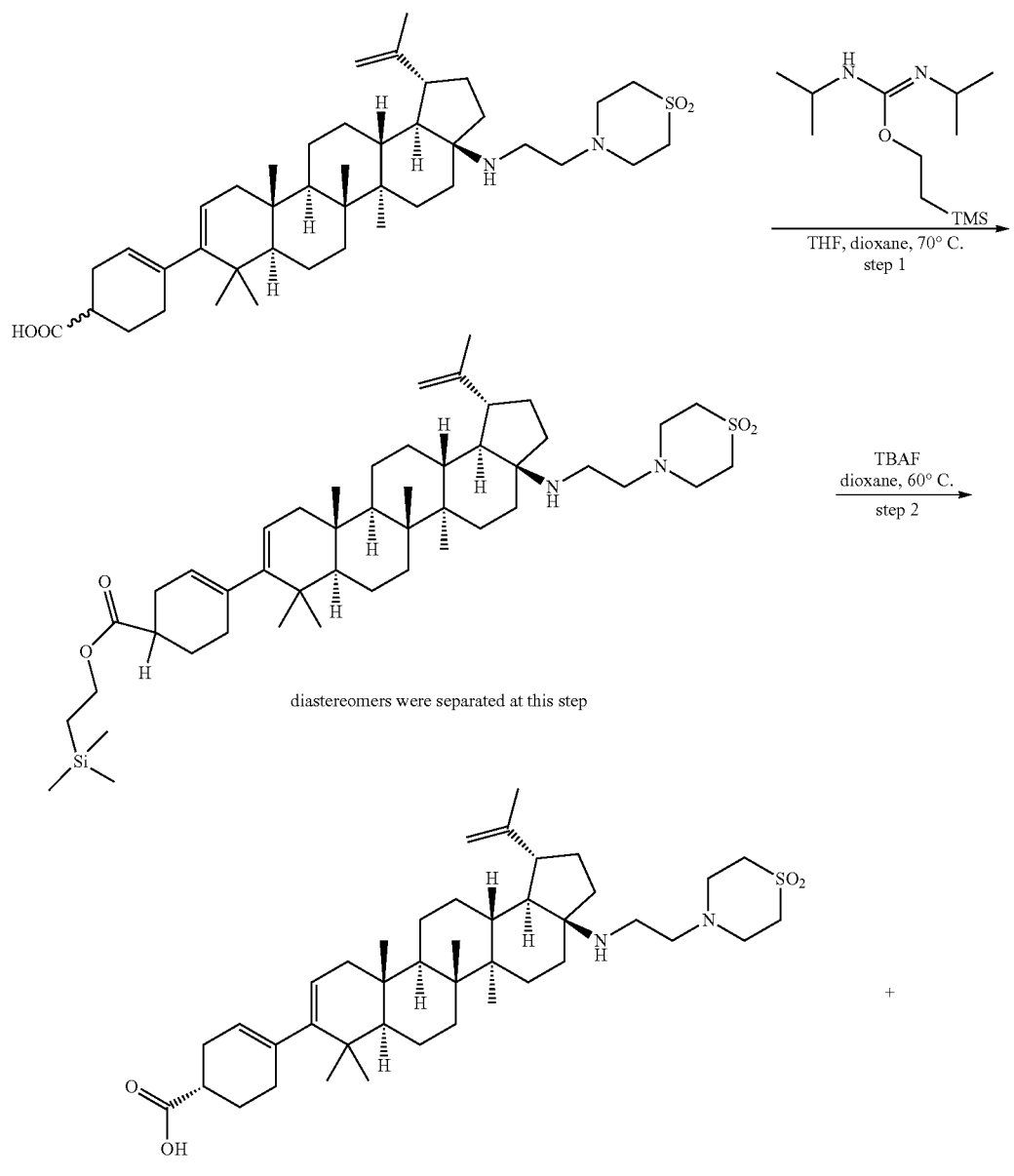

Example 9

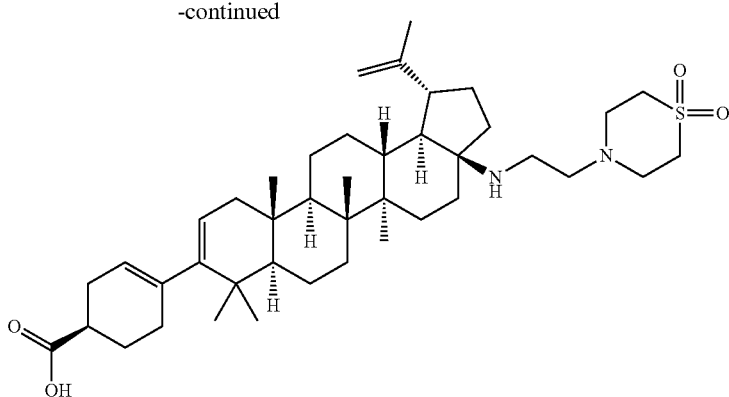

Example 10

Step 1: Preparation and separation of the diasteriomers of 2-(trimethylsilyl)ethyl 4-((1R,3aS,5aR, 5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7, 7a,8,11,11a,11b,12,13,13a,13b-octadecahydro-1H-cyclopenta[a]chrysen-9-yl)cyclohex-3-enecarboxylate To a vial containing a suspension of 4-((1R,3aS,5aR,5bR, 7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a, 13b-octadecahydro-1H-cyclopenta[a]chrysen-9-yl) cyclohex-3-enecarboxylic acid (0.025 g, 0.036 mmol) in THF (1 mL) was added (Z)-2-(trimethylsilyl)ethyl N,N'-diisopropylcarbamimidate (0.017 g, 0.070 mmol). The vial was sealed and heated to 70° C. and upon heating the solids completely dissolved. After 4.5 h of heating, the mixture was cooled to rt. LC/MS showed a mixture of starting material and product present. Since the seal on the vial started to fail, 1 mL of 1,4-dioxane was added and the mixture was again heated to 70° C. After heating the mixture for 21 h (total), the mixture was cooled to rt. LC/MS still showed starting material present, so an additional 30 mg of (Z)-2-(trimethylsilyl)ethyl N,N'-diisopropylcarbamimidate was added and the mixture was further heated to 70° C. After 7 h of heating, the mixture was cooled to rt. The mixture was purified by flash chromatography using a 0-50% ethyl acetate in hexanes gradient and a 12 g silica gel column. The fractions containing the expected product were combined and concentrated under reduced pressure to give 2-(trimethylsilyl)ethyl 4-((1R,3aS, 5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12, 13,13a,13b-octadecahydro-1H-cyclopenta[a]chrysen-9-yl) cyclohex-3-enecarboxylate (0.02 g, 0.025 mmol, 69.9% yield) as a white foam. The mixture of diastereomers was separated by SFC (Chiral SFC Method 1) and the fractions containing each isolate was concentrated under reduced pressure to give 4.7 mg of isomer 1 and 6.1 mg of isomer 2. Isomer 1: $^1$H NMR (400 MHz, chloroform-d) δ=5.35 (br. s., 1H), 5.18 (d, J=4.5 Hz, 1H), 4.71 (br. s., 1H), 4.59 (br. s., 1H), 4.21-4.14 (m, 2H), 3.16-2.95 (m, 8H), 2.75-2.39 (m, 6H), 2.30 (br. s., 2H), 2.17 (br. s., 2H), 1.69 (s, 3H), 1.06 (s, 3H), 0.98 (br. s., 3H), 0.96 (br. s., 3H), 0.90 (s, 3H), 0.86 (s, 3H), 2.04-0.83 (m, 27H), 0.065-0.04 (m, 9H). Isomer 2: $^1$H NMR (400 MHz, chloroform-d) δ=5.35 (br. s., 1H), 5.21-5.16 (m, 1H), 4.71 (br. s., 1H), 4.60 (br. s., 1H), 4.21-4.14 (m, 2H), 3.14-2.97 (m, 8H), 2.74-2.42 (m, 6H), 2.30 (br. s., 2H), 2.25-2.08 (m, 2H), 1.69 (s, 3H), 1.06 (s, 3H), 0.96 (br. s., 3H), 0.95 (s, 3H), 0.94 (s, 3H), 0.86 (s, 3H), 2.03-0.83 (m, 27H), 0.065-0.04 (m, 9H).

Step 2

To a solution of each of the two isomers in the previous step in 1,4-Dioxane (0.25 mL) was added TBAF (75% in water) (50 mg, 0.143 mmol). The mixtures were warmed to 60° C. After 4.5 h the mixtures were cooled to rt then was diluted with methanol and dioxane and were purified by prep HPLC (method 5, retention time: isomer 1: 9.7 minutes, isomer 2: 9.6 minutes). The fractions containing each product were combined and concentrated under reduced pressure to give the free carboxylic acid of isomer 1 (2.4 mg, 2.9 mmol, 49% yield) and isomer 2 (4.5 mg, 5.5 mmol, 93% yield) as off-white solids.

Example 9

(R)-4-((1R,3aS,5aR,5bR,7aR,11aS,11bR,13aR, 13bR)-3a-((2-(1,1-dioxidothiomorpholino)ethyl) amino)-5a,5b,8,8,11a-pentamethyl-1-(prop-1-en-2-yl)-2,3,3a,4,5,5a,5b,6,7,7a,8,11,11a,11b,12,13,13a, 13b-octadecahydro-1H-cyclopenta[a]chrysen-9-yl) cyclohex-3-enecarboxylic acid, TFA LCMS: m/e 695.6 (M+H)$^+$, 1.65 min (method 1). $^1$H NMR (400 MHz, Acetic) δ=5.38 (br. s., 1H), 5.23 (d, J=4.5 Hz, 1H), 4.82 (s, 1H), 4.71 (s, 1H), 3.50-3.43 (m, 1H), 3.35-3.02 (m, 11H), 2.96-2.88 (m, 1H), 2.64-2.54 (m, 1H), 1.73 (s, 3H), 1.23 (s, 3H), 1.09 (s, 3H), 1.02 (s, 3H), 0.96 (br. s., 3H), 0.95 (br. s., 3H), 2.42-0.90 (m, 28H).

Example 10

(S)-4-((1R,3aS,5aR,5bR,7aR,11aS,11bR,13aR, 13bR)-3a-((2-(1,1-dioxidothiomorpholino)ethyl) amino)-5a,5b,8,8,11a-pentamethyl-1-(prop-1-en-2-yl)-2,3,3a,4,5,5a,5b,6,7,7a,8,11,11a,11b,12,13,13a, 13b-octadecahydro-1H-cyclopenta[a]chrysen-9-yl) cyclohex-3-enecarboxylic acid, TFA LCMS: m/e 695.6 (M+H)$^+$, 1.63 min (method 1). $^1$H NMR (400 MHz, Acetic) δ=5.38 (br. s., 1H), 5.23 (d, J=5.5 Hz, 1H), 4.81 (s, 1H), 4.71 (s, 1H), 3.48 (d, J=11.8 Hz, 1H), 3.36-3.04 (m, 11H), 2.95-2.83 (m, 1H), 2.66-2.55 (m, 1H), 1.73 (s, 3H), 1.23 (s, 3H), 1.09 (s, 3H), 0.99 (s, 6H), 0.95 (s, 3H), 2.41-0.92 (m, 28H).

Preparation and purification of (R)- and (S)-benzyl 4-(4,4,5,5-tetramethyl-1,3,2-dioxaborolan-2-yl)cyclohex-3-enecarboxylate

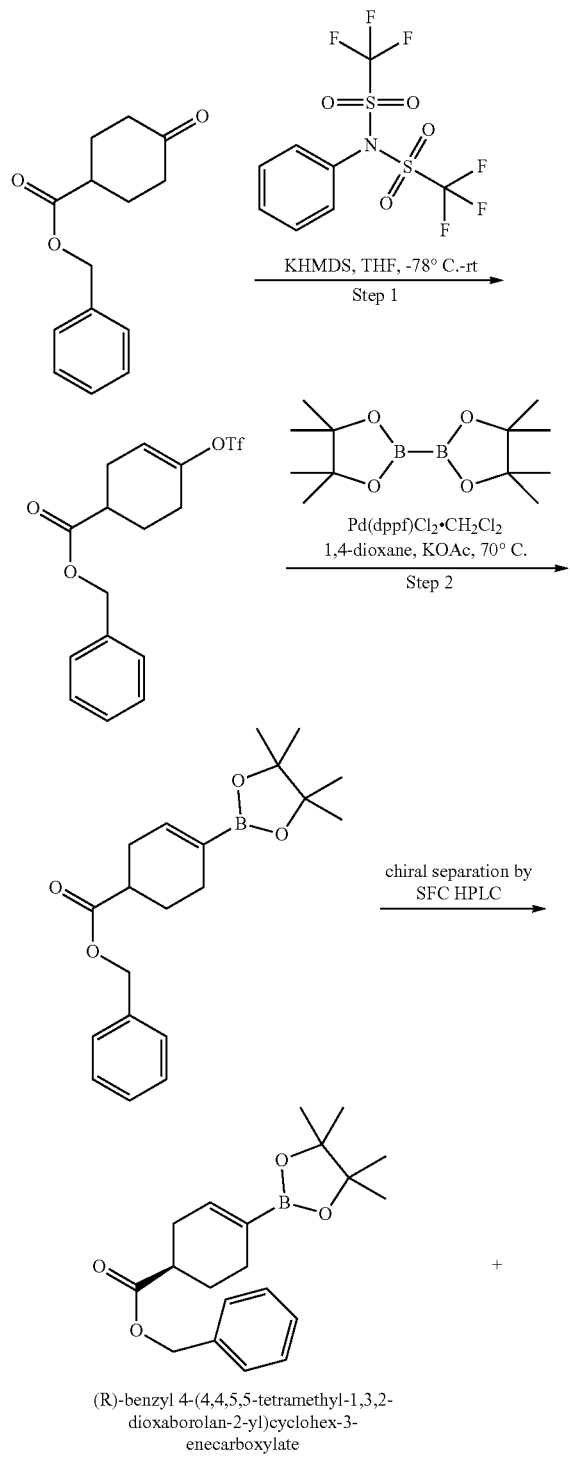

(R)-benzyl 4-(4,4,5,5-tetramethyl-1,3,2-dioxaborolan-2-yl)cyclohex-3-enecarboxylate

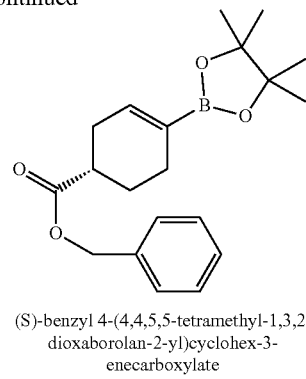

(S)-benzyl 4-(4,4,5,5-tetramethyl-1,3,2-dioxaborolan-2-yl)cyclohex-3-enecarboxylate Step 1. Preparation of benzyl 4-(((trifluoromethyl)sulfonyl)oxy)cyclohex-3-enecarboxylate A rbf containing benzyl 4-oxocyclohexanecarboxylate (6.0 g, 25.8 mmol) (see *Bioorg. Med. Chem. Lett.* 2008, 18, 5107-5110. for the preparation) and 1,1,1-trifluoro-N-phenyl-N-((trifluoromethyl)sulfonyl)methanesulfonamide (10.15 g, 28.4 mmol) was evacuated and backfilled with nitrogen three times. The mixture was diluted with THF (100 mL) and was cooled to −78° C. To the mixture was added KHMDS (0.5M in toluene) (64.6 mL, 32.3 mmol) slowly over 20 minutes. The mixture was stirred at −78° C. for 30 minutes then the ice bath was removed and it was stirred for 1.5 h at rt. The mixture was diluted with water (150 mL) and was extracted with ethyl acetate (3×150 mL). The combined organic layers were washed with brine, dried over magnesium sulfate, filtered, and concentrated under reduced pressure to give the crude benzyl 4-(((trifluoromethyl)sulfonyl)oxy)cyclohex-3-enecarboxylate as a light-red oil. The crude product was used in the next step with no additional purification. $^1$H NMR (500 MHz, CHLOROFORM-d) δ=7.42-7.29 (m, 5H), 5.79-5.76 (m, 1H), 5.18-5.13 (m, 2H), 2.70-2.61 (m, 1H), 2.52-2.34 (m, 4H), 2.20-2.13 (m, 1H), 1.99-1.90 (m, 1H).

Step 2. Preparation of benzyl 4-(4,4,5,5-tetramethyl-1,3,2-dioxaborolan-2-yl)cyclohex-3-enecarboxylate To a flask containing the crude benzyl 4-(((trifluoromethyl)sulfonyl)oxy)cyclohex-3-enecarboxylate (9.40 g, 25.8 mmol) was added bis(pinacolato)diboron (6.88 g, 27.1 mmol), potassium acetate (6.33 g, 64.5 mmol), and 1,1'-bis(diphenylphosphino)ferrocenepalladium(II) dichloride (0.637 g, 0.774 mmol). The mixture was evacuated and filled with nitrogen 3 times, then was diluted with 1,4-dioxane (100 mL) and was heated to 70° C. for 21.5 h. The mixture was cooled to rt, diluted with water (100 mL), and extracted with ethyl acetate (3×100 mL). The organic layers were washed with brine, dried over magnesium sulfate, filtered, and concentrated under reduced pressure. The residue was purified by flash chromatography using a 0-30% ethyl acetate in hexanes gradient and a 300 g silica gel column. The fractions containing the expected product were combined and concentrated under reduced pressure to give 4.26 g of the product as a clear, colorless oil. The sample was divided and one portion (1.0 g) was purified a second time by flash chromatography using a 0-7% acetone in hexanes gradient. The fractions containing the product were combined and concentrated under reduced pressure to give 0.7 g of benzyl 4-(4,4,5,5-tetramethyl-1,3,2-dioxaborolan-2-yl)cyclohex-3-enecarboxylate as a clear, colorless oil. A second portion (2.9 g), was purified by chiral SFC (chiral SFC method 2) to give the two separate enantiomers: enantiomer 1: (R)-benzyl 4-(4,4,5,5-tetramethyl-1,3,2-dioxaborolan-2-yl)cyclohex-3-enecarboxylate: 0.883 g; and enantiomer 2: (S)-benzyl 4-(4,4,5,5-tetramethyl-1,3,2-dioxaborolan-2-yl)cyclohex-3-enecarboxylate: 0.932 g. $^1$H NMR (500 MHz, chloroform-d) δ=7.42-7.32 (m, 5H), 6.59-6.55 (m, 1H), 5.15 (s, 2H), 2.65-2.58 (m, 1H), 2.42-2.37 (m, 2H), 2.34-2.26 (m, 1H), 2.20-2.03 (m, 2H), 1.71-1.59 (m, 1H), 1.28 (s, 12H).

Preparation of benzyl 1-hydroxy-4-(4,4,5,5-tetramethyl-1,3,2-dioxaborolan-2-yl)cyclohex-3-enecarboxylate

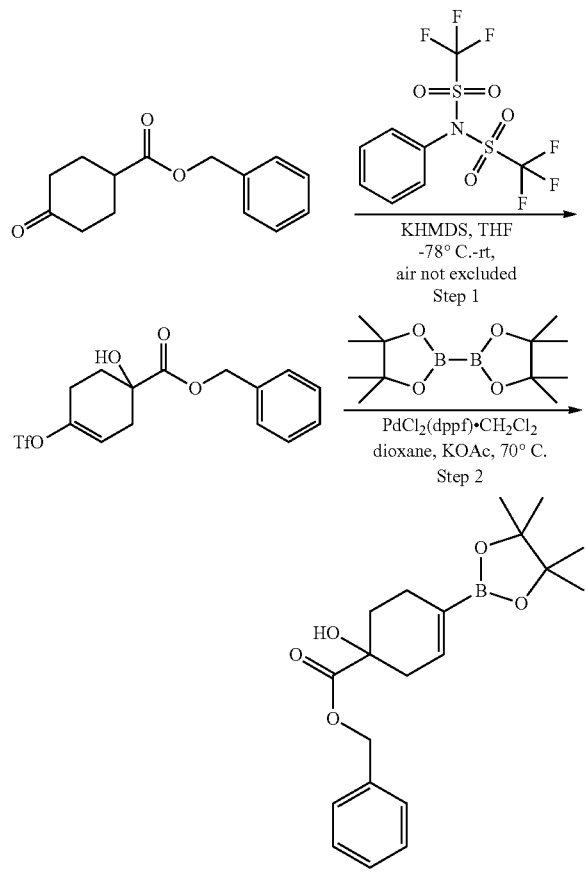

Step 1: Preparation of benzyl 1-hydroxy-4-(((trifluoromethyl)sulfonyl)oxy)cyclohex-3-enecarboxylate A rbf containing a solution of benzyl 4-oxocyclohexanecarboxylate (0.25 g, 1.076 mmol) and 1,1,1-trifluoro-N-phenyl-N-((trifluoromethyl)sulfonyl)methanesulfonamide (0.481 g, 1.345 mmol) in THF (10 mL) was cooled to −78° C. To the solution was added KHMDS (0.5M in toluene) (4.74 mL, 2.368 mmol) (Although the flask was fitted with a septum, no special attention was made to exclude air from the reaction). The mixture was stirred at −78° C. for 1 h then was warmed to rt and was stirred for 1.5 h. TLC still showed a trace of starting material present, so an additional 0.1 g of 1,1,1-trifluoro-N-phenyl-N-((trifluoromethyl)sulfonyl) methanesulfonamide was added and the mixture was further stirred at rt for 1 h then the mixture was diluted with water (30 mL) and was extracted with ethyl acetate (3×30 mL). The organic layers were washed with brine, dried over magnesium sulfate, filtered, and concentrated under reduced pressure. The residue was purified by flash chromatography using a 0-40% ethyl acetate in hexanes gradient and a 25 g silica gel column. The fractions containing the major product were combined and concentrated under reduced pressure to give benzyl 1-hydroxy-4-(((trifluoromethyl)sulfonyl)oxy)cyclohex-3-enecarboxylate (0.101 g, 0.266 mmol, 24.7% yield) as a clear film. $^1$H NMR (500 MHz, chloroform-d) δ=7.43-7.32 (m, 5H), 5.70 (dt, J=5.0, 2.2 Hz, 1H), 5.24 (s, 2H), 3.17 (s, 1H), 2.82-2.75 (m, 1H), 2.72-2.63 (m, 1H), 2.40-2.28 (m, 2H), 2.13 (ddd, J=13.3, 10.9, 6.2 Hz, 1H), 1.96 (ddt, J=13.3, 6.0, 2.6 Hz, 1H).

Step 2. Preparation of benzyl 1-hydroxy-4-(4,4,5,5-tetramethyl-1,3,2-dioxaborolan-2-yl)cyclohex-3-enecarboxylate To a flask containing benzyl 1-hydroxy-4-(((trifluoromethyl)sulfonyl)oxy)cyclohex-3-enecarboxylate (0.1 g, 0.263 mmol) was added bis(pinacolato)diboron (0.070 g, 0.276 mmol), potassium acetate (0.065 g, 0.657 mmol), and 1,1'-bis(diphenylphosphino)ferrocenepalladium(II) dichloride (6.49 mg, 7.89 μmol). The mixture was diluted with 1,4-dioxane (2 mL), flushed with nitrogen, and heated to 70° C. for 16 h. The mixture was cooled to rt, diluted with water (20 mL), and was extracted with ethyl acetate (3×20 mL). The organic layers were washed with brine, dried over magnesium sulfate, filtered, and concentrated under reduced pressure to give crude benzyl 1-hydroxy-4-(4,4,5,5-tetramethyl-1,3,2-dioxaborolan-2-yl)cyclohex-3-enecarboxylate. 113 mg of crude product were carried to the next step with no additional purification. LCMS: m/e 359.3 (M+H)$^+$, 1.79 min (method 1).

Example 11

Preparation of 4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-hydroxycyclohex-3-enecarboxylic acid, TFA

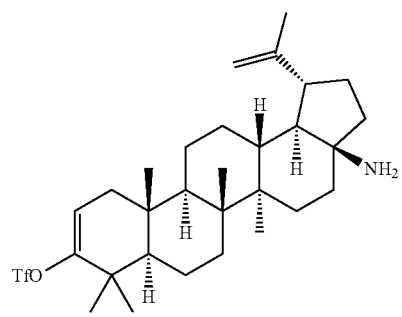

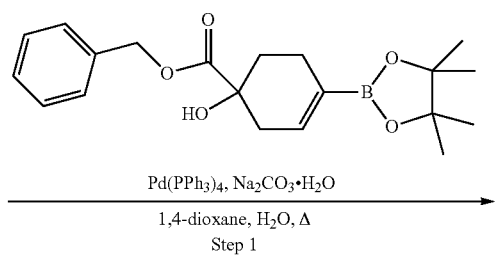

Pd(PPh$_3$)$_4$, Na$_2$CO$_3$•H$_2$O 1,4-dioxane, H$_2$O, Δ

Step 1

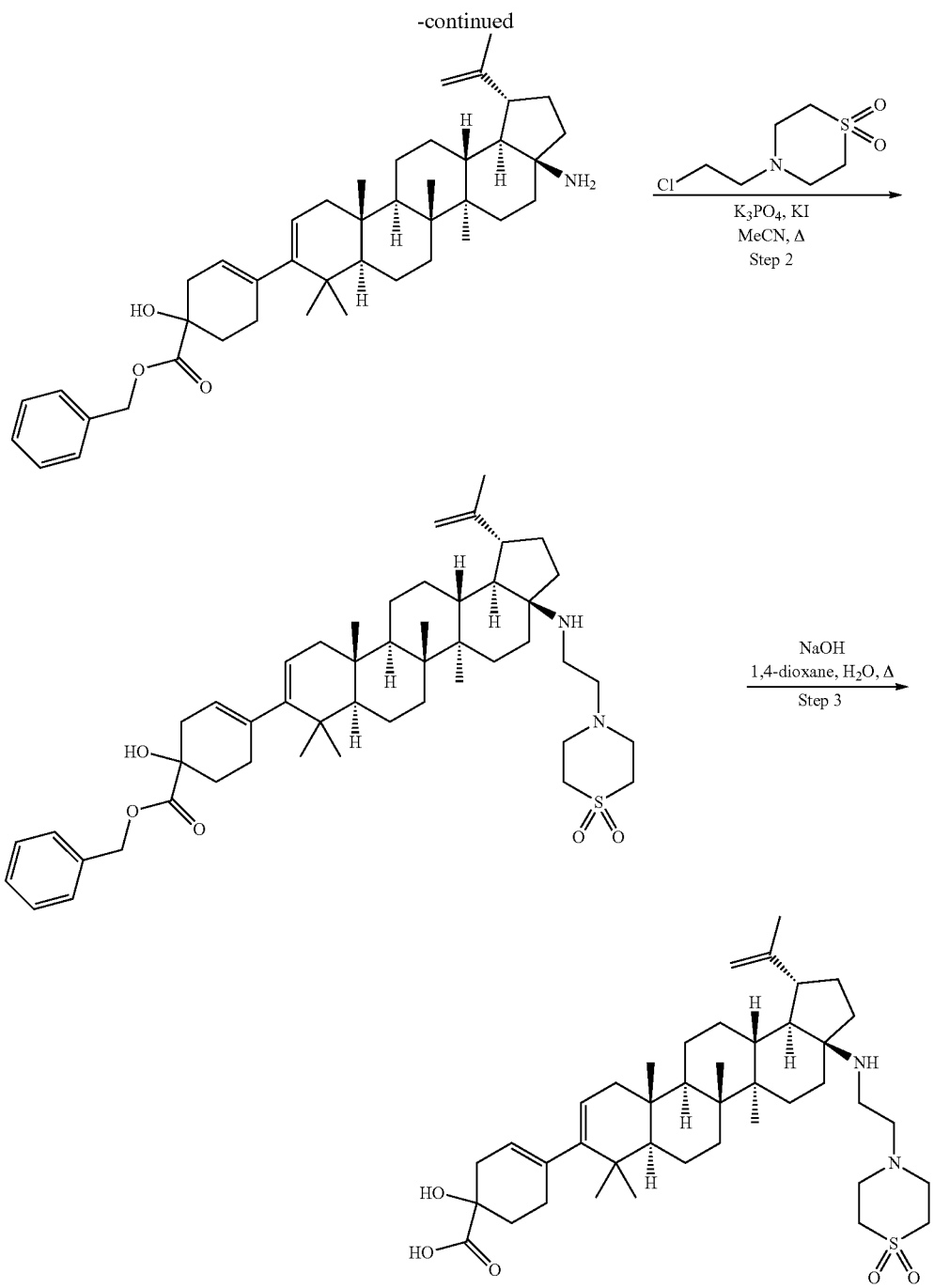

Example 11

Step 1: Preparation of benzyl 4-((1R,3aS,5aR,5bR, 7aR,11aS,11bR,13aR,13bR)-3a-amino-5a,5b,8,8, 11a-pentamethyl-1-(prop-1-en-2-yl)-2,3,3a,4,5,5a, 5b,6,7,7a,8,11,11a,11b,12,13,13a,13b-octadecahydro-1H-cyclopenta[a]chrysen-9-yl)-1-hydroxycyclohex-3-enecarboxylate A flask containing benzyl 1-hydroxy-4-(4,4,5,5-tetramethyl-1,3,2-dioxaborolan-2-yl)cyclohex-3-enecarboxylate (0.113 g, 0.221 mmol) and (1R,3aS,5aR,5bR,7aR,11aR, 11bR,13 aR,13bR)-3a-amino-5a,5b,8,8,11a-pentamethyl-1-(prop-1-en-2-yl)-2,3,3a,4,5,5a,5b,6,7,7a,8,11,11a,11b,12, 13,13a,13b-octadecahydro-1H-cyclopenta[a]chrysen-9-yl trifluoromethanesulfonate (0.082 g, 0.147 mmol) was diluted with 1,4-dioxane (1 mL) and water (0.25 mL). To the mixture was added sodium carbonate hydrate (0.075 g, 0.605 mmol) and the mixture was degassed with nitrogen for five minutes. To the mixture was added palladium tetrakis (5.10 mg, 4.41 mmol) then the flask was purged then refilled with nitrogen three times. The mixture was heated to 85° C. for 4 h then was cooled to rt and was purified by flash chromatography using a 20-80% ethyl acetate in hexanes gradient and a 25 g silica gel column. The fractions containing the expected product were combined and concentrated under reduced pressure to give benzyl 4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-hydroxycyclohex-3-enecarboxylate (0.053 g, 0.083 mmol, 56.3% yield) as an off-white foam. LCMS: m/e 640.6 (M+H)$^+$, 1.91 min (method 1).

Step 2: Preparation of benzyl 4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-hydroxycyclohex-3-enecarboxylate To a sealable vial was added benzyl 4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-hydroxycyclohex-3-enecarboxylate (0.053 g, 0.083 mmol), 4-(2-chloroethyl)thiomorpholine 1,1-dioxide, HCl (0.078 g, 0.331 mmol), potassium iodide (0.041 g, 0.248 mmol) and phosphoric acid, potassium salt (0.088 g, 0.414 mmol). The mixture was diluted with acetonitrile (1.5 mL) and flushed with nitrogen, then was sealed and heated to 100° C. for 15.25 h. The mixture was cooled to rt and was filtered to remove the solids which were washed with dichloromethane. The filtrate was concentrated under reduced pressure and adsorbed to silica gel, then was purified by flash chromatography using a 20-80% ethyl acetate in hexanes gradient and a 12 g silica gel column. The fractions containing the expected product were combined and were concentrated under reduced pressure to give benzyl 4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-hydroxycyclohex-3-enecarboxylate (0.029 g, 0.036 mmol, 43.7% yield) as a clear, colorless film. LCMS: m/e 801.7 (M+H)$^+$, 1.92 min (method 1).

Step 3

To a solution of benzyl 4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-hydroxycyclohex-3-enecarboxylate (28.8 mg, 0.036 mmol) in 1,4-dioxane (2 mL) was added NaOH (1N) (0.2 mL, 0.200 mmol). The mixture was heated to 75° C. for 4.5 h then was cooled to rt. The mixture was diluted with methanol and was purified by prep HPLC. The fractions containing the expected product were combined and concentrated under reduced pressure to give 4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-hydroxycyclohex-3-enecarboxylic acid, TFA (16 mg, 0.018 mmol, 51.2% yield) as a white solid. LCMS: m/e 711.6 (M+H)$^+$, 1.54 min (method 1)$^1$H NMR (500 MHz, acetic acid-d$_4$) δ=5.33 (br. s., 1H), 5.32-5.28 (m, 1H), 4.84 (s, 1H), 4.74 (s, 1H), 3.50 (dt, J=12.8, 3.3 Hz, 1H), 3.36-3.06 (m, 11H), 2.93-2.86 (m, 1H), 2.75-2.69 (m, 1H), 2.52-2.39 (m, 1H), 1.76 (s, 3H), 1.26 (s, 3H), 1.13 (s, 3H), 2.34-0.93 (m, 35H).

General Procedure for C-3 cyclohexene, C-17 amine formation (Examples 12-16)

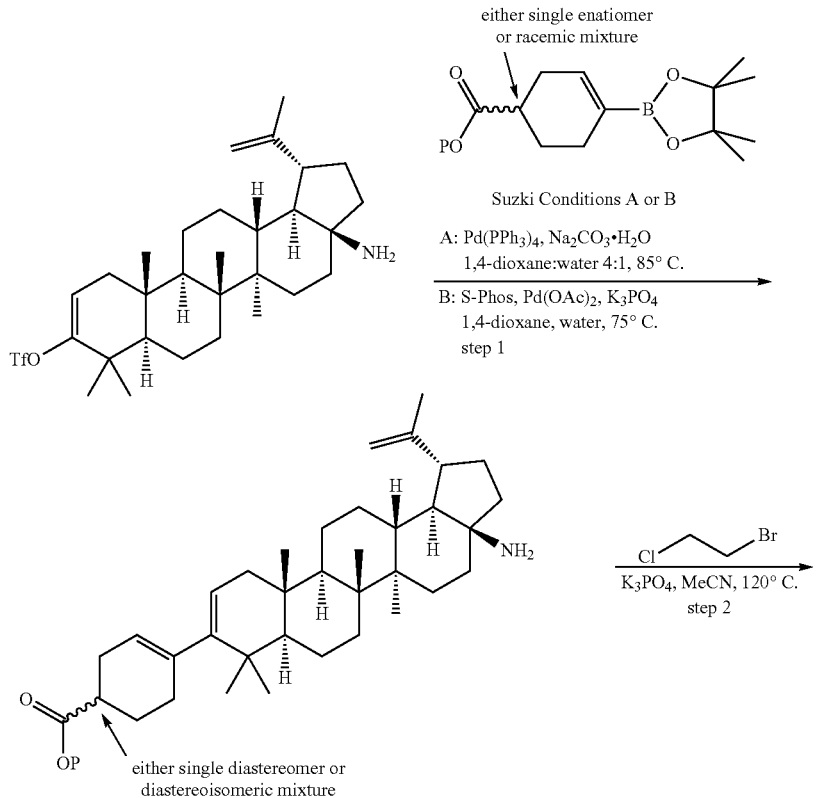

P = Protecting group; methyl, ethyl, benzyl, etc.

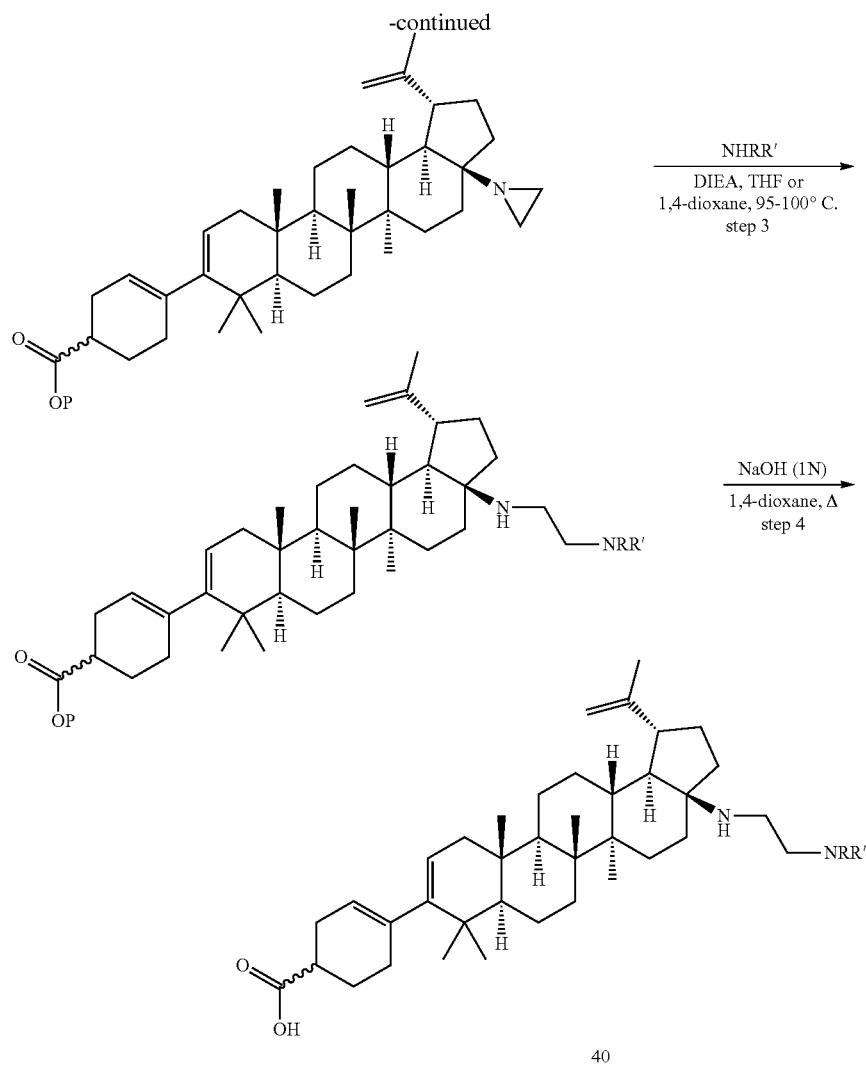
Example 12
Preparation of 4-((1R,3aS,5aR,5bR,7aR,11aS,11bR, 13aR,13bR)-5a,5b,8,8,11a-pentamethyl-3a-((2-(4-(methylsulfonyl)piperazin-1-yl)ethyl)amino)-1-(prop-1-en-2-yl)-2,3,3a,4,5,5a,5b,6,7,7a,8,11,11a, 11b,12,13,13a,13b-octadecahydro-1H-cyclopenta[a] chrysen-9-yl)cyclohex-3-enecarboxylic acid, TFA
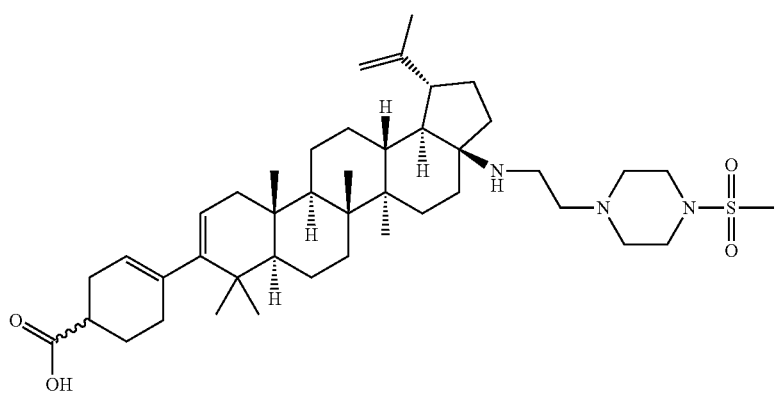

Step 1. Preparation of ethyl 4-((1R,3aS,5aR,5bR, 7aR,11aS,11bR,13aR,13bR)-3a-amino-5a,5b,8,8, 11a-pentamethyl-1-(prop-1-en-2-yl)-2,3,3a,4,5,5a, 5b,6,7,7a,8,11,11a,11b,12,13,13a,13b-octadecahydro-1H-cyclopenta[a]chrysen-9-yl) cyclohex-3-enecarboxylate To a flask containing (1R,3aS,5aR,5bR,7aR,11aR,11bR, 13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a, 13b-octadecahydro-1H-cyclopenta[a]chrysen-9-yl trifluoromethanesulfonate (1.22 g, 2.187 mmol) was added phosphoric acid, potassium salt (1.393 g, 6.56 mmol), ethyl 4-(4,4,5,5-tetramethyl-1,3,2-dioxaborolan-2-yl)cyclohex-3-enecarboxylate (0.613 g, 2.187 mmol), 2-dicyclohexylphosphino-2',6'-dimethoxy-1,1'-biphenyl (S-phos) (0.067 g, 0.164 mmol), and palladium(II)acetate (0.025 g, 0.109 mmol). The mixture was diluted with 1,4-dioxane (10 mL) and water (1 mL), was flushed with nitrogen, then was sealed and heated to 75° C. After 15 h of heating, the mixture was cooled to rt and was concentrated under reduced pressure. The residue was diluted with water (40 mL) and was extracted with ethyl acetate (3×50 mL). The organic layers were washed with brine, dried over magnesium sulfate, filtered, and concentrated under reduced pressure. The residue was purified by flash chromatography using a 10-70% EtOAc in hexanes gradient and an 80 g silica gel column. The fractions containing the expected product were combined and concentrated under reduced pressure to give ethyl 4-((1R,3aS,5aR, 5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8, 11,11a,11b,12,13,13a,13b-octadecahydro-1H-cyclopenta[a] chrysen-9-yl)cyclohex-3-enecarboxylate (806 mg, 1.434 mmol, 65.6% yield) as an off-white solid. LCMS: m/e 562.7 (M+H)$^+$, 2.17 min (method 1).

Step 2. Preparation of ethyl 4-((1R,3aS,5aR,5bR, 7aR,11aS,11bR,13aR,13bR)-3a-(aziridin-1-yl)-5a, 5b,8,8,11a-pentamethyl-1-(prop-1-en-2-yl)-2,3,3a,4, 5,5a,5b,6,7,7a,8,11,11a,11b,12,13,13a,13b-octadecahydro-1H-cyclopenta[a]chrysen-9-yl) cyclohex-3-enecarboxylate To a sealable vial was added ethyl 4-((1R,3aS,5aR,5bR, 7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11, 11a,11b,12,13,13a,13b-octadecahydro-1H-cyclopenta[a] chrysen-9-yl)cyclohex-3-enecarboxylate (0.1 g, 0.178 mmol), 1-bromo-2-chloroethane (0.148 mL, 1.780 mmol) and phosphoric acid, potassium salt (0.189 g, 0.890 mmol). The mixture was diluted with acetonitrile (1.5 mL), was flushed with nitrogen, then was sealed and heated to 120° C. After 17.5 h of heating, the mixture was cooled to rt and some of the solids were removed by filtration. The filtrate was concentrated under reduced pressure to give ethyl 4-((1R, 3aS,5aR,5bR,7aR,11aS,11bR,13aR,13bR)-3a-(aziridin-1-yl)-5a,5b,8,8,11a-pentamethyl-1-(prop-1-en-2-yl)-2,3,3a,4, 5,5a,5b,6,7,7a,8,11,11a,11b,12,13,13a,13b-octadecahydro-1H-cyclopenta[a]chrysen-9-yl)cyclohex-3-enecarboxylate as the crude product which was used in the next step with no additional purification. LCMS: m/e 588.7 (M+H)$^+$, 2.30 min (method 1).

Step 3. Preparation of ethyl 4-((1R,3aS,5aR,5bR, 7aR,11aS,11bR,13aR,13bR)-5a,5b,8,8,11a-pentamethyl-3a-((2-(4-(methylsulfonyl)piperazin-1-yl)ethyl) amino)-1-(prop-1-en-2-yl)-2,3,3a,4,5,5a,5b,6,7,7a,8, 11,11a,11b,12,13,13a,13b-octadecahydro-1H-cyclopenta[a]chrysen-9-yl)cyclohex-3-enecarboxylate To a flask containing the crude ethyl 4-((1R,3aS,5aR,5bR, 7aR,11aS,11bR,13aR,13bR)-3a-(aziridin-1-yl)-5a,5b,8,8, 11a-pentamethyl-1-(prop-1-en-2-yl)-2,3,3a,4,5,5a,5b,6,7, 7a,8,11,11a,11b,12,13,13a,13b-octadecahydro-1H-cyclopenta[a]chrysen-9-yl)cyclohex-3-enecarboxylate (0.094 g, 0.16 mmol), was added 1-Methanesulfonyl-piperazine (0.131 g, 0.800 mmol). The mixture was diluted with 1,4-dioxane (2 mL) and Hunig's base (0.168 mL, 0.960 mmol) was added. The mixture was attached to a reflux condensor and was heated to 100° C. for 24 h then was cooled to rt, concentrated under reduced pressure, and adsorbed to silica gel. The mixture was purified by flash chromatography using a 12 g silica gel column and a 20-80% ethyl acetate in hexanes gradient. The fractions containing the product were combined and concentrated under reduced pressure to give ethyl 4-((1R,3 aS,5aR,5bR,7aR,11aS,11bR,13 aR,13bR)-5a, 5b,8,8,11a-pentamethyl-3a-((2-(4-(methylsulfonyl)piperazin-1-yl)ethyl)amino)-1-(prop-1-en-2-yl)-2,3,3a,4,5,5a,5b, 6,7,7a,8,11,11a,11b,12,13,13a,13b-octadecahydro-1H-cyclopenta[a]chrysen-9-yl)cyclohex-3-enecarboxylate as an off-white solid. LCMS: m/e 752.8 (M+H)$^+$, 2.22 min (method 1).

Step 4

To a solution of ethyl 4-((1R,3aS,5aR,5bR,7aR,11aS, 11bR,13aR,13bR)-5a,5b,8,8,11a-pentamethyl-3a-((2-(4-(methylsulfonyl)piperazin-1-yl)ethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylate (75 mg, 0.100 mmol) in 1,4-dioxane (2 mL) was added sodium hydroxide (1N) (0.499 mL, 0.499 mmol). The mixture was heated to 75° C. for 3 h then was cooled to rt, and was purified by prep HPLC (method 8, retention time: 9.2 minutes). The fractions containing the expected product were combined and were concentrated under reduced pressure to give 4-((1R,3 aS,5aR,5bR,7aR,11aS,11bR,13 aR,13bR)-5a,5b,8,8,11a-pentamethyl-3a-((2-(4-(methylsulfonyl)piperazin-1-yl)ethyl)amino)-1-(prop-1-en-2-yl)-2,3, 3a,4,5,5a,5b,6,7,7a,8,11,11a,11b,12,13,13a,13b-octadecahydro-1H-cyclopenta[a]chrysen-9-yl)cyclohex-3-enecarboxylic acid, TFA (51 mg, 0.061 mmol, 61% yield) as a white solid. LCMS: m/e 724.7 (M+H)$^+$, 1.72 min (method 1). $^1$H NMR (500 MHz, acetic acid-d$_4$) δ=5.38 (br. s., 1H), 5.25-5.21 (m, 1H), 4.83 (s, 1H), 4.72 (s, 1H), 3.69-3.49 (m, 8H), 3.36 (br. s., 4H), 2.92 (s, 3H), 2.87-2.78 (m, 1H), 2.64-2.56 (m, 1H), 1.73 (s, 3H), 1.17 (s, 3H), 1.08 (s, 3H), 2.39-0.84 (m, 37H)

Example 13

Preparation of 4-((1R,3aS,5aR,5bR,7aR,11aS,11bR, 13aR,13bR)-5a,5b,8,8,11a-pentamethyl-3a-((2-(4-(methylsulfonyl)piperidin-1-yl)ethyl)amino)-1-(prop-1-en-2-yl)-2,3,3a,4,5,5a,5b,6,7,7a,8,11,11a, 11b,12,13,13a,13b-octadecahydro-1H-cyclopenta[a] chrysen-9-yl)cyclohex-3-enecarboxylic acid, TFA

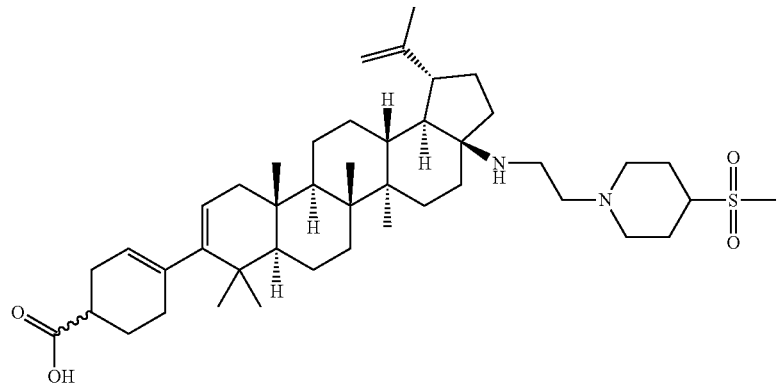

Steps 1 and 2 are the same described above in the preparation of 4-((1R,3 aS,5aR,5bR,7aR,11aS,11bR,13aR,13bR)-5a,5b,8,8,11a-pentamethyl-3a-((2-(4-(methylsulfonyl)piperazin-1-yl)ethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylic acid, TFA.

Step 3: Preparation of ethyl 4-((1R,3aS,5aR,5bR, 7aR,11aS,11bR,13aR,13bR)-5a,5b,8,8,11a-pentamethyl-3a-((2-(4-(methylsulfonyl)piperidin-1-yl)ethyl) amino)-1-(prop-1-en-2-yl)-2,3,3a,4,5,5a,5b,6,7,7a,8, 11,11a,11b,12,13,13a,13b-octadecahydro-1H-cyclopenta[a]chrysen-9-yl)cyclohex-3-enecarboxylate To a flask containing a suspension of the crude ethyl 4-((1R,3 aS,5aR,5bR,7aR,11aS,11bR,13aR,13bR)-3a-(aziridin-1-yl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylate (0.055 g, 0.094 mmol) in 1,4-dioxane (2 mL) was added Hunig's base (0.098 mL, 0.561 mmol) followed by 4-(methylsulfonyl)piperidine (0.076 g, 0.468 mmol). The mixture was heated to 100° C. for 20.5 h then was cooled to rt and was purified by flash chromatography using a 20-80% ethyl acetate in hexanes gradient and a 12 g silica gel column. The fractions containing the expected product were combined and were concentrated under reduced pressure to give ethyl 4-((1R,3aS,5aR,5bR,7aR,11aS,11bR,13aR,13bR)-5a, 5b,8,8,11a-pentamethyl-3a-((2-(4-(methylsulfonyl)piperidin-1-yl)ethyl)amino)-1-(prop-1-en-2-yl)-2,3,3a,4,5,5a,5b, 6,7,7a,8,11,11a,11b,12,13,13a,13b-octadecahydro-1H-cyclopenta[a]chrysen-9-yl)cyclohex-3-enecarboxylate (0.036 g, 0.048 mmol, 51.2% yield) as an off-white solid. LCMS: m/e 751.7 (M+H)$^+$, 2.29 min (method 1).

Step 4

To a solution of ethyl 4-((1R,3aS,5aR,5bR,7aR,11aS, 11bR,13aR,13bR)-5a,5b,8,8,11a-pentamethyl-3a-((2-(4-(methylsulfonyl)piperidin-1-yl)ethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylate (0.036 g, 0.048 mmol) in 1,4-dioxane (2 mL) was added sodium hydroxide (1N) (0.240 mL, 0.240 mmol) and the mixture was heated to 75° C. After 24 h of heating the mixture was cooled to rt and was stirred for an additional 24 h, then was diluted with methanol and dioxane and was purified by prep HPLC (method 9, retention time: 10.96 minutes).

The fractions containing the expected product were combined and concentrated under reduced pressure to give 4-((1R,3aS,5aR,5bR,7aR,11aS,11bR,13aR,13bR)-5a,5b,8, 8,11a-pentamethyl-3a-((2-(4-(methylsulfonyl)piperidin-1-yl)ethyl)amino)-1-(prop-1-en-2-yl)-2,3,3a,4,5,5a,5b,6,7,7a, 8,11,11a,11b,12,13,13a,13b-octadecahydro-1H-cyclopenta [a]chrysen-9-yl)cyclohex-3-enecarboxylic acid, TFA (0.026 g, 0.031 mmol, 65% yield) as a white solid. LCMS: m/e 723.7 (M+H)$^+$, 1.65 min (method 1).

Example 14

Preparation of 4-((1R,3aS,5aR,5bR,7aR,11aS,11bR, 13aR,13bR)-5a,5b,8,8,11a-pentamethyl-3a-((2-morpholinoethyl)amino)-1-(prop-1-en-2-yl)-2,3,3a,4,5, 5a,5b,6,7,7a,8,11,11a,11b,12,13,13a,13b-octadecahydro-1H-cyclopenta[a]chrysen-9-yl) cyclohex-3-enecarboxylic acid, TFA

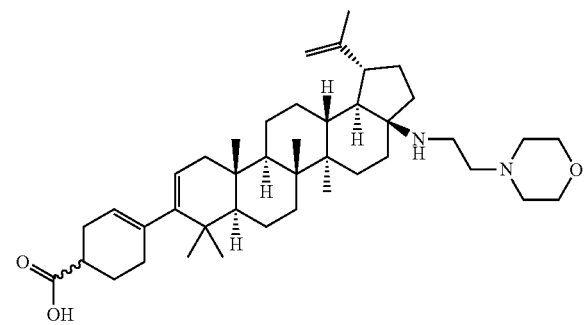

Steps 1 and 2 are the same described above in the preparation of 4-((1R,3 aS,5aR,5bR,7aR,11aS,11bR,13 aR,13bR)-5a,5b,8,8,11a-pentamethyl-3a-((2-(4-(methylsulfonyl)piperazin-1-yl)ethyl)amino)-1-(prop-1-en-2-yl)-2,3,3a,4,5,5a,5b, 6,7,7a,8,11,11a,11b,12,13,13a,13b-octadecahydro-1H-cyclopenta[a]chrysen-9-yl)cyclohex-3-enecarboxylic acid, TFA.

Step 3: Preparation of ethyl 4-((1R,3aS,5aR,5bR, 7aR,11aS,11bR,13aR,13bR)-5a,5b,8,8,11a-pentamethyl-3a-((2-morpholinoethyl)amino)-1-(prop-1-en-2-yl)-2,3,3a,4,5,5a,5b,6,7,7a,8,11,11a,11b,12,13,13a, 13b-octadecahydro-1H-cyclopenta[a]chrysen-9-yl) cyclohex-3-enecarboxylate To a flask containing a suspension of ethyl 4-((1R,3aS,5aR, 5bR,7aR,11aS,11bR,13aR,13bR)-3a-(aziridin-1-yl)-5a,5b, 8,8,11a-pentamethyl-1-(prop-1-en-2-yl)-2,3,3a,4,5,5a,5b,6, 7,7a,8,11,11a,11b,12,13,13a,13b-octadecahydro-1H-cyclopenta[a]chrysen-9-yl)cyclohex-3-enecarboxylate (0.202 g, 0.344 mmol) in 1,4-dioxane (3 mL) was added Hunig's base (0.421 mL, 2.408 mmol) followed by morpholine (0.150 mL, 1.720 mmol). The mixture was heated to 100° C. for 15.5 h then was cooled to rt. The mixture was directly purified by flash chromatography using a 0-40% ethyl acetate in hexanes gradient and a 25 g silica gel column. The fractions containing the expected product were combined and were concentrated under reduced pressure to give ethyl 4-((1R, 3aS,5aR,5bR,7aR,11aS,11bR,13aR,13bR)-5a,5b,8,8,11a-pentamethyl-3a-((2-morpholinoethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylate (0.148 g, 0.219 mmol, 63.7% yield) as a white foam. LCMS: m/e 675.8 (M+H)$^+$, 2.06 min (method 1).

Step 4

To a solution of ethyl 4-((1R,3aS,5aR,5bR,7aR,11aS, 11bR,13aR,13bR)-5a,5b,8,8,11a-pentamethyl-3a-((2-morpholinoethyl)amino)-1-(prop-1-en-2-yl)-2,3,3a,4,5,5a,5b,6, 7,7a,8,11,11a,11b,12,13,13a,13b-octadecahydro-1H-cyclopenta[a]chrysen-9-yl)cyclohex-3-enecarboxylate (0.02 g, 0.030 mmol) in 1,4-dioxane (1 mL) was added sodium hydroxide (1N) (0.148 mL, 0.148 mmol) and the mixture was heated to 75° C. After heating the mixture for 17.5 h, it was cooled to rt and was purified by prep HPLC (method 8, retention time: 8.6 minutes). The fractions containing the expected product were combined and concentrated under reduced pressure to give 4-((1R,3aS,5aR,5bR,7aR,11aS, 11bR,13aR,13bR)-5a,5b,8,8,11a-pentamethyl-3a-((2-morpholinoethyl)amino)-1-(prop-1-en-2-yl)-2,3,3a,4,5,5a,5b,6, 7,7a,8,11,11a,11b,12,13,13a,13b-octadecahydro-1H-cyclopenta[a]chrysen-9-yl)cyclohex-3-enecarboxylic acid, TFA (19 mg, 0.025 mmol, 83% yield) as a white solid. LCMS: m/e 647.7 (M+H)$^+$, 1.69 min (method 1). $^1$H NMR (500 MHz, acetic acid-d$_4$) δ=5.41 (br. s., 1H), 5.28-5.23 (m, 1H), 4.85 (s, 1H), 4.74 (s, 1H), 3.97 (br. s., 4H), 3.80-3.67 (m, 4H), 3.41 (br. s., 4H), 2.87-2.77 (m, 1H), 2.66-2.59 (m, 1H), 1.76 (s, 3H), 1.16 (s, 3H), 1.10 (s, 3H), 1.06-0.93 (m, 9H), 2.44-0.74 (m, 28H).

Example 15

Preparation of (R)-4-((1R,3aS,5aR,5bR,7aR,11aS, 11bR,13aR,13bR)-5a,5b,8,8,11a-pentamethyl-3a-((2-(4-(methylsulfonyl)piperidin-1-yl)ethyl)amino)-1-(prop-1-en-2-yl)-2,3,3a,4,5,5a,5b,6,7,7a,8,11,11a, 11b,12,13,13a,13b-octadecahydro-1H-cyclopenta[a]chrysen-9-yl)cyclohex-3-enecarboxylic acid, TFA

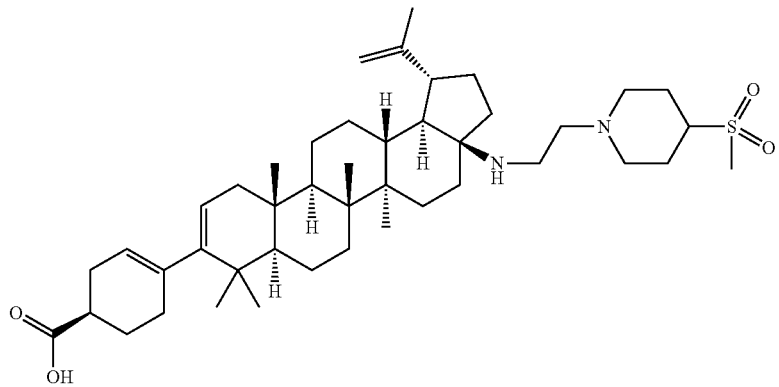

Step 1. Preparation of (R)-benzyl 4-((1R,3aS,5aR, 5bR,7aR,11aS,11bR,13aR,13bR)-3a-amino-5a,5b,8, 8,11a-pentamethyl-1-(prop-1-en-2-yl)-2,3,3a,4,5,5a, 5b,6,7,7a,8,11,11a,11b,12,13,13a,13b-octadecahydro-1H-cyclopenta[a]chrysen-9-yl) cyclohex-3-enecarboxylate To a vial containing (1R,3aS,5aR,5bR,7aR,11aR,11bR, 13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a, 13b-octadecahydro-1H-cyclopenta[a]chrysen-9-yl trifluoromethanesulfonate (0.65 g, 1.165 mmol) was added phosphoric acid, potassium salt (0.742 g, 3.50 mmol), (R)-benzyl 4-(4,4,5,5-tetramethyl-1,3,2-dioxaborolan-2-yl)cyclohex-3-enecarboxylate (0.8 g, 2.338 mmol) (enantiomer 1 prepared above), 2-dicyclohexylphosphino-2',6'-dimethoxy-1,1'-biphenyl (S-phos) (0.072 g, 0.175 mmol) and palladium (II) acetate (0.026 g, 0.117 mmol). The mixture was diluted with 1,4-dioxane (10 mL) and water (1 mL), flushed with nitrogen, then the vial was sealed and heated to 75° C. After 6 h of heating, the mixture was cooled to rt, diluted with water (20 mL) and brine (20 mL), and was extracted with dichloromethane (5×40 mL). The organic layers were dried with sodium sulfate, filtered, and concentrated under reduced pressure. The residue was purified by flash chromatography using a 10-60% ethyl acetate in hexanes gradient and a 40 g silica gel column. The fractions containing the expected product were combined and were concentrated under reduced pressure to give (R)-benzyl 4-((1R,3 aS,5aR,5bR,7aR,11aS, 11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12, 13,13a,13b-octadecahydro-1H-cyclopenta[a]chrysen-9-yl) cyclohex-3-enecarboxylate (0.488 g, 0.782 mmol, 67.1% yield) as an off-white solid. LCMS: m/e 624.65 (M+H)$^+$, 2.18 min (method 1). $^1$H NMR (500 MHz, chloroform-d) δ=7.40-

7.30 (m, 5H), 5.35 (br. s., 1H), 5.18 (dd, J=6.2, 1.8 Hz, 1H), 5.14 (s, 2H), 4.73 (d, J=2.0 Hz, 1H), 4.60 (s, 1H), 2.65-2.50 (m, 2H), 2.38-2.30 (m, 2H), 2.25-1.94 (m, 5H), 1.70 (s, 3H), 1.07 (s, 3H), 0.96 (s, 3H), 0.94 (s, 3H), 0.92 (s, 3H), 0.86 (s, 3H), 1.80-0.83 (m, 23H).

Step 2. Preparation of (R)-benzyl 4-((1R,3aS,5aR, 5bR,7aR,11aS,11bR,13aR,13bR)-3a-(aziridin-1-yl)-5a,5b,8,8,11a-pentamethyl-1-(prop-1-en-2-yl)-2,3, 3a,4,5,5a,5b,6,7,7a,8,11,11a,11b,12,13,13a,13b-octadecahydro-1H-cyclopenta[a]chrysen-9-yl) cyclohex-3-enecarboxylate To a sealable vial was added (R)-benzyl 4-((1R,3 aS,5aR, 5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8, 11,11a,11b,12,13,13a,13b-octadecahydro-1H-cyclopenta[a]chrysen-9-yl)cyclohex-3-enecarboxylate (0.075 g, 0.120 mmol), 1-bromo-2-chloroethane (0.100 mL, 1.202 mmol), and phosphoric acid, potassium salt (0.128 g, 0.601 mmol). The mixture was diluted with acetonitrile (1.5 mL), flushed with nitrogen, then the vial was sealed and heated to 120° C. After 24 h of heating, the mixture was cooled to rt and was filtered to remove solids. The solids were washed with dichloromethane and the filtrate was concentrated under reduced pressure to give (R)-benzyl 4-((1R,3aS,5aR,5bR,7aR,11aS, 11bR,13aR,13bR)-3a-(aziridin-1-yl)-5a,5b,8,8,11a-pentamethyl-1-(prop-1-en-2-yl)-2,3,3a,4,5,5a,5b,6,7,7a,8,11,11a, 11b,12,13,13a,13b-octadecahydro-1H-cyclopenta[a]chrysen-9-yl)cyclohex-3-enecarboxylate as an off-white solid that was used in the next step with no additional purification. LCMS: m/e 650.7 (M+H)$^+$, 2.22 min (method 1).

Step 3. Preparation of (R)-benzyl 4-((1R,3aS,5aR, 5bR,7aR,11aS,11bR,13aR,13bR)-5a,5b,8,8,11a-pentamethyl-3a-((2-(4-(methylsulfonyl)piperidin-1-yl)ethyl)amino)-1-(prop-1-en-2-yl)-2,3,3a,4,5,5a,5b, 6,7,7a,8,11,11a,11b,12,13,13a,13b-octadecahydro-1H-cyclopenta[a]chrysen-9-yl)cyclohex-3-enecarboxylate, TFA To a Flask containing a suspension of (R)-benzyl 4-((1R,3 aS,5aR,5bR,7aR,11aS,11bR,13 aR,13bR)-3a-(aziridin-1-yl)-5a,5b,8,8,11a-pentamethyl-1-(prop-1-en-2-yl)-2,3,3a,4, 5,5a,5b,6,7,7a,8,11,11a,11b,12,13,13a,13b-octadecahydro-1H-cyclopenta[a]chrysen-9-yl)cyclohex-3-enecarboxylate (78 mg, 0.12 mmol) in 1,4-dioxane (2 mL) was added Hunig's base (0.126 mL, 0.720 mmol) and 4-(methylsulfonyl)piperidine (98 mg, 0.600 mmol). The flask was heated to 100° C. with a reflux condensor attached for 23 h, then was cooled to rt, diluted with water (10 mL) and extracted with dichloromethane (3×10 mL). The organic layers were dried with sodium sulfate, filtered, and concentrated under reduced pressure. The residue was purified by prep HPLC (method 10). The fractions containing the expected product were combined and were concentrated under a stream of nitrogen to give (R)-benzyl 4-((1R,3aS,5aR,5bR,7aR,11aS,11bR,13aR, 13bR)-5a,5b,8,8,11a-pentamethyl-3a-((2-(4-(methylsulfonyl)piperidin-1-yl)ethyl)amino)-1-(prop-1-en-2-yl)-2,3,3a, 4,5,5a,5b,6,7,7a,8,11,11a,11b,12,13,13a,13b-octadecahydro-1H-cyclopenta[a]chrysen-9-yl)cyclohex-3-enecarboxylate, TFA (44.5 mg, 0.048 mmol, 40.0% yield) as a white foam. LCMS: m/e 813.75 (M+H)$^+$, 2.09 min (method 1). $^1$H NMR (500 MHz, chloroform-d) δ=7.39-7.30 (m, 5H), 5.35 (br. s., 1H), 5.17 (d, J=4.6 Hz, 1H), 5.14 (s, 2H), 4.78 (s, 1H), 4.70 (s, 1H), 3.45-3.21 (m, 5H), 3.19-3.09 (m, 1H), 3.07-2.98 (m, 1H), 2.90 (s, 3H), 2.81-2.54 (m, 4H), 1.69 (s, 3H), 1.11 (s, 3H), 1.02 (s, 3H), 0.93 (s, 3H), 0.93 (s, 3H), 0.87 (s, 3H), 2.40-0.82 (m, 32H).

Step 4

To a solution of (R)-benzyl 4-((1R,3aS,5aR,5bR,7aR, 11aS,11bR,13aR,13bR)-5a,5b,8,8,11a-pentamethyl-3a-((2-(4-(methylsulfonyl)piperidin-1-yl)ethyl)amino)-1-(prop-1-en-2-yl)-2,3,3a,4,5,5a,5b,6,7,7a,8,11,11a,11b,12,13,13a, 13b-octadecahydro-1H-cyclopenta[a]chrysen-9-yl) cyclohex-3-enecarboxylate (0.04 g, 0.049 mmol) in 1,4-dioxane (2 mL) was added sodium hydroxide (1N) (0.246 mL, 0.246 mmol). The mixture was heated to 60° C. for 5 h, then was cooled to rt. The mixture was diluted with methanol and dioxane and was purified by prep HPLC (method 11, retention time: 8.89 minutes). The fractions containing the expected product were combined and concentrated under reduced pressure to give (R)-4-((1R,3aS,5aR,5bR,7aR,11aS, 11bR,13aR,13bR)-5a,5b,8,8,11a-pentamethyl-3a-((2-(4-(methylsulfonyl)piperidin-1-yl)ethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylic acid, TFA (27 mg, 0.032 mmol, 65% yield) as a white solid. LCMS: m/e 723.8 (M+H)$^+$, 2.02 min (method 1). $^1$H NMR (500 MHz, acetic acid-d$_4$) δ=5.41 (br. s., 1H), 5.26 (d, J=4.6 Hz, 1H), 4.86 (s, 1H), 4.75 (s, 1H), 3.87-3.68 (m, 6H), 3.47-3.39 (m, 1H), 3.23 (q, J=9.8 Hz, 2H), 3.02 (s, 3H), 2.86-2.78 (m, 1H), 2.67-2.59 (m, 1H), 1.76 (s, 3H), 1.16 (s, 3H), 1.10 (s, 3H), 1.02 (s, 3H), 1.01 (s, 3H), 0.96 (s, 3H), 2.49-0.87 (m, 32H). The structure of this compound was confirmed by X-Ray crystallography.

Example 16

Preparation of (S)-4-((1R,3aS,5aR,5bR,7aR,11aS, 11bR,13aR,13bR)-5a,5b,8,8,11a-pentamethyl-3a-((2-(4-(methylsulfonyl)piperidin-1-yl)ethyl)amino)-1-(prop-1-en-2-yl)-2,3,3a,4,5,5a,5b,6,7,7a,8,11,11a, 11b,12,13,13a,13b-octadecahydro-1H-cyclopenta[a] chrysen-9-yl)cyclohex-3-enecarboxylic acid, TFA

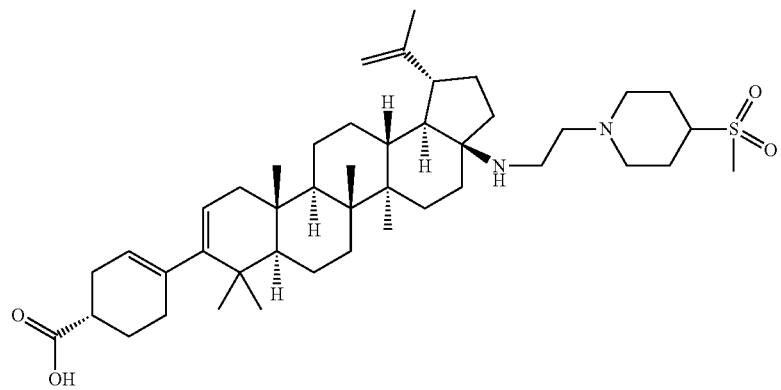

Step 1. Preparation of (S)-benzyl 4-((1R,3aS,5aR, 5bR,7aR,11aS,11bR,13aR,13bR)-3a-amino-5a,5b,8, 8,11a-pentamethyl-1-(prop-1-en-2-yl)-2,3,3a,4,5,5a, 5b,6,7,7a,8,11,11a,11b,12,13,13a,13b-octadecahydro-1H-cyclopenta[a]chrysen-9-yl) cyclohex-3-enecarboxylate To a vial containing (1R,3aS,5aR,5bR,7aR,11aR,11bR, 13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a, 13b-octadecahydro-1H-cyclopenta[a]chrysen-9-yl trifluoromethanesulfonate (0.05 g, 0.090 mmol) was added phosphoric acid, potassium salt (0.057 g, 0.269 mmol), (S)-benzyl 4-(4,4,5,5-tetramethyl-1,3,2-dioxaborolan-2-yl)cyclohex-3-enecarboxylate (0.062 g, 0.181 mmol) (enantiomer 2 prepared above), 2-dicyclohexylphosphino-2',6'-dimethoxy-1,1'-biphenyl (S-phos) (5.52 mg, 0.013 mmol), and palladium(II) acetate (2.013 mg, 8.96 mmol). The mixture was diluted with 1,4-dioxane (1 mL) and water (0.1 mL), was flushed with nitrogen, then was sealed and heated to 75° C. After 6 h of heating, the mixture was cooled to rt, was diluted with dichloromethane, and was dried with sodium sulfate. The drying agent was removed by filtration and the filtrate was concentrated under reduced pressure. The residue was purified by flash chromatography using a 10-60% ethyl acetate in hexanes gradient and a 12 g silica gel column. The fractions containing the expected product were combined and concentrated under reduced pressure to give (S)-benzyl 4-((1R,3 aS,5aR,5bR,7aR,11aS,11bR,13aR,13bR)-3a-amino-5a,5b,8,8,11a-pentamethyl-1-(prop-1-en-2-yl)-2,3, 3a,4,5,5a,5b,6,7,7a,8,11,11a,11b,12,13,13a,13b-octadecahydro-1H-cyclopenta[a]chrysen-9-yl)cyclohex-3-enecarboxylate (0.042 g, 0.067 mmol, 75% yield) as an off-white solid. $^1$H NMR (500 MHz, chloroform-d) δ=7.42-7.31 (m, 5H), 5.37 (br. s., 1H), 5.21-5.17 (m, 1H), 5.16 (s, 2H), 4.75 (d, J=1.9 Hz, 1H), 4.62 (s, 1H), 2.65-2.52 (m, 2H), 2.39-2.32 (m, 2H), 2.22-2.15 (m, 2H), 2.10-1.96 (m, 3H), 1.71 (s, 3H), 1.09 (s, 3H), 0.98 (s, 6H), 0.91 (s, 3H), 0.88 (s, 3H), 1.82-0.83 (m, 23H).

Step 2. Preparation of (S)-benzyl 4-((1R,3aS,5aR, 5bR,7aR,11aS,11bR,13aR,13bR)-3a-(aziridin-1-yl)-5a,5b,8,8,11a-pentamethyl-1-(prop-1-en-2-yl)-2,3, 3a,4,5,5a,5b,6,7,7a,8,11,11a,11b,12,13,13a,13b-octadecahydro-1H-cyclopenta[a]chrysen-9-yl) cyclohex-3-enecarboxylate To a sealable vial was added (S)-benzyl 4-((1R,3 aS,5aR, 5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8, 11,11a,11b,12,13,13a,13b-octadecahydro-1H-cyclopenta[a]chrysen-9-yl)cyclohex-3-enecarboxylate (0.042 g, 0.067 mmol), 1-bromo-2-chloroethane (0.056 ml, 0.673 mmol) and phosphoric acid, potassium salt (0.071 g, 0.337 mmol). The mixture was diluted with acetonitrile (1 mL), was flushed with nitrogen, then was sealed and heated to 120° C. After 23 h of heating, the mixture was cooled to rt and the reaction mixture was filtered to remove solids. The solids were washed with dichloromethane and the filtrate was concentrated under reduced pressure to give (S)-benzyl 4-((1R,3aS,5aR,5bR, 7aR,11aS,11bR,13aR,13bR)-3a-(aziridin-1-yl)-5a,5b,8,8, 11a-pentamethyl-1-(prop-1-en-2-yl)-2,3,3a,4,5,5a,5b,6,7, 7a,8,11,11a,11b,12,13,13a,13b-octadecahydro-1H-cyclopenta[a]chrysen-9-yl)cyclohex-3-enecarboxylate as an off-white solid. The crude product was used in the next step with no additional purification. LCMS: m/e 650.8 (M+H)$^+$, 2.26 min (method 1).

Step 3. Preparation of (S)-benzyl 4-((1R,3aS,5aR, 5bR,7aR,11aS,11bR,13aR,13bR)-5a,5b,8,8,11a-pentamethyl-3a-((2-(4-(methylsulfonyl)piperidin-1-yl)ethyl)amino)-1-(prop-1-en-2-yl)-2,3,3a,4,5,5a,5b, 6,7,7a,8,11,11a,11b,12,13,13a,13b-octadecahydro-1H-cyclopenta[a]chrysen-9-yl)cyclohex-3-enecarboxylate To a flask containing a suspension of (S)-benzyl 4-((1R,3 aS,5aR,5bR,7aR,11aS,11bR,13aR,13bR)-3a-(aziridin-1-yl)-5a,5b,8,8,11a-pentamethyl-1-(prop-1-en-2-yl)-2,3,3a,4, 5,5a,5b,6,7,7a,8,11,11a,11b,12,13,13a,13b-octadecahydro-1H-cyclopenta[a]chrysen-9-yl)cyclohex-3-enecarboxylate (0.044 g, 0.067 mmol) in 1,4-dioxane (2 mL) was added Hunig's base (0.070 mL, 0.402 mmol) followed by 4-(methylsulfonyl)piperidine, HCl (0.067 g, 0.335 mmol). The flask attached to a reflux condenser and was heated to 95° C. for 15 h, then was cooled to rt. The crude mixture was adsorbed to silica gel and was purified by flash chromatography using a 10-75% ethyl acetate in hexanes gradient and a 12 g silica gel column. The fractions containing the expected product were combined and concentrated under reduced pressure to give (S)-benzyl 4-((1R,3aS,5aR,5bR,7aR,11aS,11bR,13aR, 13bR)-5a,5b,8,8,11a-pentamethyl-3a-((2-(4-(methylsulfonyl)piperidin-1-yl)ethyl)amino)-1-(prop-1-en-2-yl)-2,3,3a, 4,5,5a,5b,6,7,7a,8,11,11a,11b,12,13,13a,13b-octadecahydro-1H-cyclopenta[a]chrysen-9-yl)cyclohex-3-enecarboxylate (0.033 g, 0.041 mmol, 60.6% yield) as a clear, colorless film. LCMS: m/e 813.8 (M+H)$^+$, 2.17 min (method 1). $^1$H NMR (500 MHz, chloroform-d) δ=7.40-7.29 (m, 5H), 5.37-5.33 (m, 1H), 5.16 (dd, J=6.1, 1.7 Hz, 1H), 5.14 (s, 2H), 4.71 (d, J=1.7 Hz, 1H), 4.59 (s, 1H), 3.17-3.06 (m, 2H), 2.83 (s, 3H), 2.86-2.78 (m, 1H), 2.65-2.53 (m, 4H), 2.49-2.42 (m, 2H), 2.38-2.30 (m, 2H), 2.19-2.12 (m, 4H), 1.69 (s, 3H), 1.08 (s, 3H), 0.96 (s, 6H), 0.89 (s, 3H), 0.85 (s, 3H), 2.12-0.82 (m, 29H).

Step 4

To a solution of (S)-benzyl 4-((1R,3aS,5aR,5bR,7aR, 11aS,11bR,13aR,13bR)-5a,5b,8,8,11a-pentamethyl-3a-((2-(4-(methylsulfonyl)piperidin-1-yl)ethyl)amino)-1-(prop-1-en-2-yl)-2,3,3a,4,5,5a,5b,6,7,7a,8,11,11a,11b,12,13,13a, 13b-octadecahydro-1H-cyclopenta[a]chrysen-9-yl) cyclohex-3-enecarboxylate (0.033 g, 0.041 mmol) in 1,4-dioxane (2 mL) was added sodium hydroxide (1N) (0.203 mL, 0.203 mmol). The mixture was heated to 60° C. for 4 h then was cooled to rt. The mixture was diluted with methanol, was filtered through a plug of glass wool and was purified by prep HPLC (method 8, retention time: 8.44 minutes). The fractions containing the expected product were combined and concentrated under reduced pressure to give (S)-4-((1R,3 aS,5aR,5bR,7aR,11aS,11bR,13 aR,13bR)-5a,5b,8,8,11a-pentamethyl-3a-((2-(4-(methylsulfonyl)piperidin-1-yl) ethyl)amino)-1-(prop-1-en-2-yl)-2,3,3a,4,5,5a,5b,6,7,7a,8, 11,11a,11b,12,13,13a,13b-octadecahydro-1H-cyclopenta[a] chrysen-9-yl)cyclohex-3-enecarboxylic acid, TFA (21.0 mg, 0.025 mmol, 61% yield) as a white solid. LCMS: m/e 723.6 (M+H)$^+$, 1.57 min (method 1). $^1$H NMR (500 MHz, acetic acid-d$_4$) δ=5.41 (br. s., 1H), 5.25 (d, J=4.7 Hz, 1H), 4.86 (s, 1H), 4.75 (s, 1H), 3.83-3.67 (m, 6H), 3.44-3.37 (m, 1H), 3.22-3.12 (m, 2H), 3.02 (s, 3H), 2.87-2.78 (m, 1H), 2.66-2.59

(m, 1H), 2.44-2.32 (m, 3H), 1.76 (s, 3H), 1.17 (s, 3H), 1.10 (s, 3H), 1.04 (s, 3H), 0.98 (s, 3H), 0.96 (s, 3H), 2.28-0.90 (m, 29H).

Example 17

Preparation of 4-((1R,3aS,5aR,5bR,7aR,11aS,11bR, 13aR,13bR)-3a-amino-5a,5b,8,8,11a-pentamethyl-1-(prop-1-en-2-yl)-2,3,3a,4,5,5a,5b,6,7,7a,8,11,11a, 11b,12,13,13a,13b-octadecahydro-1H-cyclopenta[a] chrysen-9-yl)cyclohex-3-enecarboxylic acid, HCl (prop-1-en-2-yl)-2,3,3a,4,5,5a,5b,6,7,7a,8,11,11a,11b,12, 13,13a,13b-octadecahydro-1H-cyclopenta[a]chrysen-9-yl trifluoromethanesulfonate (0.25 g, 0.448 mmol) was added ethyl 4-(4,4,5,5-tetramethyl-1,3,2-dioxaborolan-2-yl)cyclohex-3-enecarboxylate (0.138 g, 0.493 mmol), sodium carbonate hydrate (0.167 g, 1.345 mmol), and palladium tetrakis (0.016 g, 0.013 mmol). The mixture was diluted with 1,4-dioxane (4 mL) and water (1 mL) then was flushed with nitrogen and was sealed and heated to 85° C. in an oil bath. After 5 h of heating, the mixture was cooled to rt, diluted with water (20 mL), and extracted with ethyl acetate (3×20 mL). The organic layers were washed with brine, dried over mag-

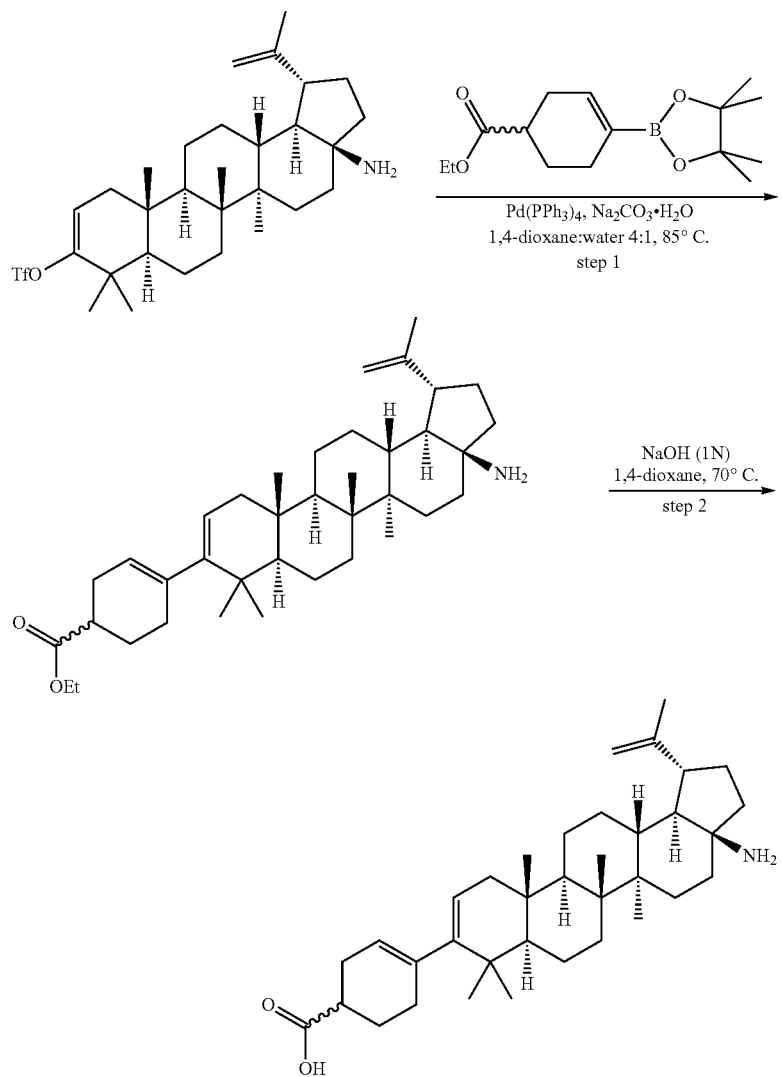

Example 17

Step 1: Preparation of ethyl 4-((1R,3aS,5aR,5bR, 7aR,11aS,11bR,13aR,13bR)-3a-amino-5a,5b,8,8, 11a-pentamethyl-1-(prop-1-en-2-yl)-2,3,3a,4,5,5a, 5b,6,7,7a,8,11,11a,11b,12,13,13a,13b-octadecahydro-1H-cyclopenta[a]chrysen-9-yl) cyclohex-3-enecarboxylate To a sealable vial containing (1R,3aS,5aR,5bR,7aR,11aR, 11bR,13aR,13bR)-3a-amino-5a,5b,8,8,11a-pentamethyl-1- nesium sulfate, filtered, and concentrated under reduced pressure. The residue was purified by flash chromatography using a 6-50% ethyl acetate in hexanes gradient and 40 g silica gel column. The fractions containing the expected product were combined and concentrated under reduced pressure to give ethyl 4-((1R,3 aS,5aR,5bR,7aR,11aS,11bR,13aR,13bR)-3a-amino-5a,5b,8,8,11a-pentamethyl-1-(prop-1-en-2-yl)-2,3, 3a,4,5,5a,5b,6,7,7a,8,11,11a,11b,12,13,13a,13b-octadecahydro-1H-cyclopenta[a]chrysen-9-yl)cyclohex-3- enecarboxylate (0.119 g, 0.212 mmol, 47.3% yield) as an off-white solid. LCMS: m/e 562.6 (M+H)$^+$, 2.13 min (method 1). $^1$H NMR (500 MHz, chloroform-d) δ=5.35 (br. s., 1H), 5.19 (d, J=6.1 Hz, 1H), 4.73 (d, J=1.9 Hz, 1H), 4.60 (s, 1H), 4.15 (q, J=7.1 Hz, 2H), 2.58-2.47 (m, 2H), 2.33-2.27 (m, 2H), 2.23-1.94 (m, 6H), 1.70 (s, 3H), 1.27 (t, 3H), 1.07 (s, 3H), 1.79-0.82 (m, 34H).

Step 2

To a suspension of ethyl 4-((1R,3aS,5aR,5bR,7aR,11aS, 11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12, 13,13a,13b-octadecahydro-1H-cyclopenta[a]chrysen-9-yl) cyclohex-3-enecarboxylate (0.02 g, 0.036 mmol) in 1,4-dioxane (1 mL) was added sodium hydroxide (1N) (0.2 mL, 0.200 mmol) and the mixture was heated to 70° C. After heating the mixture for 15.5 h, it was cooled to rt. The mixture was diluted with methanol and solids were apparent. 2 mL of 1N HCl were added and the solids that formed were collected by filtration and washed with water. The expected product, 4-((1R,3aS,5aR,5bR,7aR,11aS,11bR,13aR,13bR)-3a-amino-5a,5b,8,8,11a-pentamethyl-1-(prop-1-en-2-yl)-2,3, 3a,4,5,5a,5b,6,7,7a,8,11,11a,11b,12,13,13a,13b-octa-decahydro-1H-cyclopenta[a]chrysen-9-yl)cyclohex-3-enecarboxylic acid, HCl (0.02 g, 0.033 mmol, 94% yield), was isolated as an off-white solid. LCMS: m/e 534.6 (M+H)$^+$, 1.74 min (method 1). $^1$H NMR (500 MHz, Acetic acid-d$_4$) δ=5.41 (br. s., 1H), 5.27-5.24 (m, 1H), 4.88 (s, 1H), 4.74 (s, 1H), 2.88-2.79 (m, 1H), 2.67-2.59 (m, 1H), 1.77 (s, 3H), 1.18 (s, 3H), 1.08 (s, 3H), 2.43-0.92 (m, 37H).

Example 18

Preparation of 4-((1R,3aS,5aR,5bR,7aR,11aS,11bR, 13aR,13bR)-3a-((2-hydroxyethyl)amino)-5a,5b,8,8, 11a-pentamethyl-1-(prop-1-en-2-yl)-2,3,3a,4,5,5a, 5b,6,7,7a,8,11,11a,11b,12,13,13a,13b-octadecahydro-1H-cyclopenta[a]chrysen-9-yl) cyclohex-3-enecarboxylic acid, TFA

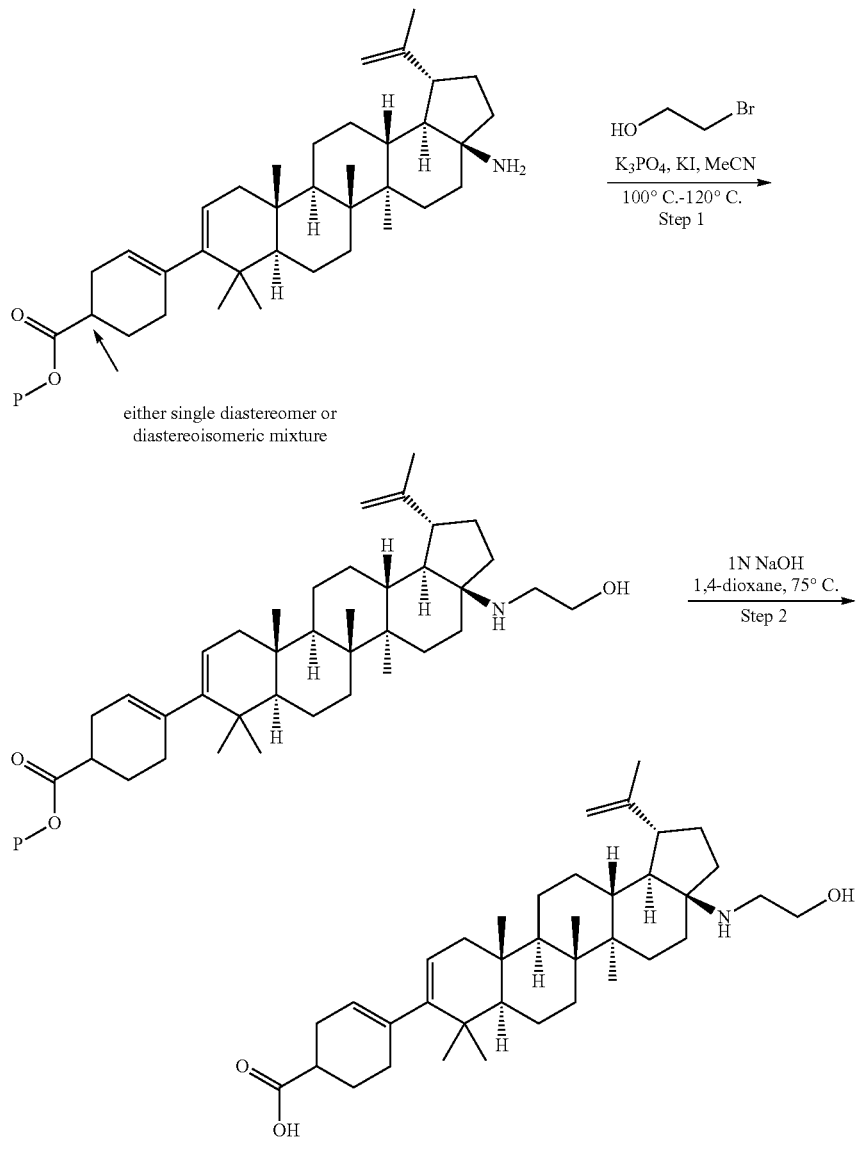

P = Methyl, Ethyl, benzyl, etc.

Example 18

Step 1: Preparation of ethyl 4-((1R,3aS,5aR,5bR, 7aR,11aS,11bR,13aR,13bR)-3a-((2-hydroxyethyl) amino)-5a,5b,8,8,11a-pentamethyl-1-(prop-1-en-2-yl)-2,3,3a,4,5,5a,5b,6,7,7a,8,11,11a,11b,12,13,13a, 13b-octadecahydro-1H-cyclopenta[a]chrysen-9-yl) cyclohex-3-enecarboxylate To a sealable vial was added ethyl 4-((1R,3aS,5aR,5bR, 7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11, 11a,11b,12,13,13a,13b-octadecahydro-1H-cyclopenta[a] chrysen-9-yl)cyclohex-3-enecarboxylate (0.156 g, 0.278 mmol), ethylene bromohydrin (0.059 mL, 0.833 mmol), potassium iodide (0.138 g, 0.833 mmol), and phosphoric acid, potassium salt (0.295 g, 1.388 mmol). The mixture was diluted with acetonitrile (2 mL), was flushed with nitrogen, then was sealed and heated to 100° C. After 15 h of heating, the mixture was cooled to rt. LC/MS still showed starting material present, so an additional 0.059 mL of ethylene bromohydrin was added, the mixture was diluted with 1 mL of acetonitrile, and it was sealed and heated to 120° C. After heating the mixture for an additional 20 h, it was cooled to rt, and diluted with 10 mL of water. The solids that formed were collected by filtration and were washed with water to give ethyl 4-((1R,3aS,5aR,5bR,7aR,11aS,11bR,13aR,13bR)-3a-((2-hydroxyethyl)amino)-5a,5b,8,8,11a-pentamethyl-1-(prop-1-en-2-yl)-2,3,3a,4,5,5a,5b,6,7,7a,8,11,11a,11b,12, 13,13a,13b-octadecahydro-1H-cyclopenta[a]chrysen-9-yl) cyclohex-3-enecarboxylate (0.145 g, 0.239 mmol, 86% yield) as an off-white solid. LCMS: m/e 606.7 (M+H)$^+$, 2.18 min (method 1).

Step 2

To a solution of ethyl 4-((1R,3aS,5aR,5bR,7aR,11aS, 11bR,13aR,13bR)-3a-((2-hydroxyethyl)amino)-5a,5b,8,8, 11a-pentamethyl-1-(prop-1-en-2-yl)-2,3,3a,4,5,5a,5b,6,7, 7a,8,11,11a,11b,12,13,13a,13b-octadecahydro-1H-cyclopenta[a]chrysen-9-yl)cyclohex-3-enecarboxylate (0.013 g, 0.022 mmol) in 1,4-dioxane (1 mL) was added NaOH (1N) (0.2 mL, 0.200 mmol). The mixture was heated to 75° C. for 15 h then was cooled to rt. The mixture was purified by prep HPLC (method 6, retention time: 14.0 minutes) and the fractions containing the product were combined and concentrated under reduced pressure. The product was purified a second time by prep HPLC (method 7, retention time: 16.9 minutes) to attain a higher level of purity. The fractions containing each product were concentrated under reduced pressure to give 4-((1R,3aS,5aR,5bR,7aR,11aS,11bR,13aR, 13bR)-3a-((2-hydroxyethyl)amino)-5a,5b,8,8,11a-pentamethyl-1-(prop-1-en-2-yl)-2,3,3a,4,5,5a,5b,6,7,7a,8, 11,11a,11b,12,13,13a,13b-octadecahydro-1H-cyclopenta[a] chrysen-9-yl)cyclohex-3-enecarboxylic acid, TFA (4.6 mg, 6.6 mmol, 30% yield). LCMS: m/e 578.6 (M+H)$^+$, 1.71 min (method 1). $^1$H NMR (500 MHz, acetic acid-d$_4$) δ=5.38 (br. s., 1H), 5.25-5.21 (m, 1H), 4.82 (s, 1H), 4.71 (s, 1H), 4.05-3.93 (m, 2H), 3.42-3.36 (m, 1H), 3.32-3.24 (m, 1H), 2.85 (td, J=10.9, 5.3 Hz, 1H), 2.64-2.56 (m, 1H), 1.74 (s, 3H), 1.13 (s, 3H), 1.09 (s, 3H), 1.03-0.90 (m, 9H), 2.40-0.89 (m, 29H).

The pure diastereomers were prepared by this method only using (R)-benzyl 4-((1R,3 aS,5aR,5bR,7aR,11aS,11bR, 13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a, 13b-octadecahydro-1H-cyclopenta[a]chrysen-9-yl) cyclohex-3-enecarboxylate as starting material in step 1 for Example 19 and (S)-benzyl 4-((1R,3aS,5aR,5bR,7aR,11aS, 11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12, 13,13a,13b-octadecahydro-1H-cyclopenta[a]chrysen-9-yl) cyclohex-3-enecarboxylate as starting material in step 1 for Example 20. Alternatively, they can be separated from the mixture described above.

Example 19

Preparation of (R)-4-((1R,3aS,5aR,5bR,7aR,11aS, 11bR,13aR,13bR)-3a-((2-hydroxyethyl)amino)-5a, 5b,8,8,11a-pentamethyl-1-(prop-1-en-2-yl)-2,3,3a,4, 5,5a,5b,6,7,7a,8,11,11a,11b,12,13,13a,13b-octadecahydro-1H-cyclopenta[a]chrysen-9-yl) cyclohex-3-enecarboxylic acid, TFA

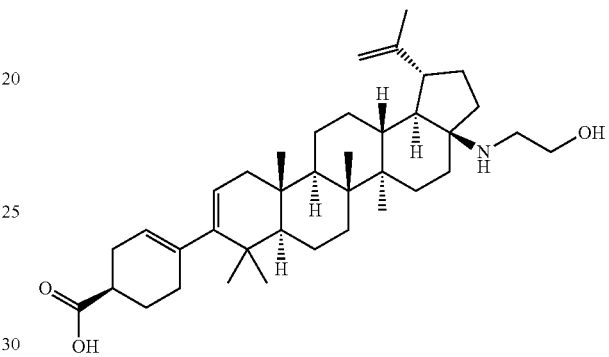

LCMS: m/e 578.7 (M+H)$^+$, 1.75 min (method 1). $^1$H NMR (500 MHz, acetic acid-d$_4$) δ=5.38 (br. s., 1H), 5.22 (dd, J=6.1, 1.6 Hz, 1H), 4.82 (s, 1H), 4.71 (s, 1H), 4.06-3.94 (m, 2H), 3.42-3.37 (m, 1H), 3.32-3.25 (m, 1H), 2.86 (td, J=11.0, 5.5 Hz, 1H), 2.63-2.56 (m, 1H), 1.74 (s, 3H), 1.13 (s, 3H), 1.09 (s, 3H), 1.01 (s, 3H), 0.95 (s, 3H), 0.92 (s, 3H), 2.41-0.85 (m, 29H).

Example 20

Preparation of (S)-4-((1R,3aS,5aR,5bR,7aR,11aS, 11bR,13aR,13bR)-3a-((2-hydroxyethyl)amino)-5a, 5b,8,8,11a-pentamethyl-1-(prop-1-en-2-yl)-2,3,3a,4, 5,5a,5b,6,7,7a,8,11,11a,11b,12,13,13a,13b-octadecahydro-1H-cyclopenta[a]chrysen-9-yl) cyclohex-3-enecarboxylic acid, TFA

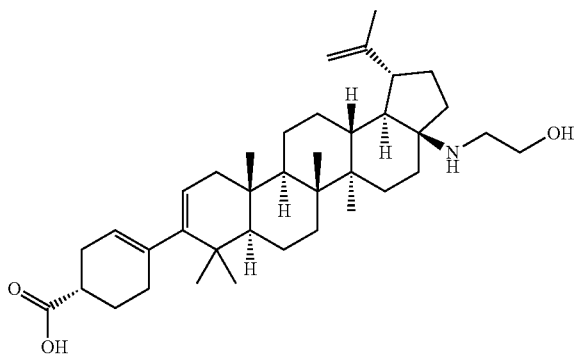

LCMS: m/e 578.6 (M+H)$^+$, 1.67 min (method 1). $^1$H NMR (500 MHz, Acetic acid-d$_4$) δ=5.38 (br. s., 1H), 5.23 (d, J=4.9

Hz, 1H), 4.82 (s, 1H), 4.71 (s, 1H), 4.05-3.91 (m, 2H), 3.39-3.33 (m, 1H), 3.30-3.24 (m, 1H), 2.92-2.83 (m, 1H), 2.64-2.56 (m, 1H), 1.74 (s, 3H), 1.13 (s, 3H), 1.08 (s, 3H), 0.99 (s, 3H), 0.98 (s, 3H), 0.93 (s, 3H), 2.41-0.83 (m, 29H).

Example 21

Preparation of 4-((1R,3aS,5aR,5bR,7aR,11aS,11bR, 13aR,13bR)-3a-((2-(1,1-dioxidothiomorpholino) ethyl)amino)-5a,5b,8,8,11a-pentamethyl-1-(prop-1-en-2-yl)-2,3,3a,4,5,5a,5b,6,7,7a,8,11,11a,11b,12,13, 13a,13b-octadecahydro-1H-cyclopenta[a]chrysen-9-yl)-N-(methylsulfonyl)cyclohex-3-enecarboxamide, TFA Step 1. Preparation of 4-((1R,3aS,5aR,5bR,7aR, 11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a, 11b,12,13,13a,13b-octadecahydro-1H-cyclopenta[a]chrysen-9-yl)cyclohex-3-enecarbonyl chloride To a suspension of 4-((1R,3aS,5aR,5bR,7aR,11aS,11bR, 13aR,13bR)-3a-((2-(1,1-dioxidothiomorpholino)ethyl)amino)-5a,5b,8,8,11a-pentamethyl-1-(prop-1-en-2-yl)-2,3, 3a,4,5,5a,5b,6,7,7a,8,11,11a,11b,12,13,13a,13b-octadecahydro-1H-cyclopenta[a]chrysen-9-yl)cyclohex-3-enecarboxylic acid (0.1 g, 0.144 mmol) in dichloromethane (4 mL) was added thionyl chloride (0.105 mL, 1.439 mmol). The mixture was attached to a reflux condensor and was

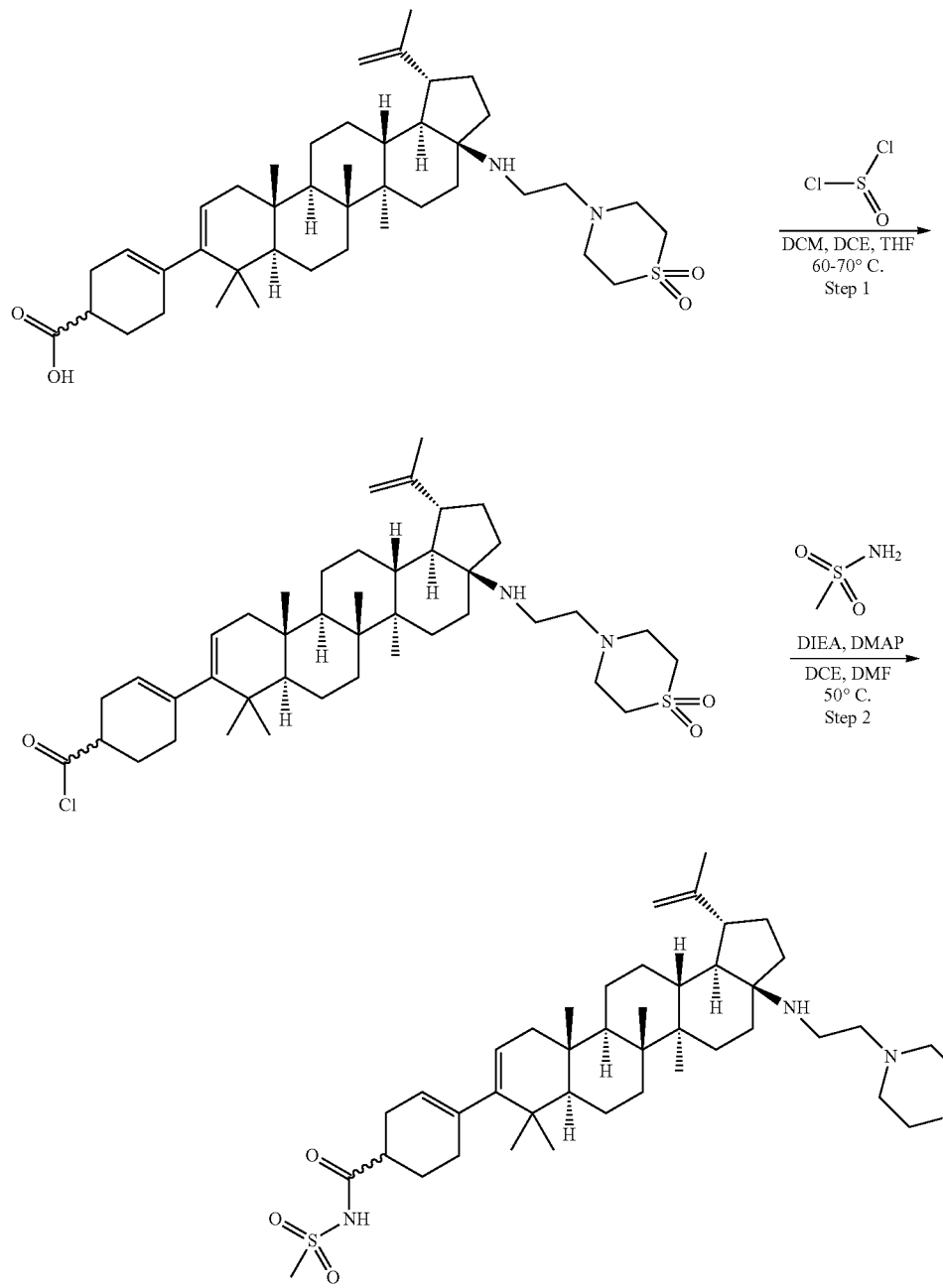

heated to reflux. The solids did not completely dissolve, so DCE (3 mL) was added and the mixture was warmed to 60° C. with a reflux condensor attached. Solids still remained, so THF (2 mL) was added and the mixture was further heated to 70° C. The solids never completely dissolved, but the reaction was allowed to reflux regardless. After 4 h of heating, the mixture was cooled to rt. LC/MS showed the methyl ester since methanol was added to analytical sample to help solubilize the product for analysis. The mixture was concentrated under reduced pressure, then was diluted with dichloromethane and concentrated two additional times. The crude product was used in the next step with no additional purification. LCMS: m/e 709.7 (M+MeOH)$^+$, 2.08 min (method 1).

Step 2

To a suspension of 4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarbonyl chloride (103 mg, 0.144 mmol) in 1,2-dichloroethane (3 mL) was added Hunig's Base (0.252 mL, 1.440 mmol). To the solution was added a solution of methanesulfonamide (68.5 mg, 0.720 mmol) (dried by azeotroping with toluene prior to use) in 1,2-dichloroethane (1.5 mL) and DMF (2 mL). DMAP (3.52 mg, 0.029 mmol) was added and the mixture was warmed to 50° C. for 40 h. The mixture was diluted with ethanol and dioxane and was purified by prep HPLC (method 5, retention time: 9.2 minutes). The fractions containing the product were combined and concentrated under reduced pressure to give the expected product still contaminated with a small amount of the parent carboxylic acid. The product was repurified by prep HPLC (method 16, retention time: 10.6 minutes). The fractions containing the product were combined and concentrated under reduced pressure to give 4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-N-(methylsulfonyl)cyclohex-3-enecarboxamide, TFA (10.4 mg, 0.011 mmol, 7.74% yield) as a white solid. LCMS: m/e 772.5 (M+H)$^+$, 1.70 min (method 1). $^1$H NMR (400 MHz, acetic acid-d$_4$) δ=5.39 (br. s., 1H), 5.24 (d, J=5.8 Hz, 1H), 4.81 (s, 1H), 4.71 (s, 1H), 3.52-3.44 (m, 1H), 3.30 (s, 3H), 3.34-3.03 (m, 12H), 2.86 (d, J=4.8 Hz, 1H), 2.61-2.48 (m, 1H), 1.73 (s, 3H), 1.23 (s, 3H), 1.10 (s, 3H), 1.05-0.92 (m, 9H), 2.39-0.88 (m, 27H).

Example A1

Preparation of 6-((1R,3aS,5aR,5bR,7aR,11aS,11bR,13aR,13bR)-3a-((tert-butoxycarbonyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)spiro[3.3]hept-5-ene-2,2-dicarboxylic acid

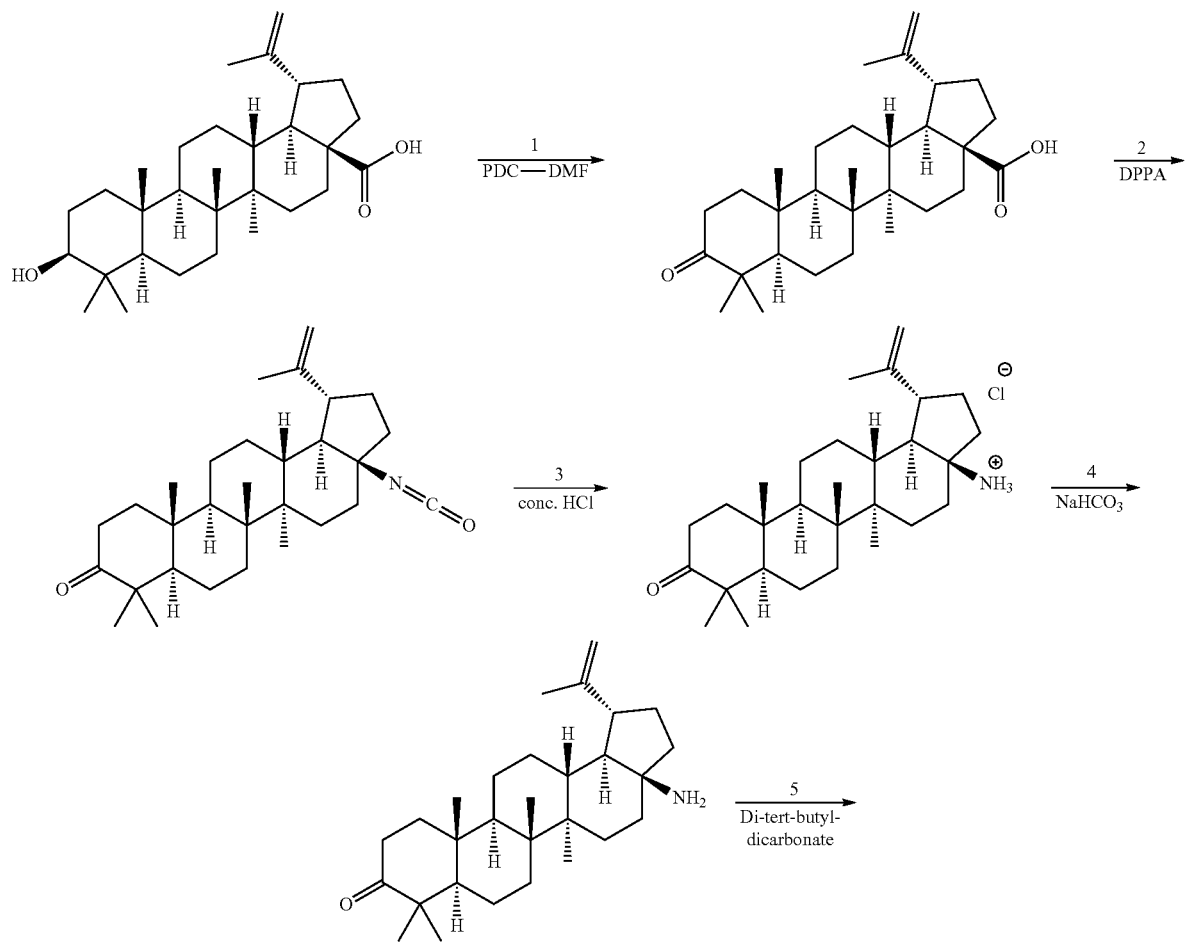

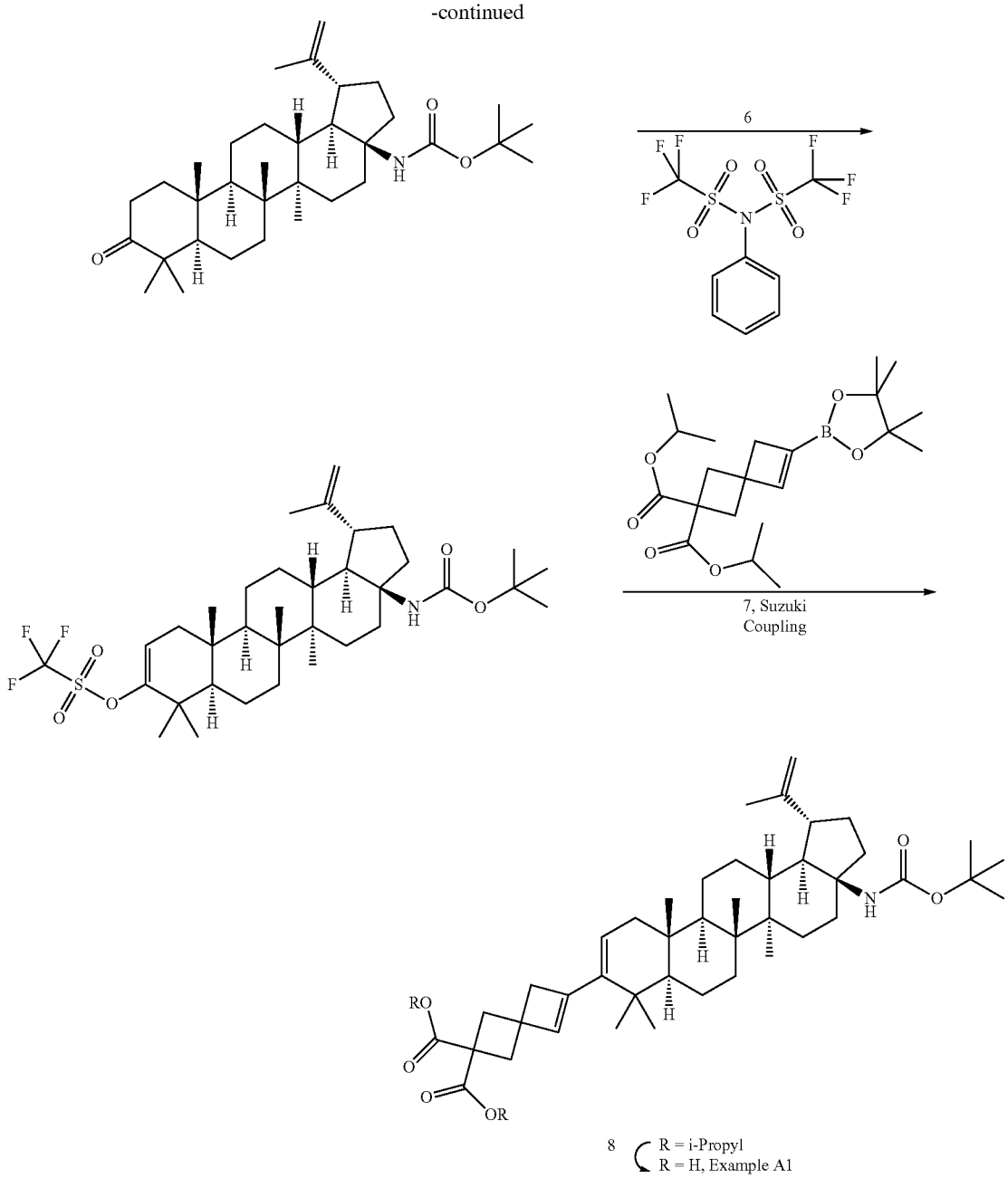

Step 1: Preparation of (1R,3aS,5aR,5bR,7aR,11aR, 11bR,13aR,13bR)-5a,5b,8,8,11a-pentamethyl-9-oxo-1-(prop-1-en-2-yl)icosahydro-1H-cyclopenta[a]chrysene-3a-carboxylic acid To a chilled solution of (1R,3 aS,5aR,5bR,7aR,9S,11aR, 11bR,13 aR,13bR)-9-hydroxy-5a,5b,8,8,11a-pentamethyl-1-(prop-1-en-2-yl)icosahydro-1H-cyclopenta[a]chrysene-3a-carboxylic acid (2.35 g, 5.15 mmol) in DMF (45 mL) at ~4° C. under nitrogen was added pyridinium dichromate (PDC 3.87 g, 10.29 mmol) in a single portion. The suspension was rapidly stirred, forming an orange solution, but rapidly changed into dark brownish with all the PDC dissolved into the reaction mixture. The reaction was kept in an ice bath, and was allowed to warm to RT slowly over 8 hours. Stirring continued for 48 hrs at RT thereafter. The PDC reaction mixture acquired a dull dark brownish appearance but no PPT was observed. The crude DMF reaction solution was poured into vigorously stirred ethyl acetate (400 mL) causing a PPT of a light brownish solid. The suspension was filtered through a short bed (~1" thick) of silica gel type-H in a large diameter filter funnel. The clear filtrate was washed with 0.1 N HCl (200 mL), then with water (3×200 mL). All the volatile solvents were removed, giving 2.1 gm (88%) as a white solid. MS: m/e 477.21 (M+Na)$^+$, 6.2 min (method 9). $^1$H NMR (400 MHz, CHLOROFORM-d) δ 4.76 (d, J=2.3 Hz, 1H), 4.63 (s, 1H), 3.06-2.98 (m, 1H), 2.55-2.37 (m, 2H), 2.28 (s, 2H), 1.99 (d, J=6.5 Hz, 2H), 1.95-1.87 (m, 1H), 1.71 (s, 3H), 1.64 (t, J=11.4 Hz, 2H), 1.59-1.20 (m, 16H), 1.08 (s, 3H), 1.03 (s, 3H), 1.00 (s, 3H), 0.99 (s, 3H), 0.94 (s, 3H).

Step 2: Preparation of (1R,3aS,5aR,5bR,7aR,11aR, 11bR,13aR,13bR)-3a-isocyanato-5a,5b,8,8,11a-pentamethyl-1-(prop-1-en-2-yl)octadecahydro-1H-cyclopenta[a]chrysen-9(5bH)-one To a solution of (1R,3aS,5aR,5bR,7aR,11aR,11bR,13aR, 13bR)-5a,5b,8,8,11a-pentamethyl-9-oxo-1-(prop-1-en-2-yl) icosahydro-1H-cyclopenta[a]chrysene-3a-carboxylic acid (2.1 g, 4.62 mmol) in dioxane (20 mL) was added diphenylphosphoryl azide (DPPA 1.294 mL, 6.00 mmol) and N,N-diisopropylethylamine (2.092 mL, 12.01 mmol) forming a clear solution. The mixture was stirred at RT for 40 minutes before it was immersed into an oil bath at 102° C. under a nitrogen atmosphere for 16 hrs. The crude mixture was evaporated to dryness, re-dissolved into 100 mL DCM, washed 3 times with water. The product was purified by silica gel chromatography eluted with mixture of 20% ethyl acetate in hexanes to give 1.91 gm (92% yield) of the title product. MS: m/e 452.35 (M+H)$^+$, 5.58 min (method 10). $^1$H NMR (400 MHz, CHLOROFORM-d) δ 4.76 (d, J=2.0 Hz, 1H), 4.66-4.64 (m, 1H), 2.60-2.47 (m, 2H), 2.43 (dd, J=7.5, 4.5 Hz, 1H), 2.11 (br. s., 1H), 1.96-1.77 (m, 5H), 1.76-1.70 (m, 1H), 1.69 (d, J=0.5 Hz, 3H), 1.64-1.42 (m, 10H), 1.42-1.29 (m, 4H), 1.23-1.15 (m, 1H), 1.10 (s, 3H), 1.09 (s, 3H), 1.04 (s, 3H), 0.96 (s, 6H).

Step 3: Preparation of (1R,3aS,5aR,5bR,7aR,11aR, 11bR,13aR,13bR)-5a,5b,8,8,11a-pentamethyl-9-oxo-1-(prop-1-en-2-yl)icosahydro-1H-cyclopenta[a]chrysen-3a-aminium chloride To a solution of (1R,3aS,5aR,5bR,7aR,11aR,11bR,13aR, 13bR)-3a-isocyanato-5a,5b,8,8,11a-pentamethyl-1-(prop-1-en-2-yl)octadecahydro-1H-cyclopenta[a]chrysen-9(5bH)-one (2.1 g, 4.65 mmol) in dioxane (30 mL) at RT was added 7 mL conc. HCl over a period of 5 minutes. The clear solution was stirred for 10 minutes, forming a slightly turbid mixture. Stirring continued for a total of 6 hours and the reaction mixture turned into a 2-layer mixture. All the volatile solvents were removed under high vacuum. The dried, crude material was dissolved into DCM (15 mL), poured over a short bed (~1" thick) of silica gel type-H, washed with 500 mL, 20% ethyl acetate in hexanes, followed by a 2:1 mixture of DCM: Ethyl acetate (0.5 L). Upon concentration, a pale gum was obtained. The material was dried under high vacuum to give 1.55 gm (72% yield). MS: m/e 426.40 M$^+$, 4.11 min (method 11). $^1$H NMR (400 MHz, CHLOROFORM-d) δ 8.24 (br. s., 3H), 4.83 (br. s., 1H), 4.66 (br. s., 1H), 2.62-2.17 (m, 4H), 2.16-1.78 (m, 5H), 1.77-1.31 (m, 17H), 1.30-1.16 (m, 5H), 1.09 (s, 3H), 1.03 (s, 3H), 0.99 (br. s., 3H), 0.93 (s, 3H).

Step 4: Preparation of (1R,3aS,5aR,5bR,7aR,11aR, 11bR,13aR,13bR)-3a-amino-5a,5b,8,8,11a-pentamethyl-1-(prop-1-en-2-yl)octadecahydro-1H-cyclopenta[a]chrysen-9(5bH)-one To a solution of (1R,3aS,5aR,5bR,7aR,11aR,11bR,13aR, 13bR)-5a,5b,8,8,11a-pentamethyl-9-oxo-1-(prop-1-en-2-yl) icosahydro-1H-cyclopenta[a]chrysen-3a-aminium chloride (462 mg, 1.000 mmol) in DCM (6 mL) was added saturated solution of sodium bicarbonate 10 mL. The 2-phase mixture was vigorously stirred, DCM layer separated, it was washed with another portion of 6 mL of saturated sodium bicarbonate solution. The mixture was extracted with 10 mL DCM three times. The combine DCM fractions was finally washed with 5 mL DI water. Upon evaporation and drying, a thick semi-solid was isolated. This crude material was used in the next step without further purification.

Step 5: Preparation of tert-butyl((1R,3aS,5aR,5bR, 7aR,11aR,11bR,13aR,13bR)-5a,5b,8,8,11a-pentamethyl-9-oxo-1-(prop-1-en-2-yl)icosahydro-1H-cyclopenta[a]chrysen-3a-yl)carbamate To the free base, (1R,3aS,5aR,5bR,7aR,11aR,11bR,13aR, 13bR)-3a-amino-5a,5b,8,8,11a-pentamethyl-1-(prop-1-en-2-yl)octadecahydro-1H-cyclopenta[a]chrysen-9(5bH)-one (394 mg, 0.926 mmol) in 2 mL of THF was added di-tert-butyl dicarbonate (400 mg, 2 mmol), the resulting solution was stirred at RT for 48 hours. The reaction was worked up by adding 8 mL of a mixture made up of 4 mL 0.5 M HCl and 4 mL of a half saturated ammonium chloride solution. The organic residues were extracted into ethyl acetate (25 mL×3), the combined organic extract was washed once with DI water (25 mL). Evaporation of solvents gave 455 mg (93%) of the desired product suitable for the next preparation without further purification. MS: m/e 548.45 (M+Na)$^+$, 5.87 min (method 12). $^1$H NMR (400 MHz, CHLOROFORM-d) δ 4.76-4.70 (m, 1H), 4.65-4.59 (m, 1H), 4.39-4.27 (m, 1H), 2.68-2.30 (m, 5H), 2.06-1.84 (m, 2H), 1.69 (s, 5H), 1.54 (s, 9H), 1.45 (s, 16H), 1.08 (s, 3H), 1.06 (s, 3H), 1.04 (s, 3H), 0.98 (s, 3H), 0.94 (s, 3H).

Step 6: Preparation of (1R,3aS,5aR,5bR,7aR,11aR, 11bR,13aR,13bR)-3a-((tert-butoxycarbonyl)amino)-5a,5b,8,8,11a-pentamethyl-1-(prop-1-en-2-yl)-2,3, 3a,4,5,5a,5b,6,7,7a,8,11,11a,11b,12,13,13a,13b-octadecahydro-1H-cyclopenta[a]chrysen-9-yl trifluoromethanesulfonate The title compound was prepared as described above in method 2 for the preparation of intermediate 1, step 6 in 72.3% yield.

Step 7: Preparation of diisopropyl 6-((1R,3aS,5aR, 5bR,7aR,11aS,11bR,13aR,13bR)-3a-((tert-butoxycarbonyl)amino)-5a,5b,8,8,11a-pentamethyl-1-(prop-1-en-2-yl)-2,3,3a,4,5,5a,5b,6,7,7a,8,11,11a,11b,12, 13,13a,13b-octadecahydro-1H-cyclopenta[a] chrysen-9-yl)spiro[3.3]hept-5-ene-2,2-dicarboxylate To a mixture of (1R,3aS,5aR,5bR,7aR,11aR,11bR,13aR, 13bR)-3a-((tert-butoxycarbonyl)amino)-5a,5b,8,8,11a-pentamethyl-1-(prop-1-en-2-yl)-2,3,3a,4,5,5a,5b,6,7,7a,8,11, 11a,11b,12,13,13a,13b-octadecahydro-1H-cyclopenta[a] chrysen-9-yl trifluoromethanesulfonate (517 mg, 0.786 mmol), diisopropyl 6-(4,4,5,5-tetramethyl-1,3,2-dioxaborolan-2-yl)spiro[3.3]hept-5-ene-2,2-dicarboxylate (364 mg, 0.928 mmol), sodium carbonate hydrate (292 mg, 2.358 mmol) and, tetrakis(triphenylphosphine)palladium (27.2 mg, 0.024 mmol) under nitrogen was added dioxane (4 mL) and water (1 mL) forming a very pale yellow suspension. The mixture was chilled to −78° C., evacuation/purging (N$_2$) cycles were repeated three times. The reaction mixture was immersed into an oil bath at 85° C. and continued there for 2 hours. The reaction was quenched with 8 mL 1:1 mixture of 0.5N HCl and a half-saturated ammonium chloride solution. The organic residues were extracted into ethyl acetate (3×25 mL). The desired product was isolated by preparative HPLC using method 14 to afford the title compound (101 mg,17%). MS: m/e 774.6 (M+H)$^+$, 7.9 min (method 14). $^1$H NMR (400 MHz, CHLOROFORM-d) δ 5.87 (br. s, 1H), 5.52 (dd, J=6.4, 1.9 Hz, 1H), 5.08 (dt, J=10.5, 6.2 Hz, 2H), 4.72 (s, 1H), 4.62

(d, J=1.5 Hz, 1H), 4.45-4.22 (m, 1H), 2.70 (s, 3H), 2.59 (d, J=2.3 Hz, 2H), 2.50-2.31 (m, 2H), 2.14-2.06 (m, 1H), 2.05-1.91 (m, 1H), 1.69 (s, 3H), 1.67-1.52 (m, 7H), 1.45 (s, 9H), 1.47-1.42 (m, 2H), 1.25 (m, 12H), 1.15 (s, 3H), 1.06 (s, 3H), 1.05 (s, 3H), 0.97 (s, 3H), 0.82 (s, 3H).

Step 8

To a solution of diisopropyl 6-((1R,3aS,5aR,5bR,7aR,11aS,11bR,13aR,13bR)-3a-((tert-butoxycarbonyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)spiro[3.3]hept-5-ene-2,2-dicarboxylate (15 mg, 0.019 mmol) in dioxane (2 mL) and MeOH (1 mL) was added 1N NaOH (1 mL, 1 mmol). The mixture was stirred at 50° C. for 4 h. The solvent was removed in vacuo. The crude product was dissolved in dioxane (1 mL) and MeOH (1 mL). H$_2$O was added dropwise, the solid formed was collected by filtration to give desired product in 88% yield. MS: m/e 688.6 (M−H)$^-$, 2.72 min (method 5). $^1$H NMR (400 MHz, METHANOL-d$_4$) δ 5.88 (s, 1H), 5.57-5.52

(m, 1H), 4.74 (d, J=1.8 Hz, 1H), 4.61 (s, 1H), 2.69 (s, 2H), 2.68-2.48 (m, 4H), 2.33-2.25 (m, 1H), 2.14 (dd, J=17.9, 6.7 Hz, 1H), 1.99-1.83 (m, 2H), 1.77-0.81 (m, 19H), 1.70 (s, 3H), 1.45 (s, 9H), 1.16 (s, 3H), 1.09 (s, 3H), 1.08 (s., 3H), 1.00 (s, 3H), 0.86 (s, 3H).

Example A2 and Example A3

Preparation of 6-((1R,3aS,5aR,5bR,7aR,11aS,11bR,13aR,13bR)-5a,5b,8,8,11a-pentamethyl-1-(prop-1-en-2-yl)-3a-((2-(1,1,1-trifluoro-N-phenylmethylsulfonamido)ethyl)amino)-2,3,3a,4,5,5a,5b,6,7,7a,8,11,11a,11b,12,13,13a,13b-octadecahydro-1H-cyclopenta[a]chrysen-9-yl)spiro[3.3]hept-5-ene-2,2-dicarboxylic acid and 6-((1R,3aS,5aR,5bR,7aR,11aS,11bR,13aR,13bR)-3a-((2-(N-(5-chloropyridin-2-yl)-1,1,1-trifluoromethylsulfonamido)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-M-cyclopenta[a]chrysen-9-yl)spiro[3.3]hept-5-ene-2,2-dicarboxylic acid

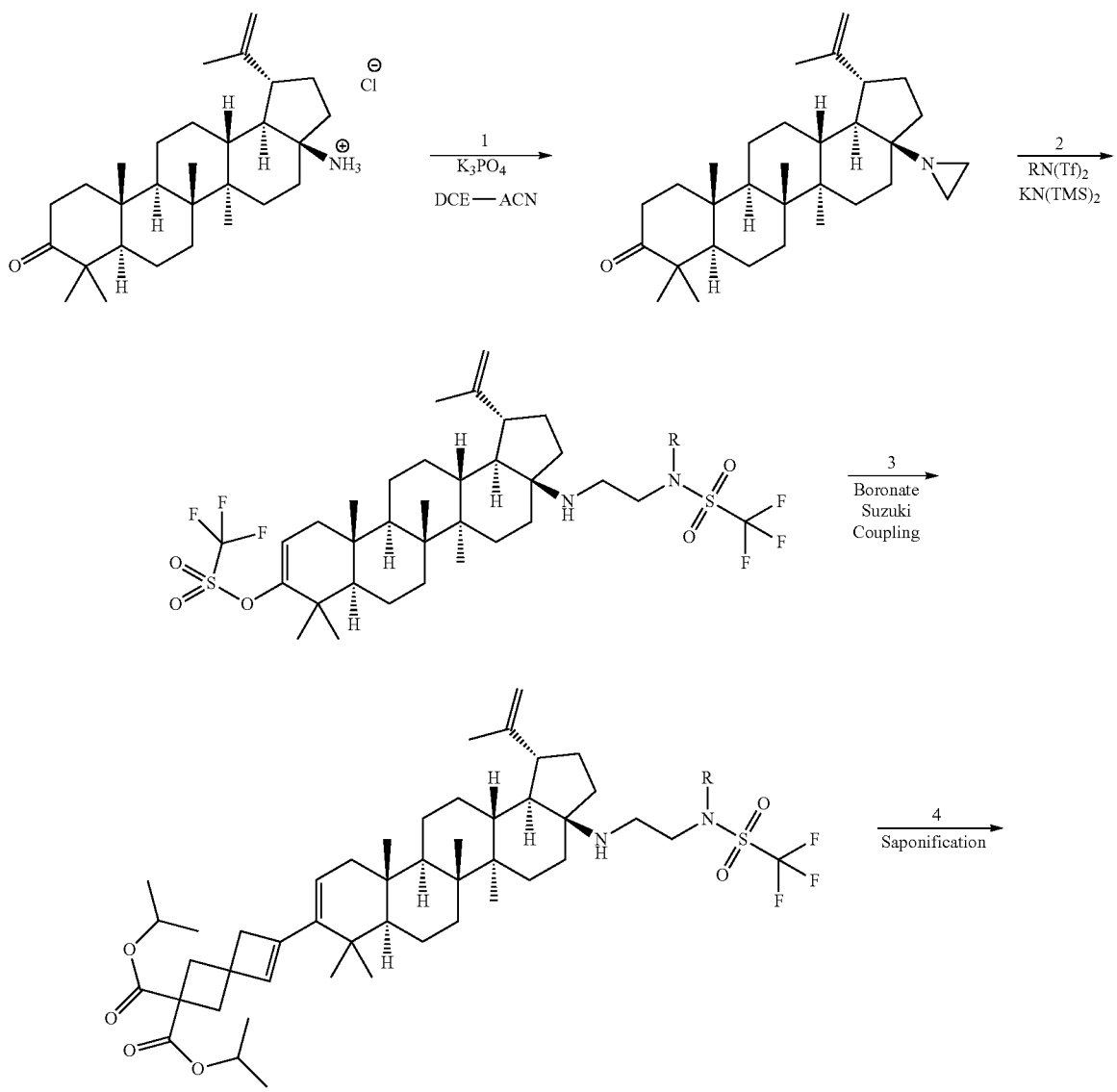

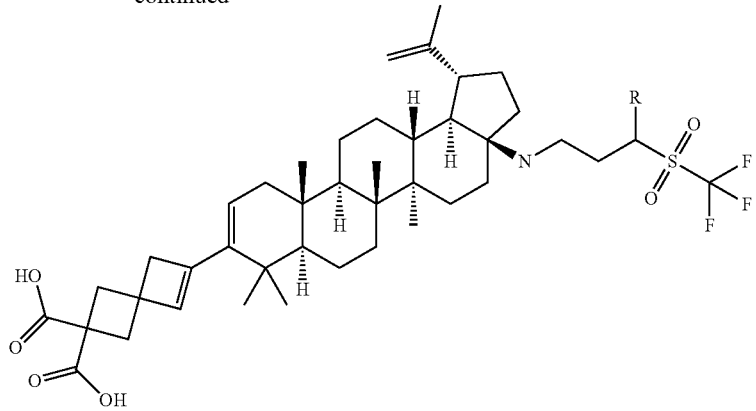

Example A2 (R = Phenyl)

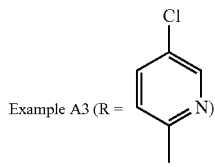

Example A3 (R = )

Step 1: Preparation of (1R,3aS,5aR,5bR,7aR,11aR, 11bR,13aR,13bR)-3a-(aziridin-1-yl)-5a,5b,8,8,11a-pentamethyl-1-(prop-1-en-2-yl)octadecahydro-1H-cyclopenta[a]chrysen-9(5bH)-one A mixture of (1R,3aS,5aR,5bR,7aR,11aR,11bR,13aR, 13bR)-5a,5b,8,8,11a-pentamethyl-9-oxo-1-(prop-1-en-2-yl) icosahydro-1H-cyclopenta[a]chrysen-3a-aminium chloride (1.09 g, 2.359 mmol) and potassium triphosphate (2.7 g, 12.72 mmol) in 1,2-dichloroethane (12 mL) and acetonitrile (24 mL) was placed in a thick-walled resealable vessel. The reaction vessel with its contents were flushed with nitrogen, sealed, and warmed to 130° C. for 36 hours. The crude reaction mixture was cooled to RT, filtered through a short bed (~1" thick) of silica gel type-H, washed with ethyl acetate (150 mL). The filtrate was concentrated into a free flowing solid (1.1 g, quantitative) which was taken to the next step without further purification. MS: m/e 452.35 (M+H)+, 3.12 min (method 21). $^1$H NMR (400 MHz, CHLOROFORM-d) δ 4.77 (d, J=2.5 Hz, 1H), 4.62 (dd, J=2.5, 1.5 Hz, 1H), 2.74-2.56 (m, 2H), 2.55-2.36 (m, 3H), 2.10-2.00 (m, 1H), 1.96-1.86 (m, 1H), 1.85-1.75 (m, 1H), 1.74-1.67 (m, 2H), 1.68 (s, 3H), 1.55-1.24 (m, 16H), 1.16-1.10 (m, 1H), 1.08 (s, 3H), 1.07 (s, 3H), 1.04 (s, 3H), 0.98 (s, 3H), 0.96 (d, J=2.8 Hz, 2H), 0.94 (s, 3H).

Step 2: Preparation of (1R,3aS,5aR,5bR,7aR,11aR, 11bR,13aR,13bR)-3a-((2-(N-(5-chloropyridin-2-yl)-1,1,1-trifluoromethylsulfonamido)ethyl)amino)-5a, 5b,8,8,11a-pentamethyl-1-(prop-1-en-2-yl)-2,3,3a,4, 5,5a,5b,6,7,7a,8,11,11a,11b,12,13,13a,13b-octadecahydro-1H-cyclopenta[a]chrysen-9-yl trifluoromethanesulfonate (1R,3aS,5aR,5bR,7aR,11aR,11bR,13aR,13bR)-3a-(aziridin-1-yl)-5a,5b,8,8,11a-pentamethyl-1-(prop-1-en-2-yl)octadecahydro-1H-cyclopenta[a]chrysen-9(5bH)-one (353 mg, 0.781 mmol) was mixed with N-(5-chloropyridin-2-yl)-1,1, 1-trifluoro-N-((trifluoromethyl)sulfonyl)methanesulfonamide (338 mg, 0.860 mmol) in THF (2 mL) under nitrogen. The solution was stirred at −78° C. under nitrogen. A 0.5 M stock solution of potassium bis(trimethylsilyl)amide (1.875 mL, 0.938 mmol) was added, and the mixture was stirred at −78° C. for an hour. The desired product was purified by silica gel chromatography eluted with mixture of ethyl acetate and hexanes (230 mg, 35%). MS: m/e 844.3/846.3 (M+H)+, 6.47 min (method 15). $^1$H NMR (400 MHz, CHLOROFORM-d) δ (key fingerprint signals) 8.45 (d, J=2.0 Hz, 1H), 7.76 (dd, J=8.7, 2.6 Hz, 1H), 7.48 (d, J=8.5 Hz, 1H), 5.57 (d, J=6.5 Hz, 1H), 4.80-4.57 (m, 3H), 3.71-3.65 (m, 1H), 2.80-2.73 (m, 1H), 2.73-2.49 (m, 2H), 2.45-2.29 (m, 1H), 2.26-2.12 (m, 2H), 2.08-1.94 (m, 2H), 1.93-1.80 (m, 2H), 1.80-1.72 (m, 3H), 1.71-1.65 (m, 6H). $^{19}$F NMR (376 MHz, CHLOROFORM-d) δ −74.84 (s), −74.85 (s).

Step 3: Preparation of diisopropyl 6-((1R,3aS,5aR, 5bR,7aR,11aS,11bR,13aR,13bR)-3a-((2-(N-(5-chloropyridin-2-yl)-1,1,1-trifluoromethylsulfonamido) ethyl)amino)-5a,5b,8,8,11a-pentamethyl-1-(prop-1-en-2-yl)-2,3,3a,4,5,5a,5b,6,7,7a,8,11,11a,11b,12,13, 13a,13b-octadecahydro-1H-cyclopenta[a]chrysen-9-yl)spiro[3.3]hept-5-ene-2,2-dicarboxylate (1R,3aS,5aR,5bR,7aR,11aR,11bR,13aR,13bR)-3a-((2-(N-(5-chloropyridin-2-yl)-1,1,1-trifluoromethylsulfonamido)ethyl)amino)-5a,5b,8,8,11a-pentamethyl-1-(prop-1-en-2-yl)-2,3,3a,4,5,5a,5b,6,7,7a,8,11,11a,11b,12,13,13a, 13b-octadecahydro-1H-cyclopenta[a]chrysen-9-yl trifluoromethanesulfonate (226 mg, 0.268 mmol) was coupled via Suzuki coupling with diisopropyl 6-(4,4,5,5-tetramethyl-1,3,2-dioxaborolan-2-yl)spiro[3.3]hept-5-ene-2,2-dicarboxylate (126 mg, 0.321 mmol) as described previously to give the desired product in 77 mg (30%). MS: m/e 960.45/ 962.45 (M+H)+, 4.41 min (method 16). $^1$H NMR (400 MHz, CHLOROFORM-d) δ 8.45 (d, J=2.8 Hz, 1H), 7.75 (dd, J=8.7, 2.6 Hz, 1H), 7.48 (d, J=8.5 Hz, 1H), 5.87 (s, 1H), 5.52 (dd, J=6.4, 1.9 Hz, 1H), 5.14-5.01 (m, 2H), 4.68 (d, J=2.3 Hz, 1H), 4.59 (d, J=1.3 Hz, 1H), 4.29-4.13 (m, 2H), 2.70 (s, 4H), 2.59 (d, J=2.8 Hz, 4H), 2.44-2.06 (m, 2H), 1.91-1.74 (m, 2H), 1.72-1.34 (m, 19H), 1.30-1.21 (m, 16H), 1.15 (s, 3H), 1.07 (s, 3H), 1.03 (s, 3H), 0.92 (s, 3H), 0.84 (s, 3H). $^{19}$F NMR (376 MHz, CHLOROFORM-d) δ −73.66 (s).

The analogous diisopropyl 6-((1R,3aS,5aR,5bR,7aR,11aS,11bR,13aR,13bR)-5a,5b,8,8,11a-pentamethyl-1-(prop-1-en-2-yl)-3a-((2-(1,1,1-trifluoro-N-phenylmethylsulfonamido)ethyl)amino)-2,3,3a,4,5,5a,5b,6,7,7a,8,11,11a,11b,12,13,13a,13b-octadecahydro-1H-cyclopenta[a]chrysen-9-yl)spiro[3.3]hept-5-ene-2,2-dicarboxylate was prepared in a similar fashion using 1,1,1-trifluoro-N-phenyl-N-((trifluoromethyl)sulfonyl)methanesulfonamide in Step 2 to first give intermediate (1R,3aS,5aR,5bR,7aR,11aR,11bR,13aR,13bR)-5a,5b,8,8,11a-pentamethyl-1-(prop-1-en-2-yl)-3a-((2-(1,1,1-trifluoro-N-phenylmethylsulfonamido)ethyl)amino)-2,3,3a,4,5,5a,5b,6,7,7a,8,11,11a,11b,12,13,13a,13b-octadecahydro-1H-cyclopenta[a]chrysen-9-yl trifluoromethanesulfonate which was then carried into the Suzuki coupling as described before. MS: m/e 925.5 (M+H)⁺, 2.84 min (method 17). $^1$H NMR (400 MHz, CHLOROFORM-d) δ 7.48-7.38 (m, 3H), 7.37-7.28 (m, 1H), 5.87 (s, 1H), 5.52 (dd, J=6.4, 1.9 Hz, 1H), 5.14-5.01 (m, 2H), 4.71 (d, J=1.8 Hz, 1H), 4.60 (d, J=1.3 Hz, 1H), 3.89 (br. s., 2H), 2.70 (s, 3H), 2.59 (d, J=2.5 Hz, 2H), 2.54 (dd, J=12.5, 6.0 Hz, 4H), 2.15-2.06 (m, 1H), 1.96-1.70 (m, 4H), 1.68 (s, 4H), 1.65-1.29 (m, 13H), 1.25 (dd, J=6.3, 5.0 Hz, 11H), 1.15 (s, 3H), 1.07 (s, 3H), 1.06 (s, 3H), 0.93 (s, 3H), 0.84 (s, 3H).

Step 4

To a solution of diisopropyl 6-((1R,3aS,5aR,5bR,7aR,11aS,11bR,13aR,13bR)-5a,5b,8,8,11a-pentamethyl-1-(prop-1-en-2-yl)-3a-((2-(1,1,1-trifluoro-N-phenylmethylsulfonamido)ethyl)amino)-2,3,3a,4,5,5a,5b,6,7,7a,8,11,11a,11b,12,13,13a,13b-octadecahydro-1H-cyclopenta[a]chrysen-9-yl)spiro[3.3]hept-5-ene-2,2-dicarboxylate (15 mg, 0.016 mmol) in dioxane (2 mL) and MeOH (1 mL) was added 1N NaOH (1 mL, 1 mmol). The mixture was stirred at 50° C. for 3 h. The mixture was neutralized by 1N HCl (1 mL) to pH ~6 and solids formed were collected by filtration. The crude product was purified by preparative HPLC using method 14 to give 6-((1R,3 aS,5aR,5bR,7aR,11aS,11bR,13aR,13bR)-5a,5b,8,8,11a-pentamethyl-1-(prop-1-en-2-yl)-3a-((2-(1,1,1-trifluoro-N-phenylmethylsulfonamido)ethyl)amino)-2,3,3a,4,5,5a,5b,6,7,7a,8,11,11a,11b,12,13,13a,13b-octadecahydro-1H-cyclopenta[a]chrysen-9-yl)spiro[3.3]hept-5-ene-2,2-dicarboxylic acid in 42% yield as a solid. MS: m/e 841.5 (M+H)⁺, 2.52 min (method 4). $^1$H NMR (400 MHz, METHANOL-d$_4$) δ 7.52-7.43 (m, 5H), 5.93 (s, 1H), 5.56-5.52 (m, 1H), 4.72 (d, J=1.8 Hz, 1H), 4.60 (s, 1H), 3.99 (s., 2H), 2.77-2.65 (m, 4H), 2.63-2.51 (m, 5H), 2.15 (dd, J=17.8, 6.5 Hz, 1H), 1.92-1.83 (m, 2H), 1.78-0.94 (m, 19H), 1.69 (s, 3H), 1.16 (s, 3H), 1.11 (s, 3H), 1.09 (s, 3H), 0.98 (s, 3H), 0.87 (s, 3H). $^{19}$F NMR (376 MHz, METHANOL-d$_4$) δ −75.37 (s., 3F).

Step 4 for example A3 was carried out in a similar manner: To a solution of diisopropyl 6-((1R,3aS,5aR,5bR,7aR,11aS,11bR,13aR,13bR)-3a-((2-(N-(5-chloropyridin-2-yl)-1,1,1-trifluoromethylsulfonamido)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)spiro[3.3]hept-5-ene-2,2-dicarboxylate (32 mg, 0.033 mmol) in dioxane (2 mL) and MeOH (1 mL) was added 1N NaOH (1 mL, 1 mmol). The mixture was stirred at 50° C. for 3 h. The mixture was neutralized by 1N HCl (1 mL) to pH ~6 and solids formed were collected by filtration. The crude product was purified by preparative HPLC using method 14 to give 6-((1R,3 aS,5aR,5bR,7aR,11aS,11bR,13aR,13bR)-3a-((2-(N-(5-chloropyridin-2-yl)-1,1,1-trifluoromethylsulfonamido)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)spiro[3.3]hept-5-ene-2,2-dicarboxylic acid in 47% yield as a solid. MS: m/e 876.5 (M+H)⁺, 2.56 min (method 4). $^1$H NMR (400 MHz, METHANOL-d$_4$) δ 8.53 (d, J=2.3 Hz, 1H), 8.00 (dd, J=8.7, 2.6 Hz, 1H), 7.57 (d, J=8.5 Hz, 1H), 5.92 (s, 1H), 5.54 (dd, J=6.4, 1.9 Hz, 1H), 4.71 (d, J=1.3 Hz, 1H), 4.60 (s, 1H), 4.34-4.17 (m, 2H), 2.76-2.65 (m, 6H), 2.62-2.53 (m, 2H), 2.43-2.33 (m, 1H), 2.15 (dd, J=17.9, 6.7 Hz, 1H), 1.86 (quin, J=10.6 Hz, 1H), 1.79-0.94 (m, 20H), 1.68 (s, 3H), 1.16 (s, 3H), 1.09 (s, 3H), 1.06 (s, 3H), 0.97 (s, 3H), 0.88 (s, 3H). $^{19}$F NMR (376 MHz, METHANOL-d$_4$) δ −75.55 (s., 3F).

Example A4

Preparation of 6-((1R,3aS,5aR,5bR,7aR,11aS,11bR,13aR,13bR)-5a,5b,8,8,11a-pentamethyl-3a-((2-morpholinoethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)spiro[3.3]hept-5-ene-2,2-dicarboxylic acid

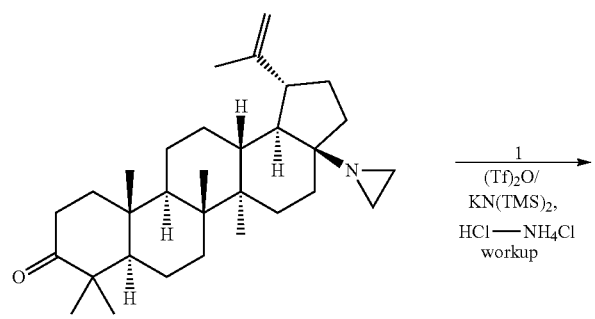

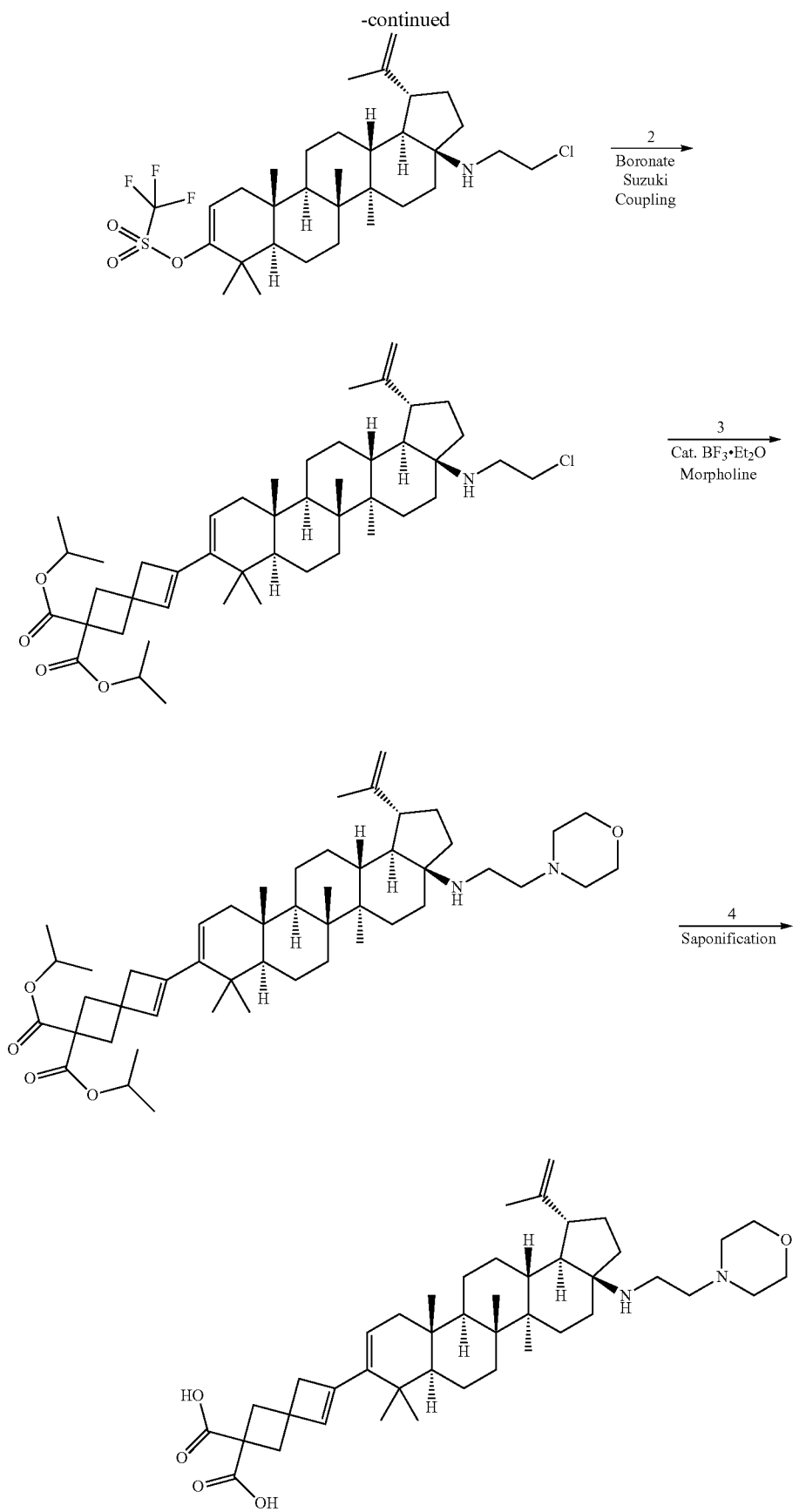

Step 1: Preparation of (1R,3aS,5aR,5bR,7aR,11aR, 11bR,13aR,13bR)-3a-((2-chloroethyl)amino)-5a,5b, 8,8,11a-pentamethyl-1-(prop-1-en-2-yl)-2,3,3a,4,5, 5a,5b,6,7,7a,8,11,11a,11b,12,13,13a,13b-octadecahydro-1H-cyclopenta[a]chrysen-9-yl trifluoromethanesulfonate To a solution of (1R,3aS,5aR,5bR,7aR,11aR,11bR,13aR, 13bR)-3a-(aziridin-1-yl)-5a,5b,8,8,11a-pentamethyl-1-(prop-1-en-2-yl)octadecahydro-1H-cyclopenta[a]chrysen-9 (5bH)-one (357 mg, 0.790 mmol) in THF (3 mL) under nitrogen at −78° C. was added trifluoromethanesulfonic anhydride (0.320 mL, 1.9 mmol), followed by a 0.5 M stock solution of potassium bis(trimethylsilyl)amide (1.897 mL, 0.948 mmol) forming a dull suspension. Stirring continued for 60 minutes at −78° C. The reaction was worked up by the addition of 8 mL mixture of 4 mL 1.0 N HCl and 4 mL of a half-saturated ammonium chloride solution. The quenched mixture was stirred at RT for 30 minutes, the organic materials were extracted into ethyl acetate. The crude mixture was separated on a silica gel column eluted with mixture of ethyl acetate in hexanes to furnish 73 mg (15%) of the desired product. MS: m/e 620.3/622.3 (M+H)$^+$, 3.93 min (method 18). $^{19}$F NMR (376 MHz, CHLOROFORM-d) δ −74.85.

Step 2: Preparation of diisopropyl 6-((1R,3aS,5aR, 5bR,7aR,11aS,11bR,13aR,13bR)-3a-((2-chloroethyl) amino)-5a,5b,8,8,11a-pentamethyl-1-(prop-1-en-2-yl)-2,3,3a,4,5,5a,5b,6,7,7a,8,11,11a,11b,12,13,13a, 13b-octadecahydro-1H-cyclopenta[a]chrysen-9-yl) spiro[3.3]hept-5-ene-2,2-dicarboxylate (1R,3aS,5 aR,5bR,7aR,11aR,11bR,13aR,13bR)-3a-((2-chloroethyl)amino)-5a,5b,8,8,11a-pentamethyl-1-(prop-1-en-2-yl)-2,3,3a,4,5,5a,5b,6,7,7a,8,11,11a,11b,12,13,13a, 13b-octadecahydro-1H-cyclopenta[a]chrysen-9-yl trifluoromethanesulfonate (73 mg, 0.118 mmol), previously dried, was mixed with diisopropyl 6-(4,4,5,5-tetramethyl-1, 3,2-dioxaborolan-2-yl)spiro[3.3]hept-5-ene-2,2-dicarboxylate (55.4 mg, 0.141 mmol) in a 50 mL RBF fitted with an air condenser and a 3-way stopcock/balloon setup. To this mixture was added sodium carbonate hydrate (43.8 mg, 0.353 mmol), tetrakis(triphenylphosphine)palladium (4.08 mg, 3.53 mmol) and dioxane (2 mL), followed by water (0.5 mL). The mixture was quickly immersed into a dry-ice bath until completely frozen. Standard evacuation/purging cycles were repeated 4 times. Under nitrogen, the frozen solid was allowed to melt at RT, forming a very pale lemon yellow solution. Once the solution became nearly homogeneous, it was immersed into an oil bath at 85° C. The reaction was allowed to remain at 85° C. for the 2 hours. LCMS analysis showed the desired product, in the forms of water and methanol adducts. The crude reaction mixture was quenched with a mixture of 4 mL saturated ammonium chloride and 4 mL 0.5 N HCl to bring aziridine back to the chloroethyl open form. The desired product was purified by silica gel chromatography eluted with mixture of ethyl acetate and hexanes to give 19 mg (22%). MS: m/e 736.5/738.5 (M+H)$^+$, 4.53 min (method 19). $^1$H NMR (400 MHz, CHLOROFORM-d) δ 5.87 (s, 1H), 5.52 (dd, J=6.5, 2.0 Hz, 1H), 5.07 (dq, J=17.1, 6.3 Hz, 2H), 4.72 (d, J=2.0 Hz, 1H), 4.62-4.57 (m, 1H), 3.73-3.62 (m, 2H), 2.86-2.72 (m, 2H), 2.70 (s, 3H), 2.59 (d, J=2.5 Hz, 2H), 2.17-1.82 (m, 4H), 1.80-1.70 (m, 3H), 1.69 (s, 3H), 1.66-1.28 (m, 18H), 1.25 (dd, J=6.3, 5.0 Hz, 12H), 1.15 (s, 3H), 1.07 (s, 3H), 1.06 (s, 3H), 0.96 (s, 3H), 0.82 (s, 3H).

Step 3: Preparation of diisopropyl 6-((1R,3aS,5aR, 5bR,7aR,11aS,11bR,13aR,13bR)-5a,5b,8,8,11a-pentamethyl-3a-((2-morpholinoethyl)amino)-1-(prop-1-en-2-yl)-2,3,3a,4,5,5a,5b,6,7,7a,8,11,11a, 11b,12,13,13a,13b-octadecahydro-1H-cyclopenta[a] chrysen-9-yl)spiro[3.3]hept-5-ene-2,2-dicarboxylate To a solution of diisopropyl 6-((1R,3aS,5aR,5bR,7aR, 11aS,11bR,13aR,13bR)-3a-((2-chloroethyl)amino)-5a,5b,8, 8,11a-pentamethyl-1-(prop-1-en-2-yl)-2,3,3a,4,5,5a,5b,6,7, 7a,8,11,11a,11b,12,13,13a,13b-octadecahydro-1H-cyclopenta[a]chrysen-9-yl)spiro[3.3]hept-5-ene-2,2-dicarboxylate (18 mg, 0.024 mmol) in a solution of borontrifluoride etherate in benzene (BF$_3$.Et$_2$O 2% by volume, 2 mL) at RT, was added morpholine (75 µl, 0.857 mmol) forming a cloudy mixture. The mixture was kept at 80° C. for 2 hours. The reaction was diluted with a saturated solution of ammonium chloride in 0.5 N HCl, organic materials were extracted into ethyl acetate (25 mL) three times. The organic extracts were combined and washed with a solution of sodium bicarbonate, the organic materials were concentrated, and purified by silica gel chromatography eluted with mixture of ethyl acetate and hexanes to give 8.1 mg (40%) of the desired product. MS: m/e 787.6 (M+H)$^+$. $^1$H NMR (400 MHz, CHLOROFORM-d) δ 5.87 (s, 1H), 5.55-5.49 (m, 1H), 5.15-5.00 (m, 2H), 4.72 (br. s., 1H), 4.59 (br. s., 1H), 3.73 (t, J=4.4 Hz, 4H), 2.70 (s, 4H), 2.59 (d, J=2.3 Hz, 3H), 2.56-2.34 (m, 6H), 2.10 (dd, J=17.9, 6.7 Hz, 1H), 1.92-1.72 (m, 4H), 1.70 (s, 4H), 1.67-1.28 (m, 14H), 1.25 (dd, J=6.3, 5.0 Hz, 14H), 1.15 (m, 5H), 1.10 (m, 5H), 1.07 (m, 5H), 0.97 (s, 3H), 0.82 (s, 3H).

Step 4

To a solution of diisopropyl 6-((1R,3aS,5aR,5bR,7aR, 11aS,11bR,13aR,13bR)-5a,5b,8,8,11a-pentamethyl-3a-((2-morpholinoethyl)amino)-1-(prop-1-en-2-yl)-2,3,3a,4,5,5a, 5b,6,7,7a,8,11,11a,11b,12,13,13a,13b-octadecahydro-1H-cyclopenta[a]chrysen-9-yl)spiro[3.3]hept-5-ene-2,2-dicarboxylate (9 mg, 0.011 mmol) in 1,4-dioxane (1 mL) and MeOH (0.5 mL) was added 1N NaOH (0.5 mL, 0.500 mmol)). The mixture was stirred at 50° C. for 3 h. The crude product was purified by Prep HPLC using method 14 to give desired product in 74% yield as a solid. MS: m/e 703.6 (M+H)$^+$, 2.42 min (method 4). $^1$H NMR (400 MHz, METHANOL-d$_4$) δ 5.96 (s, 1H), 5.54 (dd, J=6.1, 1.6 Hz, 1H), 4.81 (s, 1H), 4.70 (s, 1H), 3.80-3.67 (m, 4H), 3.15-3.01 (m, 2H), 2.94-2.76 (m, 2H), 2.76-2.58 (m, 8H), 2.52 (br. s., 2H), 2.22-2.14 (m, 1H), 2.10-1.87 (m, 2H), 1.83-1.07 (m, 19H), 1.76 (s, 3H), 1.24 (s, 3H), 1.18 (s, 4H), 1.09 (s, 6H), 0.85 (s, 3H).

151

Key Intermediate: Triflate 1

Preparation of (1R,3aS,5aR,5bR,7aR,11aR,11bR, 13aR,13bR)-3a-((2-(1,1-dioxidothiomorpholino) ethyl)amino)-5a,5b,8,8,11a-pentamethyl-1-(prop-1-en-2-yl)-2,3,3a,4,5,5a,5b,6,7,7a,8,11,11a,11b,12,13, 13a,13b-octadecahydro-1H-cyclopenta[a]chrysen-9-yl trifluoromethanesulfonate

152

Step 2: Preparation of (1R,3aS,5aR,5bR,7aR,11aR, 11bR,13aR,13bR)-3a-((2-(1,1-dioxidothiomorpholino)ethyl)amino)-5a,5b,8,8,11a-pentamethyl-1-(prop-1-en-2-yl)octadecahydro-1H-cyclopenta[a]chrysen-9(5bH)-one To a solution of (1R,3aS,5aR,5bR,7aR,11aR,11bR,13aR, 13bR)-3a-(aziridin-1-yl)-5a,5b,8,8,11a-pentamethyl-1-(prop-1-en-2-yl)octadecahydro-1H-cyclopenta[a]chrysen-9

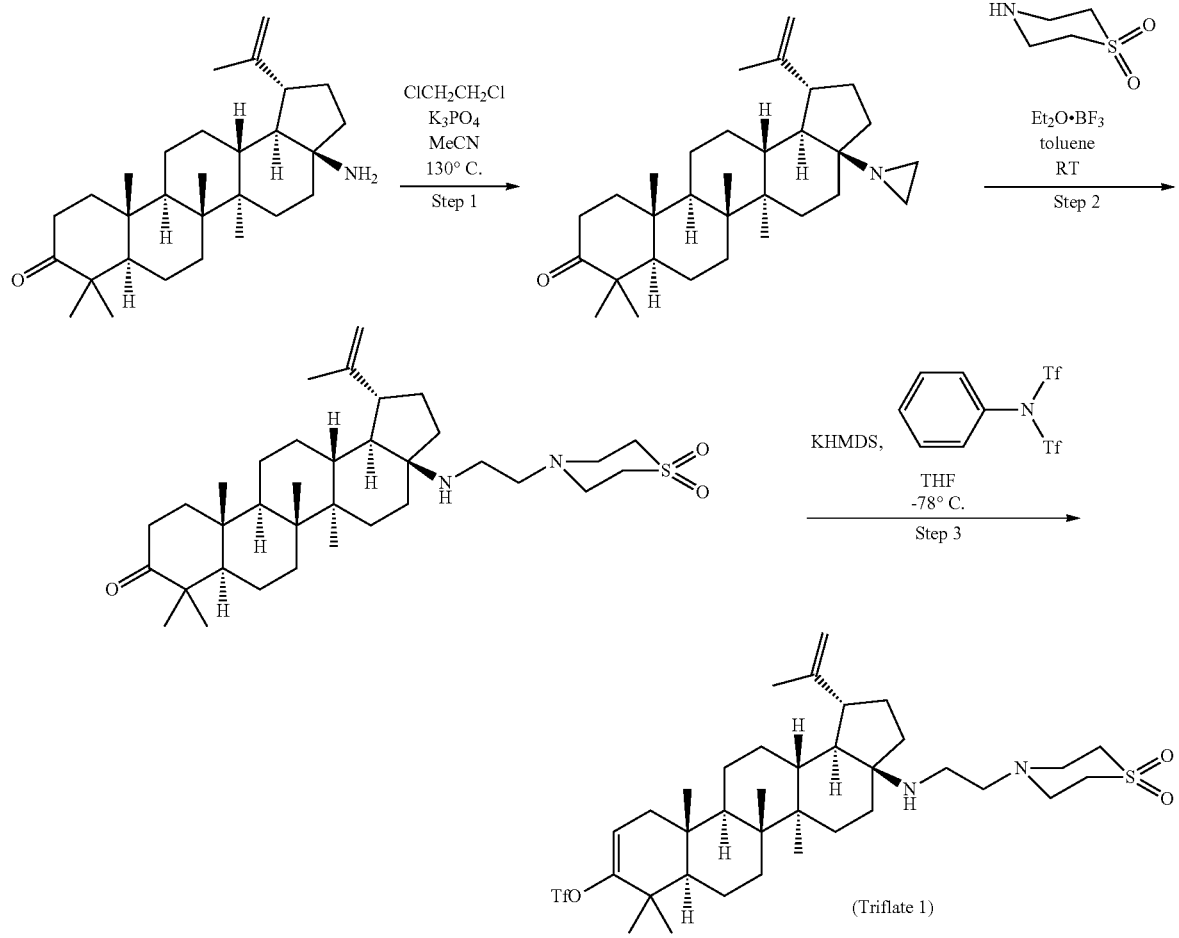

Step 1: Preparation of (1R,3aS,5aR,5bR,7aR,11aR, 11bR,13aR,13bR)-3a-(aziridin-1-yl)-5a,5b,8,8,11a-pentamethyl-1-(prop-1-en-2-yl)octadecahydro-1H-cyclopenta[a]chrysen-9(5bH)-one In a pressure vessel, a suspension of (1R,3aS,5aR,5bR, 7aR,11aR,11bR,13aR,13bR)-3a-amino-5a,5b,8,8,11a-pentamethyl-1-(prop-1-en-2-yl)octadecahydro-1H-cyclopenta[a]chrysen-9(5bH)-one (4.0 g, 9.4 mmol), $K_3PO_4$ (9.97 g, 47.0 mmol) in 1,2-dichloroethane (300 mL) and acetonitrile (30 mL) was flushed with nitrogen, sealed, and stirred at 130° C. overnight. The reaction mixture was cooled to RT, filtered through a bed of silica gel, and rinsed with EtOAc. The filtrate was concentrated in vacuo to give crude aziridine (4.0 g, 94%) as a solid which was used for the next step without purification. MS: m/e 452.5 (M+H)$^+$, 2.63 min (method 4).

(5bH)-one (4.0 g, 8.85 mmol) and thiomorpholine 1,1-dioxide (4.79 g, 35.4 mmol) in toluene (30 mL) was added boron trifluoride diethyl etherate (1 mL in 100 mL of toluene, 10 mL) forming a yellow suspension. The mixture was sonicated for 2 min, then stirred at RT for 5 days. The reaction mixture was diluted with EtOAc (200 mL), washed with $NaHCO_3$ (200 mL), dried over $Na_2SO_4$, filtered and concentrated in vacuo. The crude product was purified by a silica gel column (160 gm) eluted with 20-50% of EtOAc/Hexane to give desired ketone (2.95 g, 57%) as a solid. MS: m/e 587.5 (M+H)$^+$, 2.39 min (method 4). $^1$H NMR (400 MHz, CHLOROFORM-d) δ 4.74-4.70 (m, 1H), 4.62-4.59 (m, 1H), 3.11-2.99 (m, 7H), 2.72-2.36 (m, H), 1.98-0.82 (m. 23H), 1.69 (s, 3H), 1.08 (s, 6H), 1.04 (s, 3H), 0.98 (s, 3H), 0.95 (s, 3H).

Step 3

To a solution of (1R,3aS,5aR,5bR,7aR,11aR,11bR,13aR, 13bR)-3a-((2-(1,1-dioxidothiomorpholino)ethyl)amino)-5a, 5b,8,8,11a-pentamethyl-1-(prop-1-en-2-yl)octadecahydro-1H-cyclopenta[a]chrysen-9(5bH)-one (2.95 g, 5.03 mmol) in THF (50 mL) at −78° C. was added KHMDS (1 M in THF, 7.54 mL, 7.54 mmol). The yellow solution was stirred at −78° C. for 30 min. A solution of 1,1,1-trifluoro-N-phenyl-N-((trifluoromethyl)sulfonyl)methanesulfonamide (1.89 g, 5.28 mmol) in THF (10 mL) was added. The resulted reddish reaction mixture was stirred at −78° C. for 2 h, then warmed to RT and stirred at RT overnight (20 h). The reaction was quenched with saturated aq NH₄Cl (50 mL). The separated aqueous layer was extracted with EtOAc (2×100 mL). The combined organic layers were washed with brine (50 mL), dried over Na₂SO₄, filtered and concentrated in vacuo. The crude product was purified by a silica gel column (160 gm) eluted with 20-80% of EtOAc/Hexane to give (1R,3aS,5aR, 5bR,7aR,11aR,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12, 13,13a,13b-octadecahydro-1H-cyclopenta[a]chrysen-9-yl trifluoromethanesulfonate (triflate 1) (2.78 g, 77%) as a solid. MS: m/e 719.5 (M+H)⁺, 2.60 min (method 4). ¹H NMR (400 MHz, CHLOROFORM-d) δ 5.57 (dd, J=6.8, 2.0 Hz, 1H), 4.76-4.71 (m, 1H), 4.64-4.61 (m, 1H), 3.13-3.02 (m, 7H), 2.85-2.75 (m, 1H), 2.73-2.64 (m, 2H), 2.62-2.52 (m, 2H), 2.17 (dd, J=17.1, 6.8 Hz, 1H), 2.00-0.86 (m, 22H), 1.70 (s, 3H), 1.13 (s, 3H), 1.08 (s, 3H), 1.03 (s, 3H), 0.98 (s, 3H), 0.93 (s, 3H). ¹⁹F NMR (376 MHz, CHLOROFORM-d) δ −74.84 (s, 3F).

Key Intermediate: Triflate 2

Preparation of (1R,3aS,5aR,5bR,7aR,11aR,11bR, 13aR,13bR)-5a,5b,8,8,11a-pentamethyl-3a-((2-(4-(methylsulfonyl)piperidin-1-yl)ethyl)amino)-1-(prop-1-en-2-yl)-2,3,3a,4,5,5a,5b,6,7,7a,8,11,11a, 11b,12,13,13a,13b-octadecahydro-1H-cyclopenta[a] chrysen-9-yl trifluoromethanesulfonate

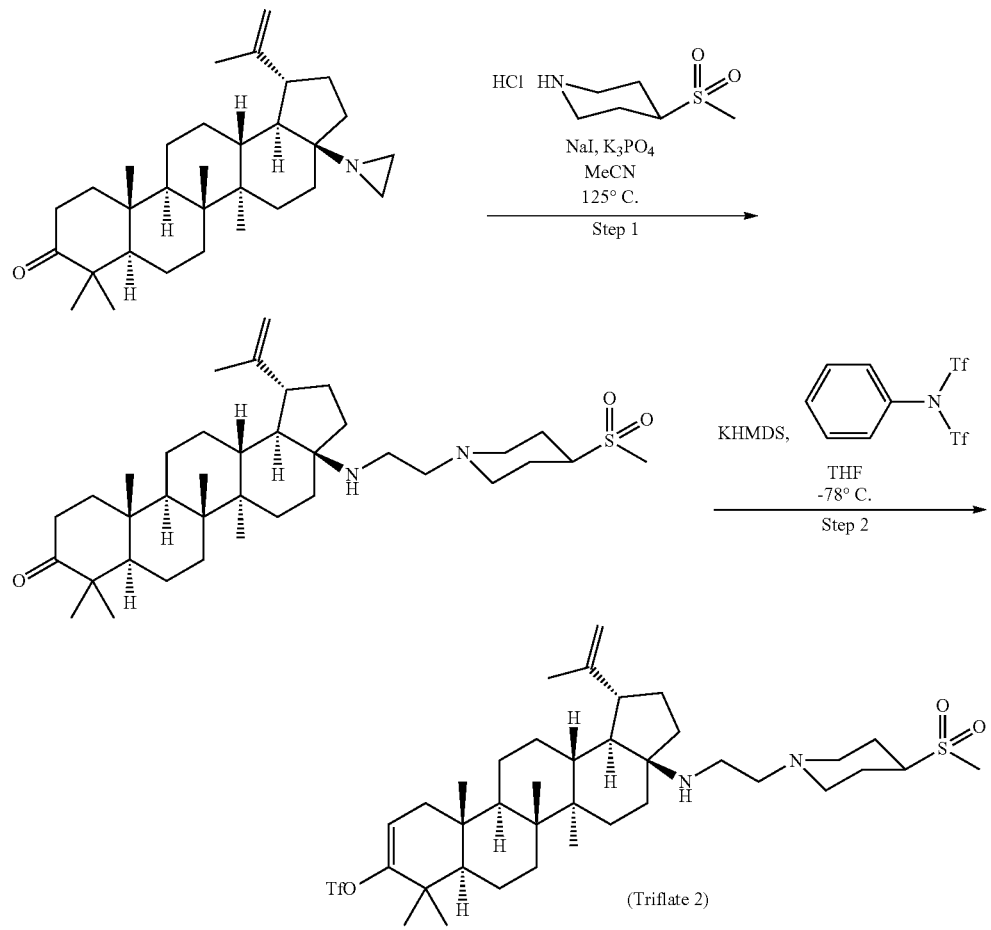

Step 1: Preparation of (1R,3aS,5aR,5bR,7aR,11aR, 11bR,13aR,13bR)-5a,5b,8,8,11a-pentamethyl-3a-((2-(4-(methylsulfonyl)piperidin-1-yl)ethyl)amino)-1-(prop-1-en-2-yl)octadecahydro-1H-cyclopenta[a] chrysen-9(5bH)-one In a pressure vessel, a suspension of (1R,3aS,5aR,5bR, 7aR,11aR,11bR,13aR,13bR)-3a-(aziridin-1-yl)-5a,5b,8,8, 11a-pentamethyl-1-(prop-1-en-2-yl)octadecahydro-1H-cyclopenta[a]chrysen-9(5bH)-one (5.0 g, 11.07 mmol), 4-(methylsulfonyl)piperidine hydrochloride (4.42 g, 22.14 mmol), NaI (1.659 g, 11.07 mmol) and K₃PO₄ (4.70 g, 22.14 mmol) in toluene (50 mL) and CH₃CN (50 mL) was flushed with nitrogen, sealed, and stirred at 125° C. for 24 h. The reaction mixture was concentrated in vacuo, and the residue was partitioned between EtOAc (100 mL) and H₂O (100 mL). The separated aqueous layer was extracted with EtOAc (2×100 mL). The combined organic layers were washed with brine (100 mL), dried over $Na_2SO_4$, filtered and concentrated in vacuo. The crude product was purified by a silica gel column (240 gm) eluted with 40-80% EtOAc/Hexane to give desired ketone (4.26 g, 63%) as a solid. MS: m/e 615.6 $(M+H)^+$, 2.40 min (method 4). $^1H$ NMR (400 MHz, CHLOROFORM-d) δ 4.67 (d, J=2.3 Hz, 1H), 4.54 (dd, J=2.3, 1.5 Hz, 1H), 3.07 (dd, J=16.7, 11.7 Hz, 2H), 2.88-2.78 (m, 1H), 2.81 (s, 3H), 2.61-2.30 (m, 7H), 2.14-2.02 (m, 3H), 1.98-1.70 (m, 9H), 1.69-0.94 (m, 16H), 1.65 (s, 3H), 1.06 (s, 3H), 1.03 (s, 3H), 0.99 (s, 3H), 0.93 (s, 3H), 0.90 (s, 3H).

Step 2

To a solution of (1R,3aS,5aR,5bR,7aR,11aR,11bR,13aR,13bR)-5a,5b,8,8,11a-pentamethyl-3a-((2-(4-(methylsulfonyl)piperidin-1-yl)ethyl)amino)-1-(prop-1-en-2-yl)octadecahydro-1H-cyclopenta[a]chrysen-9(5bH)-one (4.26 g, 6.93 mmol) in THF (80 mL) at −78° C. was added KHMDS (1 M in THF) (10.39 mL, 10.39 mmol). The resulted orange slurry was stirred at −78° C. for 20 min. A solution of 1,1,1-trifluoro-N-phenyl-N-((trifluoromethyl)sulfonyl)methanesulfonamide (2.72 g, 7.62 mmol) in THF (20 mL) was added. The resulted orange reaction mixture was stirred at −78° C. for 2 h. The reaction was quenched with saturated aq $NH_4Cl$ (100 mL). The separated aqueous layer was extracted with EtOAc (3×100 mL). The combined organic layers were washed with brine (100 mL), dried over $Na_2SO_4$, filtered and concentrated in vacuo. The crude product was purified by a silica gel column (240 gm), eluted with 40-100% EtOAc/Hexane to give (1R,3aS,5aR,5bR,7aR,11aR,11bR,13aR,13bR)-5a,5b,8,8,11a-pentamethyl-3a-((2-(4-(methylsulfonyl)piperidin-1-yl)ethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl trifluoromethanesulfonate, (triflate 2) (3.5 g, 68%) as a solid. MS: m/e 747.4 $(M+H)^+$, 2.82 min (method 4). $^1H$ NMR (400 MHz, CHLOROFORM-d) δ 5.56 (dd, J=6.7, 1.9 Hz, 1H), 4.73 (d, J=2.0 Hz, 1H), 4.60 (dd, J=2.1, 1.4 Hz, 1H), 3.17-3.07 (m, 2H), 2.88-2.79 (m, 1H), 2.85 (s, 3H), 2.69-2.54 (m, 3H), 2.52-2.42 (m, 2H), 2.19-2.07 (m, 4H), 2.03-0.88 (m, 24H), 1.69 (s, 3H), 1.12 (s, 3H), 1.08 (s, 3H), 1.02 (s, 3H), 0.96 (s, 3H), 0.91 (s, 3H). $^{19}F$ NMR (376 MHz, CHLOROFORM-d) δ −74.85 (s, 3F).

General Procedure for the Preparation of
C-3α-substituted cyclohexenecarboxylic acid
Compounds

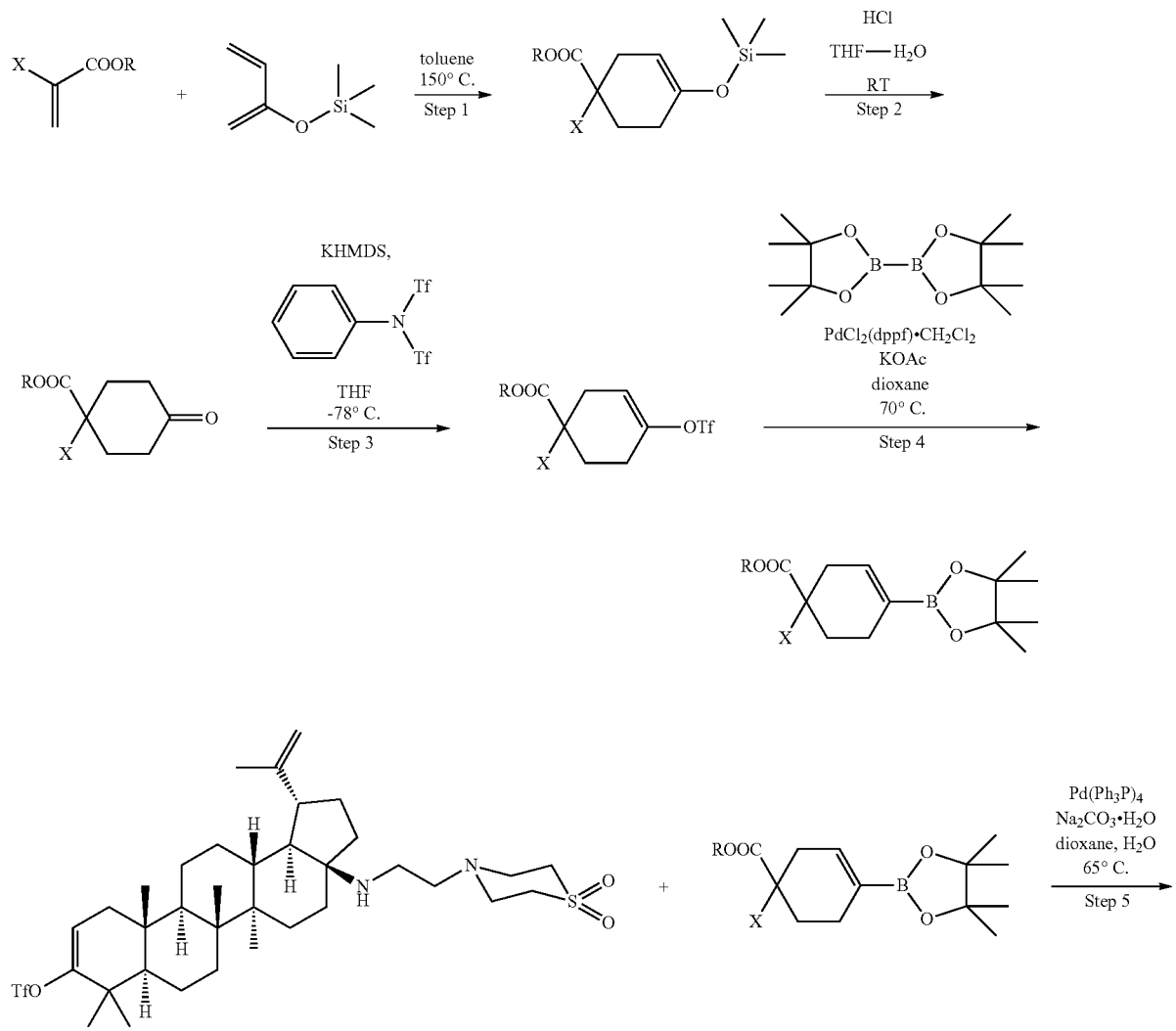

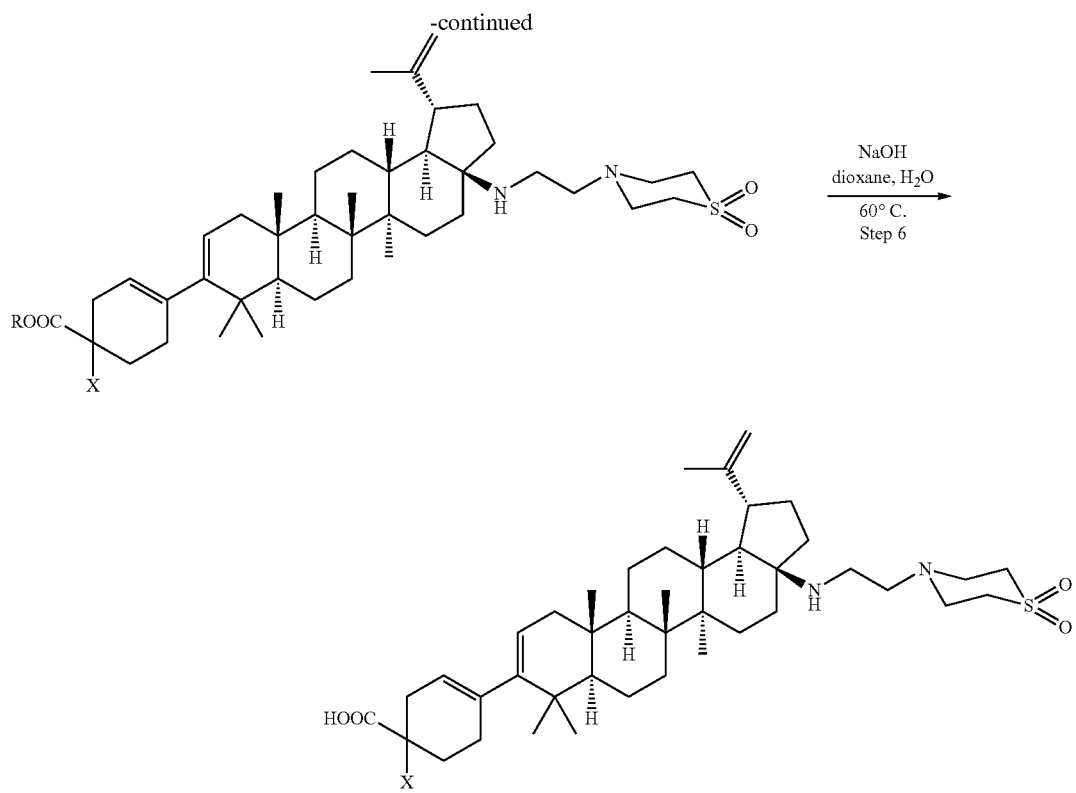

Step 1: Preparation of cyclohexenyloxytrimethylsilane

In a pressure vessel, a solution of acrylate (1 eq), (buta-1, 3-dien-2-yloxy)trimethylsilane (1.1 eq) in toluene was flushed with nitrogen, sealed and heated at 150° C. for 1-3 days. The reaction mixture was cooled to RT and concentrated in vacuo to give crude product which was used for the next step without purification.

Step 2: Preparation of ketone

To a solution of crude product from step 1 (1 eq) in THF was added 0.005 N HCl (0.005 eq). The mixture was stirred at RT overnight. The mixture was extracted with EtOAc, washed with saturated aq NaHCO$_3$ followed by brine, dried over Na$_2$SO$_4$, filtered and concentrated in vacuo. The crude product was purified by a silica gel column eluted with 0-50% of EtOAc/Hexane to give desired ketone.

Step 3: Preparation of triflate

To a solution of ketone from Step 2 (1 eq) and 1,1,1-trifluoro-N-phenyl-N-((trifluoromethyl)sulfonyl)-methanesulfonamide (1.1 eq) in THF at −78° C. was added KHMDS (1 M in THF) (1.3 eq). The resulted yellow to orange solution was stirred at −78° C. for 2 h. The reaction was quenched with saturated aq NH$_4$Cl. The mixture was extracted with EtOAc, washed with brine, dried over Na$_2$SO$_4$, filtered and concentrated in vacuo. The crude product was purified by a silica gel column eluted with 0-25% of EtOAc/Hexane to give desired triflate.

Step 4: Preparation of boronate

In a pressure vessel, a mixture of triflate from Step 3 (1 eq), bis(pinacolato)diboron (1.1 eq), KOAc (2.5 eq) and PdCl$_2$(dppf)-CH$_2$Cl$_2$ adduct (0.03 eq) in 1,4-dioxane was flushed with nitrogen, sealed and heated at 70° C. for 2 h. The mixture was diluted with water and extracted with EtOAc. The combined organic layers were washed with brine, dried over Na$_2$SO$_4$, filtered and concentrated in vacuo. The crude product was purified by a silica gel column eluted with 0-25% of EtOAc/Hexane to give desired boronate.

Step 5: Suzuki Coupling

A mixture of triflate (1 eq), boronate from Step 4 (1 eq), Na$_2$CO$_3$ H$_2$O (3 eq) and Pd(Ph$_3$P)$_4$ (0.06 eq) in dioxane and H$_2$O (4:1), was flushed with nitrogen, sealed and heated at 65° C. for 2 h, color changed to dark brown. The reaction mixture was concentrated in vacuo, and the residue was partitioned between EtOAc and H$_2$O. The separated aqueous layer was extracted with EtOAc. The combined organic layers were washed with brine dried over Na$_2$SO$_4$, filtered and concentrated in vacuo. The crude product was purified by a silica gel column eluted with 30-80% EtOAc/Hexane to give desired ester.

Step 6: Preparation of carboxylic acid

A solution of ester from Step 5 in 1,4-dioxane, MeOH and 1N NaOH (2:1:1) was stirred at 60° C. for 1-2 h. The reaction mixture was purified by Prep HPLC to give final product.

Example A5

Preparation of 1-cyano-4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylic acid

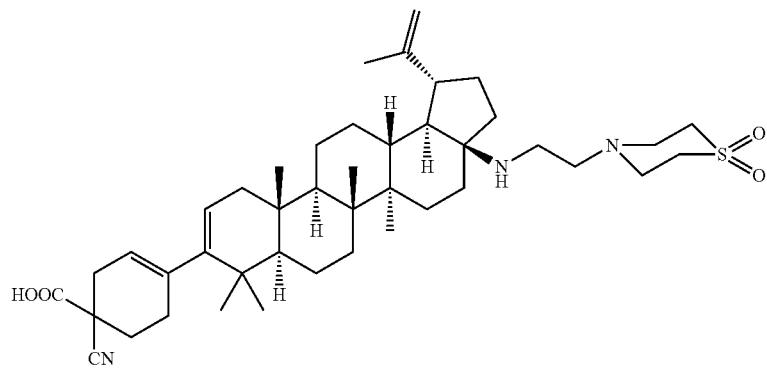

Step 1: Preparation of ethyl 1-cyano-4-(((trimethylsilyl)oxy)cyclohex-3-enecarboxylate

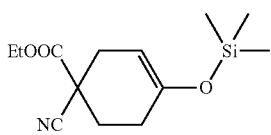 [SMILES: CCOC(=O)C1(C#N)CC=C(O[Si](C)(C)C)CC1]

The title compound was prepared following the procedure described in general procedure Step 1, using ethyl 2-cyanoacrylate as reactant and refluxing 1,4-dioxane as the solvent. The crude material was used directly in Step 2.

Step 2: Preparation of ethyl 1-cyano-4-oxocyclohexanecarboxylate

The title compound was prepared in 96% yield as an oil following the procedure described in general procedure Step 2, using ethyl 1-cyano-4-(((trimethylsilyl)oxy)cyclohex-3-enecarboxylate as reactant. MS: m/e 196.15 (M+H)$^+$, 2.75 min (method 20). $^1$H NMR (400 MHz, CHLOROFORM-d) δ 4.33 (q, J=7.3 Hz, 2H), 2.76-2.66 (m, 2H), 2.59-2.44 (m, 4H), 2.36-2.27 (m, 2H), 1.37 (t, J=7.2 Hz, 3H).

Step 3: Preparation of ethyl 1-cyano-4-(((trifluoromethyl)sulfonyl)oxy)cyclohex-3-enecarboxylate

The title compound was prepared in 64% yield as an oil following the procedure described in general procedure Step 3, using ethyl 1-cyano-4-oxocyclohexanecarboxylate as the reactant. $^1$H NMR (400 MHz, CHLOROFORM-d) δ 5.81 (ddt, J=4.6, 3.1, 1.6 Hz, 1H), 4.32 (q, J=7.0 Hz, 2H), 2.93-2.85 (m, 1H), 2.80-2.67 (m, 2H), 2.58-2.48 (m, 1H), 2.40-2.33 (m, 1H), 2.31-2.22 (m, 1H), 1.36 (t, J=7.2 Hz, 3H). $^{19}$F NMR (376 MHz, CHLOROFORM-d) δ −73.61 (s, 3F).

Step 4: Preparation of ethyl 1-cyano-4-(4,4,5,5-tetramethyl-1,3,2-dioxaborolan-2-yl)cyclohex-3-enecarboxylate

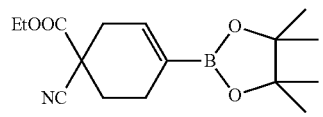

The title compound was prepared in 97% yield as an oil following the procedure described in general procedure Step 4, using ethyl 1-cyano-4-(((trifluoromethyl)sulfonyl)oxy)cyclohex-3-enecarboxylate as reactant. $^1$H NMR (400 MHz, CHLOROFORM-d) δ 6.50-6.46 (m, 1H), 4.29 (q, J=7.0 Hz, 2H), 2.78-2.58 (m, 2H), 2.52-2.32 (m, 2H), 2.24-2.17 (m, 1H), 1.95 (ddd, J=13.2, 10.8, 5.6 Hz, 1H), 1.34 (t, J=7.2 Hz, 3H), 1.27 (s, 12H)

Step 5: Preparation of ethyl 1-cyano-4-((1R,3aS,5aR, 5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a, 8,11,11a,11b,12,13,13a,13b-octadecahydro-1H-cyclopenta[a]chrysen-9-yl)cyclohex-3-enecarboxylate 1-en-2-yl)-2,3,3a,4,5,5a,5b,6,7,7a,8,11,11a,11b,12,13,13a, 13b-octadecahydro-1H-cyclopenta[a]chrysen-9-yl)cyclohex-3-enecarboxylate as reactant. The title compound was isolated as a mixture of diastereomers (solid, 84% yield). MS: m/e 720.6 (M+H)$^+$, 2.82 min (method 4). $^1$H NMR (400 MHz, CHLOROFORM-d) δ 5.35 (s., 1H), 5.24 (s., 1H), 4.78 (s., 1H), 4.66 (s, 1H), 3.23-2.40 (m, 13H), 2.29-0.81 (m, 34H), 1.70 (s, 3H), 1.14 (s, 3H), 1.01 (s., 3H), 0.88 (s, 3H).

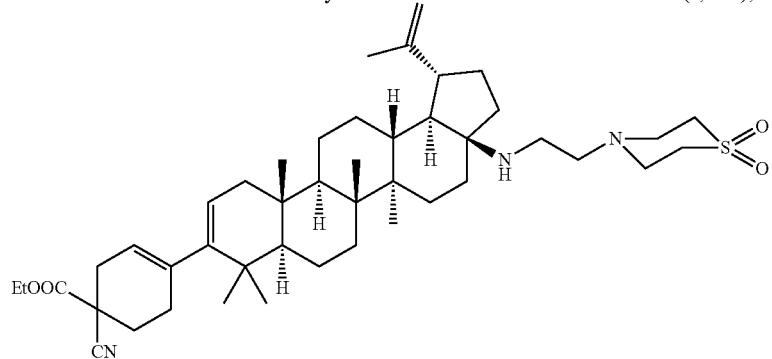

The title compound was prepared following the procedure described in general procedure Step 5, using (1R,3aS,5aR, 5bR,7aR,11aR,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12, 13,13a,13b-octadecahydro-1H-cyclopenta[a]chrysen-9-yl trifluoromethanesulfonate and ethyl 1-cyano-4-(4,4,5,5-tetramethyl-1,3,2-dioxaborolan-2-yl)cyclohex-3-enecarboxylate as reactants. The product was isolated as a mixture of diasteroisomers (solid, 61% yield). MS: m/e 748.6 (M+H)$^+$, 2.99 min (method 4). $^1$H NMR (400 MHz, CHLOROFORM-d) δ 5.35 (d, J=1.8 Hz, 1H), 5.28-5.23 (m, 1H), 4.73 (d, J=1.8 Hz, 1H), 4.61 (s, 1H), 4.29 (q, J=7.0 Hz, 2H), 3.13-3.01 (m, 8H), 2.80-2.46 (m, 9H), 2.33-2.15 (m, 2H), 2.08-0.82 (m, 22H), 1.70 (s, 3H), 1.34 (t, J=7.2 Hz, 3H), 1.07 (s, 3H), 0.97 (s, 3H), 1.03-0.92 (m, 6H), 0.86 (s, 3H).

Step 6

1-cyano-4-((1R,3aS,5aR,5bR,7aR,11aS,11bR,13aR, 13bR)-3a-((2-(1,1-dioxidothiomorpholino)ethyl)amino)-5a, 5b,8,8,11a-pentamethyl-1-(prop-1-en-2-yl)-2,3,3a,4,5,5a, 5b,6,7,7a,8,11,11a,11b,12,13,13a,13b-octadecahydro-1H-cyclopenta[a]chrysen-9-yl)cyclohex-3-enecarboxylic acid was prepared following the procedure described in general procedure Step 6, using ethyl 1-cyano-4-((1R,3aS,5aR,5bR, 7aR,11aS,11bR,13aR,13bR)-3a-((2-(1,1-dioxidothiomorpholino)ethyl)amino)-5a,5b,8,8,11a-pentamethyl-1-(prop- Example A6

Preparation of 1-cyano-4-((1R,3aS,5aR,5bR,7aR, 11aS,11bR,13aR,13bR)-5a,5b,8,8,11a-pentamethyl-3a-((2-(4-(methylsulfonyl)piperidin-1-yl)ethyl) amino)-1-(prop-1-en-2-yl)-2,3,3a,4,5,5a,5b,6,7,7a,8, 11,11a,11b,12,13,13a,13b-octadecahydro-1H-cyclopenta[a]chrysen-9-yl)cyclohex-3-enecarboxylic acid

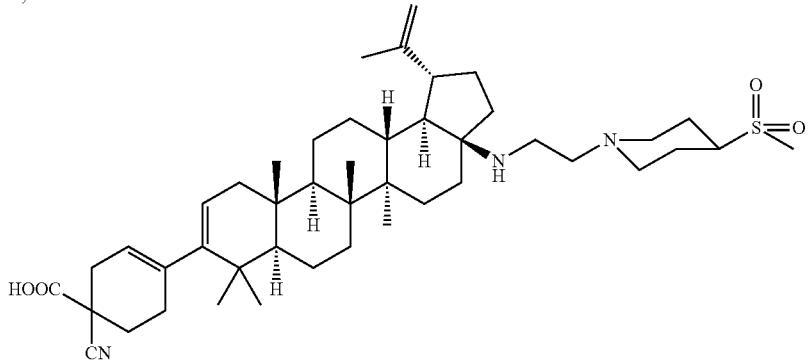

Step 1: Preparation of methyl 1-cyano-4-((trimethylsilyl)oxy)cyclohex-3-enecarboxylate

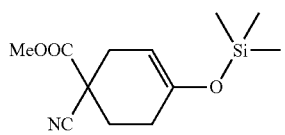 [SMILES: COC(=O)C1(C#N)CC=C(O[Si](C)(C)C)CC1]

The title compound was prepared following the procedure described in general procedure Step 1, using methyl 2-cyanoacrylate as reactant and 1,4-dioxane as solvent at 90° C.

Step 2: Preparation of methyl 1-cyano-4-oxocyclohexanecarboxylate

The title compound was prepared as following the procedure described in general procedure Step 2, using methyl 1-cyano-4-((trimethylsilyl)oxy)cyclohex-3-enecarboxylate as reactant. The crude material was isolated as an oil. $^1$H NMR (400 MHz, CHLOROFORM-d) δ 3.90 (s, 3H), 2.76-2.65 (m, 2H), 2.59-2.44 (m, 4H), 2.38-2.26 (m, 2H).

Step 3: Preparation of methyl 1-cyano-4-(((trifluoromethyl)sulfonyl)oxy)cyclohex-3-enecarboxylate

The title compound was prepared following the procedure described in general procedure Step 3, using methyl 1-cyano-4-oxocyclohexanecarboxylate as reactant. The product was isolated as an oil in 51% yield. $^1$H NMR (400 MHz, CHLOROFORM-d) δ 5.81 (qd, J=3.1, 2.0 Hz, 1H), 3.88 (s, 3H), 2.94-2.84 (m, 1H), 2.82-2.67 (m, 2H), 2.59-2.47 (m, 1H), 2.42-2.33 (m, 1H), 2.31-2.22 (m, 1H). $^{19}$F NMR (376 MHz, CHLOROFORM-d) δ −73.62 (s, 3F).

Step 4: Preparation of methyl 1-cyano-4-(4,4,5,5-tetramethyl-1,3,2-dioxaborolan-2-yl)cyclohex-3-enecarboxylate

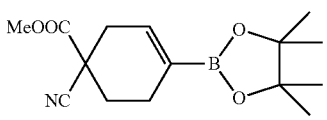 [SMILES: COC(=O)C1(C#N)CC=C(B2OC(C)(C)C(C)(C)O2)CC1]

The title compound was prepared following the procedure described in general procedure Step 4, using methyl 1-cyano-4-(((trifluoromethyl)sulfonyl)oxy)cyclohex-3-enecarboxylate as reactant. The product was obtained in 62% yield as an oil. $^1$H NMR (400 MHz, CHLOROFORM-d) δ 6.51-6.46 (m, 1H), 3.85 (s, 3H), 2.78-2.59 (m, 2H), 2.52-2.33 (m, 2H), 2.25-2.17 (m, 1H), 1.96 (ddd, J=13.1, 10.8, 5.8 Hz, 1H), 1.27 (s, 12H).

Step 5: Preparation of methyl 1-cyano-4-((1R,3aS,5aR,5bR,7aR,11aS,11bR,13aR,13bR)-5a,5b,8,8,11a-pentamethyl-3a-((2-(4-(methylsulfonyl)piperidin-1-yl)ethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylate

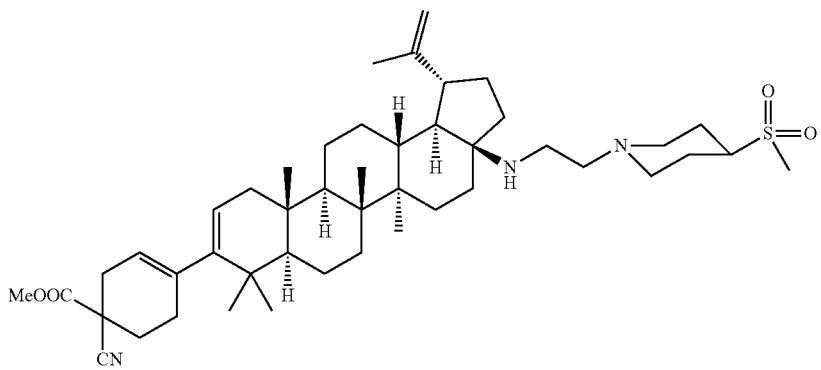

The title compound was prepared following the procedure described in general procedure Step 5, using (1R,3aS,5aR,5bR,7aR,11aR,11bR,13aR,13bR)-5a,5b,8,8,11a-pentamethyl-3a-((2-(4-(methylsulfonyl)piperidin-1-yl)ethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl trifluoromethanesulfonate and methyl 1-cyano-4-(4,4,5,5-tetramethyl-1,3,2-dioxaborolan-2-yl)cyclohex-3-enecarboxylate as reactants. The product was isolated as a mixture of diasteromers (solid, 61% yield). MS: m/e 762.6 (M+H)$^+$, 3.01 min (method 4). $^1$H NMR (400 MHz, CHLOROFORM-d) δ 5.34 (d, J=2.0 Hz, 1H), 5.28-5.22 (m, 1H), 4.71 (d, J=2.0 Hz, 1H), 4.60-4.57 (m, 1H), 3.85 (s, 3H), 3.17-3.06 (m, 3H), 2.87-2.78 (m, 2H), 2.84 (s. 3H), 2.74-2.40 (m, 10H), 2.33-0.78 (m, 27H), 1.69 (s, 3H), 1.07 (s, 3H), 1.01-0.93 (m, 6H), 0.96 (s, 3H), 0.85 (s, 3H).

Step 6

1-cyano-4-((1R,3aS,5aR,5bR,7aR,11aS,11bR,13aR,13bR)-5a,5b,8,8,11a-pentamethyl-3a-((2-(4-(methylsulfonyl)piperidin-1-yl)ethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylic acid was prepared following the procedure described in general procedure Step 6, using methyl 1-cyano-4-((1R,3aS,5aR,5bR,7aR,11aS,11bR,13aR,13bR)-5a,5b,8,8,11a-pentamethyl-3a-((2-(4-(methylsulfonyl)piperidin-1-yl)ethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylate as reactant. The product was isolated as a mixture of diastereomers (solid, 50% yield). MS: m/e 748.6 (M+H)$^+$, 2.97 min (method 4). $^1$H NMR (400 MHz, CHLOROFORM-d) δ 5.36 (s., 1H), 5.24 (d, J=5.5 Hz, 1H), 4.80 (s, 1H), 4.67 (s, 1H), 3.31-3.13 (m, 3H), 3.12-2.89 (m, 6H), 2.86 (s, 3H), 2.78-2.45 (m, 5H), 2.33-0.85 (m, 29H), 1.70 (s, 3H), 1.17 (s, 3H), 1.02-0.94 (m, 6H), 1.00 (s, 3H), 0.87 (s, 3H).

Example A7

Preparation of 1-chloro-4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylic acid

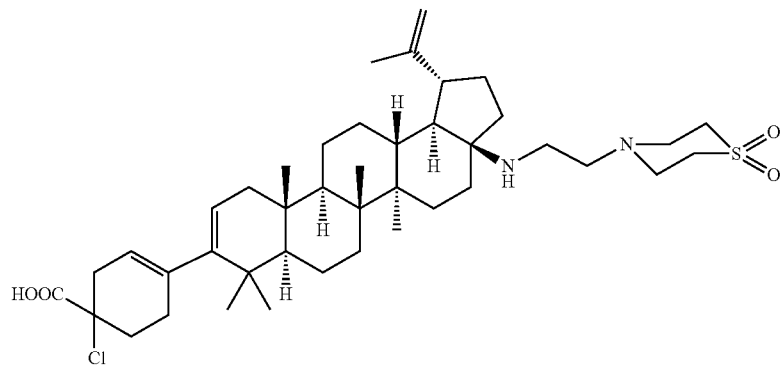

Step 1: Preparation of methyl 1-chloro-4-((trimethylsilyl)oxy)cyclohex-3-enecarboxylate

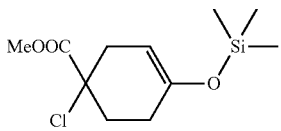 [SMILES: COC(=O)C1(Cl)CC=C(O[Si](C)(C)C)CC1]

The title compound was prepared following the procedure described in general procedure Step 1, using methyl 2-chloroacrylate as reactant.

Step 2: Preparation of methyl 1-chloro-4-oxocyclohexanecarboxylate

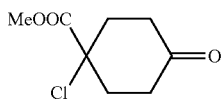

The title compound was prepared following the procedure described in general procedure Step 2, using methyl 1-chloro-4-((trimethylsilyl)oxy)cyclohex-3-enecarboxylate. The product was isolated as an oil in 46% yield. MS: m/e 191.1 (M+H)$^+$, 2.95 min (method 6). $^1$H NMR (500 MHz, CHLOROFORM-d) δ 3.86 (s, 3H), 2.80-2.71 (m, 2H), 2.55-2.39 (m, 6H).

Step 3: Preparation of methyl 1-chloro-4-(((trifluoromethyl)sulfonyl)oxy)cyclohex-3-enecarboxylate

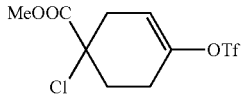

The title compound was prepared following the procedure described in general procedure Step 3, using methyl 1-chloro-4-oxocyclohexanecarboxylate as reactant. The product was isolated as an oil in 47% yield. $^1$H NMR (400 MHz, CHLOROFORM-d) δ 5.74-5.70 (m, 1H), 3.84 (s, 3H), 3.07-2.99 (m, 1H), 2.83-2.65 (m, 2H), 2.53-2.29 (m, 3H).

Step 4: Preparation of methyl 1-chloro-4-(4,4,5,5-tetramethyl-1,3,2-dioxaborolan-2-yl)cyclohex-3-enecarboxylate

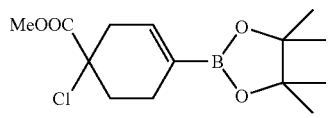

The title compound was prepared following the procedure described in general procedure Step 4, using methyl 1-chloro-4-(((trifluoromethyl)sulfonyl)oxy)cyclohex-3-enecarboxylate as reactant. The product was isolated as an oil in 28% yield. $^1$H NMR (400 MHz, CHLOROFORM-d) δ 6.45-6.41 (m, 1H), 3.81 (s, 3H), 3.00-2.91 (m, 1H), 2.71-2.63 (m, 1H), 2.50-2.10 (m, 4H), 1.27 (s, 12H).

Step 5: Preparation of methyl 1-chloro-4-((1R,3aS, 5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylate

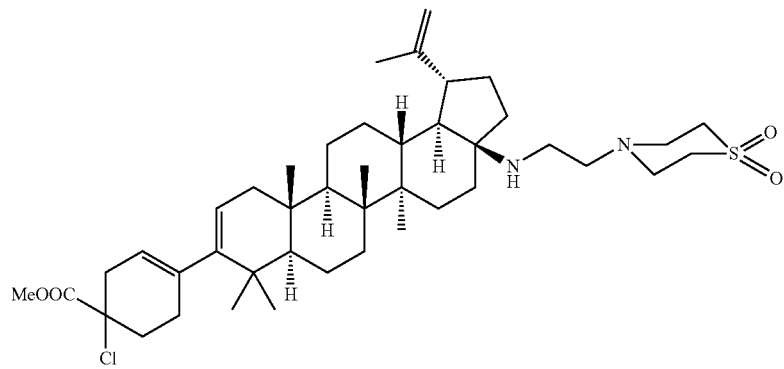

The title compound was prepared following the procedure described in general procedure Step 5, using (1R,3aS,5aR,5bR,7aR,11aR,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl trifluoromethanesulfonate and methyl 1-chloro-4-(4,4,5,5-tetramethyl-1,3,2-dioxaborolan-2-yl)cyclohex-3-enecarboxylate as reactants. The product was isolated as a mixture of diastereoisomers. MS: m/e 743.5 (M+H)⁺, 3.01 min (method 4).

Step 6

1-chloro-4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylic acid was prepared following the procedure described in general procedure Step 6, using methyl 1-chloro-4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylate as reactant. The product was isolated as a mixture of diasteromers (solid, 10% yield). MS: m/e 729.5 (M+H)⁺, 2.96 min (method 4). ¹H NMR (400 MHz, CHLOROFORM-d) δ 5.28 (s., 1H), 5.21 (d, J=4.3 Hz, 1H), 4.75 (s, 1H), 4.63 (s, 1H), 3.16-0.68 (m, 41H), 1.70 (s, 3H), 1.13 (s, 3H), 1.00 (s, 3H), 1.00-0.94 (m, 6H), 0.87 (s, 3H).

Example A8

Preparation of 1-chloro-4-((1R,3aS,5aR,5bR,7aR,11aS,11bR,13aR,13bR)-5a,5b,8,8,11a-pentamethyl-3a-((2-(4-(methylsulfonyl)piperidin-1-yl)ethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylic acid

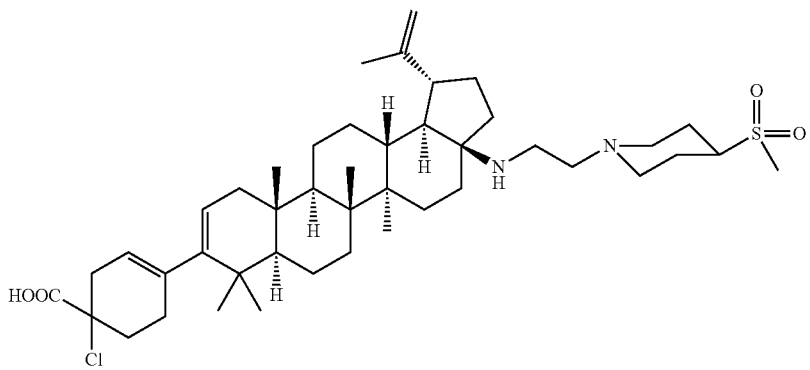

Step 1-Step 4

Same as described in example A7.

Step 5: Preparation of methyl 1-chloro-4-((1R,3aS, 5aR,5bR,7aR,11aS,11bR,13aR,13bR)-5a,5b,8,8,11a-pentamethyl-3a-((2-(4-(methylsulfonyl)piperidin-1-yl)ethyl)amino)-1-(prop-1-en-2-yl)-2,3,3a,4,5,5a,5b, 6,7,7a,8,11,11a,11b,12,13,13a,13b-octadecahydro-1H-cyclopenta[a]chrysen-9-yl)cyclohex-3-enecarboxylate

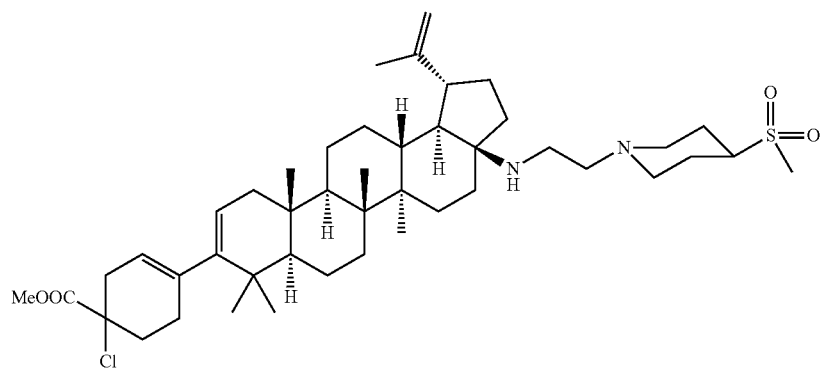

The title compound was prepared following the method described in general procedure Step 5, using (1R,3 aS,5aR, 5bR,7aR,11aR,11bR,13 aR,13bR)-5a,5b,8,8,11a-pentamethyl-3a-((2-(4-(methylsulfonyl)piperidin-1-yl)ethyl) amino)-1-(prop-1-en-2-yl)-2,3,3a,4,5,5a,5b,6,7,7a,8,11,11a, 11b,12,13,13a,13b-octadecahydro-1H-cyclopenta[a] chrysen-9-yl trifluoromethanesulfonate and methyl 1-chloro-4-(4,4,5,5-tetramethyl-1,3,2-dioxaborolan-2-yl)cyclohex-3-enecarboxylate as reactants. The product was isolated as a mixture of diastereomers, which was used in next step without purification. MS: m/e 771.5 (M+H)+, 3.06 min (method 4).

Step 6

1-chloro-4-((1R,3aS,5aR,5bR,7aR,11aS,11bR,13aR, 13bR)-5a,5b,8,8,11a-pentamethyl-3a-((2-(4-(methylsulfonyl)piperidin-1-yl)ethyl)amino)-1-(prop-1-en-2-yl)-2,3,3a, 4,5,5a,5b,6,7,7a,8,11,11a,11b,12,13,13a,13b-octadecahydro-1H-cyclopenta[a]chrysen-9-yl)cyclohex-3-enecarboxylic acid was prepared following the procedure described in general procedure Step 6, using methyl 1-chloro-4-((1R,3 aS,5aR,5bR,7aR,11aS,11bR,13 aR,13bR)-5a,5b,8,8,11a-pentamethyl-3a-((2-(4-(methylsulfonyl)piperidin-1-yl) ethyl)amino)-1-(prop-1-en-2-yl)-2,3,3a,4,5,5a,5b,6,7,7a,8, 11,11a,11b,12,13,13a,13b-octadecahydro-1H-cyclopenta[a] chrysen-9-yl)cyclohex-3-enecarboxylate as reactant. The product was isolated as a mixture of diastereomers (solid, 7% yield). MS: m/e 757.5 (M+H)+, 2.90 min (method 4). $^1$H NMR (400 MHz, CHLOROFORM-d) δ 5.31 (s, 1H), 5.24 (d, J=5.0 Hz, 1H), 4.78 (s, 1H), 4.65 (s, 1H), 3.35-2.40 (m, 14H), 2.87 (s, 3H), 2.32-0.82 (m, 28H), 1.71 (s, 3H), 1.17 (s, 3H), 1.01 (s, 6H), 0.97-0.95 (m, 3H), 0.88 (s, 3H).

Example A9

Preparation of 1-fluoro-4-((1R,3aS,5aR,5bR,7aR, 11aS,11bR,13aR,13bR)-5a,5b,8,8,11a-pentamethyl-3a-((2-(4-(methylsulfonyl)piperidin-1-yl)ethyl) amino)-1-(prop-1-en-2-yl)-2,3,3a,4,5,5a,5b,6,7,7a,8, 11,11a,11b,12,13,13a,13b-octadecahydro-1H-cyclopenta[a]chrysen-9-yl)cyclohex-3-enecarboxylic acid

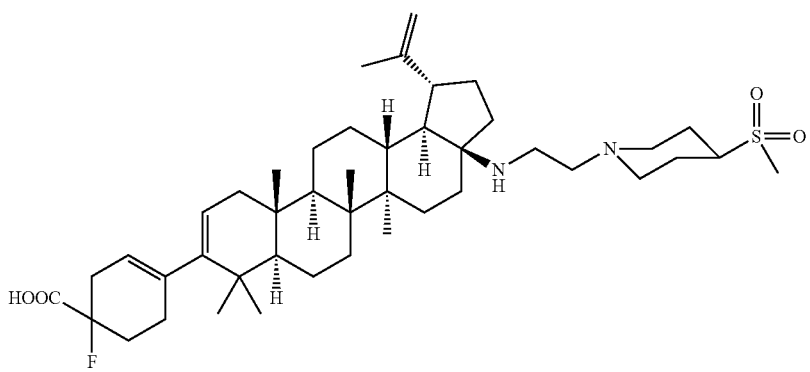

Step 1: Preparation of methyl 1-fluoro-4-((trimethylsilyl)oxy)cyclohex-3-enecarboxylate

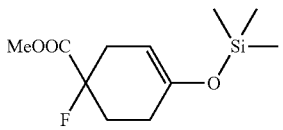 [SMILES: COC(=O)C1(F)CC=C(O[Si](C)(C)C)CC1]

The title compound was prepared following the procedure described in general procedure Step 1, using methyl 2-fluoroacrylate as reactant and taken to the next step without further purification.

Step 2: Preparation of methyl 1-fluoro-4-oxocyclohexanecarboxylate

The title compound was prepared following the procedure described in general procedure Step 2, using methyl 1-fluoro-4-((trimethylsilyl)oxy)cyclohex-3-enecarboxylate as reactant. The product was isolated as an oil in 34% yield. MS: m/e 175.1 (M+H)$^+$, 2.04 min (method 6). $^1$H NMR (400 MHz, CHLOROFORM-d) δ 3.77 (s, 3H), 2.68-2.56 (m, 2H), 2.40-2.15 (m, 6H). $^{19}$F NMR (376 MHz, CHLOROFORM-d) δ −168.02 (s, 1F).

Step 3: Preparation of methyl 1-fluoro-4-(((trifluoromethyl)sulfonyl)oxy)cyclohex-3-enecarboxylate

The title compound was prepared following the procedure described in general procedure Step 3, using methyl 1-fluoro-4-oxocyclohexanecarboxylate as reactant. The product was isolated as an oil in 16% yield. $^1$H NMR (400 MHz, CHLOROFORM-d) δ 5.74-5.70 (m, 1H), 3.85 (s, 3H), 2.94-2.77 (m, 1H), 2.73-2.57 (m, 2H), 2.47-2.38 (m, 1H), 2.35-2.10 (m, 2H). $^{19}$F NMR (376 MHz, CHLOROFORM-d) δ −73.77 (s, 3F), −163.80 (s, 1F).

Step 4: Preparation of methyl 1-fluoro-4-(4,4,5,5-tetramethyl-1,3,2-dioxaborolan-2-yl)cyclohex-3-enecarboxylate

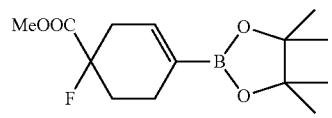 [SMILES: COC(=O)C1(F)CC=C(B2OC(C)(C)C(C)(C)O2)CC1]

The title compound was prepared following the procedure described in general procedure Step 4, using methyl 1-chloro-4-(((trifluoromethyl)sulfonyl)oxy)cyclohex-3-enecarboxylate as reactant. The product was isolated as an oil. $^1$H NMR (400 MHz, CHLOROFORM-d) δ 6.48-6.44 (m, 1H), 3.81 (s, 3H), 2.81-2.64 (m, 1H), 2.55-2.42 (m, 1H), 2.37-2.28 (m, 2H), 2.15-2.07 (m, 1H), 2.01-1.82 (m, 1H), 1.27 (s, 12H). $^{19}$F NMR (376 MHz, CHLOROFORM-d) δ −161.94 (s, 1F)

Step 5: Preparation of methyl 1-fluoro-4-((1R,3aS,5aR,5bR,7aR,11aS,11bR,13aR,13bR)-5a,5b,8,8,11a-pentamethyl-3a-((2-(4-(methylsulfonyl)piperidin-1-yl)ethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylate

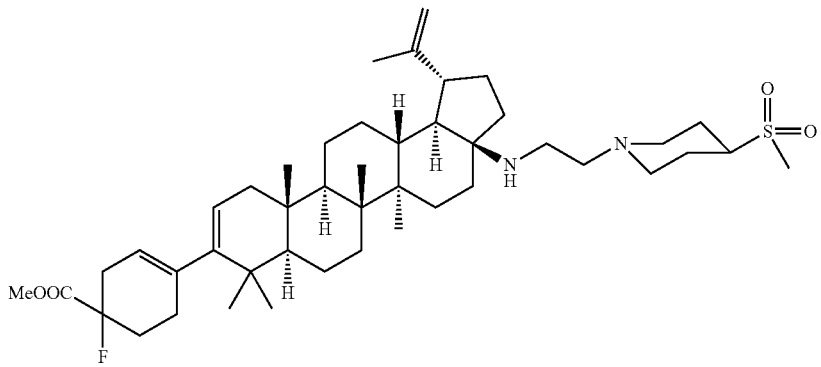

The title compound was prepared following the procedure described in general procedure Step 5, using (1R,3aS,5aR,5bR,7aR,11aR,11bR,13aR,13bR)-5a,5b,8,8,11a-pentamethyl-3a-((2-(4-(methylsulfonyl)piperidin-1-yl)ethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl trifluoromethanesulfonate and methyl 1-chloro-4-(4,4,5,5-tetramethyl-1,3,2-dioxaborolan-2-yl)cyclohex-3-enecarboxylate as reactants. The product was isolated as a mixture of diastereomers, which was used in next step without further purification. MS: m/e 755.5 (M+H)$^+$, 2.94 min (method 4).

Step 6

1-fluoro-4-((1R,3aS,5aR,5bR,7aR,11aS,11bR,13aR,13bR)-5a,5b,8,8,11a-pentamethyl-3a-((2-(4-(methylsulfonyl)piperidin-1-yl)ethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylic acid was prepared following the procedure described in general procedure Step 6, using methyl 1-chloro-4-((1R,3 aS,5aR,5bR,7aR,11aS,11bR,13 aR,13bR)-5a,5b,8,8,11a-pentamethyl-3a-((2-(4-(methylsulfonyl)piperidin-1-yl)ethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylate as reactant. The product was isolated as a mixture of diastereomers (solid, 23% yield). MS: m/e 741.6 (M+H)$^+$, 2.77 min (method 4). $^1$H NMR (400 MHz, CHLOROFORM-d) δ 5.30 (s, 1H), 5.23 (d, J=4.5 Hz, 1H), 4.76 (s, 1H), 4.64 (s, 1H), 3.24-2.73 (m, 6H), 2.85 (s, 3H), 2.61-0.80 (m, 36H), 1.69 (s, 3H), 1.14 (s, 3H), 1.00 (s, 3H), 1.00-0.92 (m, 6H), 0.86 (s, 3H). $^{19}$F NMR (376 MHz, CHLOROFORM-d) δ −157.26-158.46 (m, 1F).

Example A10

Preparation of 1-(2-hydroxyethyl)-4-((1R,3aS,5aR,5bR,7aR,11aS,11bR,13aR,13bR)-5a,5b,8,8,11a-pentamethyl-3a-((2-(4-(methylsulfonyl)piperidin-1-yl)ethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylic acid

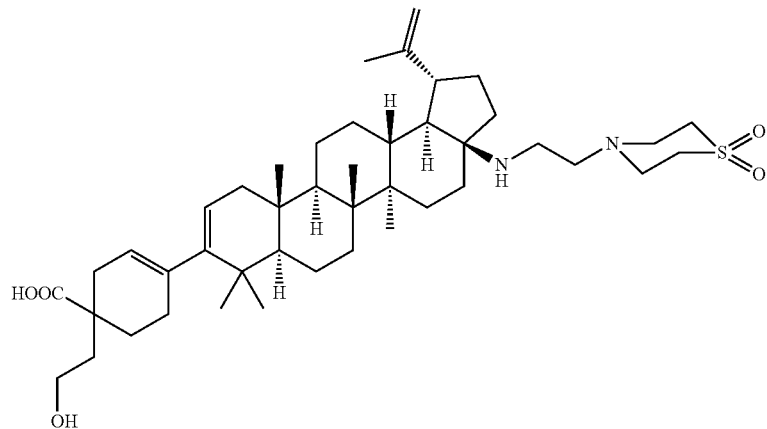

Step 1: Preparation of 8-((trimethylsilyl)oxy)-2-oxaspiro[4.5]dec-7-en-1-one

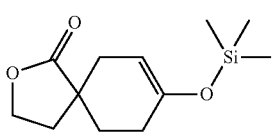 [SMILES: C[Si](C)(C)OC1=CCC2(CCOC2=O)CC1]

The title compound was prepared following the procedure described in general procedure Step 1, using 3-methylenedihydrofuran-2(3H)-one as reactant.

Step 2: Preparation of 2-oxaspiro[4.5]decane-1,8-dione

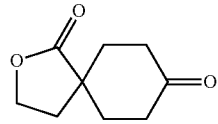 [SMILES: O=C1CCC2(CCOC2=O)CC1]

The title compound was prepared following the procedure described in general procedure Step 2, using 8-((trimethylsilyl)oxy)-2-oxaspiro[4.5]dec-7-en-1-one as reactant. The product was isolated as a solid in 48% yield. MS: m/e 169.1 (M+H)$^+$, 1.43 min (method 6). $^1$H NMR (400 MHz, CHLOROFORM-d) δ 4.38 (t, J=7.0 Hz, 2H), 2.77 (ddd, J=15.0, 8.1, 5.8 Hz, 2H), 2.40-2.31 (m, 2H), 2.31 (t, J=7.0 Hz, 2H), 2.26-2.18 (m, 2H), 1.99-1.91 (m, 2H).

Step 3: Preparation of 1-oxo-2-oxaspiro[4.5]dec-7-en-8-yl trifluoromethanesulfonate

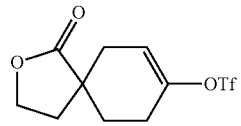 [SMILES: O=C1OCCC12CC=C(OS(=O)(=O)C(F)(F)F)CC2]

The title compound was prepared following the procedure described in general procedure Step 3, using 2-oxaspiro[4.5]decane-1,8-dione as reactant. The product was isolated as an oil in 83% yield. MS: m/e 301.1 (M+H)$^+$, 3.81 min (method 6). $^1$H NMR (400 MHz, CHLOROFORM-d) δ 5.80 (dt, J=5.7, 2.8 Hz, 1H), 4.42-4.30 (m, 2H), 2.65-2.57 (m, 1H), 2.57-2.38 (m, 2H), 2.27-2.14 (m, 3H), 2.09 (ddd, J=13.6, 10.5, 6.5 Hz, 1H), 1.84 (ddt, J=13.5, 5.6, 2.7 Hz, 1H). $^{19}$F NMR (376 MHz, CHLOROFORM-d) δ −73.83 (s, 3F).

Step 4: Preparation of 8-(4,4,5,5-tetramethyl-1,3,2-dioxaborolan-2-yl)-2-oxaspiro[4.5]dec-7-en-1-one

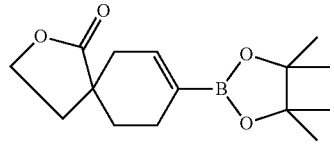 [SMILES: CC1(C)OB(C2=CCC3(CCOC3=O)CC2)OC1(C)C]

The title compound was prepared following the procedure described in general procedure Step 4, using methyl 1-oxo-2-oxaspiro[4.5]dec-7-en-8-yl trifluoromethanesulfonate as reactant. The product was isolated as a solid in 52% yield. ¹H NMR (400 MHz, CHLOROFORM-d) δ 6.53 (dd, J=4.6, 2.1 Hz, 1H), 4.35-4.23 (m, 2H), 2.53-2.33 (m, 2H), 2.18-2.02 (m, 4H), 1.83 (ddd, J=13.1, 11.6, 5.6 Hz, 1H), 1.69-1.62 (m, 1H), 1.32-1.23 (m, 12H).

Step 5: Preparation of 8-((1R,3aS,5aR,5bR,7aR, 11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a, 11b,12,13,13a,13b-octadecahydro-1H-cyclopenta[a]chrysen-9-yl)-2-oxaspiro[4.5]dec-7-en-1-one

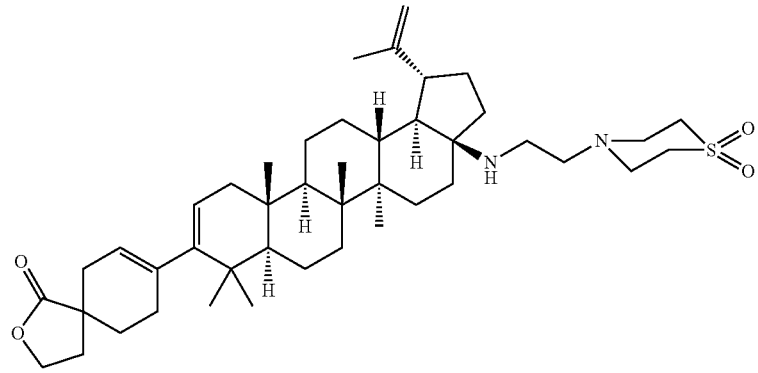

The title compound was prepared following the procedure described in general procedure Step 5, using (1R,3aS,5aR, 5bR,7aR,11aR,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12, 13,13a,13b-octadecahydro-1H-cyclopenta[a]chrysen-9-yl trifluoromethanesulfonate and 8-(4,4,5,5-tetramethyl-1,3,2-dioxaborolan-2-yl)-2-oxaspiro[4.5]dec-7-en-1-one as reactants and 85° C. The product was obtained as a mixture of diasteroisomers and was used without further purification in the next step. MS: m/e 721 (M+H)⁺, 2.72 min (method 4).

Step 6

4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8, 11,11a,11b,12,13,13a,13b-octadecahydro-1H-cyclopenta[a]chrysen-9-yl)-1-(2-hydroxyethyl)cyclohex-3-enecarboxylic acid was prepared following the procedure described in general procedure Step 6, using 8-((1R,3aS,5aR,5bR,7aR,11aS, 11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-2-oxaspiro[4.5]dec-7-en-1-one as reactant. The product was obtained as a mixture of diastereomers (solid, 13%). MS: m/e 739.5 (M+H)⁺, 2.64 min (method 4). ¹H NMR (400 MHz, METHANOL-d₄) δ 5.30 (s, 1H), 5.18 (d, J=4.5 Hz, 1H), 4.72 (s, 1H), 4.62 (s, 1H), 3.65-3.57 (m, 2H), 3.18-3.00 (m, 8H), 2.79-2.64 (m, 4H), 2.60-2.50 (m, 2H), 2.37-0.83 (29H), 1.71 (s, 3H), 1.14 (s, 3H), 1.03 (s, 3H), 0.98-0.94 (m, 6H), 0.90 (s, 3H).

Example A11

Preparation of 1-(2-hydroxyethyl)-4-((1R,3aS,5aR, 5bR,7aR,11aS,11bR,13aR,13bR)-5a,5b,8,8,11a-pentamethyl-3a-((2-(4-(methylsulfonyl)piperidin-1-yl)ethyl)amino)-1-(prop-1-en-2-yl)-2,3,3a,4,5,5a,5b, 6,7,7a,8,11,11a,11b,12,13,13a,13b-octadecahydro-1H-cyclopenta[a]chrysen-9-yl cyclohex-3-enecarboxylic acid

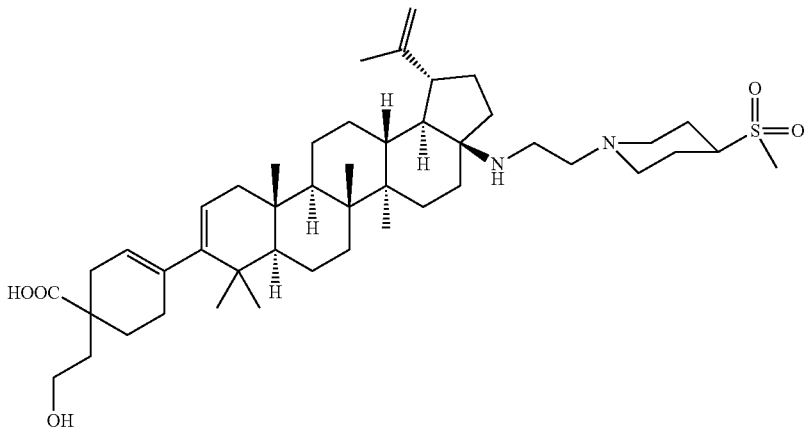

Step 1-Step 4

Same as described in example A10.

Step 5: Preparation of 8-((1R,3aS,5aR,5bR,7aR, 11aS,11bR,13aR,13bR)-5a,5b,8,8,11a-pentamethyl-3a-((2-(4-(methylsulfonyl)piperidin-1-yl)ethyl) amino)-1-(prop-1-en-2-yl)-2,3,3a,4,5,5a,5b,6,7,7a,8, 11,11a,11b,12,13,13a,13b-octadecahydro-1H-cyclopenta[a]chrysen-9-yl)-2-oxaspiro[4.5]dec-7-en-1-one

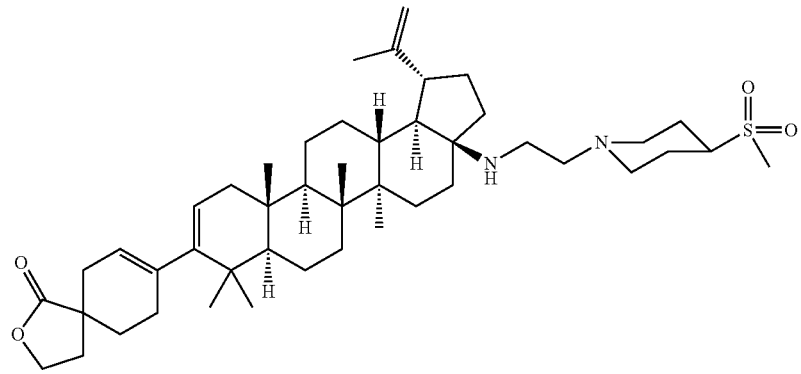

The title compound was prepared following the procedure described in general procedure Step 5, using (1R,3 aS,5aR, 5bR,7aR,11aR,11bR,13 aR,13bR)-5a,5b,8,8,11a-pentamethyl-3a-((2-(4-(methylsulfonyl)piperidin-1-yl)ethyl) amino)-1-(prop-1-en-2-yl)-2,3,3a,4,5,5a,5b,6,7,7a,8,11,11a, 11b,12,13,13a,13b-octadecahydro-1H-cyclopenta[a] chrysen-9-yl trifluoromethanesulfonate and 8-(4,4,5,5-tetramethyl-1,3,2-dioxaborolan-2-yl)-2-oxaspiro[4.5]dec-7-en-1-one as reactants. The product was isolated as diastereomers (solid, 59% yield). MS: m/e 749.7 (M+H)$^+$, 4.10 min (method 7). $^1$H NMR (400 MHz, CHLOROFORM-d) δ 5.35 (d, J=2.8 Hz, 1H), 5.24-5.19 (m, 1H), 4.72 (d, J=2.0 Hz, 1H), 4.59 (dd, J=2.3, 1.5 Hz, 1H), 4.37-4.25 (m, 2H), 3.12 (dd, J=14.6, 12.0 Hz, 2H), 2.87-2.78 (m, 1H), 2.84 (s, 3H), 2.67-2.53 (m, 3H), 2.50-2.40 (m, 3H), 2.33-0.90 (m, 35H), 1.70 (s, 3H), 1.09 (s, 3H), 0.98-0.92 (m, 6H), 0.96 (s, 3H), 0.86 (s, 3H).

Step 6

4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8, 11,11a,11b,12,13,13a,13b-octadecahydro-1H-cyclopenta[a]chrysen-9-yl)-1-(2-hydroxyethyl)cyclohex-3-enecarboxylic acid was prepared following the procedure described in general procedure Step 6, using 8-((1R,3 aS,5aR,5bR,7aR,11aS,11bR,13 aR,13bR)-5a,5b,8,8,11a-pentamethyl-3a-((2-(4-(methylsulfonyl)piperidin-1-yl)ethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-2-oxaspiro[4.5]dec-7-en-1-one as reactant. The product was isolated as a mixture of diastereomers (solid, 51% yield). MS: m/e 767.6 (M+H)$^+$, 2.35 min (method 4). $^1$H NMR (400 MHz, CHLOROFORM-d) δ 5.32 (s, 1H), 5.17 (d, J=5.5 Hz, 1H), 4.73 (s, 1H), 4.61 (s, 1H), 3.78-3.72 (m, 2H), 3.20-3.12 (m, 2H), 2.89-2.80 (m, 1H), 2.85 (s, 3H), 2.78-2.45 (m, 6H), 2.27-0.92 (m, 35H), 1.69 (s, 3H), 1.11 (s, 3H), 0.97 (s, 3H), 0.95-0.90 (m, 6H), 0.86 (s, 3H).

Example A12

Preparation of 4-((1R,3aS,5aR,5bR,7aR,11aS,11bR, 13aR,13bR)-3a-((2-(1,1-dioxidothiomorpholino) ethyl)amino)-5a,5b,8,8,11a-pentamethyl-1-(prop-1-en-2-yl)-2,3,3a,4,5,5a,5b,6,7,7a,8,11,11a,11b,12,13, 13a,13b-octadecahydro-1H-cyclopenta[a]chrysen-9-yl)-1-(hydroxymethyl)cyclohex-3-enecarboxylic acid

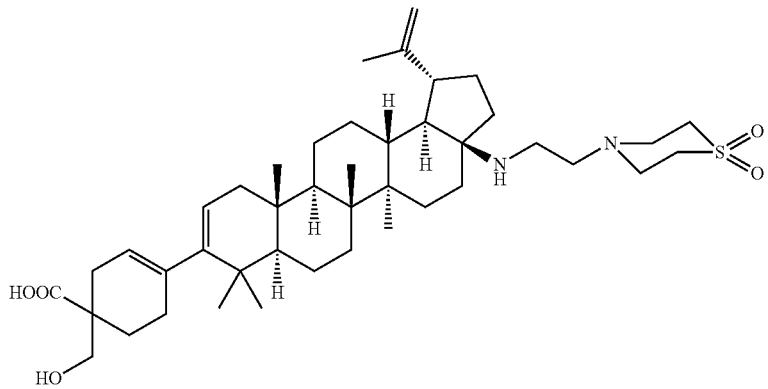

Step 1: Preparation of ethyl 1-(hydroxymethyl)-4-((trimethylsilyl)oxy)cyclohex-3-enecarboxylate

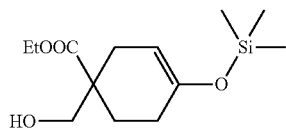

The title compound was prepared following the procedure described in general procedure Step 1, using ethyl 2-(hydroxymethyl)acrylate as reactant.

Step 2 a: Preparation of ethyl 1-(hydroxymethyl)-4-oxocyclohexanecarboxylate

The title compound was prepared following the procedure described in general procedure Step 2, using ethyl 1-(hydroxymethyl)-4-((trimethylsilyl)oxy)cyclohex-3-enecarboxylate as reactant. The product was isolated as a solid in 39% yield. MS: m/e 201.1 (M+H)+, 1.40 min (method 2). ¹H NMR (400 MHz, CHLOROFORM-d) δ 4.28 (q, J=7.0 Hz, 2H), 3.74 (d, J=6.3 Hz, 2H), 2.54-2.33 (m, 6H), 2.08 (t, J=6.4 Hz, 1H), 1.83-1.72 (m, 2H), 1.32 (t, J=7.2 Hz, 3H).

b: Preparation of (1-(ethoxycarbonyl)-4-oxocyclohexyl)methyl benzoate

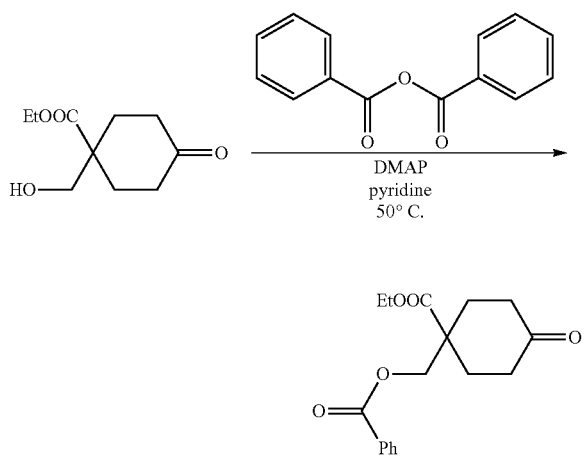

To a solution of ethyl 1-(hydroxymethyl)-4-oxocyclohexanecarboxylate from Step 2a (200 mg, 1 mmol) in pyridine (5 mL) was added DMAP (24.4 mg, 0.2 mmol). The mixture was heated to 50° C. and benzoic anhydride (249 mg, 1.1 mmol) was added. The reaction mixture was stirred at 50° C. for 3 h. The reaction mixture was concentrated in vacuo. The residue was dissolved in CH₂Cl₂ (10 mL), washed with NaHCO₃ (10 mL), dried over Na₂SO₄, filtered and concentrated in vacuo. The crude product was purified by a silica gel column eluted with 20% EtOAc/Hexane to give desired product (288 mg, 95%) as an oil. MS: m/e 305.1 (M+H)+, 3.75 min (method 6). ¹H NMR (400 MHz, CHLOROFORM-d) δ 8.03-7.99 (m, 2H), 7.62-7.56 (m, 1H), 7.49-7.43 (m, 2H), 4.45 (s, 2H), 4.28 (q, J=7.0 Hz, 2H), 2.61-2.38 (m, 6H), 1.90-1.80 (m, 2H), 1.28 (t, J=7.0 Hz, 3H).

Step 3: Preparation of (1-(ethoxycarbonyl)-4-(((trifluoromethyl)sulfonyl)oxy)cyclohex-3-en-1-yl)methyl benzoate

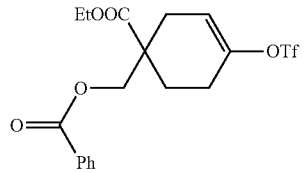 [SMILES: CCOC(=O)C1(COC(=O)c2ccccc2)CC=C(OS(=O)(=O)C(F)(F)F)CC1]

The title compound was prepared following the procedure described in general procedure Step 3, using (1-(ethoxycarbonyl)-4-oxocyclohexyl)methyl benzoate as reactant. The product was isolated as an oil in 89% yield. MS: m/e 437.2 (M+H)+, 4.30 min (method 6). ¹H NMR (400 MHz, CHLOROFORM-d) δ 8.03-7.98 (m, 2H), 7.62-7.56 (m, 1H), 7.48-7.42 (m, 2H), 5.79 (td, J=3.3, 1.8 Hz, 1H), 4.47-4.38 (m, 2H), 4.21 (qd, J=7.2, 2.1 Hz, 2H), 2.91-2.83 (m, 1H), 2.58-2.27 (m, 4H), 1.94 (ddd, J=13.4, 8.5, 6.4 Hz, 1H), 1.24 (t, J=7.0 Hz, 3H). ¹⁹F NMR (376 MHz, CHLOROFORM-d) δ −73.84 (s, 3F).

Step 4: Preparation of (1-(ethoxycarbonyl)-4-(4,4,5,5-tetramethyl-1,3,2-dioxaborolan-2-yl)cyclohex-3-en-1-yl)methyl benzoate

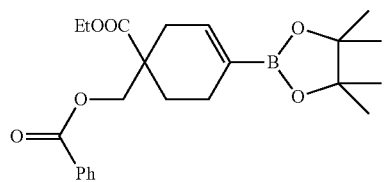 [SMILES: CCOC(=O)C1(COC(=O)c2ccccc2)CC=C(B2OC(C)(C)C(C)(C)O2)CC1]

The title compound was prepared following the procedure described in general procedure Step 4, using (1-(ethoxycarbonyl)-4-(((trifluoromethyl)sulfonyl)oxy)cyclohex-3-en-1-yl)methyl benzoate as reactant. The product was isolated as an oil in 90% yield. ¹H NMR (400 MHz, CHLOROFORM-d) δ 8.00 (dd, J=8.3, 1.3 Hz, 2H), 7.59-7.54 (m, 1H), 7.44 (d, J=8.0 Hz, 2H), 6.56-6.52 (m, 1H), 4.45-4.36 (m, 2H), 4.17 (q, J=7.0 Hz, 2H), 2.76-2.68 (m, 1H), 2.28-2.19 (m, 3H), 2.04-1.96 (m, 1H), 1.91-1.83 (m, 1H), 1.27 (s, 12H), 1.21 (t, J=7.2 Hz, 3H).

Step 5: Preparation of (4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-(ethoxycarbonyl)cyclohex-3-en-1-yl)methyl benzoate 11,11a,11b,12,13,13a,13b-octadecahydro-1H-cyclopenta[a]chrysen-9-yl)-1-(hydroxymethyl)cyclohex-3-enecarboxylic acid was prepared following the procedure described in general procedure Step 6, using (4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-1-

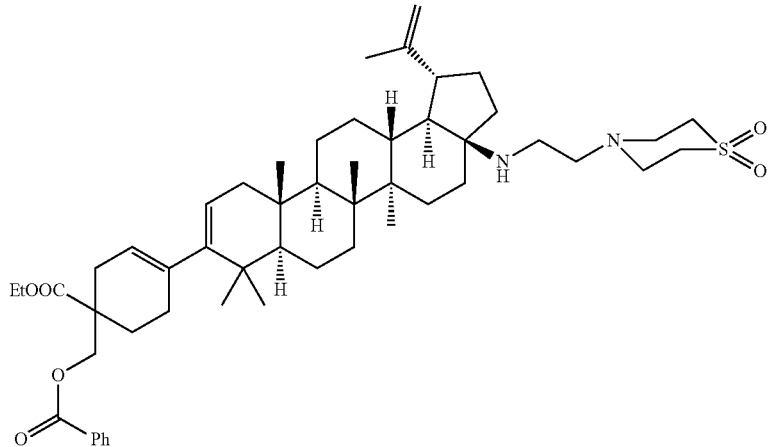

The title compound was prepared following the procedure described in general procedure Step 5, using (1R,3aS,5aR,5bR,7aR,11aR,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl trifluoromethanesulfonate and (1-(ethoxycarbonyl)-4-(4,4,5,5-tetramethyl-1,3,2-dioxaborolan-2-yl)cyclohex-3-en-1-yl)methyl benzoate as reactants at 85° C. The product was obtained as a mixture of diastereomers, which was used in next step without purification. MS: m/e 857.6 (M+H)+, 2.97 min (method 4).

Step 6

4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8, (ethoxycarbonyl)cyclohex-3-en-1-yl)methyl benzoate as reactant. The product was obtained as a mixture of diastereomers (solid, 10%). MS: m/e 725.6 (M+H)+, 2.61 min (method 4). $^1$H NMR (400 MHz, CHLOROFORM-d) δ 5.30 (s, 1H), 5.17 (s, 1H), 4.72 (s, 1H), 4.60 (s, 1H), 3.11-3.04 (m, 2H), 2.78-0.83 (m, 41H) 1.70 (s, 3H), 1.27 (s, 3H), 1.06 (s, 3H), 0.97-0.90 (m, 6H), 0.85 (s., 3H).

Example A13

Preparation of 1-(hydroxymethyl)-4-((1R,3aS,5aR,5bR,7aR,11aS,11bR,13aR,13bR)-5a,5b,8,8,11a-pentamethyl-3a-((2-(4-(methylsulfonyl)piperidin-1-yl)ethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylic acid

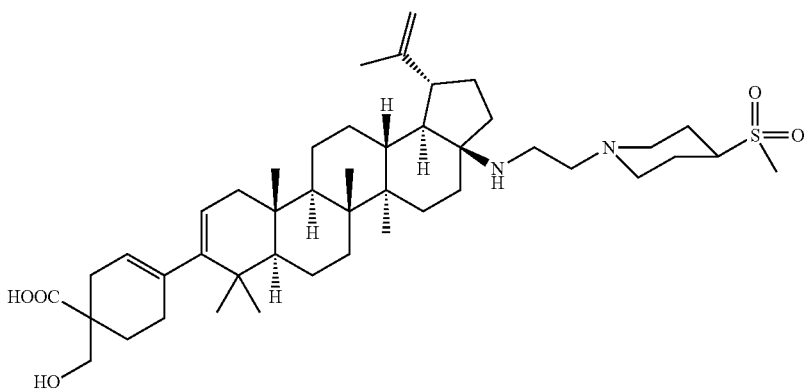

Step 1-Step 4

Same as described in example A12.

Step 5: Preparation of (1-(ethoxycarbonyl)-4-((1R,3aS,5aR,5bR,7aR,11aS,11bR,13aR,13bR)-5a,5b,8,8,11a-pentamethyl-3a-((2-(4-(methylsulfonyl)piperidin-1-yl)ethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-en-1-yl)methyl benzoate

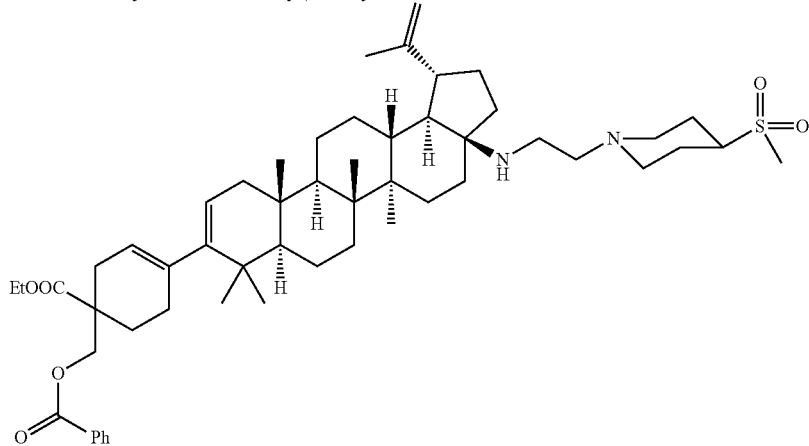

The title compound was prepared as following the procedure described in general procedure Step 5, using (1R,3aS,5aR,5bR,7aR,11aR,11bR,13aR,13bR)-5a,5b,8,8,11a-pentamethyl-3a-((2-(4-(methylsulfonyl)piperidin-1-yl)ethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl trifluoromethanesulfonate and (1-(ethoxycarbonyl)-4-(4,4,5,5-tetramethyl-1,3,2-dioxaborolan-2-yl)cyclohex-3-en-1-yl)methyl benzoate as reactants. The product was obtained as a mixture of diastereomers. MS: m/e 885.6 (M+H)$^+$, 2.80 min (method 4). $^1$H NMR (400 MHz, CHLOROFORM-d) δ 8.01 (dd, J=8.3, 1.3 Hz, 2H), 7.58-7.52 (m, 1H), 7.46-7.40 (m, 2H), 5.35 (s, 1H), 5.19 (d, J=5.8 Hz, 1H), 4.71 (d, J=1.8 Hz, 1H), 4.58 (s, 1H), 4.49-4.38 (m, 2H), 4.21-4.14 (m, 2H), 3.11 (t, J=12.3 Hz, 2H), 2.87-2.77 (m, 1H), 2.83 (s, 3H), 2.72-2.53 (m, 4H), 2.51-2.41 (m, 2H), 2.27-0.78 (m, 33H). 1.69 (s, 3H), 1.22 (t, J=7.0 Hz, 3H), 1.07 (s, 3H), 0.96 (s, 3H), 0.97-0.90 (m, 6H), 0.85 (s, 3H).

Step 6

1-(hydroxymethyl)-4-((1R,3aS,5aR,5bR,7aR,11aS,11bR,13aR,13bR)-5a,5b,8,8,11a-pentamethyl-3a-((2-(4-(methylsulfonyl)piperidin-1-yl)ethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylic acid was prepared following the procedure described in general procedure Step 6, using (1-(ethoxycarbonyl)-4-((1R,3aS,5aR,5bR,7aR,11aS,11bR,13aR,13bR)-5a,5b,8,8,11a-pentamethyl-3a-((2-(4-(methylsulfonyl)piperidin-1-yl)ethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-en-1-yl)methyl benzoate as reactant. The product was obtained as a mixture of diastereomers (solid, 47%). MS: m/e 753.5 (M+H)$^+$, 2.32 min (method 4). $^1$H NMR (400 MHz, CHLOROFORM-d) δ 5.31 (s, 1H), 5.18 (s. 1H), 4.74 (s, 1H), 4.63 (s, 1H), 3.65 (s, 2H), 3.17 (t, J=11.3 Hz, 2H), 2.93-2.66 (m, 5H), 2.85 (s, 3H), 2.62-2.49 (m, 2H), 2.27-0.82 (m, 33H). 1.69 (s, 3H), 1.14 (s, 3H), 0.99 (s, 3H), 0.97-0.90 (m, 6H), 0.86 (s, 3H).

Example A14

Preparation of 6-((1R,3aS,5aR,5bR,7aR,11aS,11bR,13aR,13bR)-3a-(((3-(1,1-dioxidothiomorpholino)propyl)amino)methyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)spiro[3.3]hept-5-ene-2,2-dicarboxylic acid

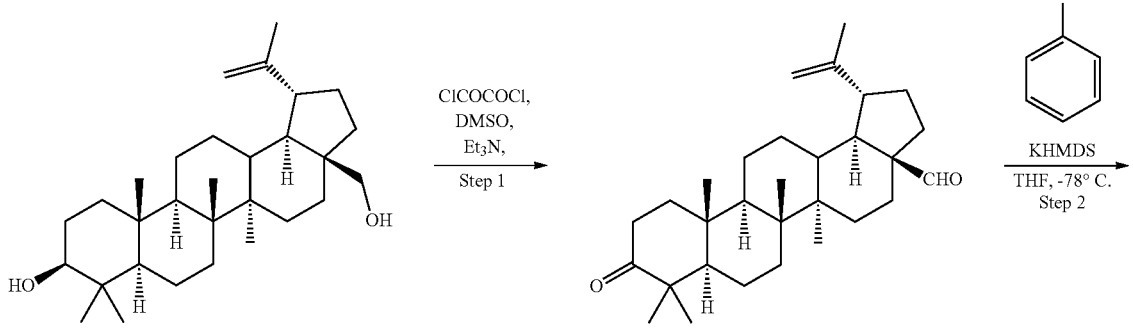

-continued
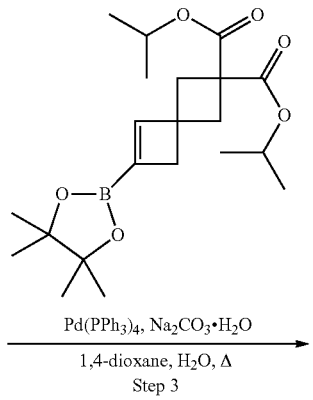
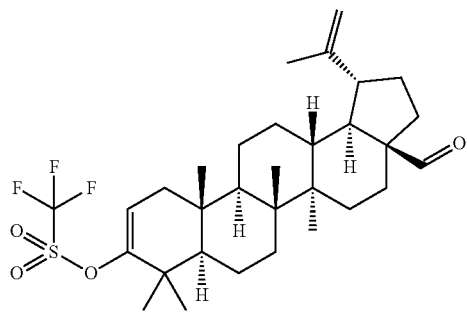
Pd(PPh₃)₄, Na₂CO₃•H₂O
———————————————→
1,4-dioxane, H₂O, Δ
Step 3
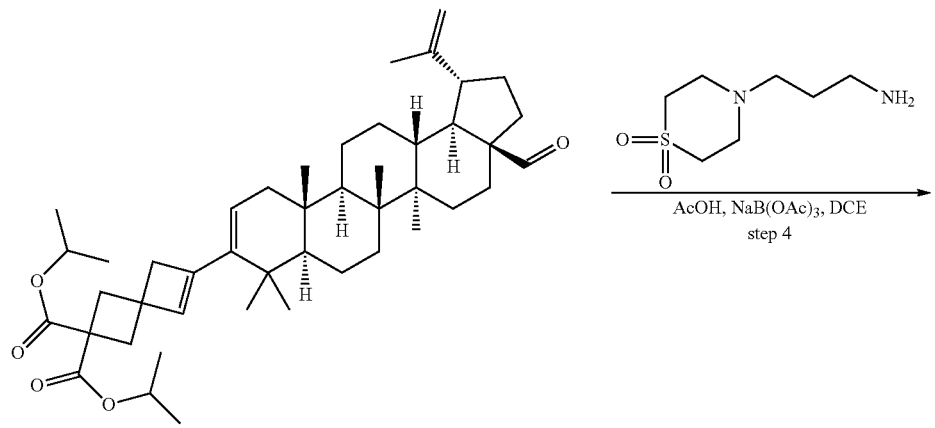
AcOH, NaB(OAc)₃, DCE
———————————————→
step 4
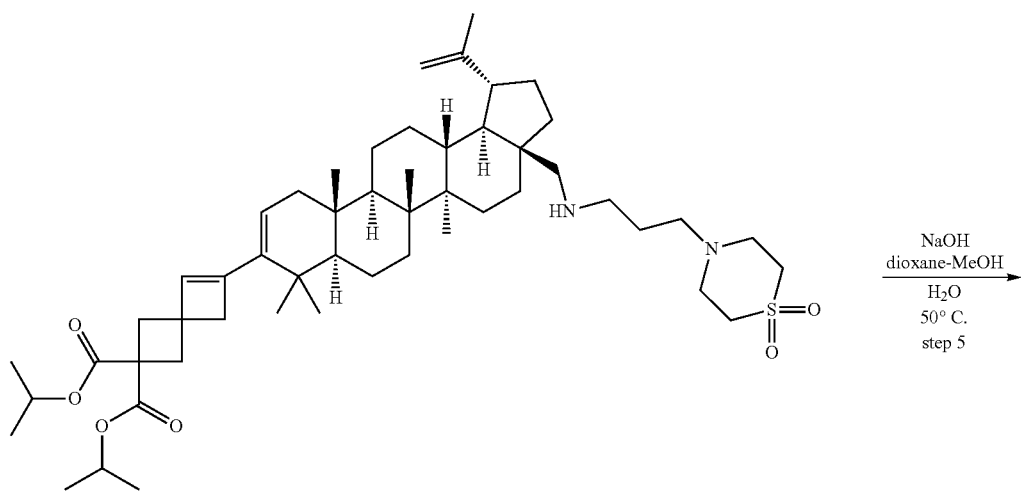
NaOH
dioxane-MeOH
H₂O
50° C.
step 5

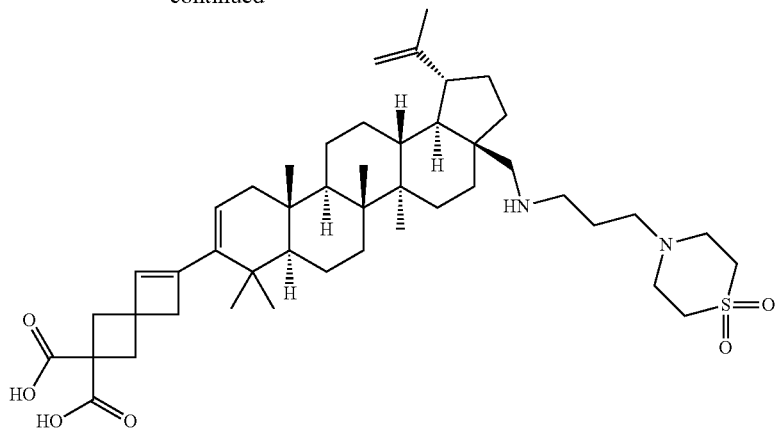

Example A14

Step 1: Preparation of (1R,3aS,5aR,5bR,7aR,11aR, 11bR,13bR)-5a,5b,8,8,11a-pentamethyl-9-oxo-1-(prop-1-en-2-yl)icosahydro-1H-cyclopenta[a]chrysene-3a-carbaldehyde Step 2: Preparation of (1R,3aS,5aR,5bR,7aR,11aR, 11bR,13aR,13bR)-3a-formyl-5a,5b,8,8,11a-pentamethyl-1-(prop-1-en-2-yl)-2,3,3a,4,5,5a,5b,6,7,7a,8, 11,11a,11b,12,13,13a,13b-octadecahydro-1H-cyclopenta[a]chrysen-9-yl trifluoromethanesulfonate

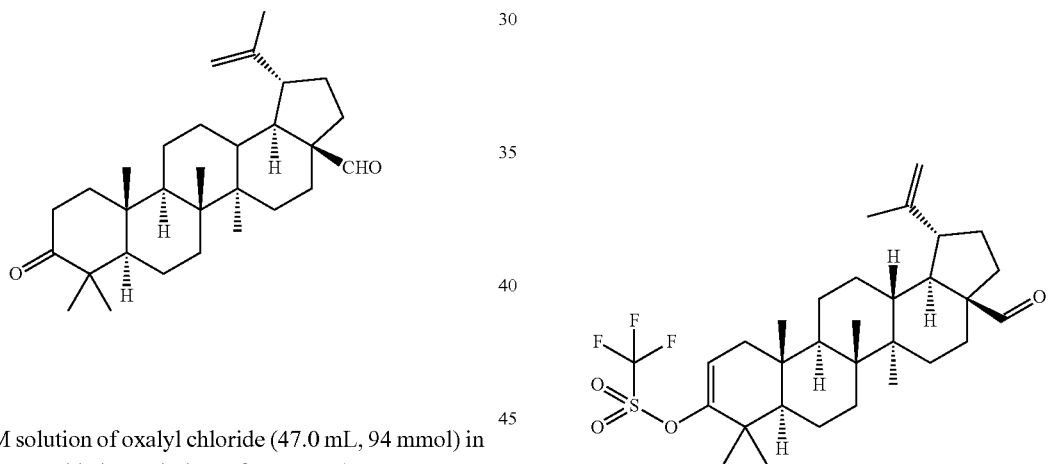

To a 2M solution of oxalyl chloride (47.0 mL, 94 mmol) in CH₂Cl₂, was added a solution of DMSO (13.7 mL, 192 mmol) in CH₂Cl₂ (20 mL) dropwise at −15° C. After 5 min, a solution of (1R,3aS,5aR,5bR,7aR,9S,11aR,11bR,13bR)-3a-(hydroxymethyl)-5a,5b,8,8,11a-pentamethyl-1-(prop-1-en-2-yl)icosahydro-1H-cyclopenta[a]chrysen-9-ol (4.43 g, 10.01 mmol) in a mixture of DMSO (30 mL) and CH₂Cl₂ (50 mL) was added at −15° C. Triethylamine (56 mL) was added 15 minutes later and the stirring was continued for another 10 min. The reaction mixture was allowed to warm up to RT. The reaction was quenched by addition of water (100 mL), and the reaction mixture was extracted with CH₂Cl₂ (70 mL×3). The combined organic layers were washed with brine (30 mL×3), dried over MgSO₄, filtered and concentrated. The crude material was purified using silica gel chromatography eluted with a mixture of ethyl acetate and hexanes, to give the product as a solid (3.3 g 75%). LCMS: m/e 461.15 (M+Na)⁺, 2.91 min (method 2).

The title compound was prepared following the procedure described in method 1 for the preparation of intermediate 1, Step 5, using (1R,3aS,5aR,5bR,7aR,11aR,11bR,13bR)-5a, 5b,8,8,11a-pentamethyl-9-oxo-1-(prop-1-en-2-yl)icosahydro-1H-cyclopenta[a]chrysene-3a-carbaldehyde as the starting material. (71% yield). $^1$H NMR (400 MHz, CHLOROFORM-d) δ 9.69 (d, J=1.8 Hz, 1H), 5.58 (dd, J=6.7, 2.1 Hz, 1H), 4.89-4.54 (m, 2H), 2.90 (td, J=11.0, 5.8 Hz, 1H), 2.28-2.00 (m, 3H), 2.00-1.64 (m, 7H), 1.60-1.55 (m, 3H), 1.53-1.18 (m, 11H), 1.14 (s, 3H), 1.08 (d, J=7.8 Hz, 1H), 1.03 (s, 3H), 1.00 (s, 3H), 0.97 (s, 3H), 0.93 (s, 3H)

Step 3: Preparation of diisopropyl 6-((1R,3aS,5aR, 5bR,7aR,11aS,11bR,13aR,13bR)-3a-formyl-5a,5b,8, 8,11a-pentamethyl-1-(prop-1-en-2-yl)-2,3,3a,4,5,5a, 5b,6,7,7a,8,11,11a,11b,12,13,13a,13b-octadecahydro-1H-cyclopenta[a]chrysen-9-yl)spiro [3.3]hept-5-ene-2,2-dicarboxylate

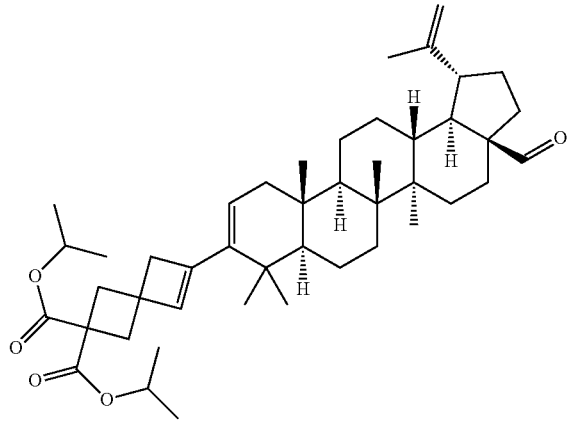

The title compound was prepared following the method for the preparation of Example 1, Step 1 described above, using (1R,3aS,5aR,5bR,7aR,11aR,11bR,13aR,13bR)-3a-formyl-5a,5b,8,8,11a-pentamethyl-1-(prop-1-en-2-yl)-2,3,3a,4,5, 5a,5b,6,7,7a,8,11,11a,11b,12,13,13a,13b-octadecahydro-1H-cyclopenta[a]chrysen-9-yl trifluoromethanesulfonate as the reactant (83% yield). MS: m/e 687.5 (M+H)$^+$, 4.16 min (method 8). $^1$H NMR (400 MHz, CHLOROFORM-d) δ 9.68 (d, J=1.3 Hz, 1H), 5.86 (s, 1H), 5.51 (dd, J=6.1, 1.9 Hz, 1H), 5.16-4.97 (m, 2H), 4.77 (d, J=1.5 Hz, 1H), 4.64 (s, 1H), 2.89 (td, J=11.1, 5.9 Hz, 1H), 2.74-2.66 (m, 4H), 2.61-2.49 (m, 2H), 2.21-2.01 (m, 3H), 1.96-1.18 (m, 33H), 1.17 (s, 3H), 1.05 (m, 4H), 0.98 (s, 3H), 0.94 (s, 3H), 0.81 (s, 3H)

Step 4: Preparation of diisopropyl 6-((1R,3aS,5aR, 5bR,7aR,11aS,11bR,13aR,13bR)-3a-(((3-(1,1-dioxidothiomorpholino)propyl)amino)methyl)-5a,5b,8,8, 11a-pentamethyl-1-(prop-1-en-2-yl)-2,3,3a,4,5,5a, 5b,6,7,7a,8,11,11a,11b,12,13,13a,13b-octadecahydro-1H-cyclopenta[a]chrysen-9-yl)spiro [3.3]hept-5-ene-2,2-dicarboxylate To a solution of diisopropyl 6-((1R,3aS,5aR,5bR,7aR, 11aS,11bR,13aR,13bR)-3a-formyl-5a,5b,8,8,11a-pentamethyl-1-(prop-1-en-2-yl)-2,3,3a,4,5,5a,5b,6,7,7a,8,11,11a, 11b,12,13,13a,13b-octadecahydro-1H-cyclopenta[a] chrysen-9-yl)spiro[3.3]hept-5-ene-2,2-dicarboxylate (100 mg, 0.146 mmol) from Step 3 in DCE (2 mL) was added acetic acid (0.017 mL, 0.291 mmol) and 4-(3-aminopropyl) thiomorpholine 1,1-dioxide (56.0 mg, 0.291 mmol). The mixture was stirred at RT for 2 h, then to the mixture was added sodium triacetoxyborohydride (154 mg, 0.728 mmol) and it was stirred for 24 hours. The mixture was diluted with 7 mL of sat. NaHCO$_3$ and extracted with dichloromethane (3×7 mL). The organic layers were combined and dried with Na$_2$SO$_4$. The drying agent was removed by filtration and the filtrate was concentrated under reduced pressure. The crude product was purified over a silica gel column eluted with mixture of ethyl acetate and hexanes. The fractions containing the expected product were combined to give the title compound as a white solid (90 mg, 71.6% yield). MS: m/e 863.9 (M+H)$^+$, 3.03 min (method 2). $^1$H NMR (400 MHz, CHLOROFORM-d) δ 5.85 (s, 1H), 5.54-5.43 (m, 1H), 5.14-4.96 (m, 2H), 4.68 (d, J=2.0 Hz, 1H), 4.57 (s, 1H), 3.12-2.90 (m, 9H), 2.83-2.63 (m, 7H), 2.63-2.50 (m, 4H), 2.42 (td, J=11.0, 5.8 Hz, 1H), 2.28-2.17 (m, 1H), 2.13-2.03 (m, 1H), 1.98-1.29 (m, 17H), 1.27-1.18 (m, 16H), 1.13 (s, 3H), 1.09-1.00 (m, 10H), 0.97 (s, 3H), 0.84-0.75 (m, 3H).

Step 5

To a solution of diisopropyl 6-((1R,3aS,5aR,5bR,7aR, 11aS,11bR,13aR,13bR)-3a-(((3-(1,1-dioxidothiomorpholino)propyl)amino)methyl)-5a,5b,8,8,11a-pentamethyl-1-(prop-1-en-2-yl)-2,3,3a,4,5,5a,5b,6,7,7a,8,11,11a,11b,12, 13,13a,13b-octadecahydro-1H-cyclopenta[a]chrysen-9-yl) spiro[3.3]hept-5-ene-2,2-dicarboxylate (90 mg, 0.104 mmol) in dioxane (3 mL) and MeOH (2 mL) was added 1N NaOH (2 mL, 2 mmol). The mixture was stirred at 50° C. for 12 h. The crude product was purified by preparative HPLC using method 14. The fractions containing the expected product were combined and concentrated to give 6-((1R,3aS,5aR, 5bR,7aR,11aS,11bR,13aR,13bR)-3a-(((3-(1,1-dioxidothiomorpholino)propyl)amino)methyl)-5a,5b,8,8,11a-pentamethyl-1-(prop-1-en-2-yl)-2,3,3a,4,5,5a,5b,6,7,7a,8,11,11a,

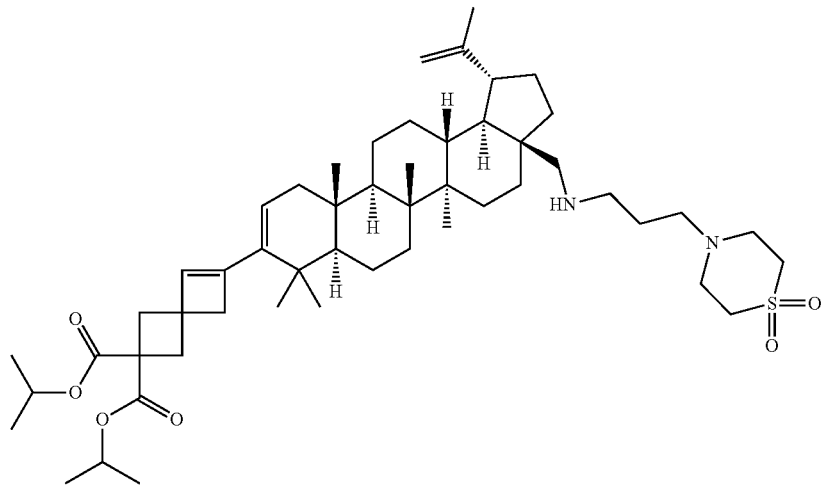

11b,12,13,13a,13b-octadecahydro-1H-cyclopenta[a]chrysen-9-yl)spiro[3.3]hept-5-ene-2,2-dicarboxylic acid as a white solid (2 mg, 2.46%). MS: m/e 779.5 (M+H)$^+$, 2.31 min (method 2). $^1$H NMR (400 MHz, DMSO-d$_6$) δ 6.02 (s, 1H), 5.48 (d, J=4.5 Hz, 1H), 4.71 (s, 1H), 4.60 (s, 1H), 3.12 (d, J=4.8 Hz, 5H), 3.01 (br. s., 4H), 2.91 (br. s., 5H), 2.72-2.64 (m, 1H), 2.57-2.49 (m 6H), 2.17-1.96 (m, 2H), 1.82 (d, J=5.8 Hz, 5H), 1.67 (m, 8H), 1.53-1.17 (m, 12H), 1.13 (s, 3H), 1.05 (m, 6H), 0.97 (s, 3H), 0.78 (s, 3H).

Example A15

Preparation of 2-(3-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclopent-3-en-1-yl)acetic acid

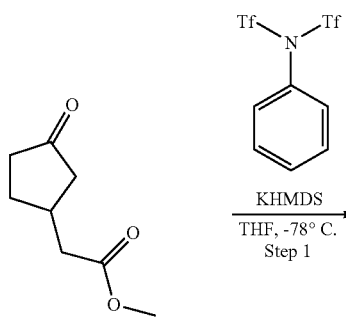
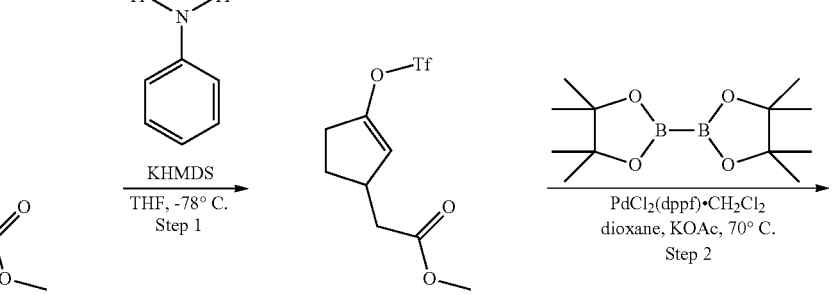

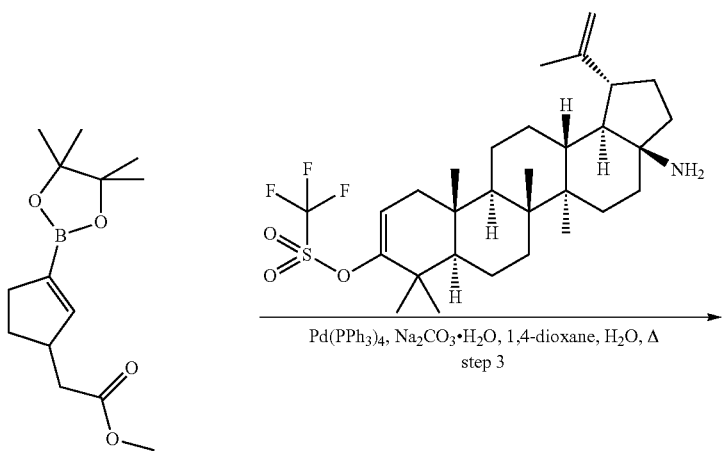

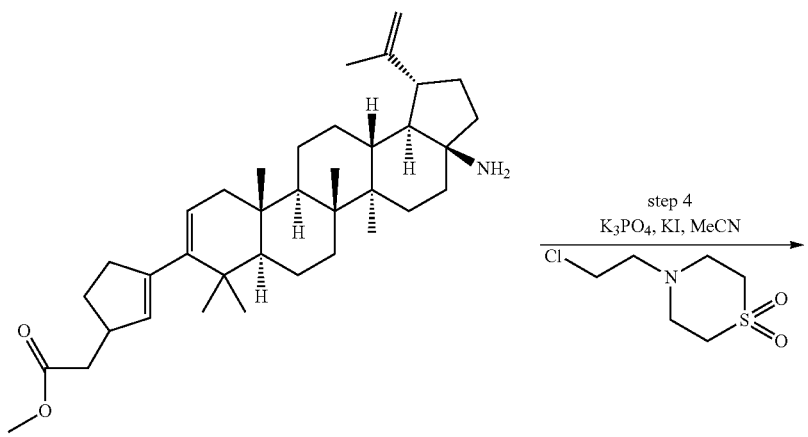

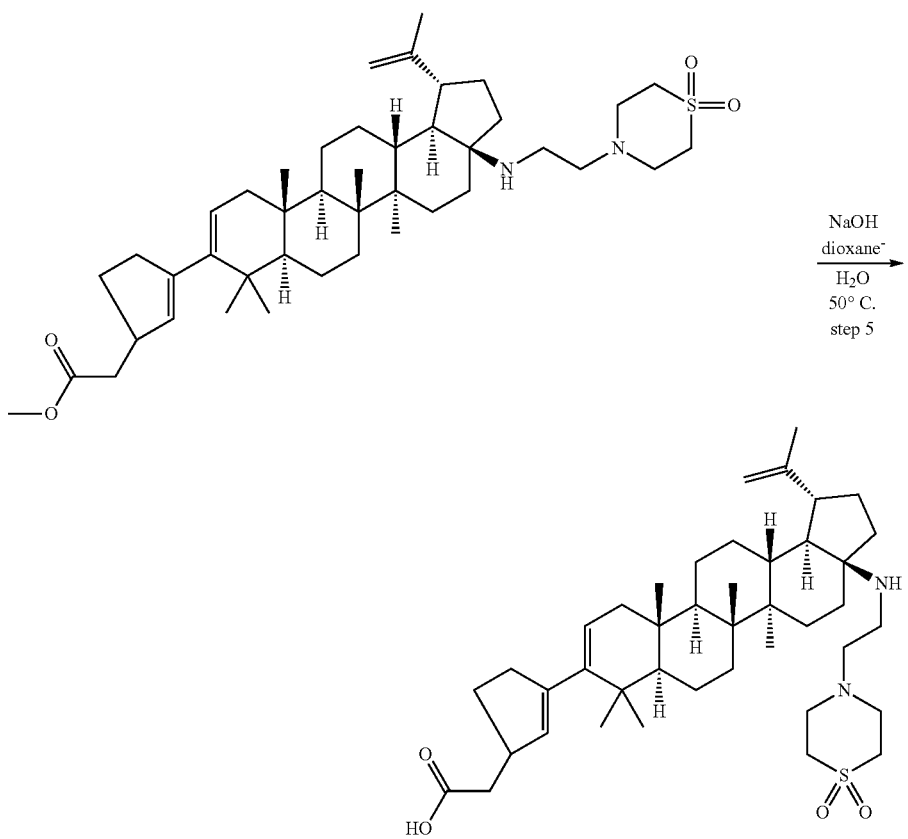

Example A15

Step 1: Preparation of methyl 2-(3-(((trifluoromethyl)sulfonyl)oxy)cyclopent-3-en-1-yl)acetate Step 2: Preparation of methyl 2-(3-(4,4,5,5-tetramethyl-1,3,2-dioxaborolan-2-yl)cyclopent-2-en-1-yl)acetate

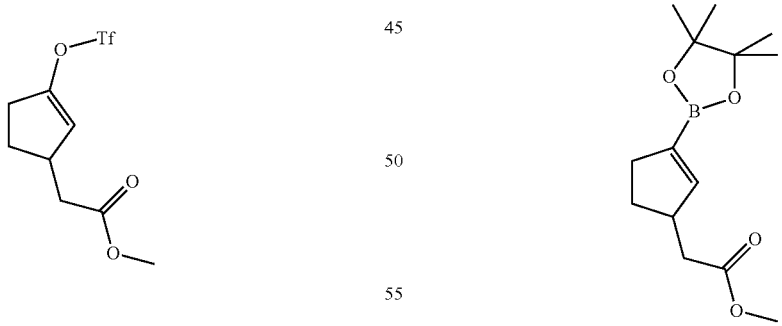

The title compound was prepared following the procedure described in method 2 for the preparation of intermediate 1, Step 6, using methyl 2-(3-oxocyclopentyl)acetate as the reactant. (50.1% yield). $^1$H NMR (400 MHz, CHLOROFORM-d) δ 5.66 (q, J=2.1 Hz, 1H), 3.73 (br. s., 3H), 3.29-3.13 (m, 1H), 2.95-2.78 (m, 1H), 2.67-2.57 (m, 2H), 2.49-2.40 (m, 1H), 2.40-2.28 (m, 1H), 1.77-1.63 (m, 1H). $^{19}$F NMR (376 MHz, CHLOROFORM-d) δ −73.53 (s, 3F).

The title compound was prepared following the method for the preparation of methyl 6-(4,4,5,5-tetramethyl-1,3,2-dioxaborolan-2-yl)spiro[3.3]hept-5-ene-2-carboxylate, Step 2 described above, using methyl 2-(3-(((trifluoromethyl)sulfonyl)oxy)cyclopent-3-en-1-yl) acetate as the reactant. (65.0% yield). $^1$H NMR (400 MHz, CHLOROFORM-d) δ 6.44 (q, J=2.0 Hz, 1H), 3.72-3.62 (m, 3H), 3.24-3.09 (m, 1H), 2.77-2.65 (m, 1H), 2.49-2.38 (m, 1H), 2.38-2.24 (m, 1H), 2.21-2.09 (m, 2H), 1.52-1.38 (m, 1H), 1.29 (s, 12H).

195

Step 3: Preparation of methyl 2-(3-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclopent-2-en-1-yl)acetate

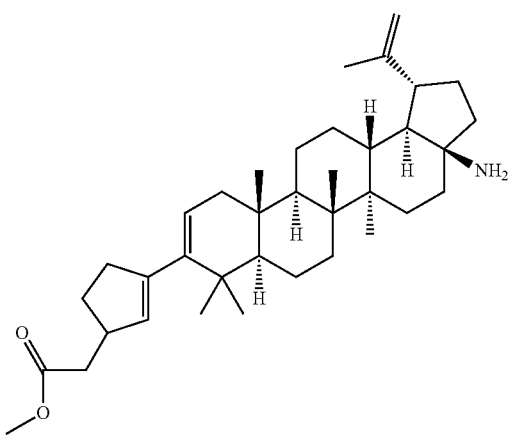

The title compound was prepared as a mixture of diastereomers in 55.7% yield following the method for the preparation of Example 1, Step 1 described above, using (1R,3aS,5aR,5bR,7aR,11aR,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl trifluoromethanesulfonate and methyl 2-(3-(4,4,5,5-tetramethyl-1,3,2-dioxaborolan-2-yl)cyclopent-2-en-1-yl)acetate as the reactant. MS: m/e 531.5 (M−16)$^+$, 2.69 min (method 3). $^1$H NMR (400 MHz, CHLOROFORM-d) δ 5.54 (s, 1H), 5.50-5.44 (m, 1H), 4.73 (s, 1H), 4.60 (s, 1H), 3.67 (s, 3H), 3.14 (t, J=7.0 Hz, 1H), 2.81-2.61 (m, 1H), 2.59-2.27 (m, 5H), 2.16-1.96 (m, 4H), 1.79-1.18 (m, 20H), 1.09-1.02 (m, 11H), 0.96 (s, 3H), 0.85 (s, 3H).

196

Step 4: Preparation of methyl 2-(3-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclopent-2-en-1-yl)acetate

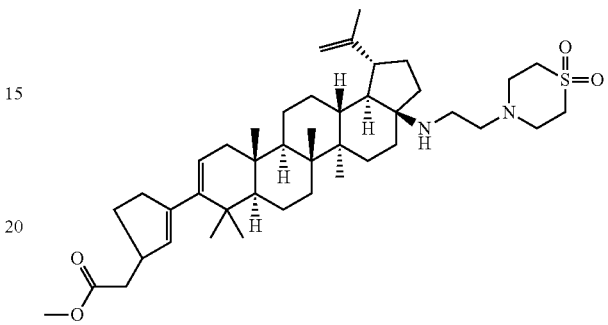

The title compound was prepared following the method of Example 1, Step 2 described above, using methyl 2-(3-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclopent-2-en-1-yl)acetate as the reactant. The product was isolated as a mixture of diastereomers in quantitative yield. MS: m/e 709.8 (M+H)$^+$, 3.126 min (method 3). $^1$H NMR (400 MHz, CHLOROFORM-d) δ 5.60-5.52 (m, 1H), 5.50-5.45 (m, 1H), 4.71 (br. s., 1H), 4.59 (br. s., 1H), 3.76-3.59 (m, 3H), 3.17-2.96 (m, 13H), 2.76-2.52 (m, 4H), 2.50-2.27 (m, 3H), 2.22-1.98 (m, 3H), 1.95-1.21 (m, 20H), 1.13-1.01 (m, 11H), 0.94 (s, 3H), 0.83 (s, 3H).

Step 5

2-(3-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclopent-2-en-1-yl)acetic acid was prepared following the method for the preparation of Example 4, Step 3 described above, purified by prep HPLC with method 8, using methyl 2-(3-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclopent-2-en-1-yl)acetate as the reactant. The product was obtained as a mixture of diastereomers in 3% yield. MS: m/e 695.8 (M+H)$^+$, 2.542 min (method 3). $^1$H NMR (400 MHz, METHANOL-d$_4$) δ 5.68-5.54 (m, 1H), 5.51-5.38 (m, 1H), 4.74 (br. s., 1H), 4.64 (s, 1H), 3.22-3.00 (m, 9H), 2.98-2.69 (m, 5H), 2.65-2.31 (m, 2H), 2.31-2.18 (m, 2H), 2.06 (m, 2H), 1.97-1.83 (m, 9H), 1.77-1.68 (m, 3H), 1.66-1.22 (m, 12H), 1.17 (s, 3H), 1.09 (m, 2H), 1.02 (m, 6H), 0.87 (s, 3H).

Example A16
Preparation of 4-((1R,3aS,5aR,5bR,7aR,11aS,11bR, 13aR,13bR)-3a-((2-(1,1-dioxidothiomorpholino) ethyl)amino)-5a,5b,8,8,11a-pentamethyl-1-(prop-1-en-2-yl)-2,3,3a,4,5,5a,5b,6,7,7a,8,11,11a,11b,12,13, 13a,13b-octadecahydro-1H-cyclopenta[a]chrysen-9-yl)-2-methylcyclohexa-1,3-dienecarboxylic acid
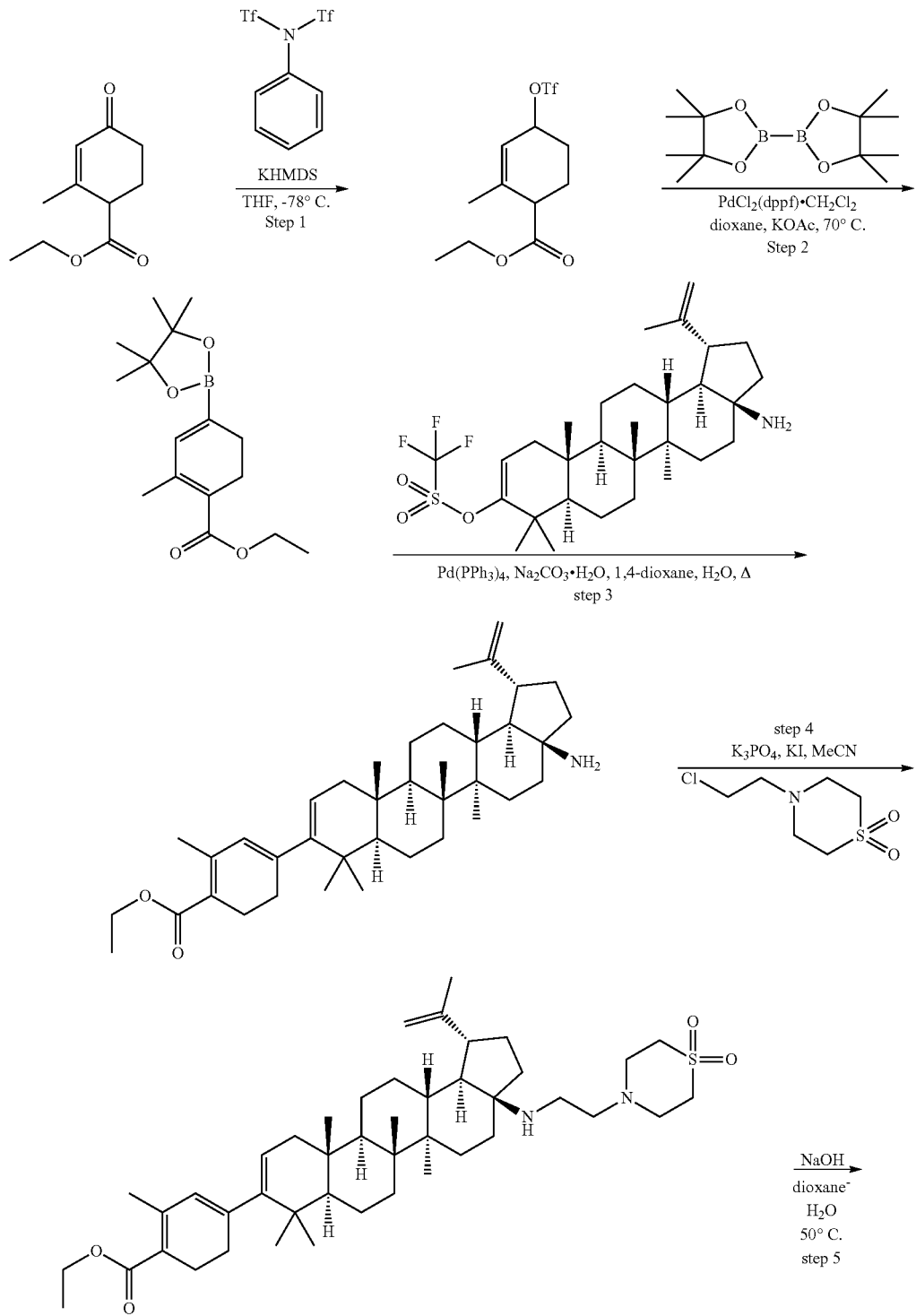

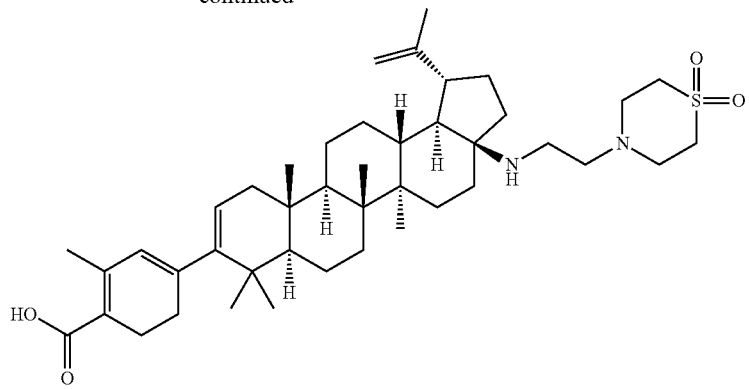

Example A16

Step 1: Preparation of ethyl 2-methyl-4-(((trifluoromethyl)sulfonyl)oxy)cyclohexa-2,4-dienecarboxylate

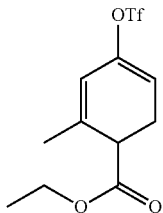 [SMILES: CCOC(=O)C1CC=C(OS(=O)(=O)C(F)(F)F)C=C1C]

The title compound was prepared following the procedure described in Method 2 for the preparation of Intermediate 1, Step 6, using ethyl 2-methyl-4-oxocyclohex-2-enecarboxylate as the reactant. (62.7% yield). $^1$H NMR (400 MHz, CHLOROFORM-d) δ 5.93 (t, J=1.3 Hz, 1H), 4.30-4.09 (m, 2H), 2.83-2.68 (m, 2H), 2.62-2.43 (m, 2H), 2.18 (t, J=1.9 Hz, 3H), 1.37-1.20 (m, 3H). $^{19}$F NMR (376 MHz, CHLOROFORM-d) δ −73.63 (s, 3F).

Step 2: Preparation of ethyl 2-methyl-4-(4,4,5,5-tetramethyl-1,3,2-dioxaborolan-2-yl)cyclohexa-1,3-dienecarboxylate

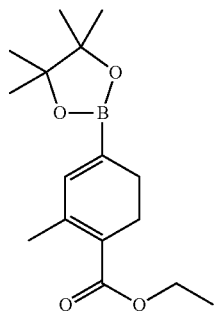 [SMILES: CCOC(=O)C1=C(C)C=C(B2OC(C)(C)C(C)(C)O2)CC1]

The title compound was prepared following the method for the preparation of methyl 6-(4,4,5,5-tetramethyl-1,3,2-dioxaborolan-2-yl)spiro[3.3]hept-5-ene-2-carboxylate, Step 2 described above in page 65-67, using ethyl 2-methyl-4-(((trifluoromethyl)sulfonyl)oxy)cyclohexa-2,4-dienecarboxylate as the reactant. (57.8% yield). $^1$H NMR (400 MHz, CHLOROFORM-d) δ 6.64 (t, J=1.6 Hz, 1H), 4.28-4.15 (m, 2H), 2.46-2.32 (m, 2H), 2.29-2.19 (m, 2H), 2.18 (t, J=1.8 Hz, 3H), 1.38-1.25 (m, 15H).

Step 3: Preparation of ethyl 4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-2-methylcyclohexa-1,3-dienecarboxylate The title compound was prepared following the method for the preparation of Example 1, Step 1 described above, using (1R,3aS,5aR,5bR,7aR,11aR,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl trifluoromethanesulfonate and ethyl 2-methyl-4-(4,4,5,5-tetramethyl-1,3,2-dioxaborolan-2-yl)cyclohexa-1,3-dienecarboxylate as reactants. MS: m/e 557.4 (M−16)$^+$, 2.47 min (method 2). $^1$H NMR (400 MHz, CHLOROFORM-d) δ 5.65 (s, 1H), 5.28 (d, J=5.8 Hz, 1H), 4.72 (s, 1H), 4.59 (s, 1H), 4.25-4.16 (m, 2H), 2.62-2.48 (m, 1H), 2.48-2.34 (m, 2H), 2.31-2.17 (m, 2H), 2.15 (s, 3H), 2.09-1.97 (m, 2H), 1.80-1.35 (m, 17H), 1.35-1.18 (m, 9H), 1.18-1.04 (m, 6H), 1.02-1.00 (s, 3H), 0.96 (s, 3H), 0.89 (s, 3H).

Step 4: Preparation of ethyl 4-((1R,3aS,5aR,5bR, 7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-2-methylcyclohexa-1,3-dienecarboxylate

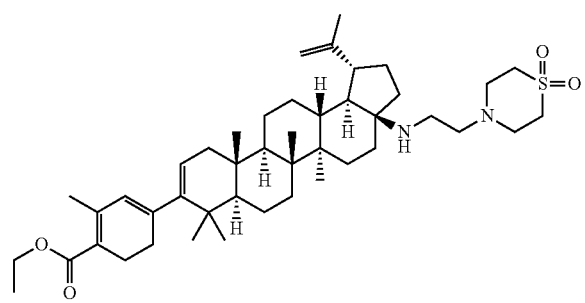

The title compound was prepared following the method described above in Step 2 for the preparation of 6-((1R,3aS,5aR,5bR,7aR,11aS,11bR,13aR,13bR)-3a-(((3-(1,1-dioxidothiomorpholino)propyl)amino)methyl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)spiro[3.3]hept-5-ene-2,2-dicarboxylic acid (example A14), using ethyl 4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-2-methylcyclohexa-1,3-dienecarboxylate as the reactant. (quantitative yield). MS: m/e 735.8 (M+H)$^+$, 3.41 min (method 3). $^1$H NMR (400 MHz, CHLOROFORM-d) δ 5.65 (s, 1H), 5.28 (dd, J=6.0, 1.5 Hz, 1H), 4.71 (s, 1H), 4.59 (s, 1H), 4.19 (q, J=7.1 Hz, 2H), 3.15-2.97 (m, 8H), 2.73-2.51 (m, 4H), 2.50-2.38 (m, 3H), 2.22 (q, J=8.3 Hz, 2H), 2.15 (s, 3H), 2.06-1.18 (m, 25H), 1.11-1.04 (m, 6H), 1.00 (s, 3H), 0.98-0.95 (m, 6H), 0.88 (s, 3H).

Step 5

4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-2-methylcyclohexa-1,3-dienecarboxylic acid was prepared in 5.46% yield following the method described above in Step 3 for the preparation of Example 4, using ethyl 4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-2-methylcyclohexa-1,3-dienecarboxylate as the reactant. The crude was purified by preparative HPLC with method 14 to afford the title compound in 83% yield. MS: m/e 707.7 (M+H)$^+$, 2.573 min (method 3). $^1$H NMR (400 MHz, CHLOROFORM-d) δ 5.70 (s, 1H), 5.32 (br. s., 1H), 4.78 (br. s., 1H), 4.65 (br. s., 1H), 3.29-3.00 (m, 9H), 2.94-2.63 (m, 4H), 2.53-2.42 (m, 2H), 2.35-2.24 (m, 2H), 2.22 (s, 3H), 2.15-2.01 (m, 2H), 2.01-1.81 (m, 4H), 1.72 (m, 3H), 1.67-1.17 (m, 15H), 1.04-0.96 (m, 9H), 0.91 (s, 3H).

Intermediate A

Preparation of (R)-ethyl 2-methyl-5-(4,4,5,5-tetramethyl-1,3,2-dioxaborolan-2-yl)-4H-1,3-dioxine-2-carboxylate

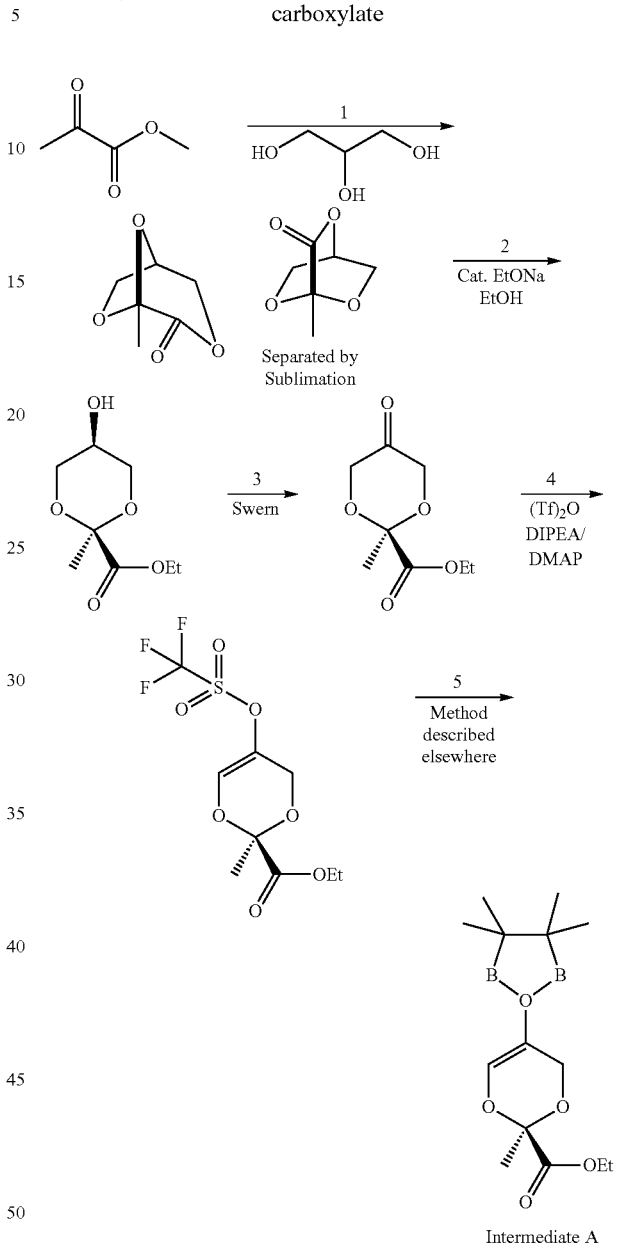

Step 1: Preparation of 1-methyl-2,5,7-trioxabicyclo[2.2.2]octan-6-one

The procedure of Gelas and Thiallier [Carbohydrate Research, 30 (1973) 21-34] was used to prepare a mixture of 5-methyl-3,6,8-trioxabicyclo[3.2.1]octan-4-one and 1-methyl-2,5,7-trioxabicyclo[2.2.2]octan-6-one. Further separation of the isomeric mixture was achieved by vacuum sublimation of the gummy mixture material at 35 micron Hg at bath temperature <56° C. The more volatile, symmetrical, desired [2.2.2]product condensed as a hard solid (43%), the other unsymmetrical [3.2.1] isomer remained as a thick gummy substance in the pot (45%). $^1$H NMR (400 MHz, CHLOROFORM-d) δ 4.80-4.77 (m, 1H), 4.14 (d, J=1.5 Hz, 4H), 1.57 (s, 3H).

Step 2: Preparation of ethyl 5-hydroxy-2-methyl-1,3-dioxane-2-carboxylate

A solution of sodium ethoxide was prepared by dissolving metallic sodium (0.05 g, 2.175 mmol) in absolute ethanol (15 mL). To this, was added 1-methyl-2,5,7-trioxabicyclo[2.2.2]octan-6-one (1.29 g, 8.95 mmol) from Step 1 forming a clear solution. Ring opening was allowed to proceed at RT for 5 hours. The reaction was quenched by the addition of acidic Dowex resin (50W 8X-200, ~equivalent with respect to the amount of sodium used) with stirring. The mixture was filtered and concentrated into a syrup 2.1 gm (82%). $^1$H NMR (400 MHz, CHLOROFORM-d) δ 4.32 (q, J=7.1 Hz, 2H), 3.99-3.89 (m, 1H), 3.57-3.49 (m, 2H), 1.54 (s, 3H), 1.36 (t, J=7.2 Hz, 3H).

Step 3: Preparation of ethyl 2-methyl-5-oxo-1,3-dioxane-2-carboxylate

To a chilled (−78° C.) DCM solvent (10 mL) under nitrogen was added a 2 M stock solution of oxalyl chloride (6.03 mL, 12.05 mmol), followed by the slow addition of dimethyl sulfoxide (0.927 mL, 13.06 mmol). Once evolution of gases stopped, stirring continued for another 20 minutes forming a snow white suspension. A solution of the crude ethyl 5-hydroxy-2-methyl-1,3-dioxane-2-carboxylate (Step 2, 1.91 g, 10.04 mmol) in 5 mL of DCM was transferred into the cold Swern solution over a period of 2 minutes via a cannula. The reaction was allowed to proceed at −78° C. for 30 minutes, followed by the slow addition of triethylamine (3.36 mL, 24.10 mmol). The resulting pale suspension was stirred at −78° C. for a further 30 minutes, then at 4° C. (ice bath) for 15 minutes. The Rx was quenched with saturated sodium bicarbonate solution (20 mL), followed by extraction with DCM (5×25 mL). The organic layers were combined, evaporated to an oily material (1.81 gm, 96%). $^1$H NMR (400 MHz, CHLOROFORM-d) δ 4.45-4.37 (m, 2H), 4.31 (q, J=7.3 Hz, 2H), 4.33-4.26 (m, 2H), 1.58 (s, 3H), 1.36 (t, J=7.2 Hz, 3H).

Step 4: Preparation of ethyl 2-methyl-5-(((trifluoromethyl)sulfonyl)oxy)-4H-1,3-dioxine-2-carboxylate To a chilled (−78° C.) solution of ethyl 2-methyl-5-oxo-1,3-dioxane-2-carboxylate (350 mg, 1.860 mmol) and N,N-dimethylpyridin-4-amine (250 mg, 2.046 mmol) in DCM (4 mL) was added N-ethyl-N-isopropylpropan-2-amine (0.356 mL, 2.046 mmol) and trifluoromethanesulfonic anhydride (0.344 mL, 2.046 mmol) forming a reddish suspension. The mixture was stirred in a dry-ice bath under nitrogen such that the bath temperature was allowed to rise to −15° C. over a period of 4 hours. The crude reaction mixture was diluted with 20 mL DCM forming a clear solution, followed by the addition of 20 mL of hexanes forming a light suspension. It was quickly filtered through a short bed (~½") of silica gel (type-H), washed with a 1:1 v/v mixture of DCM and hexanes, the filtrate was collected for concentration under vacuum at sub-ambient temperature (~15-17° C.) to give a semi-solid. It was only briefly dried before it was stored at −20° C. in the fridge readying for the next step without further purification. $^1$H NMR (400 MHz, CHLOROFORM-d) δ 6.93 (t, J=1.6 Hz, 1H), 4.56 (dd, J=15.1, 1.5 Hz, 1H), 4.35 (dd, J=14.9, 1.9 Hz, 1H), 4.30 (q, J=7.2 Hz, 2H), 1.68 (s, 3H), 1.34 (t, J=7.2 Hz, 3H). $^{19}$F NMR (376 MHz, CHLOROFORM-d) δ −72.61.

Step 5

To a crude sample (Step 4) of ethyl 2-methyl-5-(((trifluoromethyl)sulfonyl)oxy)-4H-1,3-dioxine-2-carboxylate (68 mg, 0.212 mmol) was added reagents: potassium acetate (50.0 mg, 0.510 mmol), 4,4,4',4',5,5,5',5'-octamethyl-2,2'-bi(1,3,2-dioxaborolane) (64.7 mg, 0.255 mmol) and 1,1'-bis(diphenylphosphino)ferrocene-palladium(II) dichloride dichloromethane complex (8.67 mg, 10.62 mmol), and finally dioxane (2 mL). The reaction vessel was rapidly chilled to −78° C., purged with nitrogen 4 times. The frozen mixture was allowed to warm into a bright orange solution. It was immersed into an oil bath at 60° C. for 100 minutes. The flask was removed from the oil bath, cooled to RT and filtered through a short bed of silica gel, washed with a 1:1 mixture of DCM and Hexanes. All the volatile solvents were evaporated at RT and the crude product was sufficiently pure for the next step without further purification. $^1$H NMR (400 MHz, CHLOROFORM-d) δ 7.04 (t, J=1.8 Hz, 1H), 4.45-4.39 (m, 1H), 4.30 (dd, J=15.7, 1.9 Hz, 1H), 4.31-4.24 (m, 2H), 1.64 (s, 3H), 1.32 (t, J=7.2 Hz, 3H), 1.27 (s, 12H).

Example A17

Preparation of 5-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-2-methyl-4H-1,3-dioxine-2-carboxylic acid

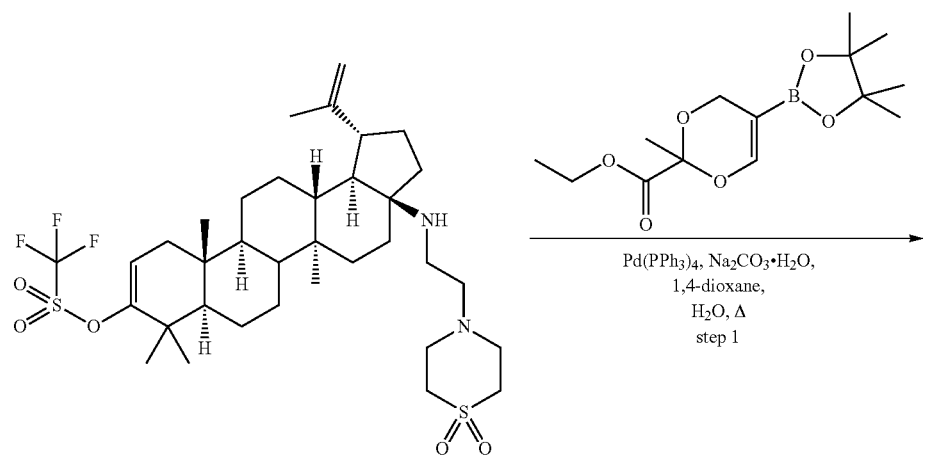

-continued

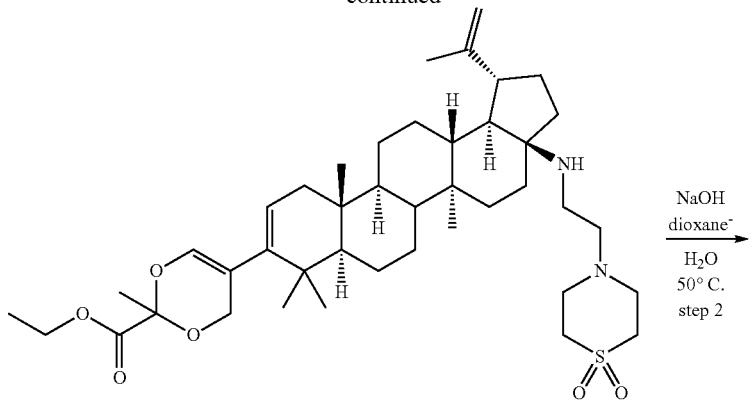

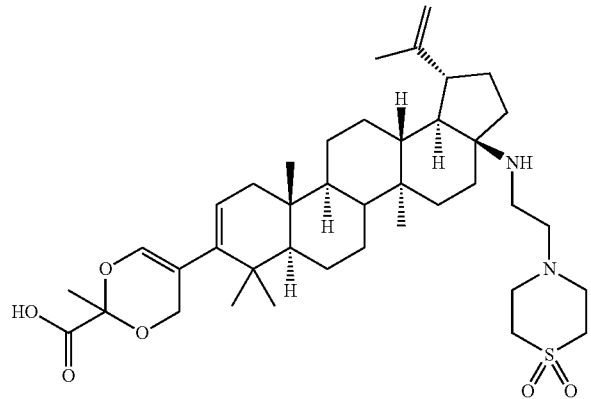

Example A17

Step 1: Preparation of ethyl 5-((1R,3aS,5aR,5bR, 7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-2-methyl-4H-1,3-dioxine-2-carboxylate

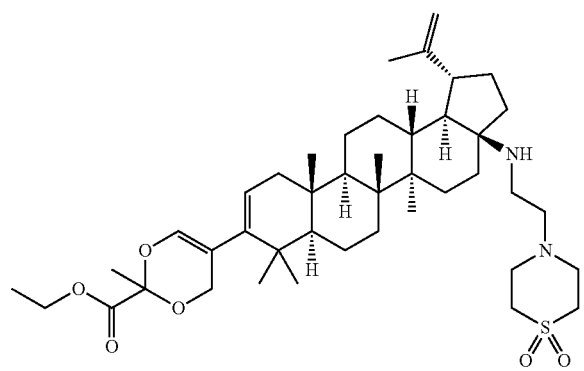

The title compound was prepared following the method described in step 1 for the preparation of Example 1, using (1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl trifluoromethanesulfonate and ethyl 2-methyl-5-(4,4,5,5-tetramethyl-1,3,2-dioxaborolan-2-yl)-4H-1,3-dioxine-2-carboxylate as the reactants. The product was isolated as a mixture of diasteromers in 13.3% yield. MS: m/e 741.55 (M+H)+, 2.72 min (method 8). $^1$H NMR (400 MHz, CHLOROFORM-d) δ 6.35-6.30 (m, 1H), 5.36 (d, J=5.5 Hz, 1H), 4.73 (s, 1H), 4.60 (s, 1H), 4.42 (ddd, J=15.4, 7.6, 1.4 Hz, 1H), 4.33-4.21 (m, 2H), 4.20-4.12 (m, 1H), 3.14-3.00 (m, 11H), 2.80-2.47 (m, 2H), 2.12-1.73 (m, 2H), 1.69 (s, 3H), 1.62 (s, 3H), 1.55-1.19 (m, 11H), 1.10-1.02 (m, 12H), 1.00-0.94 (m, 6H), 0.92-0.87 (m, 3H), 0.86-0.78 (m, 6H).

Step 2

5-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-2-methyl-4H-1,3-dioxine-2-carboxylic acid was prepared following the method described in step 3 for the preparation of Example 4 using ethyl 5-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)-2-methyl-4H-1,3-dioxine-2-carboxylate as the reactant. The crude was purified by prep HPLC with method 13 to afford the title compound as a mixture of diasteromers in 17.8% yield. MS: m/e 713.8 (M+H)+, 2.41 min (method 3). $^1$H NMR (400 MHz, CHLOROFORM-d) δ 6.41-6.27 (m, 1H), 5.41-5.29 (m, 1H), 4.79-4.70 (m, 1H), 4.67-4.61 (m, 1H), 4.54-4.39 (m, 1H), 4.29-4.12 (m, 1H), 3.14 (br. s., 13H), 2.39-1.81 (m, 15H), 1.71 (s, 3H), 1.65-1.2 (m, 10H), 1.11 (br. s., 3H), 1.01 (br. s., 6H), 0.90 (br. s., 3H), 0.83 (br. s., 3H).

Example A18
Preparation of 3-((1R,3aS,5aR,5bR,7aR,11aS,11bR, 13aR,13bR)-3a-((2-(1,1-dioxidothiomorpholino) ethyl)amino)-5a,5b,8,8,11a-pentamethyl-1-(prop-1-en-2-yl)-2,3,3a,4,5,5a,5b,6,7,7a,8,11,11a,11b,12,13, 13a,13b-octadecahydro-1H-cyclopenta[a]chrysen-9-yl)bicyclo[3.1.0]hex-2-ene-6-carboxylic acid
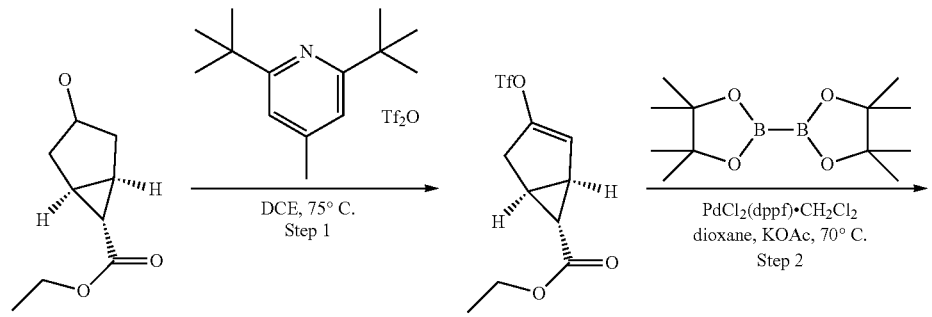
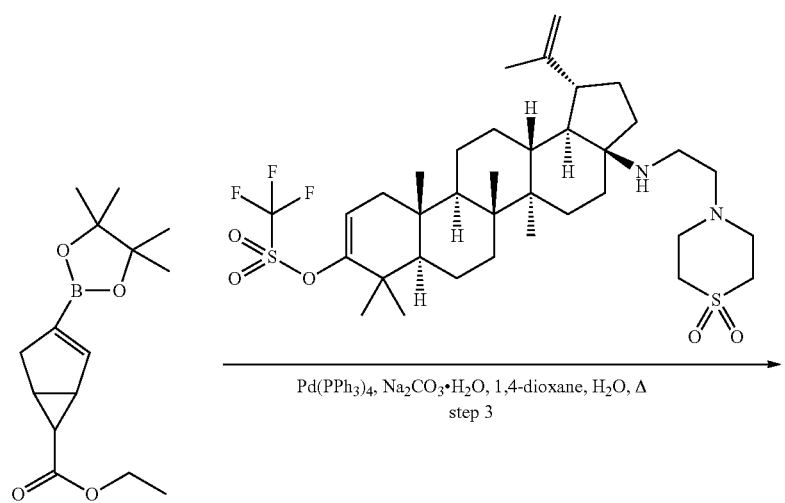
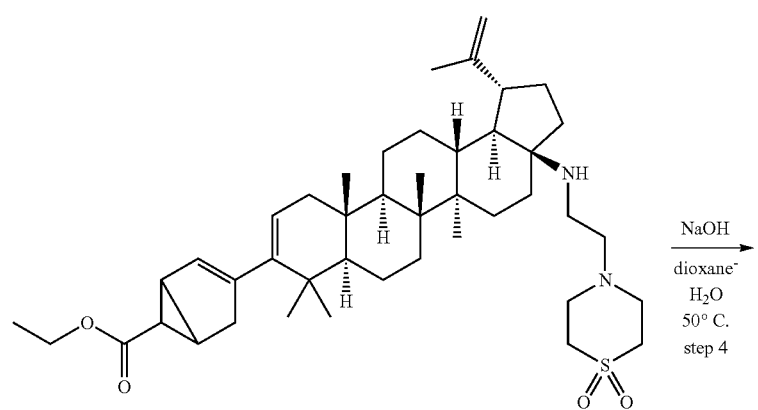

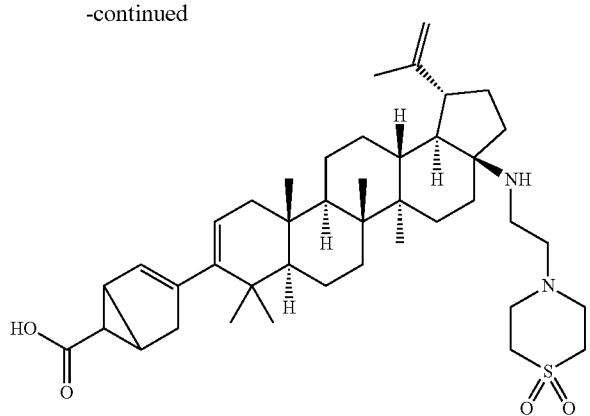

Example A18

Step 1: Preparation of (1S,5S,6R)-ethyl 3-(((trifluoromethyl)sulfonyl)oxy)bicyclo[3.1.0]hex-2-ene-6-carboxylate

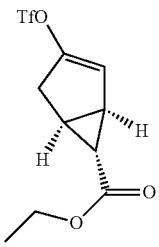 [SMILES: CCOC(=O)[C@H]1[C@@H]2C=C(OS(=O)(=O)C(F)(F)F)C[C@@H]21]

The title compound was prepared in 34.5% yield following the procedure described in WO 2012/003497, using (±)-(1R,5S,6R)-ethyl 3-oxobicyclo[3.1.0]hexane-6-carboxylate (racemic fragment unless otherwise noted) as the reactant. And (±)-(1R,5S,6R)-ethyl 3-oxobicyclo[3.1.0]hexane-6-carboxylate was prepared following procedures described in WO 2011/075515. MS: m/e 301.05 (M+H)$^+$, 2.689 min (method 8) $^1$H NMR (400 MHz, CHLOROFORM-d) δ 5.89 (d, J=1.8 Hz, 1H), 4.24-4.05 (m, 2H), 3.01 (ddd, J=18.1, 7.2, 1.8 Hz, 1H), 2.70 (d, J=18.3 Hz, 1H), 2.41 (dq, J=7.1, 2.6 Hz, 1H), 2.19 (td, J=7.2, 3.3 Hz, 1H), 1.41-1.33 (m, 1H), 1.30-1.20 (m, 3H), $^{19}$F NMR (376 MHz, CHLOROFORM-d) δ −73.22 (s, 3F).

Step 2: Preparation of ethyl 3-(4,4,5,5-tetramethyl-1,3,2-dioxaborolan-2-yl)bicyclo[3.1.0]hex-2-ene 6-carboxylate

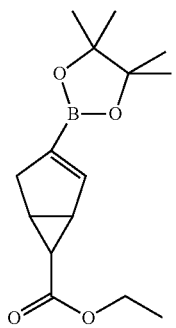 [SMILES: CCOC(=O)C1C2C=C(B3OC(C)(C)C(C)(C)O3)CC21]

The title compound was prepared in quantitative yield following the method described in step 2 for the preparation of methyl 6-(4,4,5,5-tetramethyl-1,3,2-dioxaborolan-2-yl)spiro[3.3]hept-5-ene-2-carboxylate, using (±)-(1S,5S,6R)-ethyl 3-(((trifluoromethyl)sulfonyl)oxy)bicyclo[3.1.0]hex-2-ene-6-carboxylate as the reactant. $^1$H NMR (500 MHz, CHLOROFORM-d) δ 6.67 (q, J=2.0 Hz, 1H), 4.27-3.98 (m, 2H), 2.89-2.72 (m, 1H), 2.63-2.53 (m, 1H), 2.54-2.41 (m, 1H), 2.28 (td, J=6.2, 3.3 Hz, 1H), 1.33-1.15 (m, 16H).

Step 3: Preparation of ethyl 3-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)bicyclo[3.1.0]hex-2-ene-6-carboxylate

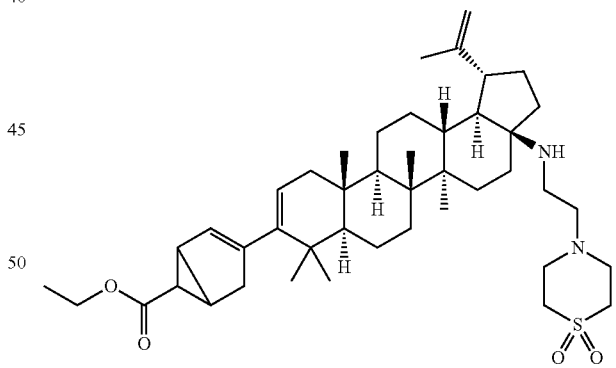

The title compound was prepared following the method described in step 1 for the preparation of Example 1, using (1R,3aS,5aR,5bR,7aR,11aR,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl trifluoromethanesulfonate and ethyl 3-(4,4,5,5-tetramethyl-1,3,2-dioxaborolan-2-yl)bicyclo[3.1.0]hex-2-ene 6-carboxylate as the reactants. The title compound was obtained as a mixture of diastereomers in 54% yield. MS: m/e 721.55 (M+H)$^+$, 2.901 min (method 8). $^1$H NMR (400 MHz, CHLOROFORM-d) δ 5.81 (dd, J=6.3, 1.5 Hz, 1H), 5.50-5.37

(m, 1H), 4.72 (d, J=2.0 Hz, 1H), 4.60 (d, J=0.8 Hz, 1H), 4.19-4.05 (m, 3H), 3.11-3.00 (m, 7H), 2.97-2.82 (m, 1H), 2.74-2.43 (m, 6H), 2.17 (td, J=6.6, 3.1 Hz, 1H), 2.09-2.01 (m, 2H), 2.00-1.73 (m, 3H), 1.70 (s, 3H), 1.66-1.18 (m, 20H), 1.16-1.01 (m, 11H), 0.97 (m, 3H), 0.83 (m, 3H).

Step 4

3-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)bicyclo[3.1.0]hex-2-ene-6-carboxylic acid was prepared following the method described in step 3 for the preparation of Example 4 using ethyl 3-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)bicyclo[3.1.0]hex-2-ene-6-carboxylate as the reactant. The crude was purified by prep HPLC with method 13 to afford the title compound as a mixture of diastereomers in 43.1% yield. MS: m/e 693.55 (M+H)$^+$, 2.649 min (method 8). $^1$H NMR (400 MHz, CHLOROFORM-d) δ 5.86 (s, 1H), 5.43 (d, J=4.5 Hz, 1H), 4.76 (s, 1H), 4.65 (s, 1H), 3.20-3.01 (m, 8H), 3.00-2.81 (m, 3H), 2.78-2.56 (m, 5H), 2.51 (d, J=2.3 Hz, 1H), 2.24-1.74 (m, 12H), 1.71 (s, 3H), 1.65-1.19 (m, 9H), 1.15 (s, 3H), 1.12 (s, 3H), 1.07-1.02 (m, 2H), 1.02-0.99 (m, 6H), 0.80 (s, 3H).

Examples A19 and A20

Preparation of 4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclopent-3-ene-1,2-dicarboxylic acid, Isomer 1 and Isomer 2

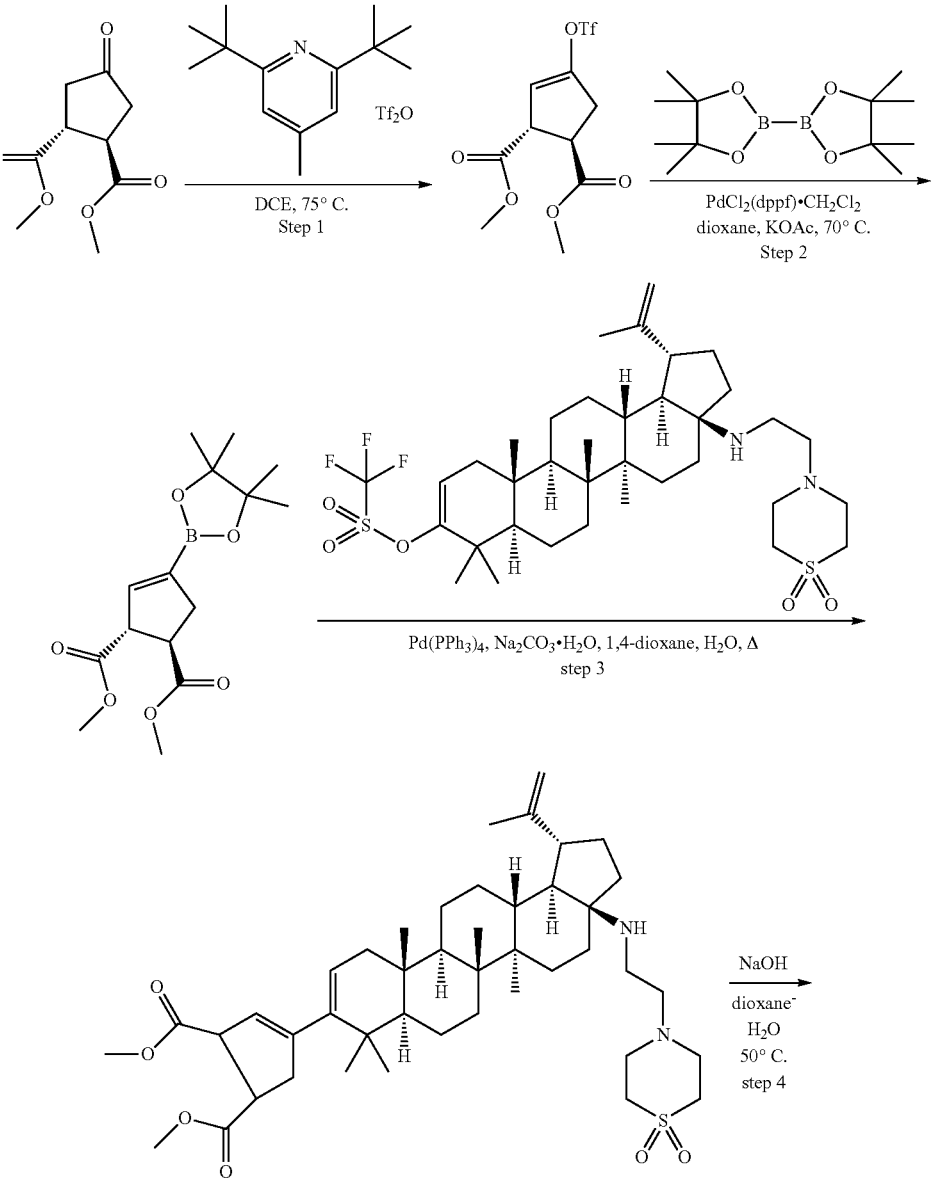

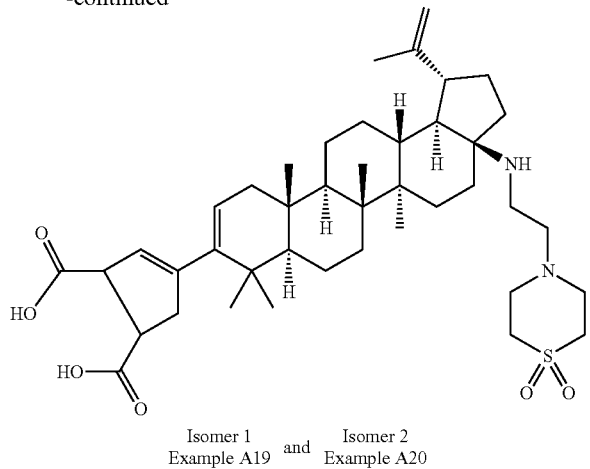

Isomer 1 Example A19 and Isomer 2 Example A20

Step 1: Preparation of dimethyl 4-(((trifluoromethyl)sulfonyl)oxy)cyclopent-3-ene-1,2-dicarboxylate

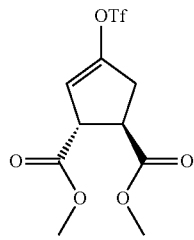 [SMILES: COC(=O)[C@@H]1C=C(OS(=O)(=O)C(F)(F)F)C[C@H]1C(=O)OC]

The title compound was prepared in 72.3% yield following the procedure described in WO 2012/003497, using 4-oxo-cyclopentane-trans-1,2-dicarboxylic acid dimethyl ester, as the reactant. MS: m/e 301.05 (M+H)$^+$, 2.689 min (method 8) $^1$HNMR (500 MHz, CHLOROFORM-d) δ 5.71 (q, J=2.1 Hz, 1H), 4.08-3.98 (m, 1H), 3.78 (d, J=1.7 Hz, 6H), 3.73-3.67 (m, 1H), 3.06-2.91 (m, 2H). $^{19}$F NMR (376 MHz, CHLOROFORM-d) δ −73.3 (s, 3F).

Step 2: Preparation of dimethyl 4-(4,4,5,5-tetramethyl-1,3,2-dioxaborolan-2-yl)cyclopent-3-ene-trans-1,2-dicarboxylate

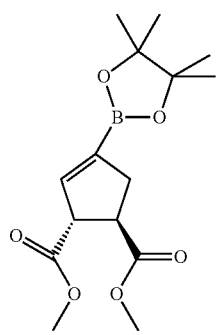 [SMILES: COC(=O)[C@@H]1C=C(B2OC(C)(C)C(C)(C)O2)C[C@H]1C(=O)OC]

The title compound was prepared in 56.8% yield following the method described in step 2 for the preparation of methyl 6-(4,4,5,5-tetramethyl-1,3,2-dioxaborolan-2-yl)spiro[3.3]hept-5-ene-2-carboxylate, using dimethyl 4-(((trifluoromethyl)sulfonyl)oxy)cyclopent-3-ene-trans-1,2-dicarboxylate as the reactant. $^1$H NMR (400 MHz, CHLOROFORM-d) δ 6.36 (q, J=2.3 Hz, 1H), 4.13-4.04 (m, 1H), 3.69 (d, J=2.5 Hz, 6H), 3.59-3.47 (m, 1H), 3.04-2.85 (m, 1H), 2.72 (d, J=7.3 Hz, 1H), 1.36-1.15 (m, 12H).

Step 3: Preparation of dimethyl 4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclopent-3-ene-1,2-dicarboxylate

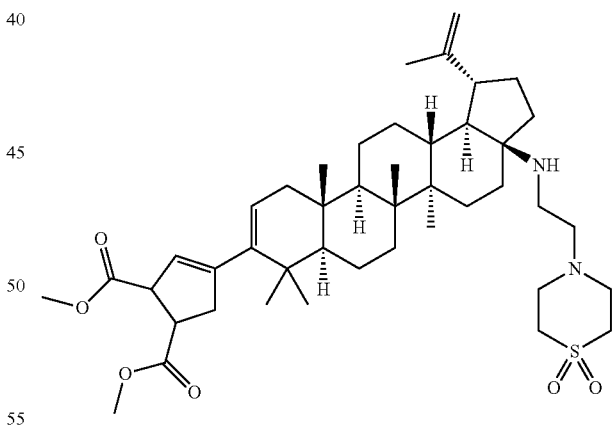

The title compound was prepared following the method described in step 1 for the preparation of Example 1, using (1R,3aS,5aR,5bR,7aR,11aR,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl trifluoromethanesulfonate and dimethyl 4-(4,4,5,5-tetramethyl-1,3,2-dioxaborolan-2-yl)cyclopent-3-ene-trans-1,2-dicarboxylate as the reactants. The title compound was obtained as a mixture of diastereomers in 72.7% yield. MS: m/e 753.6 (M+H)$^+$, 2.96 min (method 8). $^1$H NMR (400

MHz, CHLOROFORM-d) δ 5.55 (s, 1H), 5.53-5.49 (m, 1H), 4.71 (d, J=1.8 Hz, 1H), 4.59 (s, 1H), 4.05-3.99 (m, 1H), 3.75-3.70 (m, 6H), 3.57-3.46 (m, 1H), 3.14-3.00 (m, 8H), 2.98-2.41 (m, 7H), 2.08 (d, J=6.5 Hz, 1H), 2.00-1.71 (m, 5H), 1.69 (s, 3H), 1.66-1.29 (m, 13H), 1.13-1.00 (m, 13H), 0.96 (s, 3H), 0.87-0.81 (m, 3H).

Step 4

The title compounds were prepared following the method described in step 3 for the preparation of Example 4, using dimethyl 4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclopent-3-ene-trans-1,2-dicarboxylate as the reactant. The isomers were purified and isolated by prep HPLC with method 13:

Example A19: Isomer 1: (2.2% yield), MS: m/e 725.55 (M+H)+, 2.534 min (method 8). 1H NMR (400 MHz, CHLOROFORM-d) δ 5.66 (br. s., 1H), 5.44 (br. s., 1H), 4.76-4.70 (m, 1H), 4.68 (br. s., 1H), 3.70 (br. s., 1H), 3.23-3.04 (m, 9H), 2.98 (br. s., 2H), 2.91-2.76 (m, 4H), 2.66 (br. s., 1H), 2.00-1.78 (m, 7H), 1.71 (s, 3H), 1.66-1.38 (m, 11H), 1.29 (d, J=6.8 Hz, 4H), 1.16 (br. s., 3H), 1.10 (br. s., 3H), 1.02 (br. s., 3H), 0.99 (br. s., 3H), 0.86 (br. s., 3H).

Example A20: Isomer 2: (5% yield), MS: m/e 725.55 (M+H)+, 2.517 min (method 8). 1H NMR (400 MHz, DICHLOROMETHANE-d2) δ 5.76 (br. s., 1H), 5.55 (br. s., 1H), 4.75 (br. s., 1H), 4.68 (br. s., 1H), 3.72-3.59 (m, 1H), 3.25-2.98 (m, 11H), 2.91 (br. s., 4H), 2.62 (br. s., 1H), 2.17-1.86 (m, 8H), 1.71 (s, 3H), 1.68-1.24 (m, 14H), 1.22 (s, 3H), 1.14-1.07 (m, 6H), 1.04 (br. s., 3H), 0.88 (br. s., 3H).

Example A21 and Example A22

Preparation of 3-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclopent-2-enecarboxylic acid and 3-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclopent-3-enecarboxylic acid

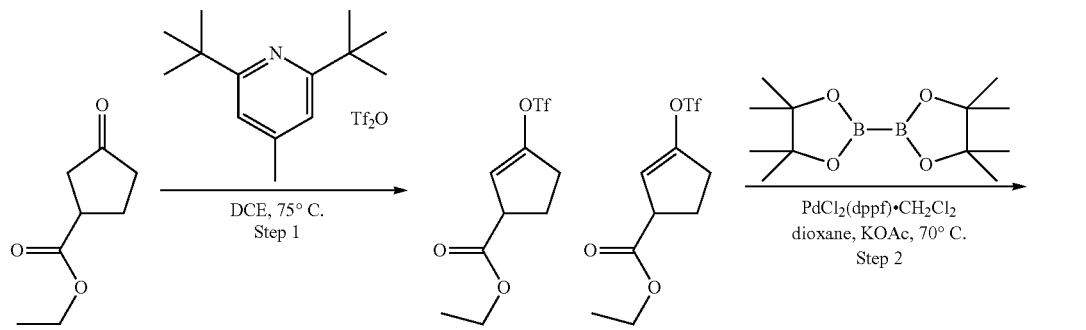

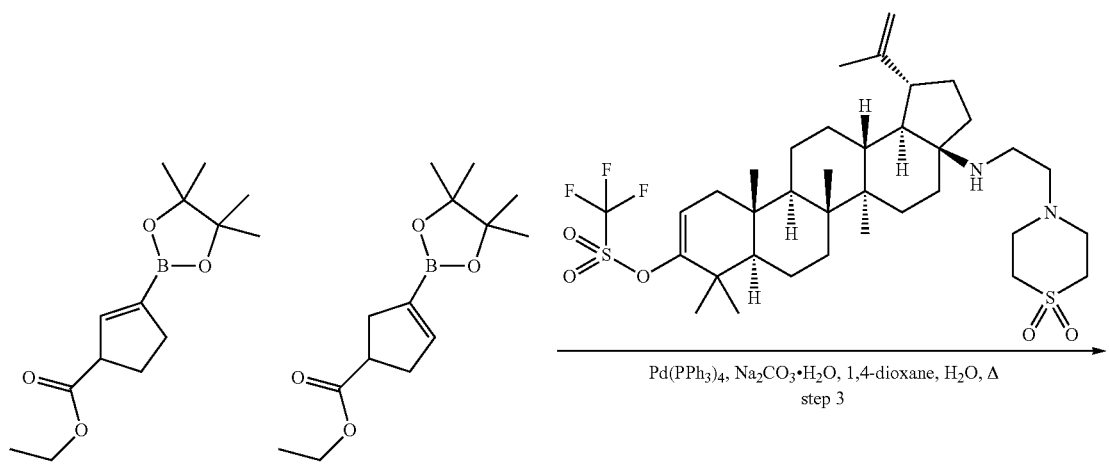

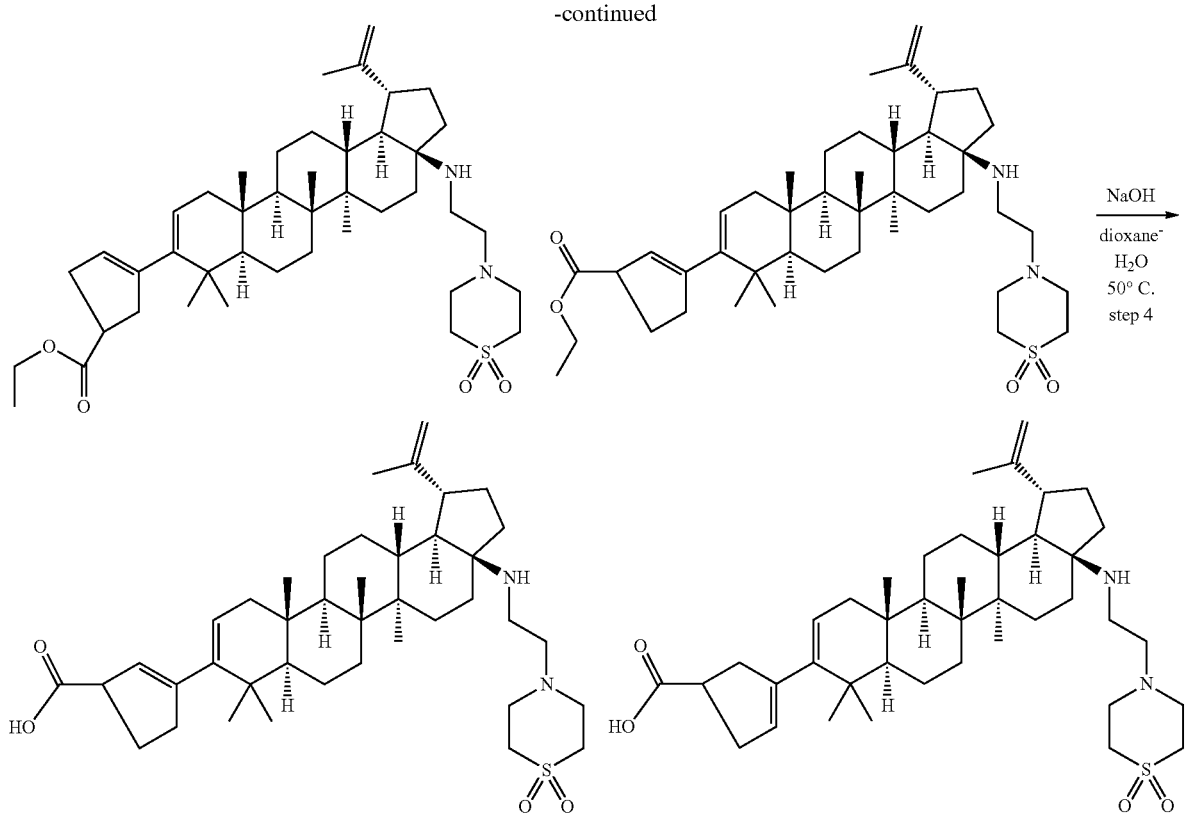

Step 1: Preparation of ethyl 3-(((trifluoromethyl)sulfonyl)oxy)cyclopent-2-enecarboxylate and ethyl 3-(((trifluoromethyl)sulfonyl)oxy)cyclopent-3-enecarboxylate

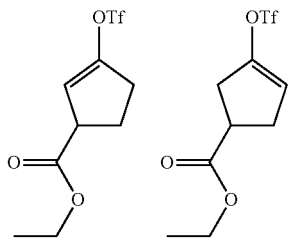

The title compounds were prepared following the procedure described in WO 2012/003497, using ethyl 3-oxocyclopentanecarboxylate, as the reactant. The product was obtained as a mixture of two isomers in 84% yield. MS: m/e 289.08 (M+H)$^+$, 2.20 min (method 3). Ethyl 3-(((trifluoromethyl)sulfonyl)oxy)cyclopent-2-enecarboxylate: $^1$H NMR (400 MHz, CHLOROFORM-d) δ 5.72 (q, J=2.1 Hz, 1H), 4.27-4.05 (m, 2H), 3.67-3.56 (m, 1H), 2.78-2.71 (m, 2H), 2.43-2.17 (m, 2H), 1.36-1.18 (m, 3H). Ethyl 3-(((trifluoromethyl)sulfonyl)oxy)cyclopent-3-enecarboxylate: $^1$H NMR (400 MHz, CHLOROFORM-d) δ 5.60 (quin, J=2.3 Hz, 1H), 4.20-4.04 (m, 2H), 3.35-3.21 (m, 1H), 3.06-2.93 (m, 1H), 2.88-2.79 (m, 1H), 2.71-2.57 (m, 2H), 1.31-1.20 (m, 3H). $^{19}$F NMR (376 MHz, CHLOROFORM-d) δ −73.3 (s, 3F) for both structures.

Step 2: Preparation of ethyl 3-(4,4,5,5-tetramethyl-1,3,2-dioxaborolan-2-yl)cyclopent-2-enecarboxylate and ethyl 3-(4,4,5,5-tetramethyl-1,3,2-dioxaborolan-2-yl)cyclopent-3-enecarboxylate

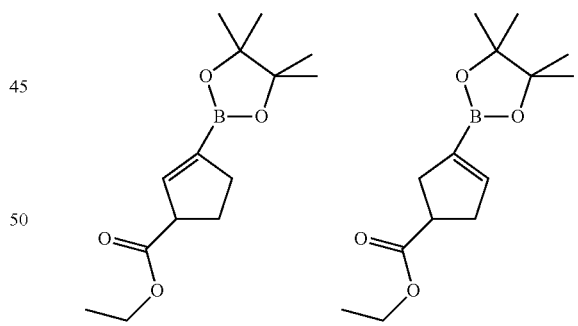

The title compounds were prepared following the method described on step 2 for the preparation of methyl 6-(4,4,5,5-tetramethyl-1,3,2-dioxaborolan-2-yl)spiro[3.3]hept-5-ene-2-carboxylate, using the mixture of ethyl 3-(((trifluoromethyl)sulfonyl)oxy)cyclopent-2-enecarboxylate and ethyl 3-(((trifluoromethyl)sulfonyl)oxy)cyclopent-3-enecarboxylate as the reactant. The product was obtained as a mixture of two isomers in 69.9% yield. Ethyl 3-(4,4,5,5-tetramethyl-1,3,2-dioxaborolan-2-yl)cyclopent-2-enecarboxylate: $^1$H NMR (400 MHz, CHLOROFORM-d) δ 6.53-6.37 (m, 1H), 4.24-4.04 (m, 2H), 3.75-3.55 (m, 1H), 2.69-2.56 (m, 1H), 2.52-2.40 (m, 1H), 2.28-2.06 (m, 2H), 1.33-1.19 (m, 15H).

Ethyl 3-(4,4,5,5-tetramethyl-1,3,2-dioxaborolan-2-yl)cyclopent-3-enecarboxylate: ¹H NMR (400 MHz, CHLOROFORM-d) δ 6.53-6.34 (m, 1H), 4.24-4.04 (m, 2H), 3.13 (tt, J=9.3, 7.3 Hz, 1H), 2.91-2.68 (m, 4H), 1.32-1.24 (m, 15H).

Step 3: Preparation of ethyl 3-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclopent-2-enecarboxylate and ethyl 3-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclopent-3-enecarboxylate

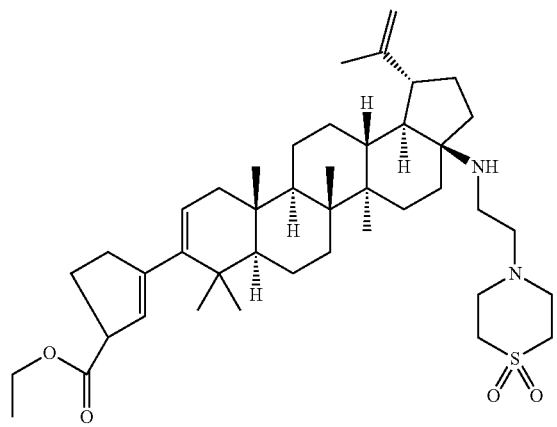

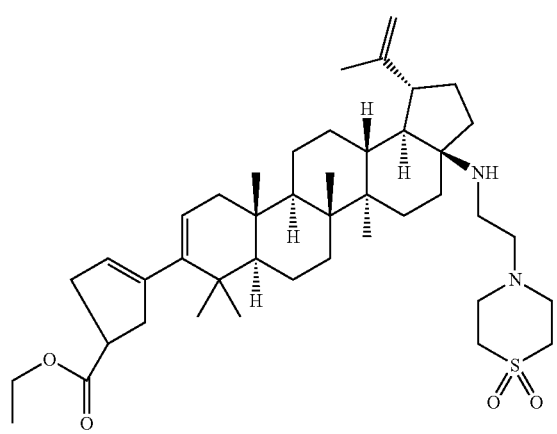

The title compounds were prepared following the method described in step 1 for the preparation of Example 1, using (1R,3aS,5aR,5bR,7aR,11aR,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl trifluoromethanesulfonate and the mixture of ethyl 3-(4,4,5,5-tetramethyl-1,3,2-dioxaborolan-2-yl)cyclopent-2-enecarboxylate and ethyl 3-(4,4,5,5-tetramethyl-1,3,2-dioxaborolan-2-yl)cyclopent-3-enecarboxylate as the reactants. The product was obtained as a mixture of two isomers in 77% yield. MS: m/e 709.65 (M+H)⁺, 2.961 min (method 8). ¹H NMR (400 MHz, CHLOROFORM-d) δ 5.71-5.32 (m, 2H), 4.73 (d, J=2.0 Hz, 1H), 4.61 (d, J=1.3 Hz, 1H), 4.23-4.09 (m, 2H), 3.71-2.08 (m, 19H), 2.00-1.73 (m, 4H), 1.71 (s, 3H), 1.67-1.18 (m, 18H), 1.14-1.04 (m, 11H), 1.00-0.95 (m, 3H), 0.89-0.83 (m, 3H).

Step 4

The title compounds were prepared following the method described in step 3 for the preparation of Example 4, using the mixture of ethyl 3-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclopent-2-enecarboxylate and ethyl 3-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclopent-3-enecarboxylate as the reactant. The products were purified and isolated by preparative HPLC with method 13 to afford two isomeric products:

Example A21: 3-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclopent-2-enecarboxylic acid: (1.7% yield), MS: m/e 681.55 (M+H)⁺, 2.63 min (method 8). ¹H NMR (400 MHz, CHLOROFORM-d) δ 5.71-5.44 (m, 2H), 4.73 (s, 1H), 4.62 (s, 1H), 3.67 (br. s., 1H), 3.19-3.01 (m, 8H), 2.88-2.47 (m, 7H), 2.24-2.06 (m, 3H), 1.72 (s, 3H), 1.50-1.21 (m, 16H), 1.16-1.03 (m, 14H), 0.99 (s, 3H), 0.90 (br. s., 3H).

Example A22: 3-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclopent-3-enecarboxylic acid: (2.1% yield). MS: m/e 681.55 (M+H)⁺, 2.65 min (method 8). ¹H NMR (400 MHz, CHLOROFORM-d) δ 5.68-5.44 (m, 2H), 4.78-4.69 (m, 1H), 4.65-4.57 (m, 1H), 3.09 (m, 8H), 2.95-2.42 (m, 8H), 2.30-1.77 (m, 3H), 1.71 (s, 3H), 1.67-1.20 (m, 17H), 1.17-1.02 (m, 13H), 1.00-0.97 (m, 3H), 0.87 (s, 3H).

Example A23 and Example A24

Preparation of Preparation of 2-(3-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclopent-2-en-1-yl)-2,2-difluoroacetic acid and 2-(3-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclopent-3-en-1-yl)-2,2-difluoroacetic acid

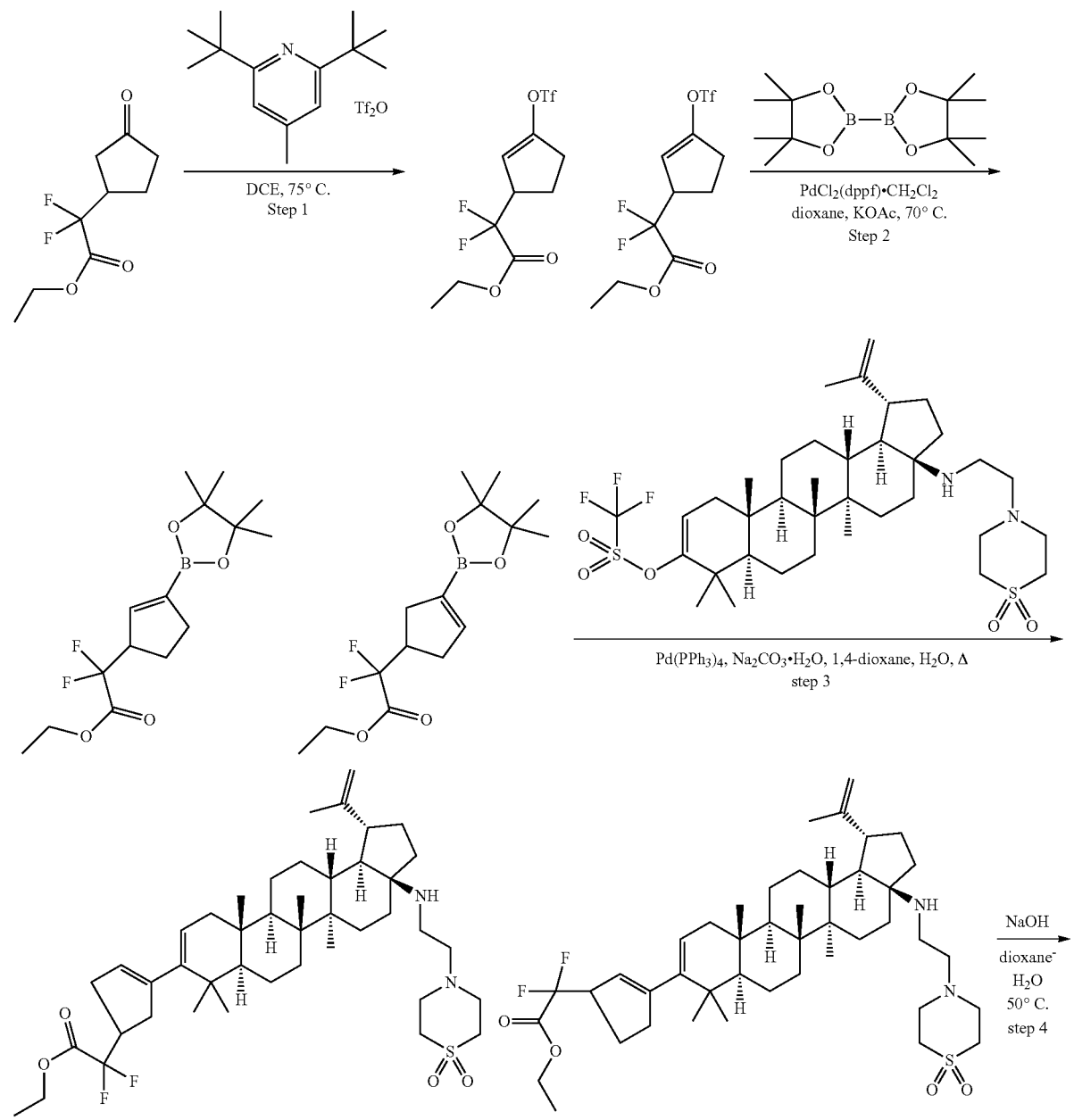

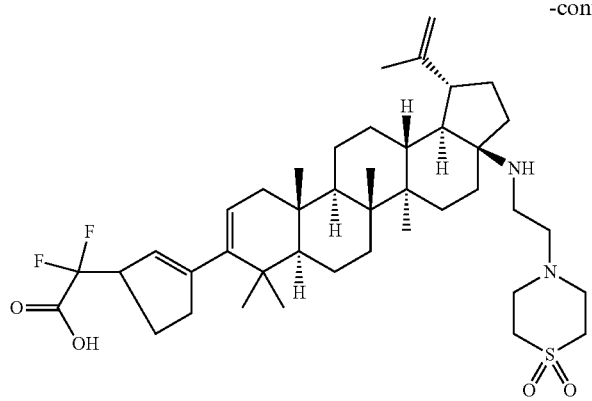

Example A23

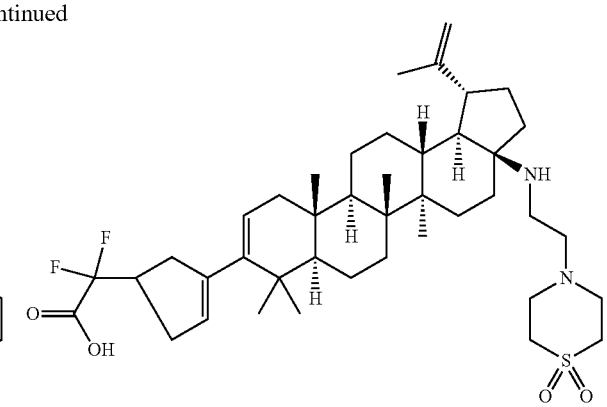

Example A24

Step 1: Preparation of ethyl 2,2-difluoro-2-(3-(((trifluoromethyl)sulfonyl)oxy)cyclopent-2-en-1-yl)acetate and ethyl 2,2-difluoro-2-(3-(((trifluoromethyl)sulfonyl)oxy)cyclopent-3-en-1-yl)acetate

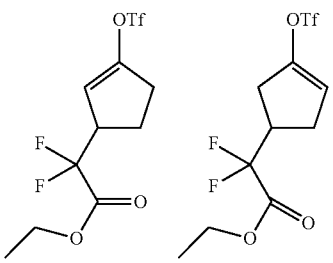 [SMILES: CCOC(=O)C(F)(F)C1C=C(OS(=O)(=O)C(F)(F)F)CC1 ; CCOC(=O)C(F)(F)C1CC=C(OS(=O)(=O)C(F)(F)F)C1]

The title compounds were prepared following the procedure described in WO 2012/003497, using ethyl 2,2-difluoro-2-(3-oxocyclopentyl)acetate (prepared as described below) as the reactant. The product was obtained as a mixture of isomers in 36.6% yield. Isomer 1: Ethyl 2,2-difluoro-2-(3-(((trifluoromethyl)sulfonyl)oxy)cyclopent-2-en-1-yl)acetate: $^1$H NMR (400 MHz, CHLOROFORM-d) δ 5.71-5.55 (m, 1H), 4.48-4.26 (m, 2H), 3.66-3.43 (m, 1H), 2.66-2.57 (m, 2H), 2.32-2.13 (m, 2H), 1.41-1.34 (m, 3H). Isomer 2: Ethyl 2,2-difluoro-2-(3-(((trifluoromethyl)sulfonyl)oxy)cyclopent-3-en-1-yl)acetate: $^1$H NMR (400 MHz, CHLOROFORM-d) δ 5.72-5.56 (m, 1H), 4.49-4.28 (m, 2H), 3.32-3.09 (m, 1H), 2.92-2.62 (m, 4H), 1.43-1.26 (m, 3H). $^{19}$F NMR (376 MHz, CHLOROFORM-d) δ −71.69-−75.04 (m, 3F), −108.53-−114.83 (m, 2F) for both structures.

The method of Kumadaki et. al. [Journal of Fluorine Chemistry 125 (2004) 509-515] was adapted to the preparation of ethyl 2,2-difluoro-2-(3-oxocyclopentyl)acetate. To a thick-walled, re-sealable tube was placed cyclopent-2-enone (190 mg, 2.314 mmol) and ethyl 2-bromo-2,2-difluoroacetate (900 mg, 4.43 mmol) in THF (5 mL), followed by ~800 mg of a copper catalyst prepared in accordance with the method of Brewster and Groening in Org. Synthesis Coll. Vol. II (1948) 445-446. The suspension was flushed with nitrogen and warmed to 75° C. for 2 hours. After cooling to RT, TMEDA was added (0.4 mL) and the vessel was flushed with nitrogen, re-sealed and warmed to 75° C. for another 16 hours. It was diluted with 5 mL chloroform and 5 mL of hexanes, the suspension was stirred and filtered over a short bed of silica gel (type-H, ~½" thick) and washed with mixtures of ethyl acetate and hexanes. The filtrate was concentrated under slight vacuum (25-30 mmHg) at RT to give a pale orange substance. A small amount of the unreacted cyclopent-2-enone was easily removed under this vacuum conditions. The material obtained was used in the next step without further purification (49%). MS: m/e 207.10 (M+H)$^+$, 3.06 min (method 20). $^1$H NMR (400 MHz, CHLOROFORM-d) δ 4.37 (q, J=7.3 Hz, 2H), 3.10-2.89 (m, 2H), 2.50-2.32 (m, 2H), 2.31-2.15 (m, 2H), 2.12-1.97 (m, 1H), 1.38 (t, J=7.2 Hz, 3H). $^{19}$F NMR (376 MHz, CHLOROFORM-d) d −110.90-−111.94 (m, 1F), −113.16-−114.39 (m, 1F).

Step 2: Preparation of ethyl 2,2-difluoro-2-(3-(4,4,5,5-tetramethyl-1,3,2-dioxaborolan-2-yl)cyclopent-2-en-1-yl)acetate and ethyl 2,2-difluoro-2-(3-(4,4,5,5-tetramethyl-1,3,2-dioxaborolan-2-yl)cyclopent-3-en-1-yl)acetate

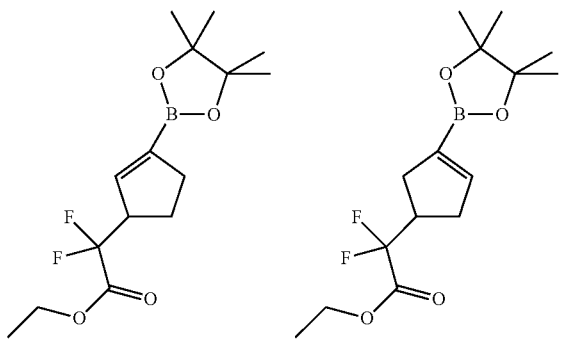 [SMILES: CCOC(=O)C(F)(F)C1C=C(B2OC(C)(C)C(C)(C)O2)CC1 ; CCOC(=O)C(F)(F)C1CC=C(B2OC(C)(C)C(C)(C)O2)C1]

The title compounds were prepared following the method described in step 2 for the preparation of methyl 6-(4,4,5,5-tetramethyl-1,3,2-dioxaborolan-2-yl)spiro[3.3]hept-5-ene-2-carboxylate, using the mixture of ethyl 2,2-difluoro-2-(3-(((trifluoromethyl)sulfonyl)oxy)cyclopent-2-en-1-yl)acetate and ethyl 2,2-difluoro-2-(3-(((trifluoromethyl)sulfonyl)oxy)cyclopent-3-en-1-yl)acetate as the reactant. The product was obtained as a mixture of isomers in 37% yield. Isomer 1: Ethyl 2,2-difluoro-2-(3-(4,4,5,5-tetramethyl-1,3,2-dioxaborolan-2-yl)cyclopent-2-en-1-yl)acetate: $^1$H NMR (400 MHz, CHLOROFORM-d) δ 6.34 (q, J=2.2 Hz, 1H), 4.44-4.26 (m, 2H), 3.50 (dddd, J=14.2, 9.4, 4.9, 2.4 Hz, 1H), 2.66-2.62 (m, 2H), 2.13-1.91 (m, 2H), 1.36 (td, J=7.2, 0.8 Hz, 3H), 1.28 (d, J=3.3 Hz, 12H). Isomer 2: Ethyl 2,2-difluoro-2-(3-(4,4,5,5-tetramethyl-1,3,2-dioxaborolan-2-yl)cyclopent-3-en-1-yl)acetate: $^1$H NMR (400 MHz, CHLOROFORM-d) δ 6.41 (s, 1H), 4.42-4.25 (m, 2H), 3.15-2.92 (m, 1H), 2.67-2.41 (m, 4H), 1.40-1.33 (m, 3H), 1.31-1.26 (m, 12H).

Step 3: Preparation of ethyl 2-(3-((1R,3aS,5aR,5bR, 7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclopent-2-en-1-yl)-2,2-difluoroacetate and ethyl 2-(3-((1R,3aS,5aR,5bR, 7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclopent-3-en-1-yl)-2,2-difluoroacetate

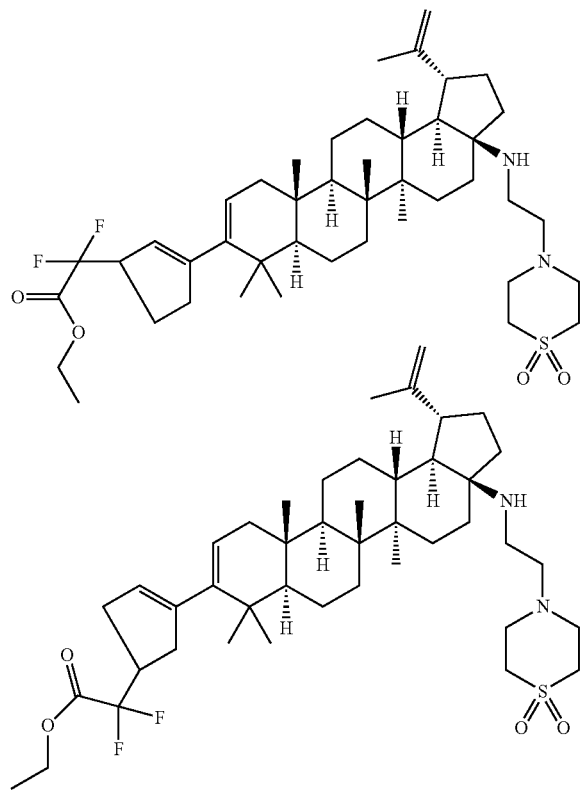

The title compounds were prepared following the method described in step 1 for the preparation of Example 1, using (1R,3aS,5aR,5bR,7aR,11aR,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl trifluoromethanesulfonate and the mixture of ethyl 2,2-difluoro-2-(3-(4,4,5,5-tetramethyl-1,3,2-dioxaborolan-2-yl)cyclopent-2-en-1-yl)acetate and ethyl 2,2-difluoro-2-(3-(4,4,5,5-tetramethyl-1,3,2-dioxaborolan-2-yl)cyclopent-3-en-1-yl)acetate as the reactants. The product was obtained as a mixture of isomers in 100% yield. MS: m/e 759.55 (M+H)$^+$, 2.86 min (method 8). $^1$H NMR (400 MHz, CHLOROFORM-d) δ 5.57-5.51 (m, 1H), 5.48 (dd, J=4.3, 1.8 Hz, 1H), 4.73 (d, J=1.8 Hz, 1H), 4.61 (s, 1H), 4.40-4.26 (m, 2H), 3.18-2.90 (m, 9H), 2.81-2.33 (m, 9H), 2.15-1.73 (m, 6H), 1.71 (s, 3H), 1.67-1.32 (m, 14H), 1.30-1.18 (m, 3H), 1.15-1.02 (m, 1H), 0.98 (s, 3H), 0.86 (s, 3H).

Step 4

The title compounds were prepared following the method described in step 3 for the preparation of Example 4, using the mixture of ethyl 2-(3-((1R,3aS,5aR,5bR,7aR,11aS,11bR, 13aR,13bR)-3a-((2-(1,1-dioxidothiomorpholino)ethyl) amino)-5a,5b,8,8,11a-pentamethyl-1-(prop-1-en-2-yl)-2,3, 3a,4,5,5a,5b,6,7,7a,8,11,11a,11b,12,13,13a,13b-octadecahydro-1H-cyclopenta[a]chrysen-9-yl)cyclopent-2-en-1-yl)-2,2-difluoroacetate and ethyl 2-(3-((1R,3aS,5aR, 5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8, 11,11a,11b,12,13,13a,13b-octadecahydro-1H-cyclopenta[a] chrysen-9-yl)cyclopent-3-en-1-yl)-2,2-difluoroacetate as the reactant. The products were purified and isolated by prep HPLC with method 13 to afford two isomers. Structures were assigned tentatively as follows:

Example A23: Isomer 1: (13% yield). MS: m/e 731.55 (M+H)$^+$, 2.72 min (method 8). $^1$H NMR (400 MHz, CHLOROFORM-d) δ 5.72 (br. s., 1H), 5.44 (br. s., 1H), 4.74 (s, 1H), 4.69 (s, 1H), 3.31-2.96 (m, 11H), 2.92-2.17 (m, 7H), 2.11-1.88 (m, 6H), 1.72 (s, 3H), 1.65-1.26 (m, 13H), 1.24 (br. s., 3H), 1.19 (m, 3H), 1.06 (d, J=11.5 Hz, 6H), 0.82 (s, 3H), 0.85-0.79 (m, 3H).

Example A24: Isomer 2: (10.4%). MS: m/e 731.55 (M+H)$^+$, 2.72 min (method 8). $^1$H NMR (400 MHz, CHLOROFORM-d) δ 5.83 (br. s., 1H), 5.43 (d, J=6.3 Hz, 1H), 4.74 (s, 1H), 4.70 (s, 1H), 3.26-2.54 (m, 18H), 2.24 (d, J=7.3 Hz, 3H), 2.14-1.82 (m, 9H), 1.74 (s, 3H), 1.68-1.40 (m, 10H), 1.23 (br. s., 6H), 1.07 (d, J=9.5 Hz, 6H), 0.81 (s, 3H).

Example A25

Preparation of 2-(4-((1R,3aS,5aR,5bR,7aR,11aS, 11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a, 11b,12,13,13a,13b-octadecahydro-1H-cyclopenta[a] chrysen-9-yl)cyclohex-3-en-1-yl)acetic acid

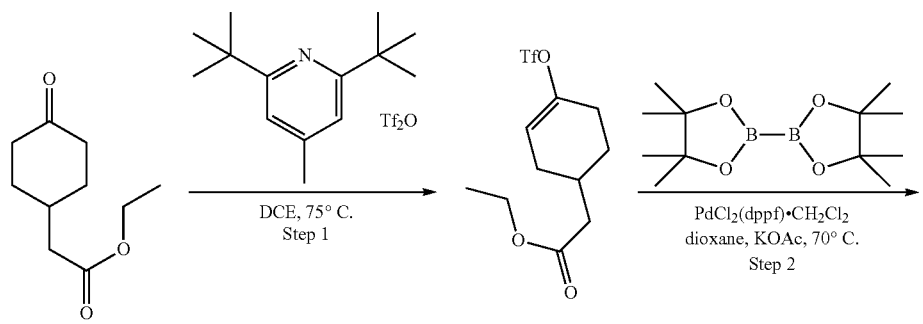

-continued
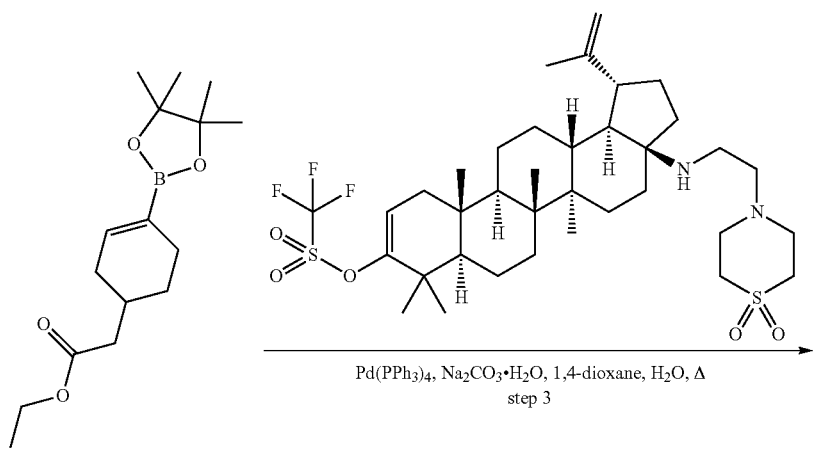
Pd(PPh3)4, Na2CO3·H2O, 1,4-dioxane, H2O, Δ
step 3
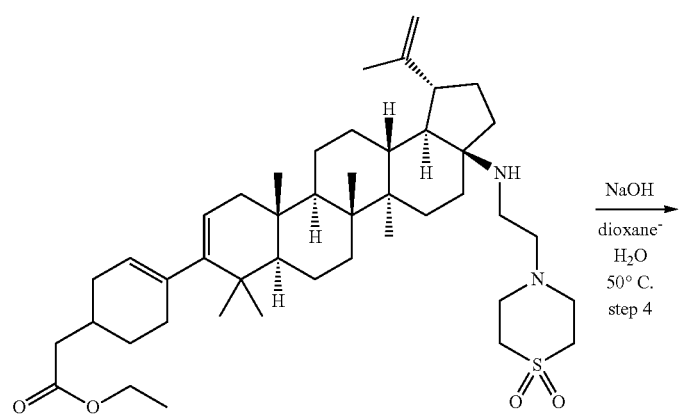
NaOH
dioxane-
H2O
50° C.
step 4
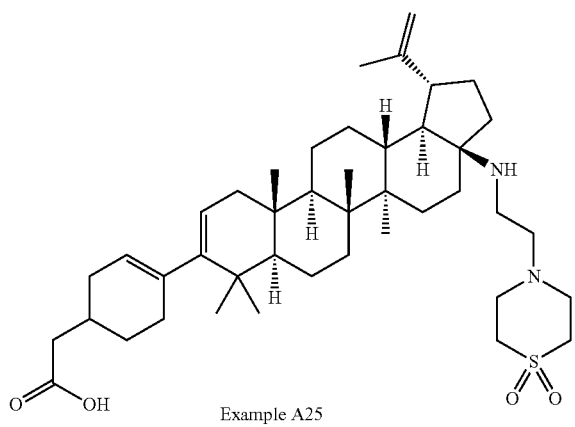
Example A25

229

Step 1: Preparation of ethyl 2-(4-(((trifluoromethyl) sulfonyl)oxy)cyclohex-3-en-1-yl)acetate

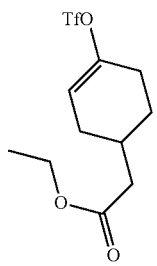 [SMILES: CCOC(=O)CC1CC=C(OS(=O)(=O)C(F)(F)F)CC1]

The title compound was prepared in 80.0% yield following the procedure described in WO 2012/003497, using ethyl 2-(4-oxocyclohexyl)acetate, as the reactant. $^1$H NMR (400 MHz, CHLOROFORM-d) δ 5.89-5.62 (m, 1H), 4.24-4.07 (m, 2H), 2.53-2.41 (m, 1H), 2.40-2.34 (m, 2H), 2.32 (d, J=7.0 Hz, 2H), 2.22-2.09 (m, 1H), 2.01-1.89 (m, 2H), 1.58-1.49 (m, 1H), 1.28 (td, J=7.1, 2.6 Hz, 3H). $^{19}$F NMR (376 MHz, CHLOROFORM-d) δ −73.897 (s, 3F).

Step 2: Preparation of ethyl 2-(4-(4,4,5,5-tetramethyl-1,3,2-dioxaborolan-2-yl)cyclohex-3-en-1-yl) acetate

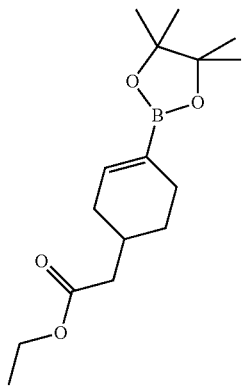 [SMILES: CCOC(=O)CC1CC=C(B2OC(C)(C)C(C)(C)O2)CC1]

The title compound was prepared following the method described in step 2 for the preparation of methyl 6-(4,4,5,5-tetramethyl-1,3,2-dioxaborolan-2-yl)spiro[3.3]hept-5-ene-2-carboxylate, using ethyl 2-(4-(((trifluoromethyl)sulfonyl) oxy)cyclohex-3-en-1-yl)acetate as the reactant. (99% yield), MS: m/e 295.2 (M+H)$^+$, 2.28 min (method 3). $^1$H NMR (400 MHz, CHLOROFORM-d) δ 6.54 (d, J=2.3 Hz, 1H), 4.15 (q, J=7.3 Hz, 2H), 2.41-1.99 (m, 7H), 1.93-1.71 (m, 2H), 1.38-1.22 (m, 15H).

230

Step 3: Preparation of ethyl 2-(4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-en-1-yl) acetate

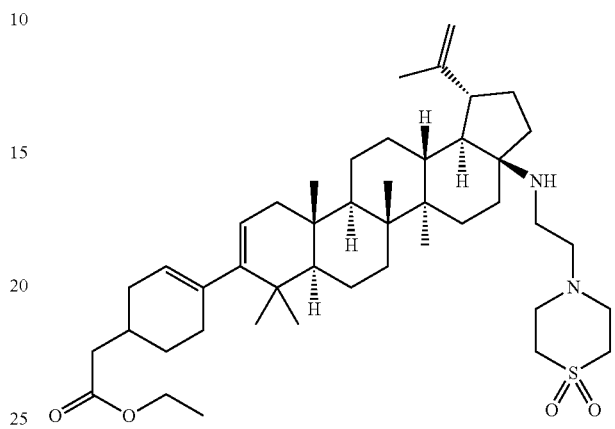

The title compound was prepared following the method described in step 1 for the preparation of Example 1, using (1R,3aS,5aR,5bR,7aR,11aR,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl trifluoromethanesulfonate and ethyl 2-(4-(4,4,5,5-tetramethyl-1,3,2-dioxaborolan-2-yl)cyclohex-3-en-1-yl)acetate as the reactants. The product was obtained as a mixture of diasteromers in 42.7% yield. MS: m/e 737.65 (M+H)$^+$, 2.939 min (method 8). $^1$H NMR (400 MHz, CHLOROFORM-d) δ 5.32 (br. s., 1H), 5.19 (d, J=5.8 Hz, 1H), 4.72 (d, J=1.8 Hz, 1H), 4.61 (d, J=1.5 Hz, 1H), 4.21-4.09 (m, 2H), 3.15-2.96 (m, 8H), 2.77-2.54 (m, 4H), 2.52-2.40 (m, 1H), 2.34-2.08 (m, 4H), 2.03-1.72 (m, 7H), 1.70 (s, 3H), 1.61-1.39 (m, 9H), 1.39-1.19 (m, 10H), 1.12-1.04 (m, 7H), 1.01-0.97 (m, 6H), 0.96-0.91 (m, 3H), 0.87 (s, 3H).

Step 4

2-(4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-en-1-yl)acetic acid was prepared following the method described in step 3 for the preparation of Example 4, using ethyl 2-(4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl) cyclohex-3-en-1-yl)acetate as the reactant. The crude was purified by prep HPLC with method 15 to afford the title compound as a mixture of diastereomers in 19.9% yield. MS: m/e 709.6 (M+H)$^+$, 2.679 min (method 8). $^1$H NMR (400 MHz, METHANOL-d$_4$) δ 5.34 (br. s., 1H), 5.22 (d, J=6.3 Hz, 1H), 4.87 (s, 1H), 4.76 (s, 1H), 3.30-3.17 (m, 8H), 3.16-3.07 (m, 3H), 3.02-2.90 (m, 1H), 2.80 (td, J=11.0, 5.4 Hz, 1H), 2.28 (d, J=7.0 Hz, 2H), 2.25-2.00 (m, 9H), 1.90-1.80 (m, 4H), 1.78 (s, 3H), 1.75-1.23 (m, 15H), 1.20 (s, 3H), 1.17 (d, J=2.8 Hz, 1H), 1.13 (s, 3H), 1.03 (s, 1.5H), 1.01 (s, 1.5H), 1.00 (s, 1.5H), 0.97 (s, 1.5H), 0.95 (s, 3H).

Example A26
Preparation of (6S)-3-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)bicyclo[3.1.0]hex-2-ene-6-carboxylic acid
5
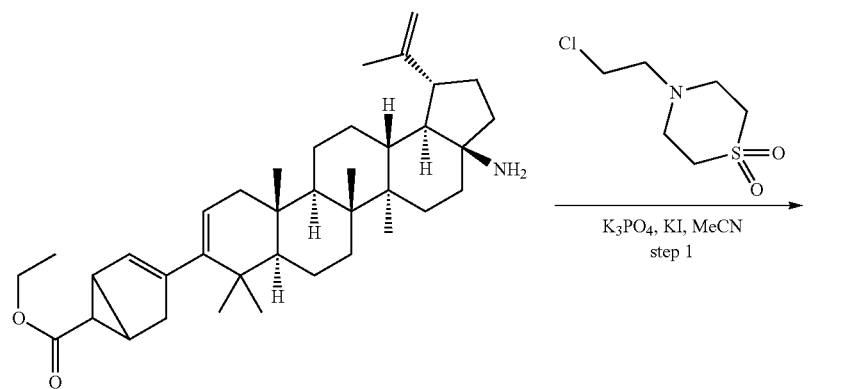
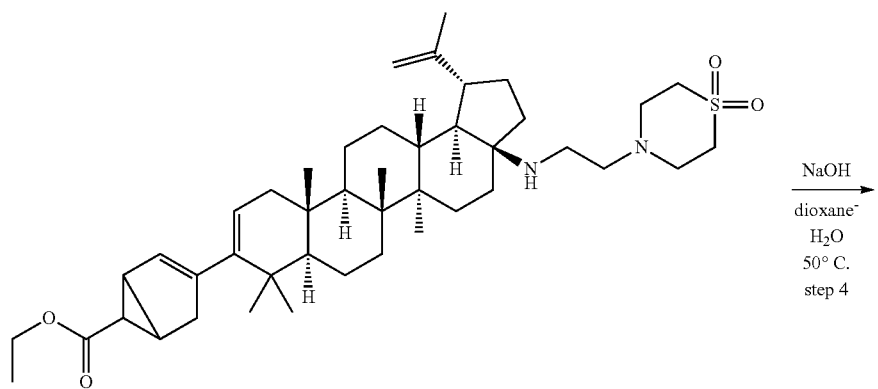
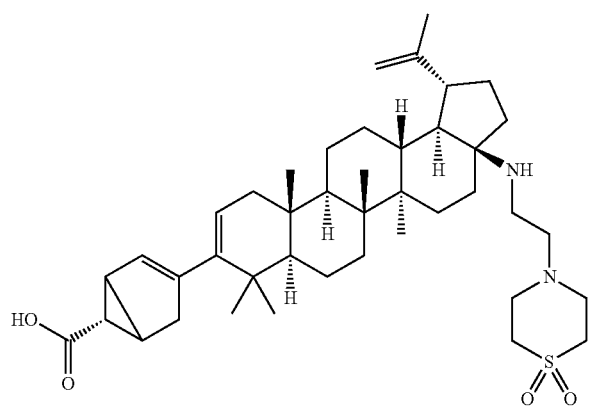
Example A26

Step 1: Preparation of 3-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)bicyclo[3.1.0]hex-2-ene-6-carboxylic acid

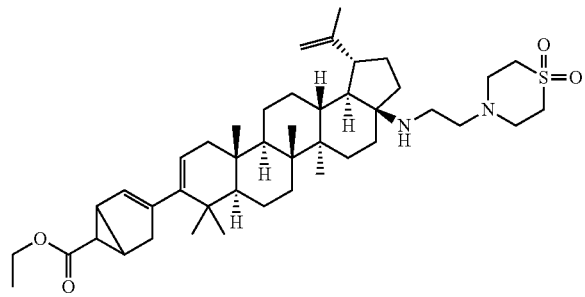

The title compound was prepared following the method described in step 2 for the preparation of Example 1, using ethyl 3-((1R,3 aS,5aR,5bR,7aR,11 aS,11bR,13 aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)bicyclo[3.1.0]hex-2-ene-6-carboxylate as the reactant. The product was obtained in 29.9% yield as a single isomer. MS: m/e 721.55 (M+H)+, 2.879 min (method 8). ¹H NMR (400 MHz, CHLOROFORM-d) δ 5.86-5.69 (m, 1H), 5.48-5.32 (m, 1H), 4.71 (d, J=1.8 Hz, 1H), 4.60 (d, J=1.5 Hz, 1H), 4.23-3.99 (m, 2H), 3.16-2.97 (m, 9H), 2.96-2.80 (m, 1H), 2.75-2.39 (m, 7H), 2.16 (td, J=6.6, 3.1 Hz, 1H), 2.09-1.99 (m, 2H), 1.98-1.72 (m, 5H), 1.69 (s, 3H), 1.65-1.30 (m, 11H), 1.29-1.21 (m, 5H), 1.11 (dd, J=5.3, 2.5 Hz, 2H), 1.07 (s, 1.5H), 1.06 (s, 3H), 1.03 (d, J=1.3 Hz, 3H), 0.97 (s, 1.5H), 0.97 (s, 3H), 0.83 (s, 1.5H), 0.82 (s, 1.5H).

Step 2

3-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)bicyclo[3.1.0]hex-2-ene-6-carboxylic acid compound was prepared following the method described in step 3 for the preparation of Example 4, using ethyl 341R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)bicyclo[3.1.0]hex-2-ene-6-carboxylate as the reactant. The crude was purified by preparative HPLC with method 15 to afford the title compound as a single isomer (this isomer can be found in the mixture of isomers obtained in the preparation of example A18). The stereochemistry was arbitrarily assigned. MS: m/e 693.55 (M+H)+, 2.65 min (method 8). ¹H NMR (400 MHz, CHLOROFORM-d) δ 5.94 (s, 1H), 5.48 (d, J=4.8 Hz, 1H), 4.82 (s, 1H), 4.73 (s, 1H), 3.27-3.00 (m, 9H), 2.97-2.84 (m, 3H), 2.80-2.58 (m, 3H), 2.28-2.13 (m, 2H), 2.10-1.87 (m, 6H), 1.82-1.74 (m, 1H), 1.71 (s, 3H), 1.68-1.25 (m, 13H), 1.22 (s, 3H), 1.16 (s, 3H), 1.11-1.07 (m, 2H), 1.06 (s, 6H), 0.99 (d, J=2.3 Hz, 1H), 0.76 (s, 3H).

Example A27 and Example A28

Preparation of 3-((1R,3aS,5aR,5bR,7aR,11aS,11bR,13aR,13bR)-5a,5b,8,8,11a-pentamethyl-3a-((2-(4-(methylsulfonyl)piperidin-1-yl)ethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)bicyclo[3.1.0]hex-2-ene-6-carboxylic acid (Isomer 1 and Isomer 2)

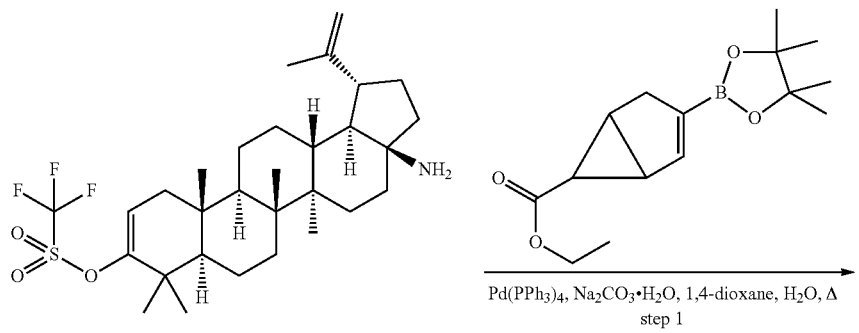

Pd(PPh₃)₄, Na₂CO₃·H₂O, 1,4-dioxane, H₂O, Δ
step 1

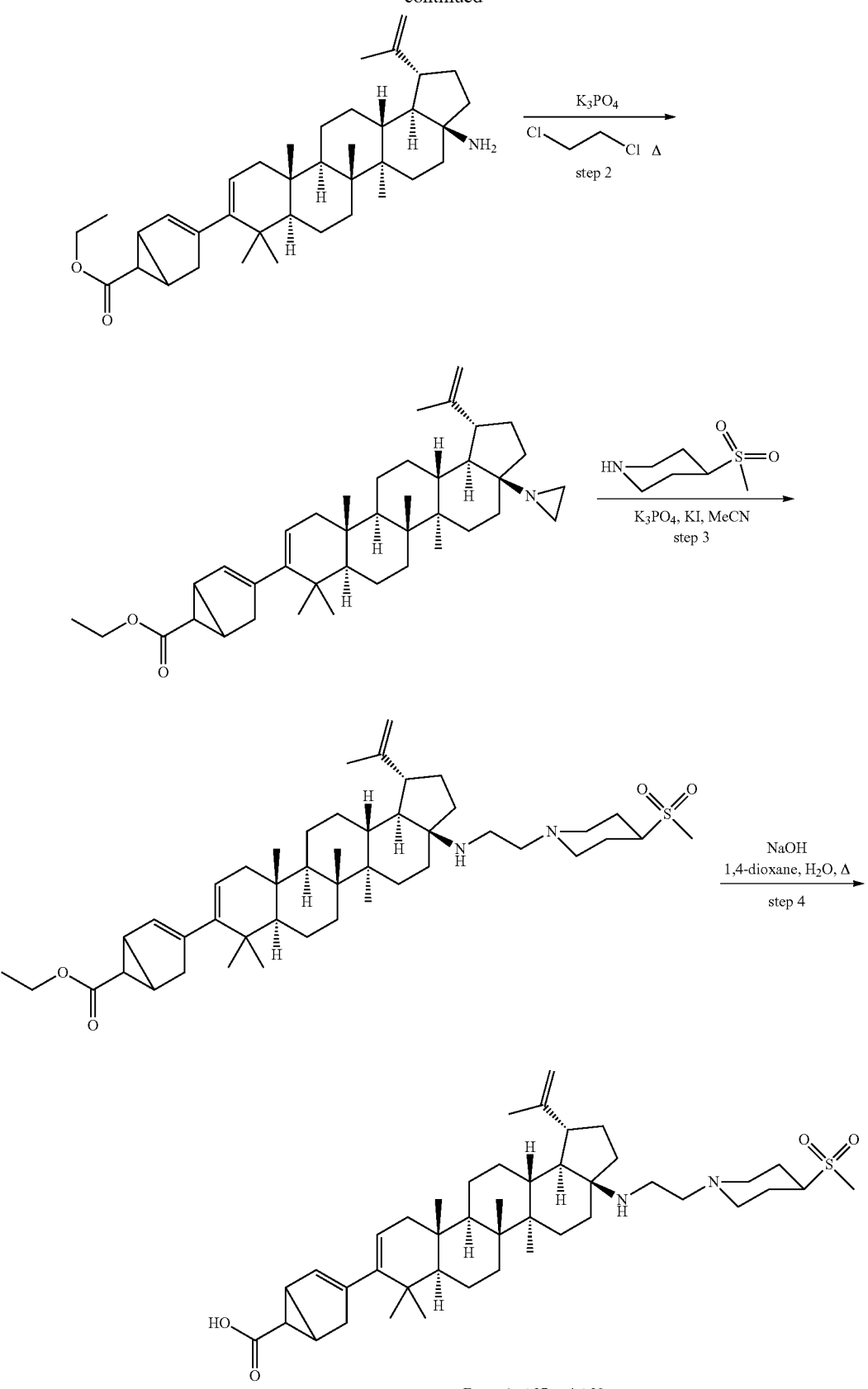
Example A27 and A28

Step 1: Preparation of ethyl 3-((1R,3aS,5aR,5bR, 7aR,11aS,11bR,13aR,13bR)-3a-amino-5a,5b,8,8, 11a-pentamethyl-1-(prop-1-en-2-yl)-2,3,3a,4,5,5a, 5b,6,7,7a,8,11,11a,11b,12,13,13a,13b-octadecahydro-1H-cyclopenta[a]chrysen-9-yl) bicyclo[3.1.0]hex-2-ene-6-carboxylate Step 2: Preparation of ethyl 3-((1R,3aS,5aR,5bR, 7aR,11aS,11bR,13aR,13bR)-3a-(aziridin-1-yl)-5a, 5b,8,8,11a-pentamethyl-1-(prop-1-en-2-yl)-2,3,3a,4, 5,5a,5b,6,7,7a,8,11,11a,11b,12,13,13a,13b-octadecahydro-1H-cyclopenta[a]chrysen-9-yl) bicyclo[3.1.0]hex-2-ene-6-carboxylate

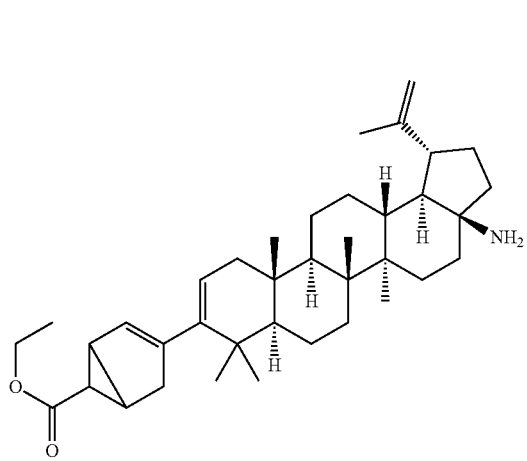

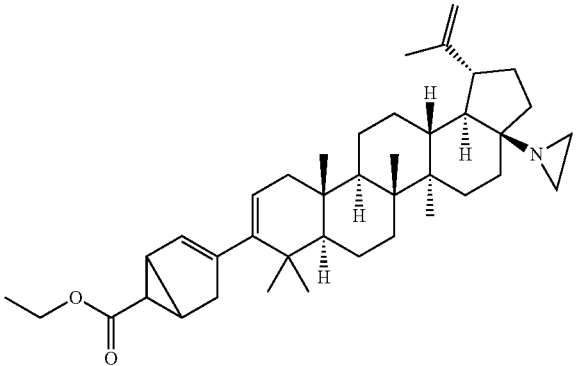

To a flame dried 75 mL thick-walled resealable vessel was placed ethyl 3-((1R,3aS,5aR,5bR,7aR,11aS,11bR,13aR, 13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)bicyclo [3.1.0]hex-2-ene-6-carboxylate (0.453 g, 0.809 mmol) and flame dried potassium phosphate (0.859 g, 4.05 mmol), followed by 1,2-dichloroethane (24 mL) and acetonitrile (12 mL). The reaction mixture was flushed with nitrogen, sealed, and warmed to 130° C. for 36 hours. The crude reaction mixture was cooled to room temperature and filtered through a short bed of silica gel, washed with ethyl acetate to obtain a very pale orange solution, it was evaporated to dryness. White solid was obtained (0.3 g, 0.512 mmole, 63.3%), and used as it is. MS: m/e 586.55 (M+H)$^+$, 2.791 min.

The titled compound was prepared in 86.6% yield following the method described in step 1 for the preparation of Example 1 described above, using (1R,3aS,5aR,5bR,7aR, 11aR,11bR,13aR,13bR)-3a-amino-5a,5b,8,8,11a-pentamethyl-1-(prop-1-en-2-yl)-2,3,3a,4,5,5a,5b,6,7,7a,8,11,11a, 11b,12,13,13a,13b-octadecahydro-1H-cyclopenta[a] chrysen-9-yl trifluoromethanesulfonate and ethyl 3-(4,4,5,5-tetramethyl-1,3,2-dioxaborolan-2-yl)bicyclo[3.1.0]hex-2-ene-6-carboxylate as the reactants. MS: m/e 543.5 (M−16)$^+$, 2.87 min. $^1$H NMR (400 MHz, CHLOROFORM-d) δ 5.84-5.72 (m, 1H), 5.47-5.32 (m, 1H), 4.72 (s, 1H), 4.59 (s, 1H), 4.24-3.99 (m, 2H), 3.09-2.74 (m, 1H), 2.67-2.40 (m, 3H), 2.26-2.10 (m, 1H), 2.09-1.92 (m, 3H), 1.69 (s, 3H), 1.67-1.65 (m, 1H), 1.64-1.31 (m, 9H), 1.29-1.22 (m, 5H), 1.17-1.05 (m, 4H), 1.02 (s, 6H), 0.98-0.93 (m, 7H), 0.82 (m, 3H).

Step 3: Preparation of ethyl 3-((1R,3aS,5aR,5bR, 7aR,11aS,11bR,13aR,13bR)-5a,5b,8,8,11a-pentamethyl-3a-((2-(4-(methylsulfonyl)piperidin-1-yl)ethyl) amino)-1-(prop-1-en-2-yl)-2,3,3a,4,5,5a,5b,6,7,7a,8, 11,11a,11b,12,13,13a,13b-octadecahydro-1H-cyclopenta[a]chrysen-9-yl)bicyclo[3.1.0]hex-2-ene-6-carboxylate

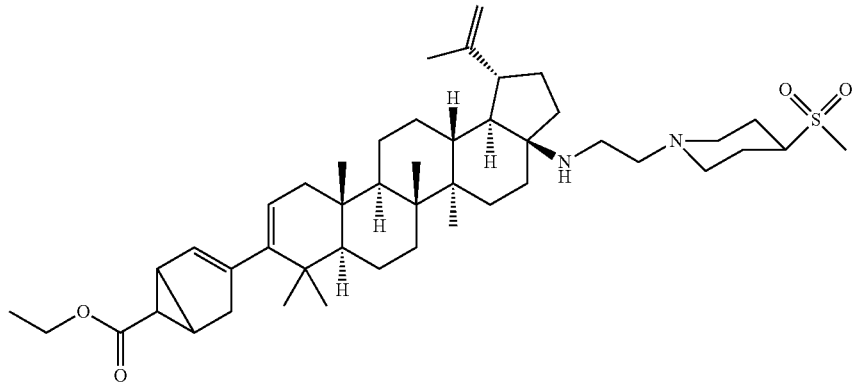

The title compound was prepared following the method describe on step 1 for the preparation of (1R,3aS,5aR,5bR,7aR,11aR,11bR,13aR,13bR)-3a-(aziridin-1-yl)-5a,5b,8,8,11a-pentamethyl-1-(prop-1-en-2-yl)octadecahydro-1H-cyclopenta[a]chrysen-9(5bH)-one using 4-(methylsulfonyl)piperidine and ethyl 3-((1R,3aS,5aR,5bR,7aR,11aS,11bR,13aR,13bR)-3a-(aziridin-1-yl)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)bicyclo[3.1.0]hex-2-ene-6-carboxylate as the reactants. The product was obtained as a mixture of diastereomers in 33.2% yield. MS: m/e 749.6 (M+H)$^+$, 2.794 min (method 8). $^1$H NMR (400 MHz, CHLOROFORM-d) δ 5.84-5.75 (m, 1H), 5.49-5.38 (m, 1H), 4.69 (br. s., 1H), 4.59 (br. s., 1H), 4.19-4.04 (m, 2H), 3.12 (dd, J=15.6, 12.8 Hz, 1H), 2.98-2.74 (m, 7H), 2.68-2.51 (m, 5H), 2.45 (d, J=7.5 Hz, 4H), 2.22-2.10 (m, 3H), 2.09-1.74 (m, 8H), 1.69 (s, 3H), 1.65-1.30 (m, 12H), 1.26 (m, 6H), 1.06 (br. s., 5.5H), 1.02 (s, 3H), 0.98-0.92 (m, 4.5H), 0.85-0.78 (m, 3H).

Step 4

3-((1R,3aS,5aR,5bR,7aR,11aS,11bR,13aR,13bR)-5a,5b,8,8,11a-pentamethyl-3a-((2-(4-(methylsulfonyl)piperidin-1-yl)ethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)bicyclo[3.1.0]hex-2-ene-6-carboxylic acid, (Isomer 1 and Isomer 2) were prepared following the method described in step 3 for the preparation of Example 4, using ethyl 3-((1R,3aS,5aR,5bR,7aR,11aS,11bR,13aR,13bR)-5a,5b,8,8,11a-pentamethyl-3a-((2-(4-(methylsulfonyl)piperidin-1-yl)ethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)bicyclo[3.1.0]hex-2-ene-6-carboxylate as the reactant. The crude was purified by prep HPLC with method 15, to afford two isomers:

Example A27: Isomer 1: (16.3%), MS: m/e 721.6 (M+H)$^+$, 2.613 min (method 8). $^1$H NMR (400 MHz, METHANOL-d$_4$) δ 5.82 (d, J=1.5 Hz, 1H), 5.53-5.37 (m, 1H), 4.85 (br. s., 1H), 4.74 (br. s., 1H), 3.26-3.16 (m, 4H), 3.04 (t, J=9.3 Hz, 1H), 2.97 (s, 3H), 2.95-2.82 (m, 2H), 2.82-2.71 (m, 2H), 2.67-2.52 (m, 2H), 2.48-2.35 (m, 2H), 2.26-1.98 (m, 9H), 1.98-1.74 (m, 5H), 1.76 (s, 3H), 1.71-1.30 (m, 12H), 1.20 (s, 3H), 1.18-1.13 (m, 1H), 1.09 (s, 3H), 1.06 (s, 6H), 1.02 (br. s., 1H), 0.89 (s, 3H).

Example A28: Isomer 2: (13.4%), MS: m/e 721.6 (M+H)$^+$, 2.649 min (method 8). $^1$H NMR (400 MHz, METHANOL-d$_4$) δ 5.83 (d, J=1.8 Hz, 1H), 5.47 (dd, J=6.4, 1.9 Hz, 1H), 4.86 (s, 1H), 4.75 (s, 1H), 3.29-3.17 (m, 4H), 3.04 (d, J=9.0 Hz, 1H), 2.98 (s, 3H), 2.94-2.71 (m, 4H), 2.68-2.57 (m, 2H), 2.44 (dq, J=6.6, 2.2 Hz, 2H), 2.27-1.97 (m, 9H), 1.94-1.79 (m, 4H), 1.78 (s, 3H), 1.74-1.26 (m, 14H), 1.22 (s, 3H), 1.11 (s, 6H), 1.04-1.00 (m, 4H), 0.89 (s, 3H).

Example A29

Preparation of 4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohexa-1,3-dienecarboxylic acid

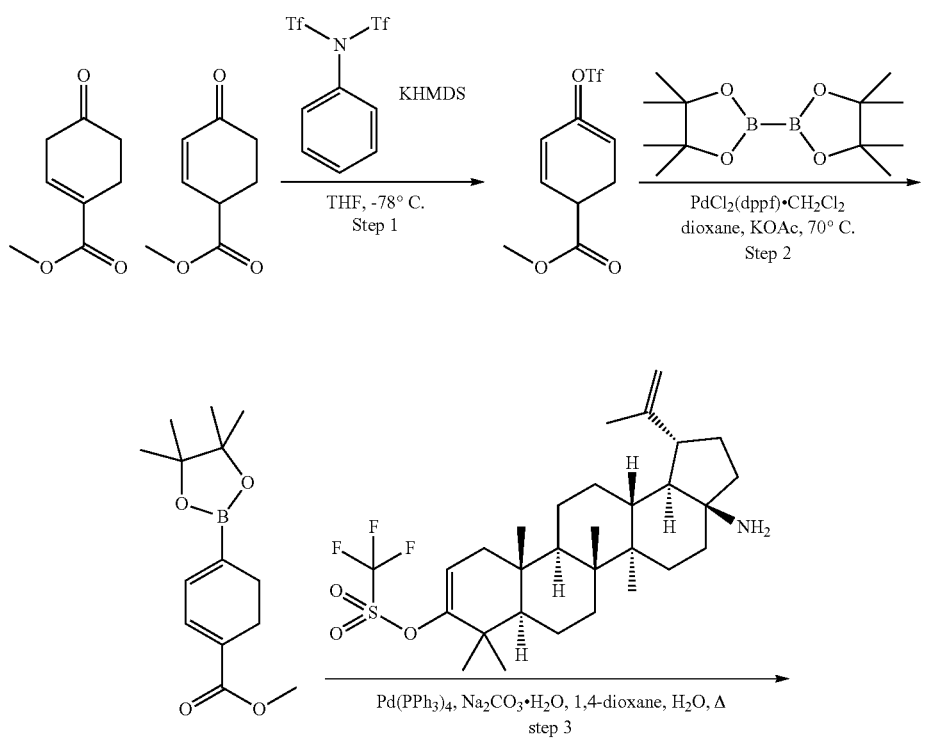

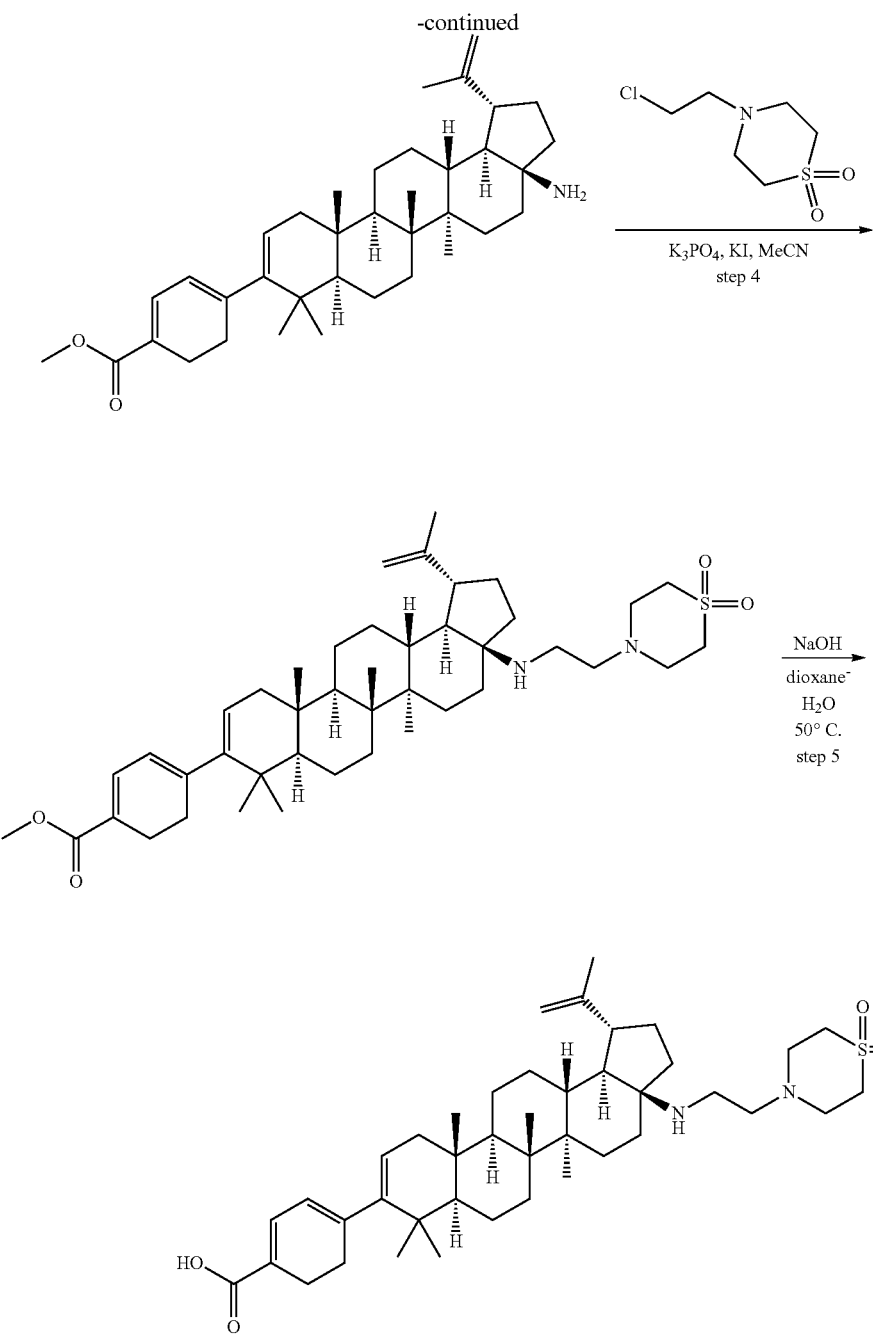

Example A29

Step 1: Preparation of methyl 4-(((trifluoromethyl)sulfonyl)oxy)cyclohexa-1,3-dienecarboxylate

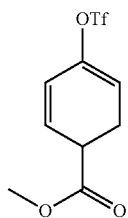

The title compound was prepared in 53.9% yield following the procedure described in step 6 of method 2 for the preparation of intermediate 1, using methyl 4-oxocyclohex-1-enecarboxylate and methyl 4-oxocyclohex-2-enecarboxylate as the reactants. Methyl 4-oxocyclohex-1-enecarboxylate and methyl 4-oxocyclohex-2-enecarboxylate were prepared following the procedures described in *Tet. Lett. Vol.* 53, issue 7, page 819-821. m/e 287.05 (M+H)$^+$, 2.435 min (method 8). $^1$H NMR (400 MHz, CHLOROFORM-d) δ 6.96 (dt, J=6.3, 1.5 Hz, 1H), 6.07 (dt, J=6.4, 1.4 Hz, 1H), 3.78 (s, 3H), 2.81-2.73 (m, 2H), 2.67-2.59 (m, 2H). $^{19}$F NMR (376 MHz, CHLOROFORM-d) δ −73.55 (s, 3F).

Step 2: Preparation of methyl 4-(4,4,5,5-tetramethyl-1,3,2-dioxaborolan-2-yl)cyclohexa-1,3-dienecarboxylate

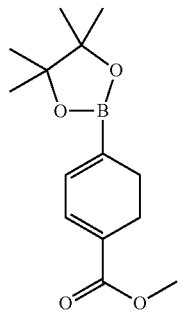

The title compound was prepared following the method described in step 2 for the preparation of methyl 6-(4,4,5,5-tetramethyl-1,3,2-dioxaborolan-2-yl)spiro[3.3]hept-5-ene-2-carboxylate, using methyl 4-(((trifluoromethyl)sulfonyl)oxy)cyclohexa-1,3-dienecarboxylate as the reactant. (46.6% yield). $^1$H NMR (400 MHz, CHLOROFORM-d) δ 7.00 (dt, J=5.3, 1.5 Hz, 1H), 6.75 (dt, J=5.3, 1.6 Hz, 1H), 3.74 (s, 3H), 2.42-2.35 (m, 2H), 2.34-2.27 (m, 2H), 1.26 (s, 12H).

Step 3: Preparation of methyl 4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohexa-1,3-dienecarboxylate

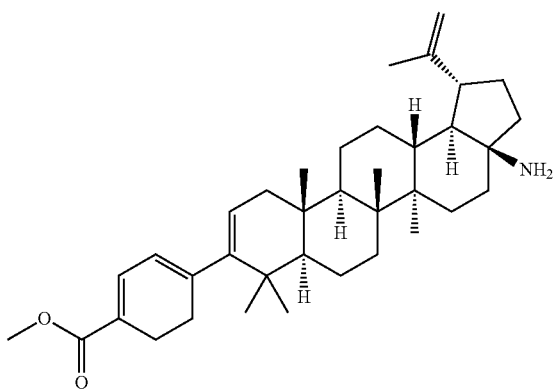

The title compound was prepared following the method described in step 1 for the preparation of Example 1, using (1R,3aS,5aR,5bR,7aR,11aR,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl trifluoromethanesulfonate and methyl 4-(4,4,5,5-tetramethyl-1,3,2-dioxaborolan-2-yl)cyclohexa-1,3-dienecarboxylate as the reactants. (60.8% yield). MS: m/e 529.5 (M−16)$^+$, 2.816 min (method 8). $^1$H NMR (400 MHz, CHLOROFORM-d) δ 6.99 (d, J=5.8 Hz, 1H), 5.78 (d, J=5.8 Hz, 1H), 5.27 (dd, J=6.0, 1.8 Hz, 1H), 4.70 (d, J=2.0 Hz, 1H), 4.57 (d, J=1.3 Hz, 1H), 3.72 (s, 3H), 2.52 (td, J=10.8, 5.3 Hz, 1H), 2.48-2.39 (m, 1H), 2.36-2.29 (m, 1H), 2.09-1.95 (m, 2H), 1.76-1.20 (m, 22H), 1.66 (s, 3H), 1.05 (s, 3H), 0.98 (s, 3H), 0.94 (s, 6H), 0.86 (s, 3H).

Step 4: Preparation of methyl 4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohexa-1,3-dienecarboxylate

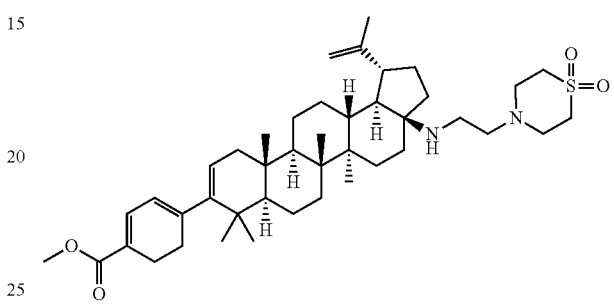

The title compound was prepared following the method described in step 2 for the preparation of Example 1, using methyl 4-((1R,3aS,5aR,5bR,7aR,11aS,11bR,13aR,13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohexa-1,3-dienecarboxylate as the reactant. (30.9% yield). MS: m/e 707.7 (M+H)$^+$, 3.20 min (method 2). $^1$H NMR (400 MHz, CHLOROFORM-d) δ 7.00 (d, J=5.8 Hz, 1H), 5.78 (d, J=5.8 Hz, 1H), 5.30-5.23 (m, 1H), 4.68 (d, J=2.0 Hz, 1H), 4.57 (d, J=1.3 Hz, 1H), 3.73 (s, 3H), 3.11-2.95 (m, 9H), 2.67-2.50 (m, 4H), 2.47-2.39 (m, 3H), 2.34-2.27 (m, 1H), 2.14-1.01 (m, 22H), 1.66 (s, 3H), 1.23 (s, 3H), 1.04 (s, 3H), 0.95 (s, 3H), 0.94 (s, 3H), 0.86 (s, 3H).

Step 5:

4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohexa-1,3-dienecarboxylic acid was following the method described in step 3 for the preparation of Example 4, using methyl 4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohexa-1,3-dienecarboxylate as the reactant. The crude was purified by prep HPLC with method 13 to afford the title compound in 34% yield MS: m/e 693.51 (M+H)$^+$, 2.2 min (method 2). $^1$H NMR (400 MHz, CHLOROFORM-d) δ 7.08 (d, J=5.5 Hz, 1H), 5.81 (d, J=5.5 Hz, 1H), 5.29 (d, J=4.8 Hz, 1H), 4.73 (s, 1H), 4.63 (s, 1H), 3.19-2.89 (m, 10H), 2.83-2.66 (m, 3H), 2.49-2.27 (m, 4H), 2.16-1.02 (m, 22H), 1.69 (s, 3H), 1.13 (s, 3H), 1.01 (s, 3H), 1.00 (s, 3H), 0.97 (s, 3H), 0.89 (s, 3H).

Example A30

Preparation of 4-((1R,3aS,5aR,5bR,7aR,11aS,11bR, 13aR,13bR)-5a,5b,8,8,11a-pentamethyl-3a-((2-(phenylsulfonyl)ethyl)amino)-1-(prop-1-en-2-yl)-2,3,3a, 4,5,5a,5b,6,7,7a,8,11,11a,11b,12,13,13a,13b-octadecahydro-1H-cyclopenta[a]chrysen-9-yl) cyclohexa-1,3-dienecarboxylic acid

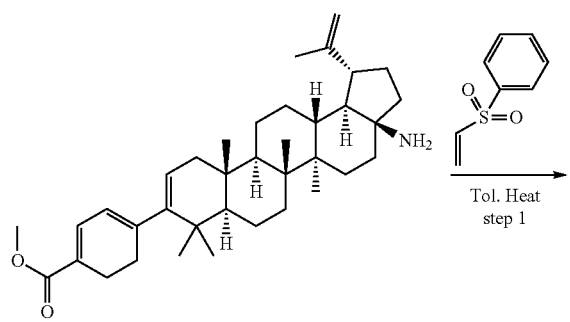

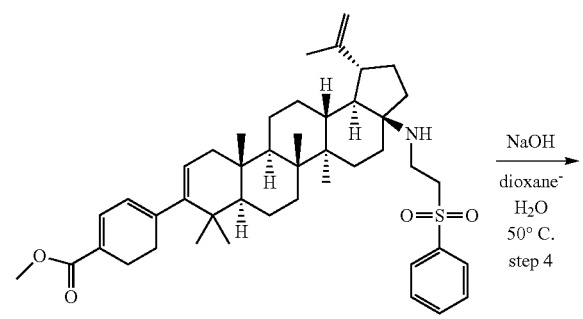

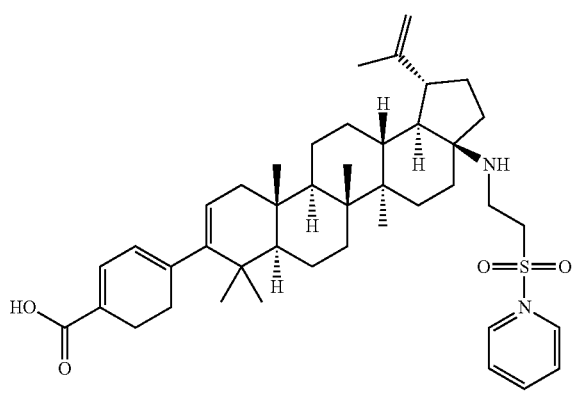

Example A30

Step 1: Preparation of methyl 4-((1R,3aS,5aR,5bR, 7aR,11aS,11bR,13aR,13bR)-5a,5b,8,8,11a-pentamethyl-3a-((2-(phenylsulfonyl)ethyl)amino)-1-(prop-1-en-2-yl)-2,3,3a,4,5,5a,5b,6,7,7a,8,11,11a,11b,12, 13,13a,13b-octadecahydro-1H-cyclopenta[a] chrysen-9-yl)cyclohexa-1,3-dienecarboxylate

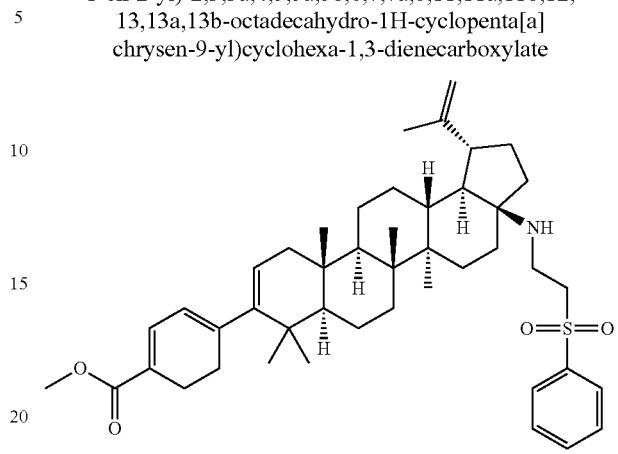

Methyl 4-((1R,3aS,5aR,5bR,7aR,11aS,11bR,13aR, 13bR)-3a-amino-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohexa-1, 3-dienecarboxylate (200 mg, 0.366 mmol) and (vinylsulfonyl)benzene (80 mg, 0.476 mmol) were dissolved in toluene (1 mL). The solution was warmed to 90° C. for 9 hours. The crude reaction mixture was applied onto a 12 gm silica gel column, purified with 0-10% ethyl acetate/hexanes as eluent to afford the title compound as a white solid (100 mg, 0.14 mmole, 38.2%). MS: m/e 714.53 (M+H)$^+$, 2.46 min (method 2). $^1$H NMR (400 MHz, CHLOROFORM-d) δ 8.03-7.89 (m, 2H), 7.73-7.66 (m, 1H), 7.66-7.57 (m, 2H), 7.08-7.01 (m, 1H), 5.83 (d, J=5.5 Hz, 1H), 5.30 (d, J=1.8 Hz, 1H), 4.70 (d, J=2.5 Hz, 1H), 4.65-4.55 (m, 1H), 3.82-3.71 (m, 3H), 3.42-3.24 (m, 2H), 3.03-2.86 (m, 1H), 2.86-2.70 (m, 1H), 2.56-2.40 (m, 3H), 2.40-2.26 (m, 1H), 2.09-2.00 (m, 1H), 1.98-1.85 (m, 1H), 1.85-1.73 (m, 2H), 1.71-1.67 (m, 3H), 1.67-1.38 (m, 7H), 1.37-1.11 (m, 12H), 1.10-1.07 (m, 3H), 1.04-1.01 (m, 3H), 0.98 (d, J=3.3 Hz, 3H), 0.97-0.94 (m, 3H), 0.92-0.89 (m, 3H).

Step 2

4-((1R,3aS,5aR,5bR,7aR,11aS,11bR,13aR,13bR)-5a,5b, 8,8,11a-pentamethyl-3a-((2-(phenylsulfonyl)ethyl)amino)-1-(prop-1-en-2-yl)-2,3,3a,4,5,5a,5b,6,7,7a,8,11,11a,11b,12, 13,13a,13b-octadecahydro-1H-cyclopenta[a]chrysen-9-yl) cyclohexa-1,3-dienecarboxylic acid was prepared following the method described in step 3 for the preparation of Example 4, using methyl 4-((1R,3aS,5aR,5bR,7aR,11aS,11bR,13aR, 13bR)-5a,5b,8,8,11a-pentamethyl-3a-((2-(phenylsulfonyl) ethyl)amino)-1-(prop-1-en-2-yl)-2,3,3a,4,5,5a,5b,6,7,7a,8, 11,11a,11b,12,13,13a,13b-octadecahydro-1H-cyclopenta[a] chrysen-9-yl)cyclohexa-1,3-dienecarboxylate as the reactant. The crude was purified by prep HPLC with method 13 to afford the title compound in 11.3% yield. MS: m/e 700.55 (M+H)$^+$, 2.838 min (method 8). $^1$H NMR (400 MHz, CHLOROFORM-d) δ 8.05-7.92 (m, 2H), 7.78-7.67 (m, 1H), 7.65-7.53 (m, 2H), 7.17 (d, J=5.8 Hz, 1H), 5.86 (d, J=5.8 Hz, 1H), 5.47-5.21 (m, 1H), 4.71 (d, J=2.0 Hz, 1H), 4.60 (s, 1H), 3.33 (td, J=6.1, 2.0 Hz, 1H), 2.92 (dt, J=12.7, 6.2 Hz, 1H), 2.85-2.68 (m, 1H), 2.53-2.29 (m, 6H), 2.24-1.85 (m, 5H), 1.84-1.70 (m, 3H), 1.69 (s, 3H), 1.67-1.11 (m, 13H), 1.09 (s, 3H), 1.03 (s, 3H), 1.00 (s, 3H), 0.95 (s, 3H), 0.91 (s, 3H).

Example A31
Preparation of 1-acetamido-4-((1R,3aS,5aR,5bR, 7aR,11aS,11bR,13aR,13bR)-3a-((2-(1,1-dioxidot- hiomorpholino)ethyl)amino)-5a,5b,8,8,11a-pentam- ethyl-1-(prop-1-en-2-yl)-2,3,3a,4,5,5a,5b,6,7,7a,8, 11,11a,11b,12,13,13a,13b-octadecahydro-1H- cyclopenta[a]chrysen-9-yl)cyclohex-3-enecarboxylic acid
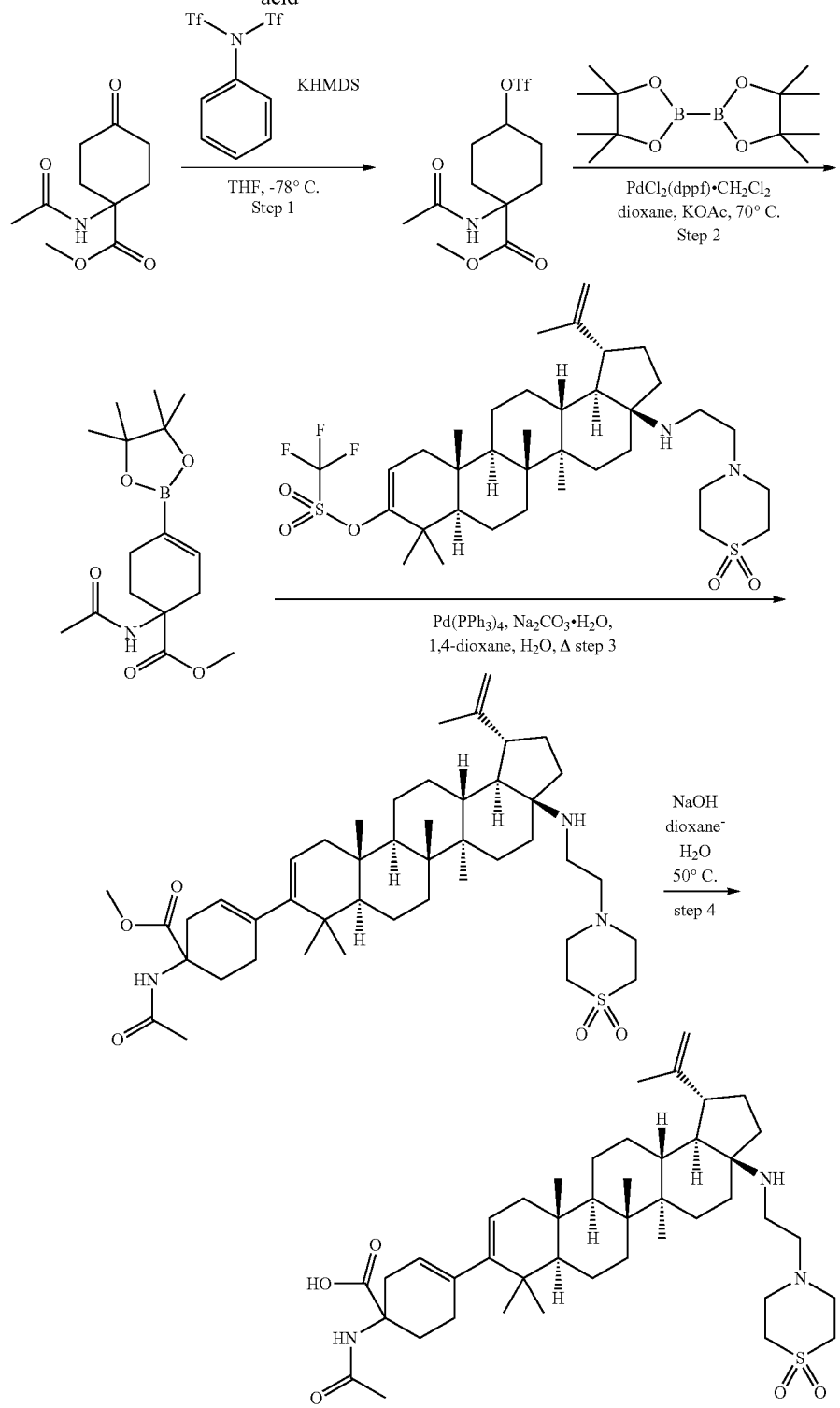
Example A31

Step 1: Preparation of methyl 1-acetamido-4-(((trifluoromethyl)sulfonyl)oxy)cyclohex-3-enecarboxylate

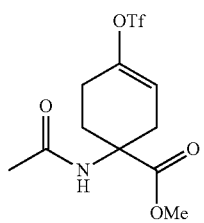 [SMILES: COC(=O)C1(NC(C)=O)CC=C(OS(=O)(=O)C(F)(F)F)CC1]

The title compound was prepared following the procedure described on step 6 of method 2 for the preparation of intermediate 1, using methyl 1-acetamido-4-oxocyclohexanecarboxylate, as the reactant. 1-acetamido-4-oxocyclohexanecarboxylate was prepared following the procedures described in *Journal of Chem. Soc., Perkin Trans. I*, 1999, pp. 3375-3379. (84.0% yield), MS: m/e 346.1 (M+H)+, 2.213 min (method ?). ¹H NMR (400 MHz, CHLOROFORM-d) δ 6.24 (s, 1H), 5.69 (td, J=3.3, 1.4 Hz, 1H), 3.82-3.58 (m, 3H), 2.87-2.67 (m, 1H), 2.61-2.44 (m, 2H), 2.42-2.33 (m, 2H), 2.19-2.07 (m, 1H), 2.01-1.94 (m, 3H). ¹⁹F NMR (376 MHz, CHLOROFORM-d) δ −74.02 (s, 3F).

Step 2: Preparation of methyl 1-acetamido-4-(4,4,5,5-tetramethyl-1,3,2-dioxaborolan-2-yl)cyclohex-3-enecarboxylate

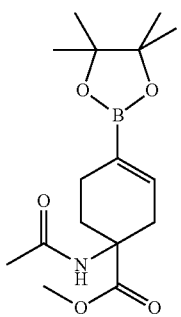 [SMILES: COC(=O)C1(NC(C)=O)CC=C(B2OC(C)(C)C(C)(C)O2)CC1]

The title compound was prepared following the method described in step 2 for the preparation of methyl 6-(4,4,5,5-tetramethyl-1,3,2-dioxaborolan-2-yl)spiro[3.3]hept-5-ene-2-carboxylate, using methyl 1-acetamido-4-(((trifluoromethyl)sulfonyl)oxy)cyclohex-3-enecarboxylate as the reactant. (48.4% yield). MS: m/e 325.25 (M+H)+, 2.126 min (method 8). ¹H NMR (400 MHz, CHLOROFORM-d) δ 6.42 (br. s., 1H), 5.90 (s, 1H), 3.83-3.59 (m, 3H), 2.65 (d, J=18.8 Hz, 1H), 2.35 (d, J=18.1 Hz, 1H), 2.25 (d, J=11.0 Hz, 2H), 2.13-2.03 (m, 1H), 1.98-1.90 (m, 3H), 1.88-1.75 (m, 1H), 1.36-1.18 (m, 12H).

Step 3: Preparation of methyl 1-acetamido-4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylate

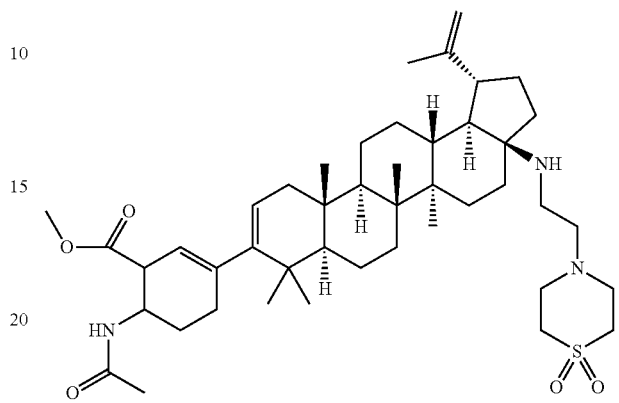

The title compound was prepared following the method described in step 1 for the preparation of Example 1, using (1R,3aS,5aR,5bR,7aR,11aR,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl trifluoromethanesulfonate and methyl 1-acetamido-4-(4,4,5,5-tetramethyl-1,3,2-dioxaborolan-2-yl)cyclohex-3-enecarboxylate as the reactants. The product was obtained as a mixture of diastereomers in 65.7% yield. MS: m/e 766.8 (M+H)+, 2.72 min (method 3). ¹H NMR (400 MHz, CHLOROFORM-d) δ 5.82 (d, J=3.0 Hz, 1H), 5.26 (br. s., 1H), 5.21-5.12 (m, 1H), 4.70 (d, J=2.0 Hz, 1H), 4.58 (d, J=1.3 Hz, 1H), 3.78-3.68 (m, 3H), 3.14-2.90 (m, 7H), 2.75-2.42 (m, 6H), 2.40-2.19 (m, 3H), 2.13-2.05 (m, 1H), 1.98 (d, J=2.0 Hz, 3H), 1.95-1.69 (m, 6H), 1.68 (s, 3H), 1.65-1.30 (m, 7H), 1.25 (m, 11H), 1.10-1.01 (m, 6H), 0.98-0.87 (m, 6H), 0.87-0.83 (m, 3H).

Step 4

1-acetamido-4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylic acid was prepared following the method described in step 3 for the preparation of Example 4, using methyl 1-acetamido-4-((1R,3aS,5aR,5bR,7aR,11aS,11bR,13aR,13bR)-3a-((2-(1,1-dioxidothiomorpholino)ethyl)amino)-5a,5b,8,8,11a-pentamethyl-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylate as the reactant. The crude was purified by preparative HPLC with method 13 to afford the title compound as a mixture of diastereomers in 41.5% yield. MS: m/e 752.55 (M+H)+, 2.53 min (method 8). ¹H NMR (500 MHz, CHLOROFORM-d) δ 6.38-6.05 (m, 1H), 5.27 (br. s., 1H), 5.22 (d, J=5.0 Hz, 1H), 4.73 (br. s., 1H), 4.62 (s, 1H), 3.26-2.90 (m, 9H), 2.89-2.49 (m, 5H), 2.46-2.23 (m, 3H), 2.22-2.06 (m, 4H), 2.00 (m, 2H), 1.97 (s, 3H), 1.90 (d, J=7.2 Hz, 4H), 1.70 (s, 3H), 1.63-1.15 (m, 14H), 1.11 (br. s., 3H), 1.03-0.97 (m, 6H), 0.94 (br. s., 3H), 0.87 (br. s., 3H).

Example A32
Preparation of 1-acetamido-4-((1R,3aS,5aR,5bR,7aR,11aS,11bR,13aR,13bR)-5a,5b,8,8,11a-pentamethyl-3a-((2-(4-(methylsulfonyl)piperidin-1-yl)ethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl cyclohex-3-enecarboxylic acid
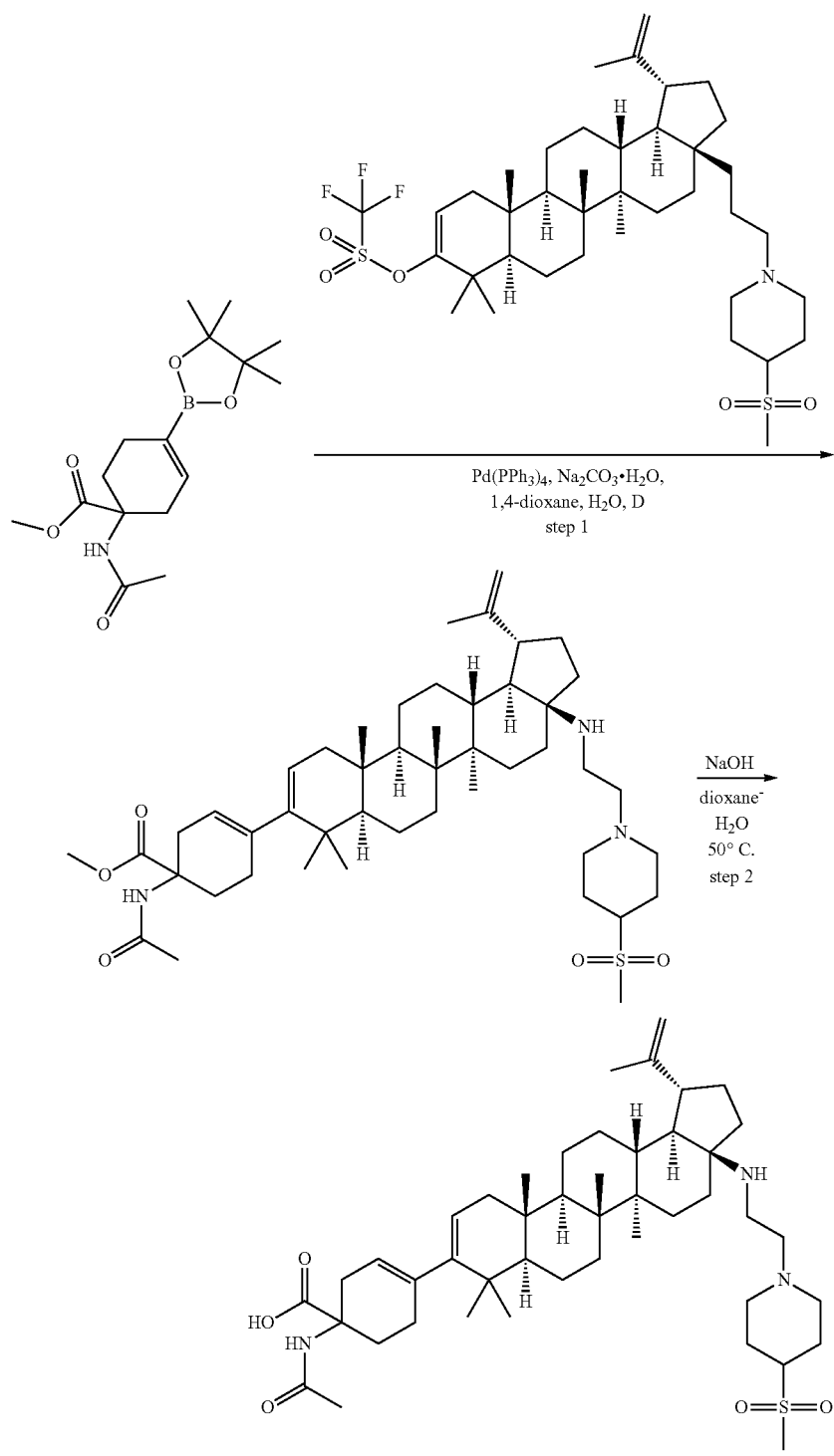
Example A32

Step 1: Preparation of methyl 1-acetamido-4-((1R,3aS,5aR,5bR,7aR,11aS,11bR,13aR,13bR)-5a,5b,8,8,11a-pentamethyl-3a-((2-(4-(methylsulfonyl)piperidin-1-yl)ethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylate

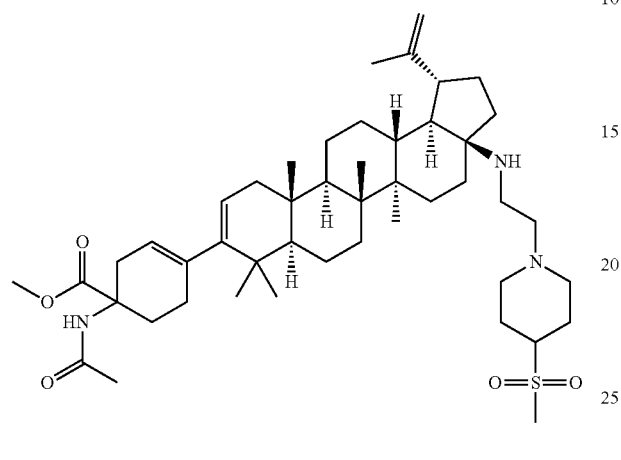

The title compound was prepared following the method described in step 1 for the preparation of Example 1, using (1R,3aS,5aR,5bR,7aR,11aR,11bR,13aR,13bR)-5a, 5b,8,8,11a-pentamethyl-3a-((2-(4-(methylsulfonyl)piperidin-1-yl)ethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl trifluoromethanesulfonate (triflate-2) and methyl 1-acetamido-4-(4,4,5,5-tetramethyl-1,3,2-dioxaborolan-2-yl)cyclohex-3-enecarboxylate as the reactants. The product was obtained as a mixture of diastereomers in 58.3% yield. MS: m/e 794.6 (M+H)$^+$, 2.718 min (method 8). $^1$H NMR (400 MHz, CHLOROFORM-d) δ 5.71 (d, J=5.5 Hz, 1H), 5.28 (br. s., 1H), 5.22 (s, 1H), 4.73 (br. s., 1H), 4.60 (br. s., 1H), 3.75 (s, 3H), 3.15 (d, J=10.5 Hz, 2H), 2.92-2.79 (m, 4H), 2.73-2.53 (m, 4H), 2.52-2.22 (m, 7H), 2.20-2.08 (m, 5H), 2.03 (br. s., 1H), 2.00 (d, J=1.8 Hz, 3H), 1.98-1.75 (m, 7H), 1.70 (s, 3H), 1.68-1.20 (m, 15H), 1.14-1.04 (m, 6H), 1.00-0.91 (m, 6H), 0.86 (s, 3H).

Step 2

1-acetamido-4-((1R,3aS,5aR,5bR,7aR,11aS,11bR,13aR,13bR)-5a,5b,8,8,11a-pentamethyl-3a-((2-(4-(methylsulfonyl)piperidin-1-yl)ethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylic acid was prepared following the method described in step 3 for the preparation of Example 4, using methyl 1-acetamido-4-((1R,3 aS,5aR,5bR,7aR,11aS,11bR,13 aR,13bR)-5a,5b,8,8,11a-pentamethyl-3a-((2-(4-(methylsulfonyl)piperidin-1-yl)ethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-enecarboxylate as the reactant. The crude was purified by preparative HPLC with method 13 to afford the title compound as a mixture of diastereomers in 41.9% yield. MS: m/e 780.55 (M+H)$^+$, 2.57 min (method 8). $^1$H NMR (400 MHz, CHLOROFORM-d) δ 6.22 (br. s., 1H), 5.36-5.24 (m, 1H), 5.21 (br. s., 1H), 4.85-4.70 (m, 1H), 4.63 (s, 1H), 3.30-3.09 (m, 2H), 2.87 (m, 5H), 2.81-2.50 (m, 5H), 2.42 (br. s., 2H), 2.27-2.03 (m, 10H), 1.98 (m, 4H), 1.92 (m, 5H), 1.91-1.68 (m, 4H), 1.70 (s, 3H), 1.65-1.19 (m, 12H), 1.14 (s, 3H), 1.08-0.91 (m, 9H), 0.86 (br. s., 3H).

Example A33

Preparation of 2-(4-((1R,3aS,5aR,5bR,7aR,11aS,11bR,13aR,13bR)-5a,5b,8,8,11a-pentamethyl-3a-((2-(4-(methylsulfonyl)piperidin-1-yl)ethyl)amino)-1-(prop-1-en-2-yl)-2,3,3a,4,5,5a,5b,6,7,7a,8,11,11a,11b,12,13,13a,13b-octadecahydro-1H-cyclopenta[a]chrysen-9-yl)cyclohex-3-en-1-yl)acetic acid

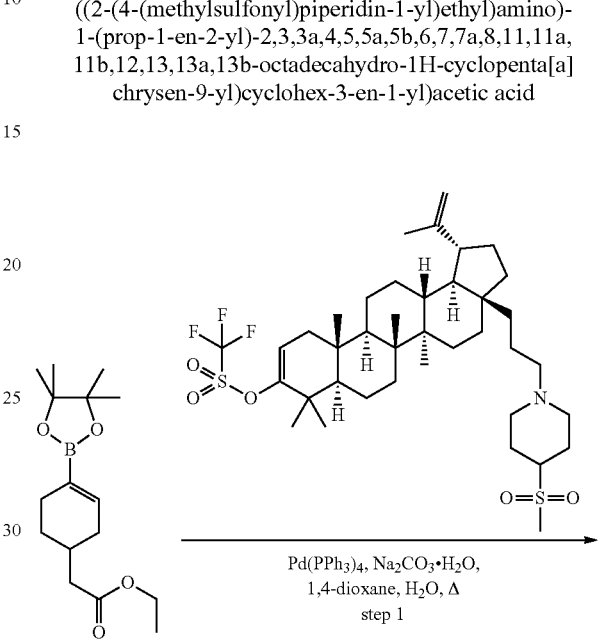

Pd(PPh$_3$)$_4$, Na$_2$CO$_3$·H$_2$O,
1,4-dioxane, H$_2$O, Δ
step 1

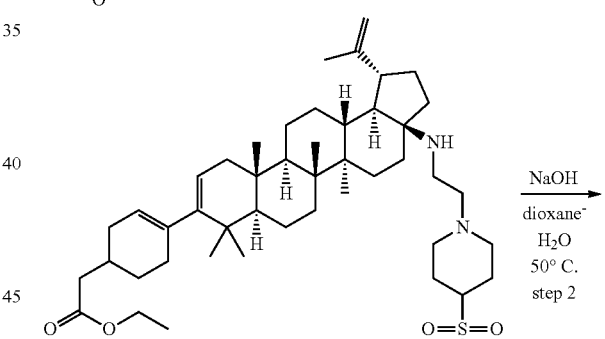

NaOH
dioxane-
H$_2$O
50° C.
step 2

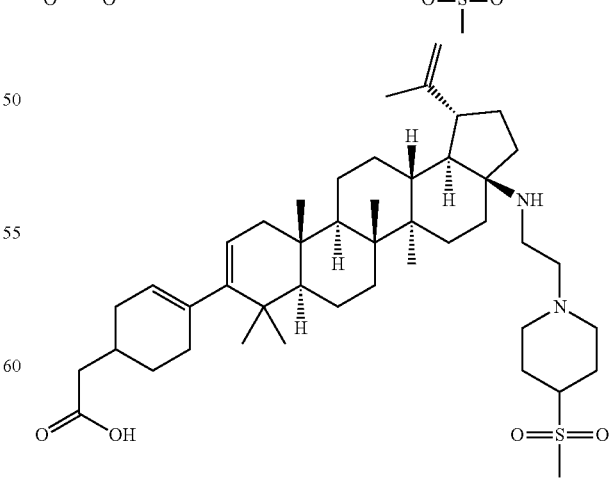

Example A33

Step 1: Preparation of ethyl 2-(4-((1R,3aS,5aR,5bR, 7aR,11aS,11bR,13aR,13bR)-5a,5b,8,8,11a-pentamethyl-3a-((2-(4-(methylsulfonyl)piperidin-1-yl)ethyl) amino)-1-(prop-1-en-2-yl)-2,3,3a,4,5,5a,5b,6,7,7a,8, 11,11a,11b,12,13,13a,13b-octadecahydro-1H-cyclopenta[a]chrysen-9-yl)cyclohex-3-en-1-yl) acetate

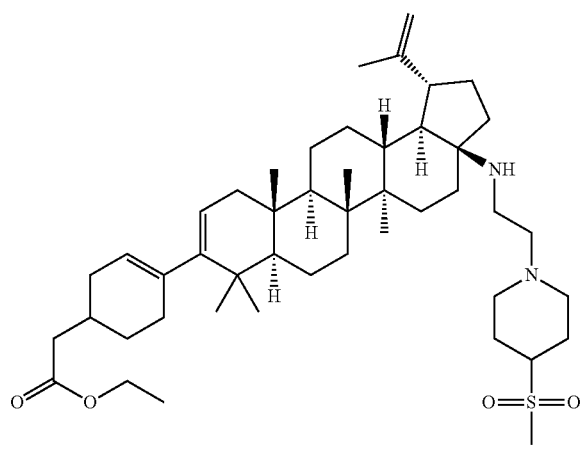

The title compound was prepared following the method described in step 1 for the preparation of Example 1, using (1R,3aS,5aR,5bR,7aR,11aR,11bR,13aR,13bR)-5a, 5b,8,8, 11a-pentamethyl-3a-((2-(4-(methylsulfonyl)piperidin-1-yl) ethyl)amino)-1-(prop-1-en-2-yl)-2,3,3a,4,5,5a,5b,6,7,7a,8, 11,11a, 11b,12,13,13a,13b-octadecahydro-1H-cyclopenta [a]chrysen-9-yl trifluoromethanesulfonate and methyl 1-acetamido-4-(4,4,5,5-tetramethyl-1,3,2-dioxaborolan-2-yl)cyclohex-3-enecarboxylate from as the reactants. The title compound was obtained as a mixture of diastereomers in 29.3% yield. MS: m/e 765.55 (M+H)$^+$, 3.03 min (method 8). $^1$H NMR (500 MHz, CHLOROFORM-d) δ 5.30 (s, 1H), 5.20-5.16 (m, 1H), 4.72 (d, J=1.8 Hz, 1H), 4.59 (d, J=1.2 Hz, 1H), 4.17-4.11 (m, 2H), 3.12 (t, J=11.9 Hz, 2H), 2.87-2.78 (m, 1H), 2.83 (s, 3H), 2.70-2.55 (m, 3H), 2.52-2.43 (m, 2H), 2.32-0.94 (m, 40H), 1.69 (s, 3H), 1.07 (s, 3H), 0.97-0.91 (m, 6H), 0.96 (s, 3H), 0.85 (s, 3H).

Step 2

2-(4-((1R,3aS,5aR,5bR,7aR,11aS,11bR,13aR,13bR)-5a, 5b,8,8,11a-pentamethyl-3a-((2-(4-(methylsulfonyl)piperidin-1-yl)ethyl)amino)-1-(prop-1-en-2-yl)-2,3,3a,4,5,5a,5b, 6,7,7a,8,11,11a,11b,12,13,13a,13b-octadecahydro-1H-cyclopenta[a]chrysen-9-yl)cyclohex-3-en-1-yl)acetic acid was prepared following the method described in step 3 for the preparation of Example 4, using methyl 1-acetamido-4-((1R, 3aS,5aR,5bR,7aR,11aS,11bR,13aR,13bR)-5a,5b,8,8,11a-pentamethyl-3a-((2-(4-(methylsulfonyl)piperidin-1-yl) ethyl)amino)-1-(prop-1-en-2-yl)-2,3,3a,4,5,5a,5b,6,7,7a,8, 11,11a,11b,12,13,13a,13b-octadecahydro-1H-cyclopenta[a] chrysen-9-yl)cyclohex-3-enecarboxylate as the reactant. The crude was purified by prep HPLC with method 13 to afford the title compound as a mixture of diastereomers in 39.4% yield MS: m/e 737.55 (M+H)$^+$, 2.928 min (method 8). $^1$H NMR (400 MHz, CHLOROFORM-d) δ 5.31 (s, 1H), 5.17 (d, J=6.3 Hz, 1H), 4.73 (s, 1H), 4.62 (s, 1H), 3.18 (t, J=12.4 Hz, 2H), 2.90-2.68 (m, 5H), 2.84 (s, 3H), 2.58-2.50 (m, 1H), 2.32-1.02 (m, 37H). 1.69 (s, 3H), 1.13 (s, 3H), 0.98 (s, 3H), 0.98-0.90 (m, 6H), 0.85 (s, 3H).

Biology Data for the Examples

"μM" means micromolar;

"mL" means milliliter;

"μl" means microliter;

"mg" means milligram;

"μg" means microgram;

The materials and experimental procedures used to obtain the results reported in Tables 1-2 are described below.

HIV Cell Culture Assay—

MT-2 cells and 293T cells were obtained from the NIH AIDS Research and Reference Reagent Program. MT-2 cells were propagated in RPMI 1640 media supplemented with 10% heat inactivated fetal bovine serum, 100 μg/ml penicillin G and up to 100 units/ml streptomycin. The 293T cells were propagated in DMEM media supplemented with 10% heat inactivated fetal bovine serum (FBS), 100 units/ml penicillin G and 100 μg/ml streptomycin. The proviral DNA clone of $NL_{4-3}$ was obtained from the NIH AIDS Research and Reference Reagent Program. A recombinant $NL_{4-3}$ virus, in which a section of the nef gene from NL4-3 was replaced with the Renilla luciferase gene, was used as a reference virus. In addition, residue Gag P373 was converted to P373S. Briefly, the recombinant virus was prepared by transfection of the altered proviral clone of $NL_{4-3}$. Transfections were performed in 293T cells using LipofectAMINE PLUS from Invitrogen (Carlsbad, Calif.), according to manufacturer's instruction. The virus was titered in MT-2 cells using luciferase enzyme activity as a marker. Luciferase was quantitated using the Dual Luciferase kit from Promega (Madison, Wis.), with modifications to the manufacturer's protocol. The diluted Passive Lysis solution was pre-mixed with the re-suspended Luciferase Assay Reagent and the re-suspended Stop & Glo Substrate (2:1:1 ratio). Fifty (50) μL of the mixture was added to each aspirated well on assay plates and luciferase activity was measured immediately on a Wallac TriLux (Perkin-Elmer). Antiviral activities of inhibitors toward the recombinant virus were quantified by measuring luciferase activity in cells infected for 4-5 days with NLRluc recombinants in the presence serial dilutions of the inhibitor. The $EC_{50}$ data for the compounds is shown in Table 1.

Results

TABLE 1

| Example # | Structure | EC$_{50}$ (μM) |
|---|---|---|
| 1 | 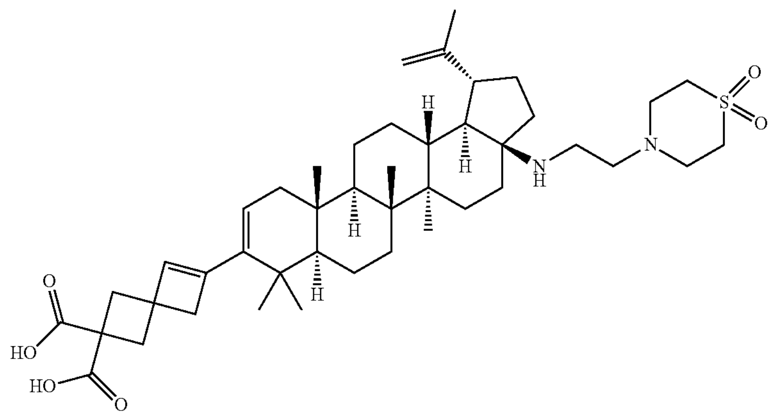 | 0.01 |
| 2 | 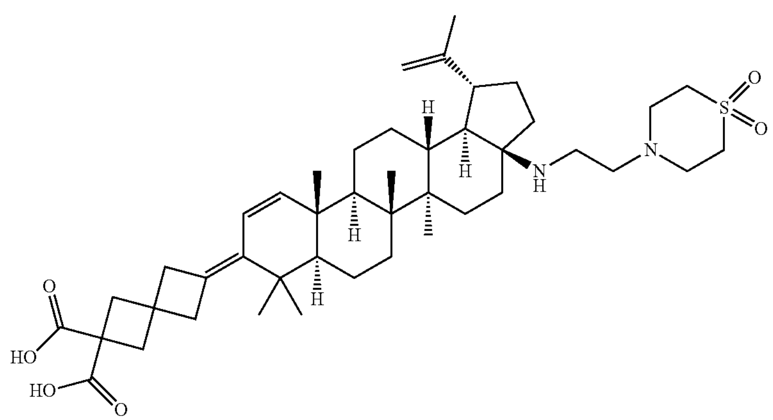 | 0.03 |
| 3 | 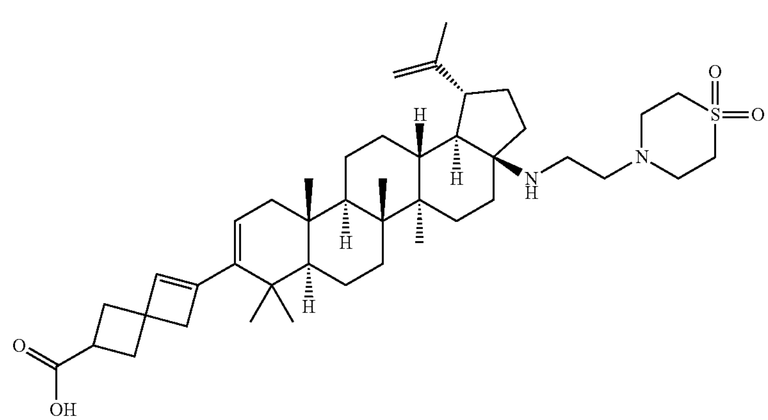 | 1.54E−03 |

TABLE 1-continued

| Example # | Structure | EC$_{50}$ (μM) |
|---|---|---|
| 4 | 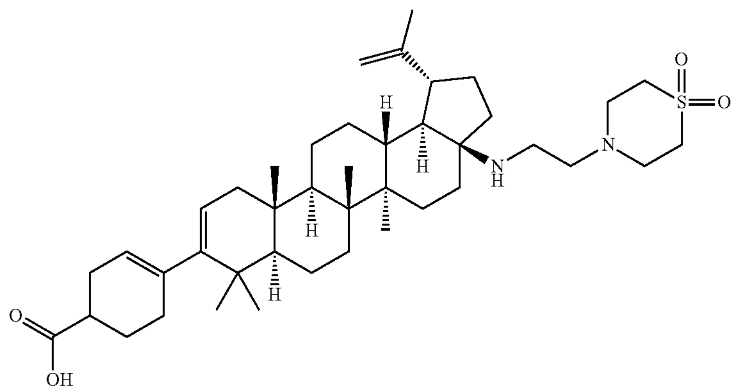 | 6.59E−04 |
| 5 | 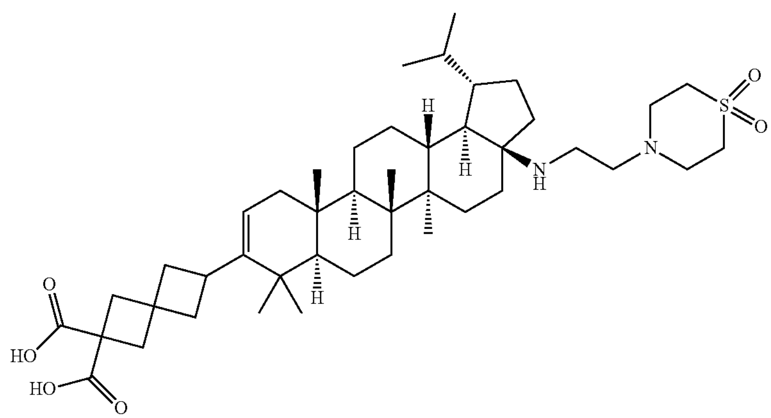 | 0.04 |
| 6 | 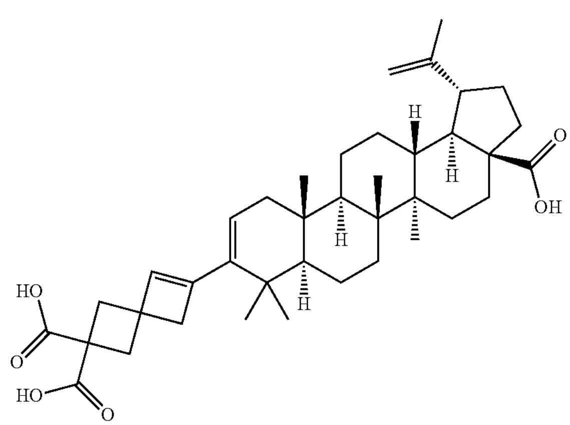 | 0.03 |

TABLE 1-continued

| Example # | Structure | EC$_{50}$ (µM) |
|---|---|---|
| 7 | 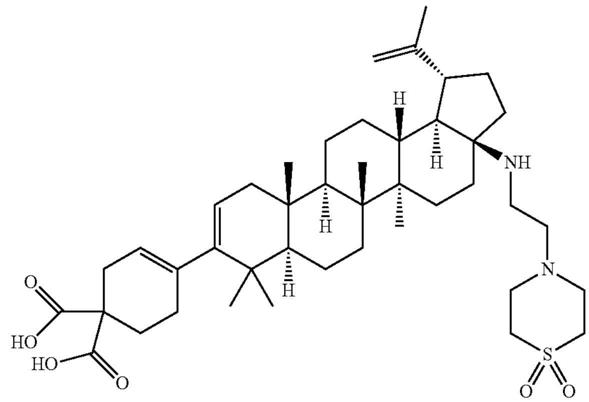 | 0.10 |
| 8 | 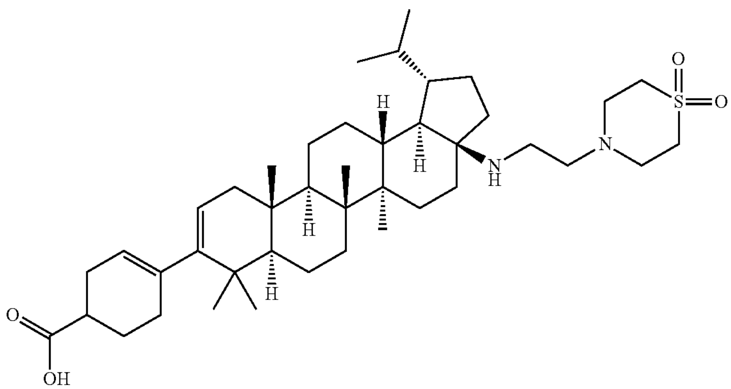 | 1.01E−03 |
| 9 | 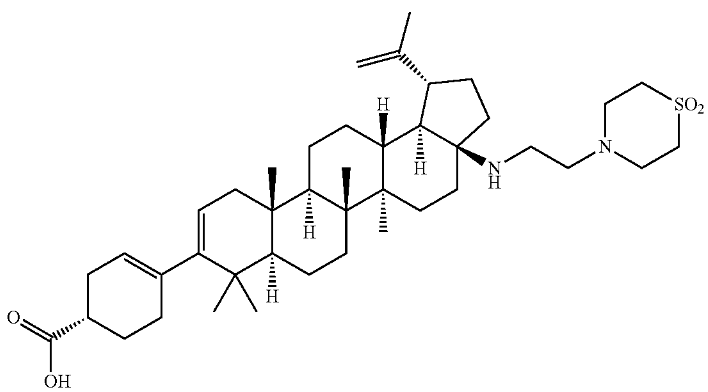 | 8.92E−04 |
| 10 | 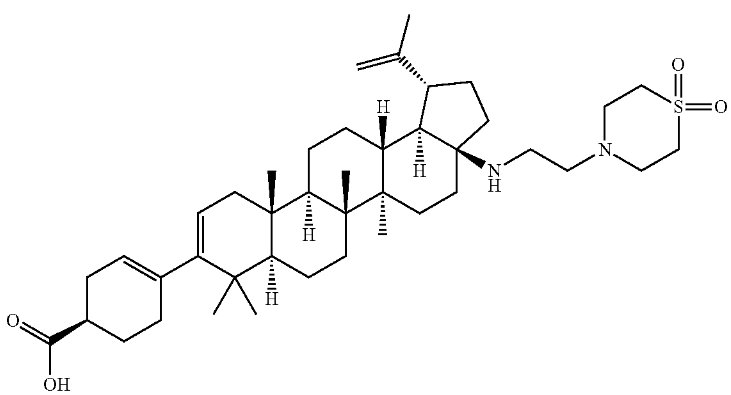 | 1.26E−03 |

TABLE 1-continued
| Example # | Structure | EC$_{50}$ (μM) |
|---|---|---|
| 11 | 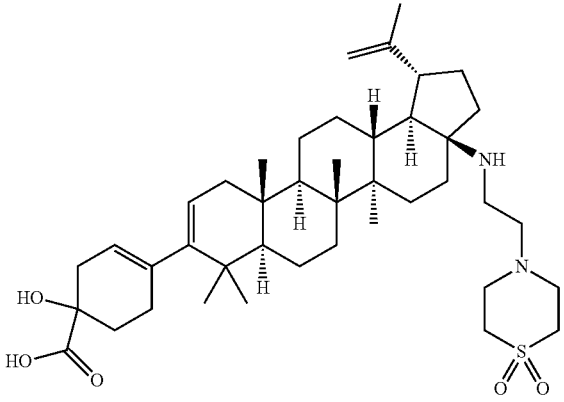 | 1.99E−03 |
| 12 | 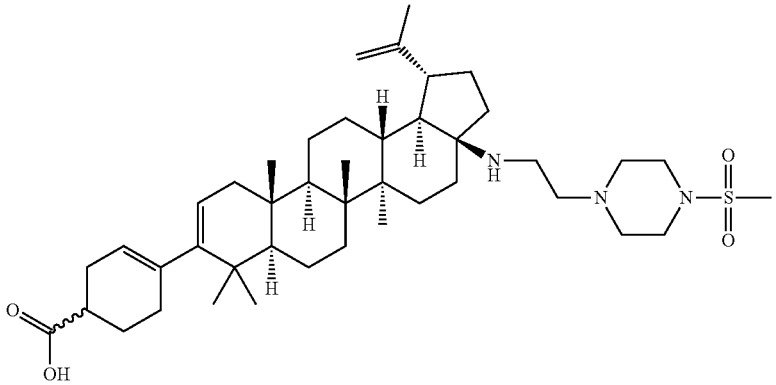 | 3.03E−03 |
| 13 | 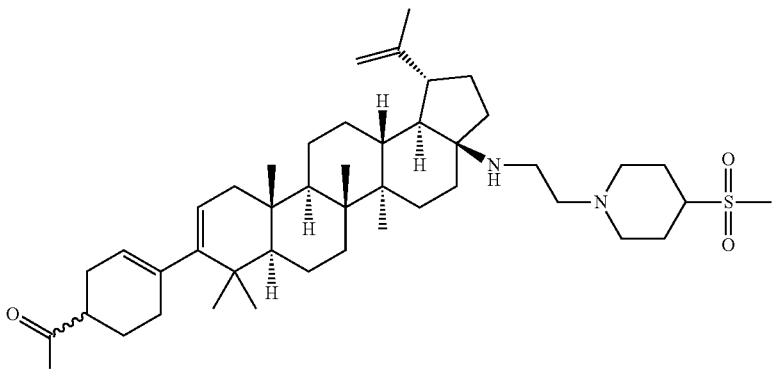 | 9.75E−04 |

TABLE 1-continued

| Example # | Structure | EC$_{50}$ (μM) |
|---|---|---|
| 14 | 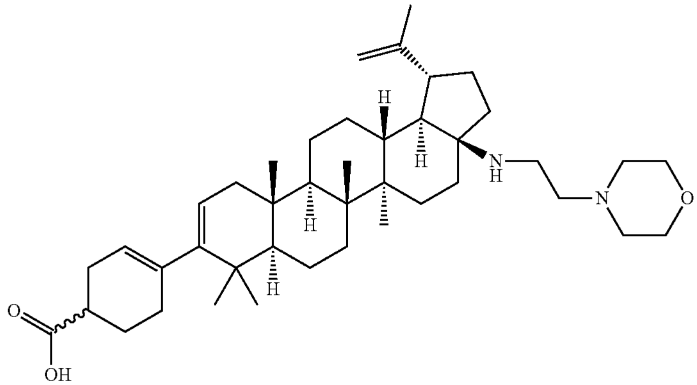 | 5.61E−03 |
| 15 | 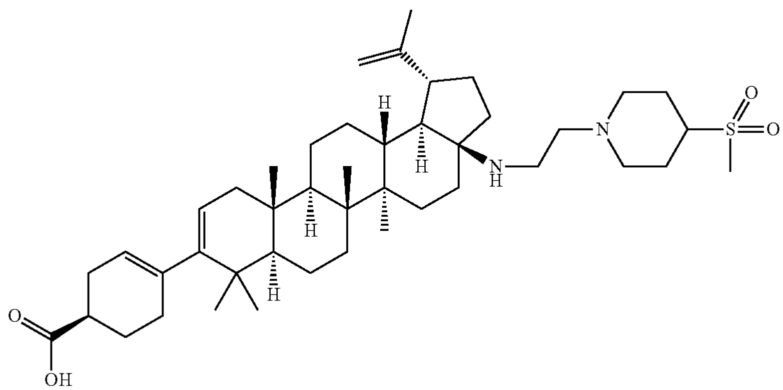 | 1.36E−03 |
| 16 | 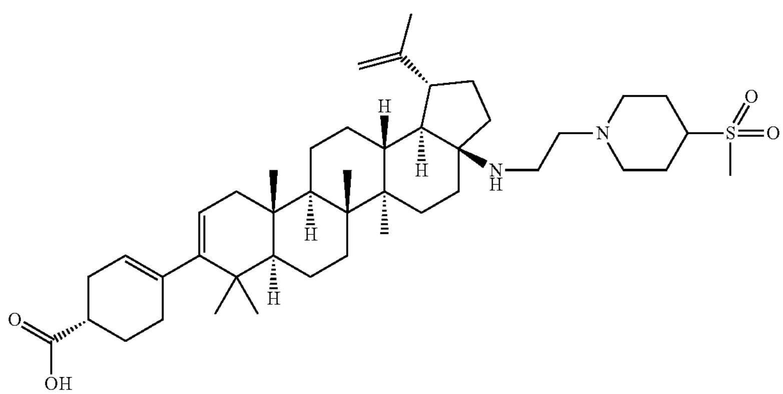 | 3.05E−03 |
| 17 | 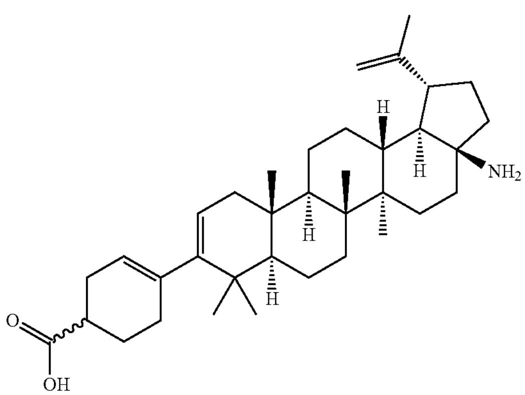 | 8.77E−04 |

TABLE 1-continued

| Example # | Structure | EC$_{50}$ (μM) |
|---|---|---|
| 18 | 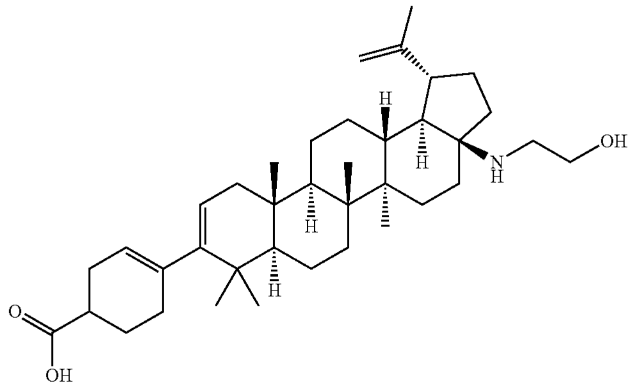 | 1.38E−03 |
| 19 | 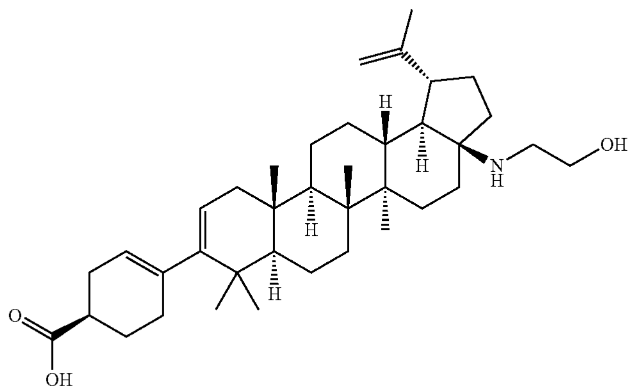 | 1.14E−03 |
| 20 | 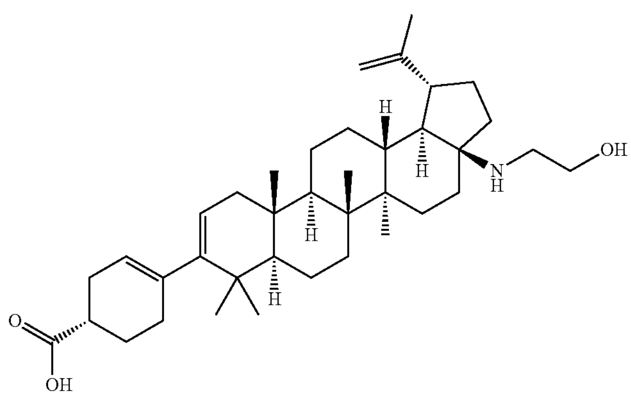 | 1.57E−03 |
| 21 | 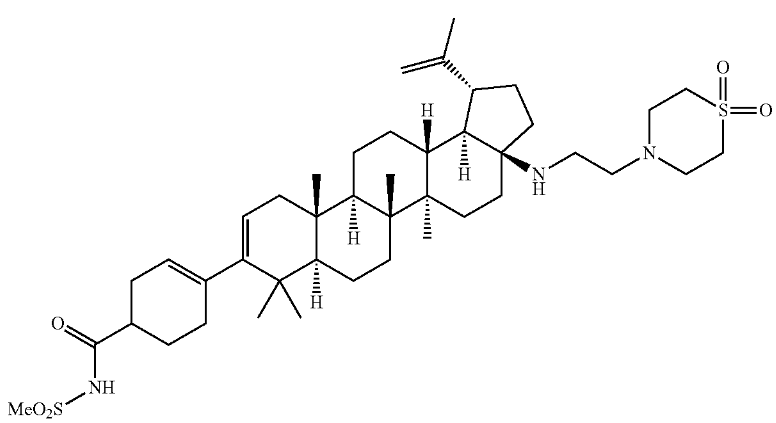 | 1.80E−03 |

TABLE 1-continued
| Example # | Structure | EC$_{50}$ (μM) |
|---|---|---|
| A1 | 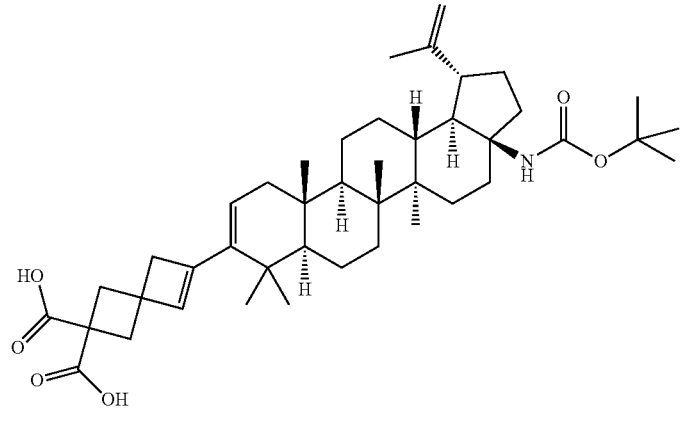 | 0.57 |
| A2 | 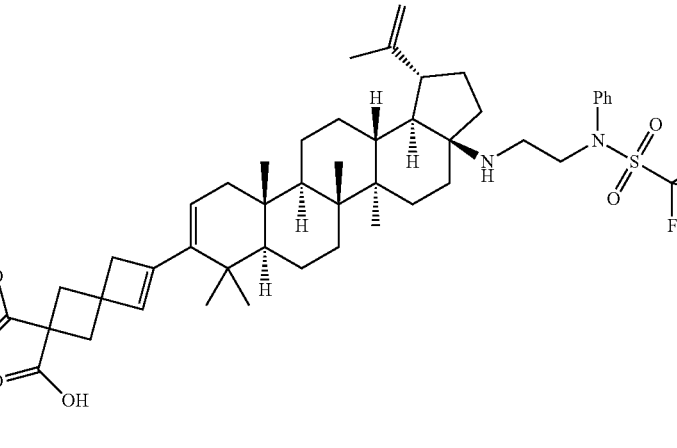 | 1.07 |
| A3 | 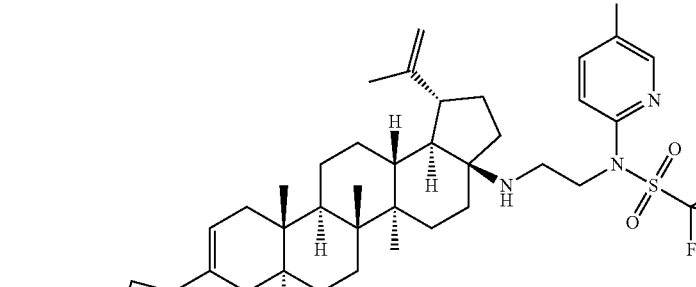 | 1.75 |

TABLE 1-continued

| Example # | Structure | EC$_{50}$ (μM) |
|---|---|---|
| A4 | 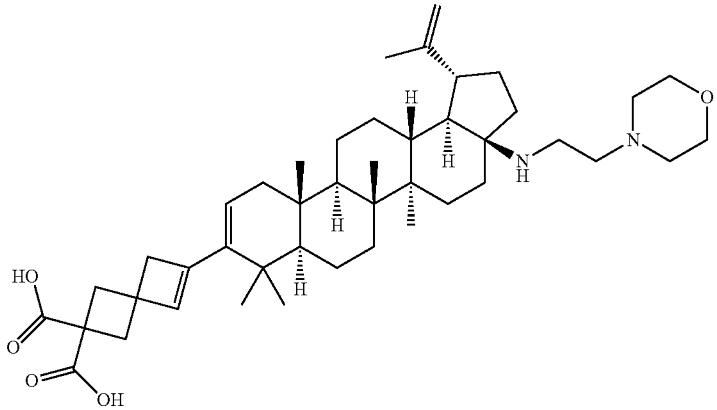 | 0.10 |
| A5 | 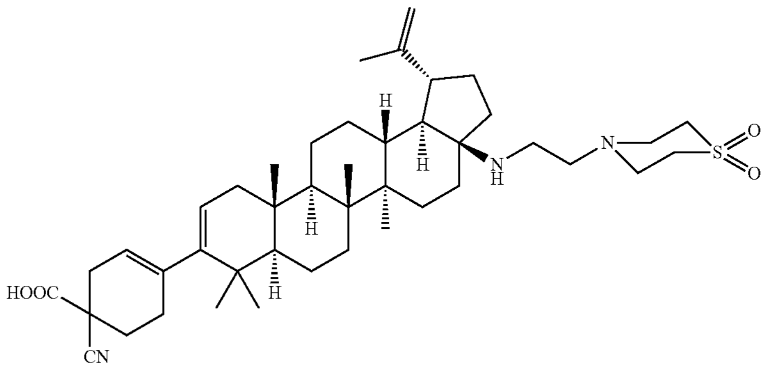 | 4.26E−03 |
| A6 | 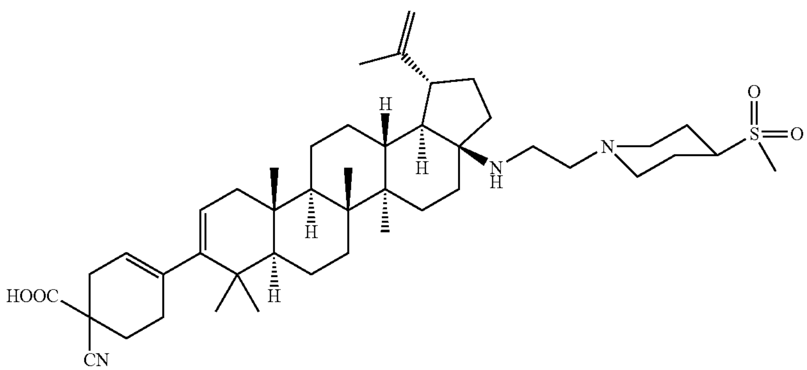 | 6.18E−03 |
| A7 | 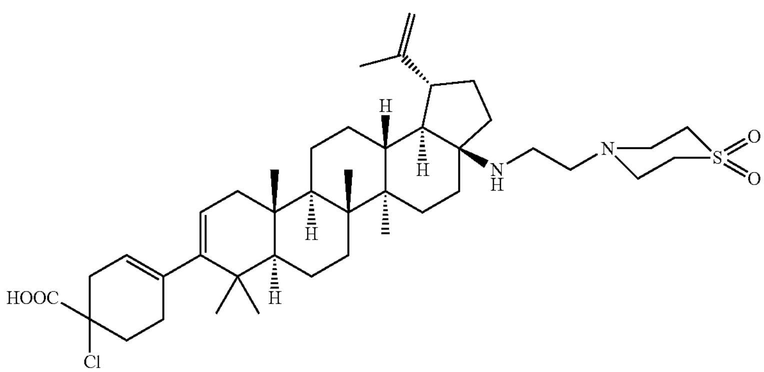 | 2.91E−03 |

TABLE 1-continued

| Example # | Structure | EC$_{50}$ (μM) |
|---|---|---|
| A8 | 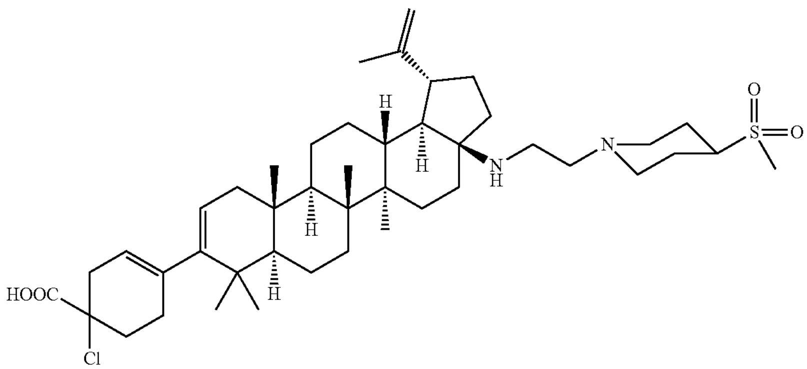 | 2.42E−03 |
| A9 | 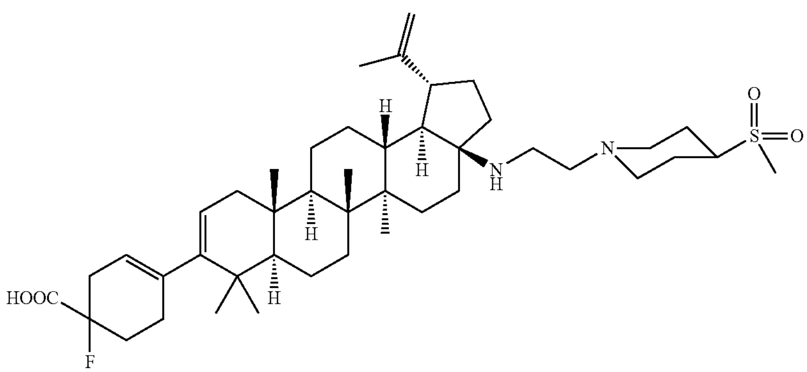 | 2.84E−03 |
| A10 | 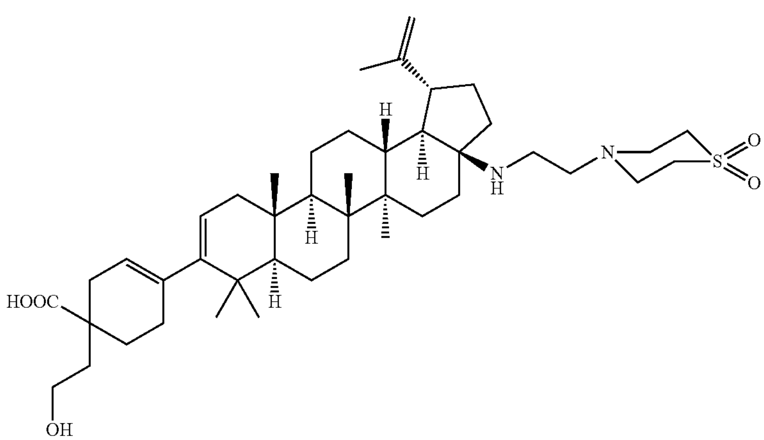 | 4.86E−03 |

TABLE 1-continued

| Example # | Structure | EC$_{50}$ (μM) |
|---|---|---|
| A11 | 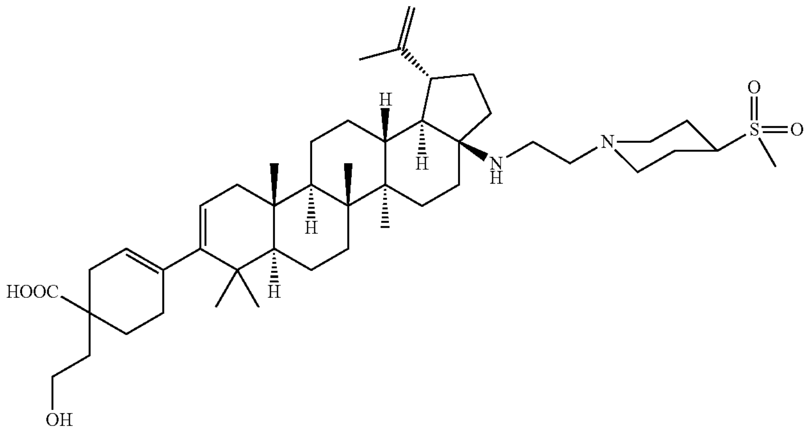 | 2.65E−03 |
| A12 | 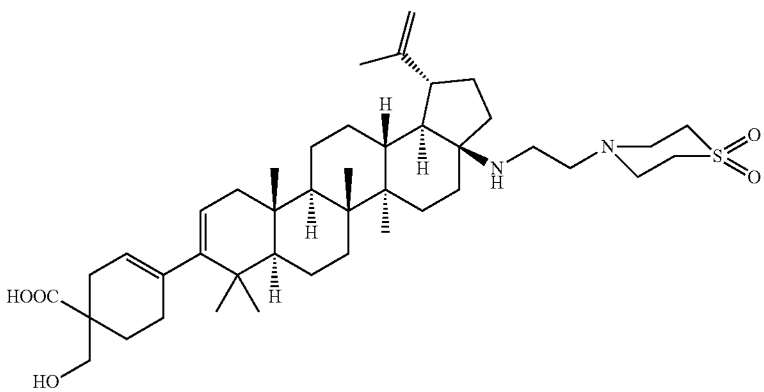 | 2.46E−03 |
| A13 | 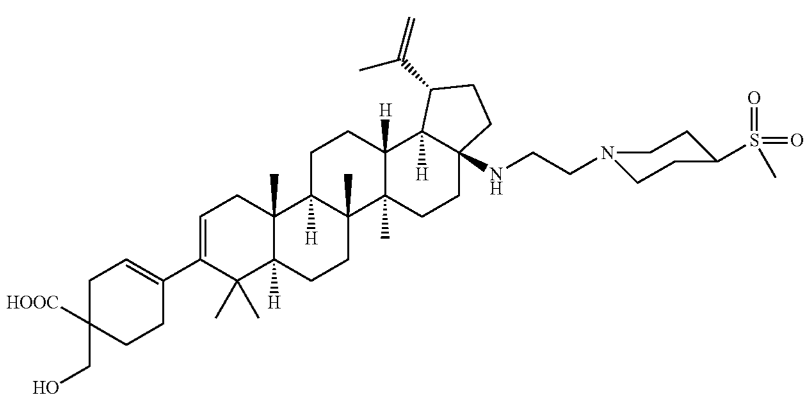 | 3.01E−04 |

TABLE 1-continued

| Example # | Structure | EC$_{50}$ (μM) |
|---|---|---|
| A14 | 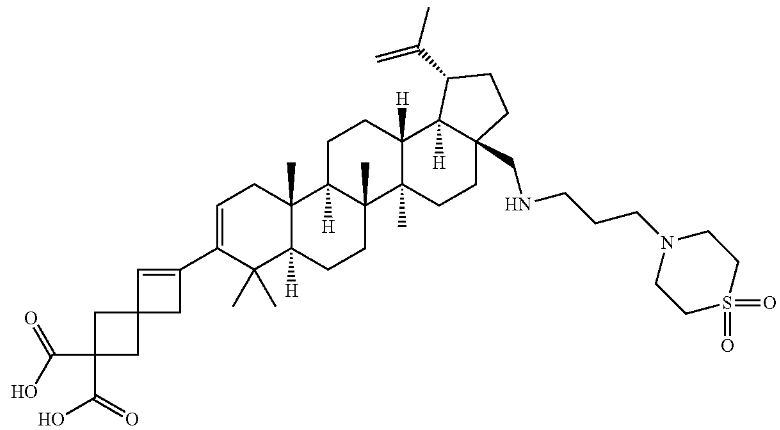 | 0.19 |
| A15 | 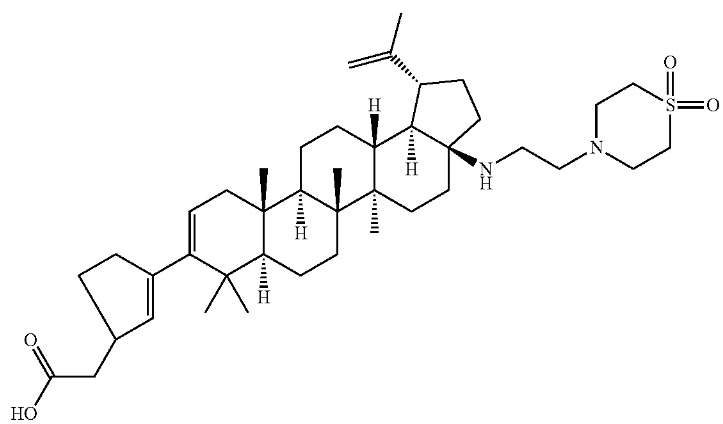 | 5.47E−04 |
| A16 | 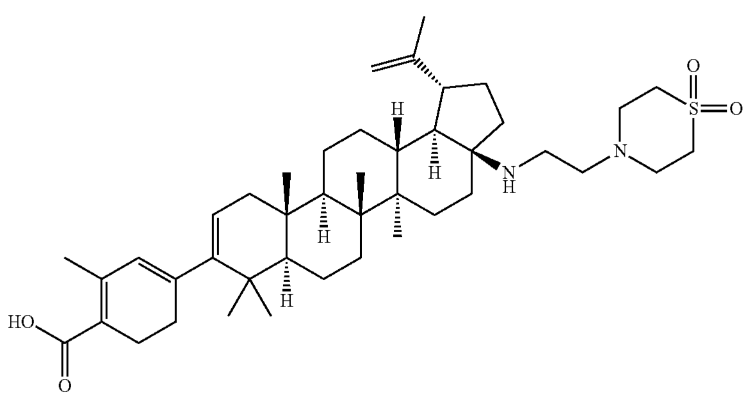 | 2.23E−03 |

TABLE 1-continued

| Example # | Structure | EC$_{50}$ (μM) |
|---|---|---|
| A17 | 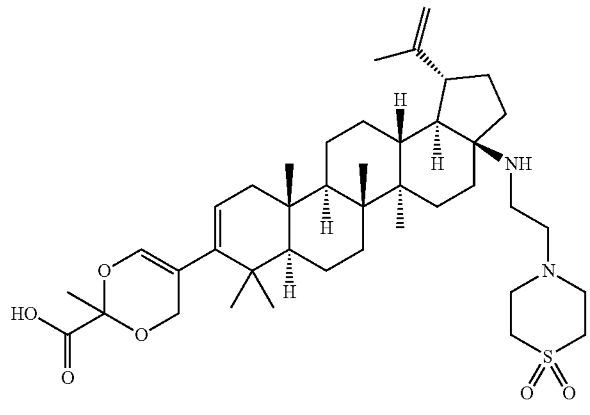 | 0.32 |
| A18 | 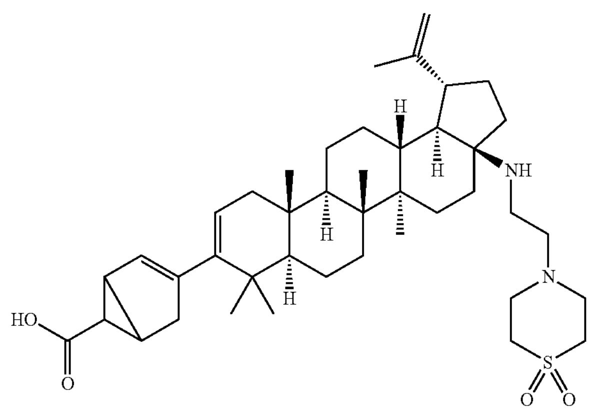 | 2.26E−03 |
| A19 | Isomer 1 | 0.10 |

TABLE 1-continued
| Example # | Structure | EC$_{50}$ (µM) |
|---|---|---|
| A20 | 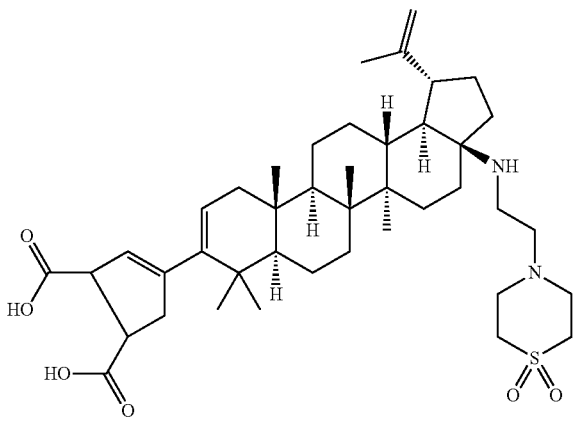 Isomer 2 | 0.06 |
| A21 | 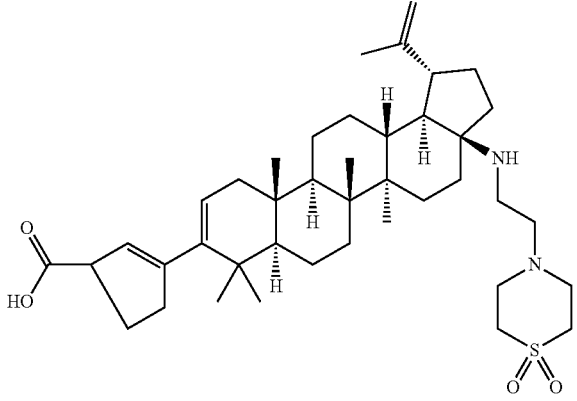 | 2.76E–03 |
| A22 | 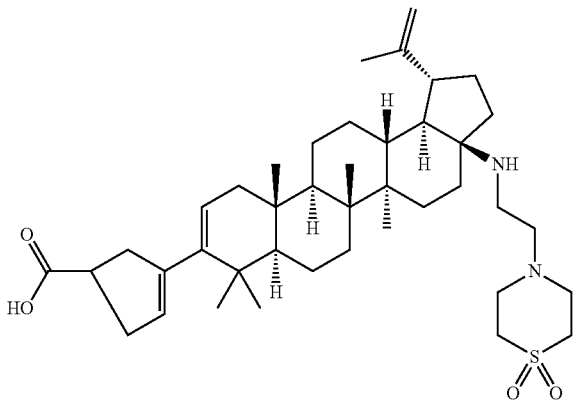 | 3.53E–03 |

TABLE 1-continued
| Example # | Structure | EC$_{50}$ (μM) |
|---|---|---|
| A23 | 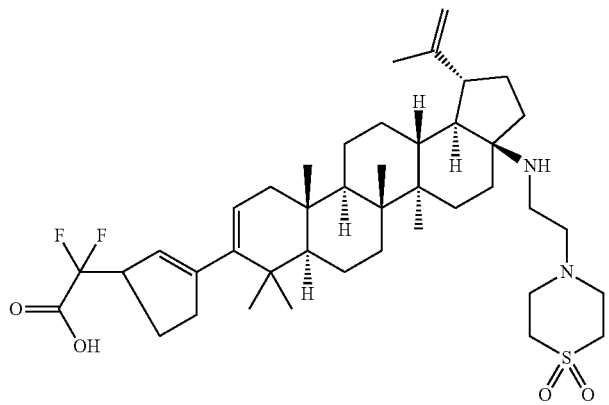 | 5.63E−03 |
| A24 | 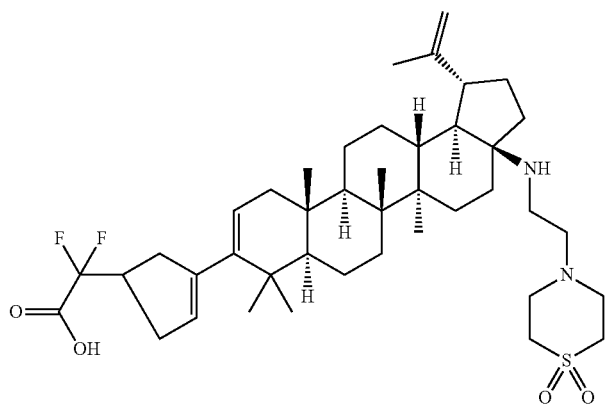 | 4.65E−03 |
| A25 | 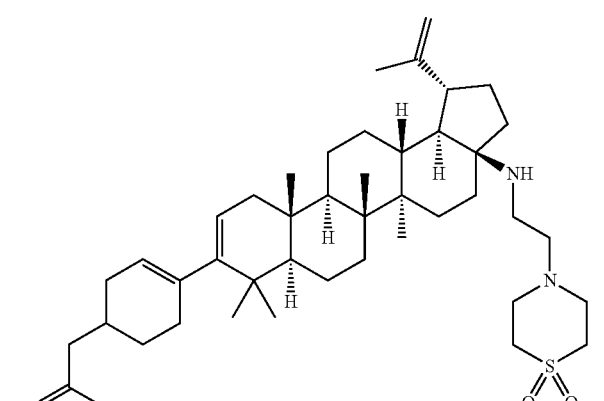 | 1.31E−03 |

TABLE 1-continued
| Example # | Structure | EC$_{50}$ (μM) |
|---|---|---|
| A26 | 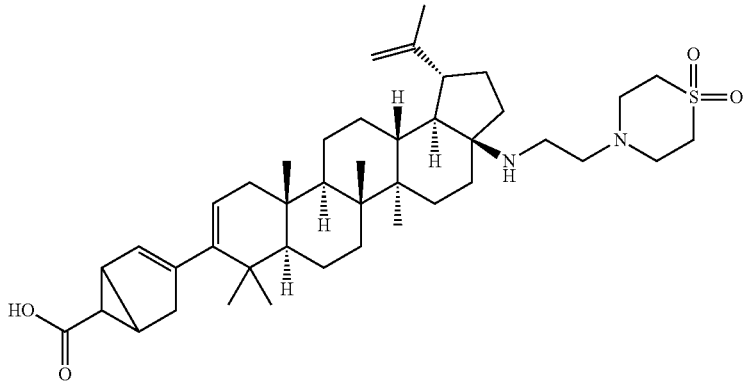<br>single isomer | 9.41E−04 |
| A27 | 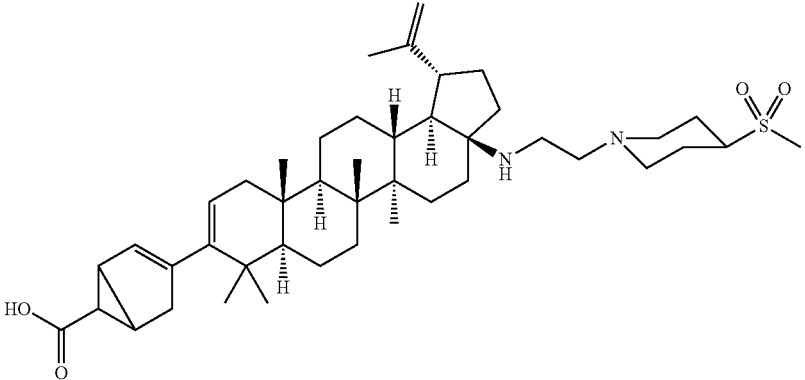<br>Isomer 1 | 9.21E−04 |
| A28 | 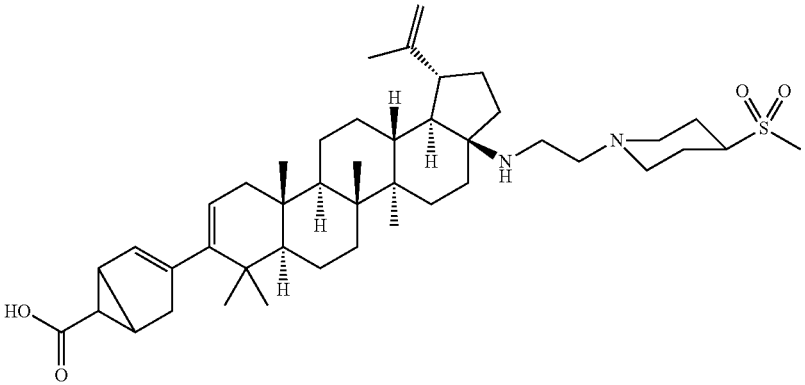<br>Isomer 2 | 6.58E−04 |

TABLE 1-continued
| Example # | Structure | EC$_{50}$ (µM) |
|---|---|---|
| A29 | 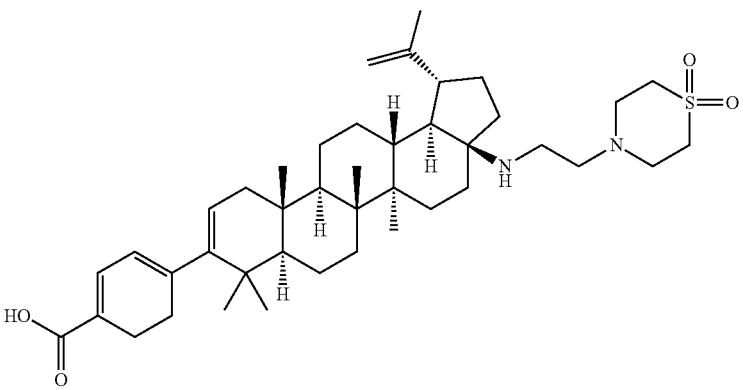 | 1.37E−03 |
| A30 | 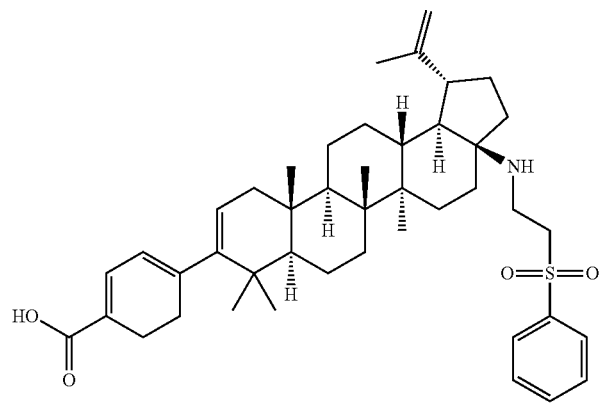 | 0.09 |
| A31 | 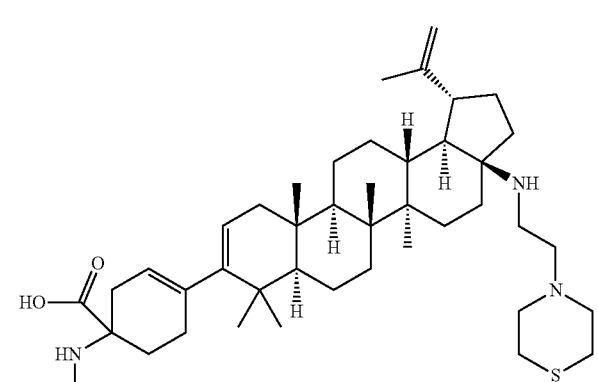 | 0.01 |

TABLE 1-continued

| Example # | Structure | EC$_{50}$ (µM) |
|---|---|---|
| A32 | 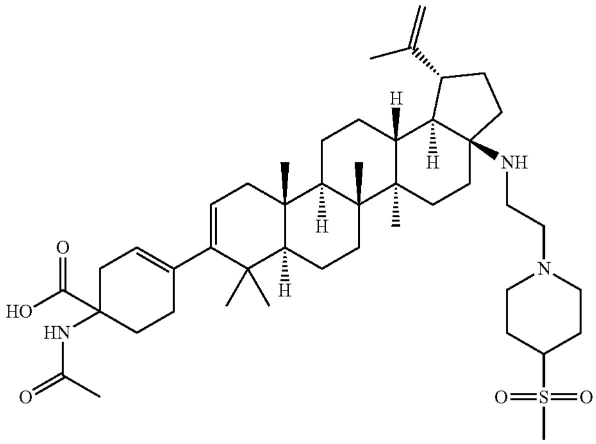 | 1.50E−03 |
| A33 | 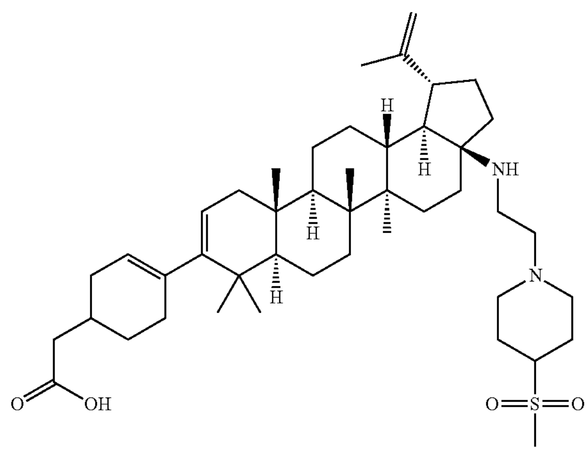 | 0.57 |

The foregoing description is merely illustrative and should not be understood to limit the scope or underlying principles of the invention in any way. Indeed, various modifications of the invention, in addition to those shown and described herein, will become apparent to those skilled in the art from the following examples and the foregoing description. Such modifications are also intended to fall within the scope of the appended claims.

What is claimed is:

1. A compound which is selected from the group consisting of:

a compound of formula I

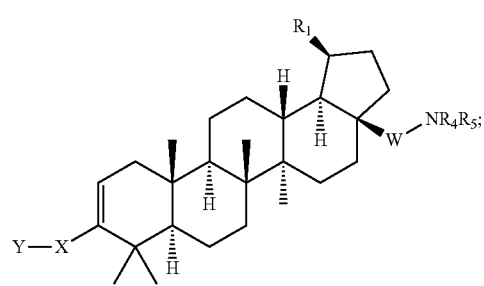

Formula I a compound of formula II

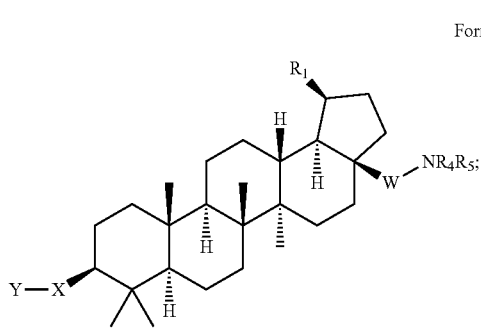

Formula II a compound of formula III

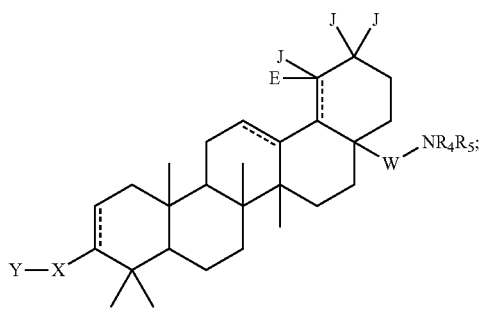

Formula III and a compound of formula IV

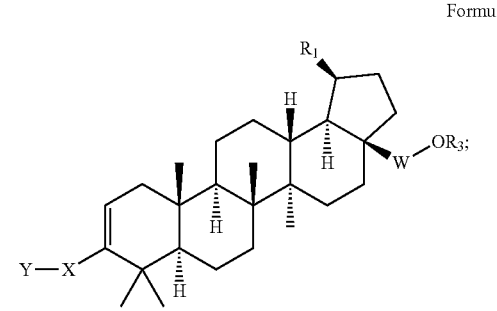

Formula IV wherein $R_1$ is isopropenyl or isopropyl;

J and E are independently —H or —$CH_3$, and E is absent when the double bond is present;

X is selected from the group of $C_{4-8}$ cycloalkyl, $C_{4-8}$ cycloalkenyl, $C_{4-9}$ spirocycloalkyl, $C_{4-9}$ spirocycloalkenyl, $C_{4-8}$ oxacycloalkyl, $C_{4-8}$ dioxacycloalkyl, $C_{6-8}$ oxacycloalkenyl, $C_{6-8}$ dioxacycloalkenyl, $C_6$ cyclodialkenyl, $C_6$ oxacyclodialkenyl, $C_{6-9}$ oxaspirocycloalkyl and $C_{6-9}$ oxaspirocycloalkenyl ring, wherein X is substituted with A, wherein A is at least one member selected from the group of —H, -halo, -hydroxyl, —$C_{1-6}$ alkyl, —$C_{1-6}$ alkoxy, —$C_{1-6}$ alkyl-Q, -alkylsubstituted $C_{1-6}$ alkyl-Q, —CN, —$CF_2Q$, —$NR_8R_9$, —$COOR_2$ and —$CONR_2R_2$;

X is also selected from the group of:

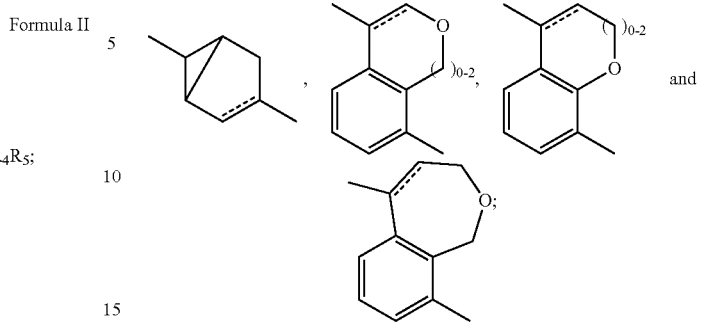

wherein Q is selected from the group of aryl, heteroaryl, substituted heteroaryl, —$OR_2$, —$COOR_3$, —$NR_2R_2$, —$SO_2R_7$, —$CONHSO_2R_3$, and —$CONHSO_2NR_2R_2$;

$R_2$ is —H, —$C_{1-6}$ alkyl, -alkylsubstituted $C_{1-6}$ alkyl or -arylsubstituted $C_{1-6}$ alkyl;

Y is selected from the group of —$COOR_2$, —C(O)$NR_2SO_2R_3$, —C(O)$NHSO_2NR_2R_2$, —$NR_2SO_2R_2$, —$SO_2NR_2R_2$, —$C_{3-6}$ cycloalkyl-$COOR_2$, —$C_{2-6}$ alkenyl-$COOR_2$, —$C_{2-6}$ alkynyl-$COOR_2$, —$C_{1-6}$ alkyl-$COOR_2$, -alkylsubstituted $C_{1-6}$ alkyl, —$COOR_2$, $CF_2$—$COOR_2$, —NHC(O)($CH_2$)$_n$—$COOR_2$, —$SO_2NR_2C(O)R_2$, _tetrazole, and —CONHOH, wherein n=1-6;

W is absent, $CH_2$ or CO;

$R_3$ is —$C_{1-6}$ alkyl or -alkylsubstituted $C_{1-6}$ alkyl;

$R_4$ is selected from the group of —H, —$C_{1-6}$ alkyl, —$C_{1-6}$alkyl-$C(OR_3)_2$—$C_{3-6}$cycloalkyl, —$C_{1-6}$ substituted alkyl, —$C_{1-6}$ alkyl-$C_{3-6}$ cycloalkyl, —$C_{1-6}$ alkyl-$Q_1$, —$C_{1-6}$ alkyl-$C_{3-6}$ cycloalkyl-$Q_1$, aryl, heteroaryl, substituted heteroaryl, —$COR_6$, —$COCOR_6$, —$SO_2R_7$, —$SO_2NR_2R_2$,

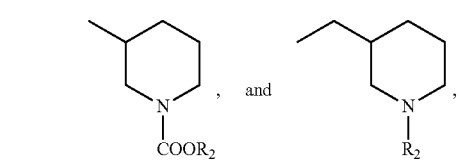

with the proviso that $R_4$ or $R_5$ cannot be $COR_6$ or $COCOR_6$ when W is CO;

wherein $Q_1$ is selected from the group of heteroaryl, substituted heteroaryl, halogen, —$CF_3$, —$OR_2$, —$COOR_2$, —$NR_8R_9$, —$CONR_{10}R_{11}$ and —$SO_2R_7$;

$R_5$ is selected from the group of —H, —$C_{1-6}$ alkyl, —$C_{3-6}$ cycloalkyl, —$C_{1-6}$ alkylsubstituted alkyl, —$C_{1-6}$alkyl-$NR_8R_9$, —$COR_{10}$, —$COR_6$, —$COCOR_6$, —$SO_2R_7$ and —$SO_2NR_2R_2$;

with the proviso that only one of $R_4$ or $R_5$ is selected from the group of —$COR_6$, —$COCOR_6$, —$SO_2R_7$ and —$SO_2NR_2R_2$;

or when W is absent or is $CH_2$, then $R_4$ and $R_5$ is taken together with the adjacent N to form

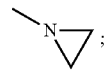

R$_6$ is selected from the group of —H, —C$_{1-6}$ alkyl, —C$_{1-6}$ alkyl-substitutedalkyl, —C$_{3-6}$ cycloalkyl, —C$_{3-6}$ substitutedcycloalkyl-Q$_2$, —C$_{1-6}$ alkyl-Q$_2$, —C$_{1-6}$ alkyl-substitutedalkyl-Q$_2$, —C$_{3-6}$ cycloalkyl-Q$_2$, aryl-Q$_2$, —NR$_{13}$R$_{14}$, and —OR$_{15}$;

wherein Q$_2$ is selected from the group of aryl, heteroaryl, substituted heteroaryl, —OR$_2$, —COOR$_2$, —NR$_8$R$_9$, SO$_2$R$_7$, —CONHSO$_2$R$_3$, and —CONHSO$_2$NR$_2$R$_2$;

R$_7$ is selected from the group of —C$_{1-6}$ alkyl, —C$_{1-6}$ substituted alkyl, —C$_{3-6}$ cycloalkyl, —CF$_3$, aryl, and heteroaryl;

R$_8$ and R$_9$ are independently selected from the group of —H, —C$_{1-6}$ alkyl, —C$_{1-6}$ substituted alkyl, aryl, heteroaryl, substituted aryl, substituted heteroaryl, —C$_{1-6}$ alkyl-Q$_2$, and —COOR$_3$, and R$_8$ and R$_9$ are also independently selected from the group of

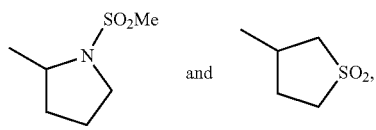

or R$_8$ and R$_9$ are taken together with the adjacent N to form a cycle selected from the group of:

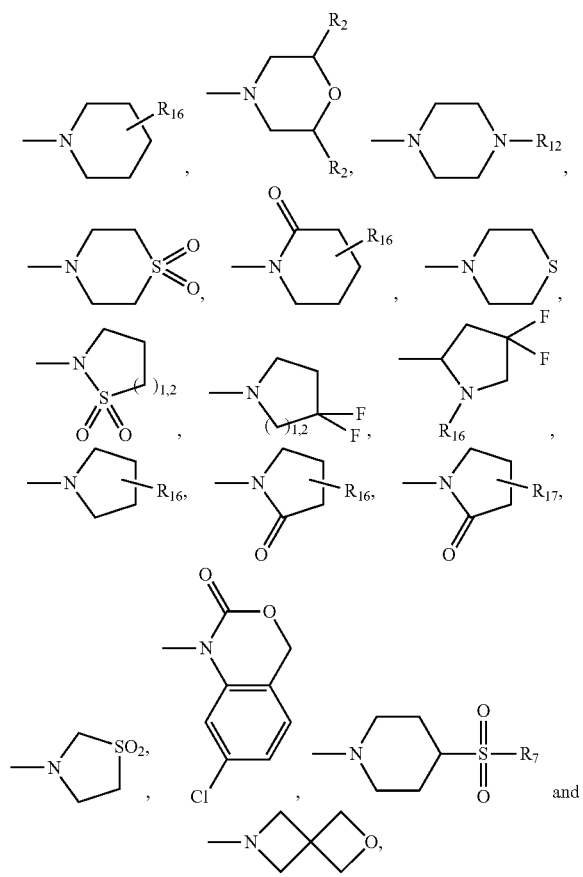

with the proviso that only one of R$_8$ or R$_9$ is —COOR$_3$;

R$_{10}$ and R$_{11}$ are independently selected from the group of —H, —C$_{1-6}$ alkyl, —C$_{1-6}$ substituted alkyl and —C$_{3-6}$ cycloalkyl, or R$_{10}$ and R$_{11}$ are taken together with the adjacent N to form the cycle

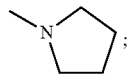

R$_{12}$ is selected from the group of —C$_{1-6}$ alkyl, —C$_{1-6}$ alkyl-OH; —C$_{1-6}$ alkyl, —C$_{1-6}$ substituted alkyl, —C$_{3-6}$ cycloalkyl, —COR$_7$, —COONR$_{22}$R$_{23}$, —SOR$_7$, and —SONR$_{24}$R$_{25}$;

R$_{13}$ and R$_{14}$ are independently selected from the group of —H, —C$_{1-6}$ alkyl, —C$_{3-6}$ cycloalkyl, —C$_{1-6}$ substituted alkyl, —C$_{1-6}$ alkyl-Q$_3$, —C$_{1-6}$ alkyl-C$_{3-6}$ cycloalkyl-Q$_3$, C$_{1-6}$ substituted alkyl-Q$_3$ and

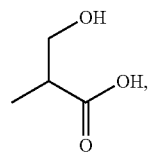

or R$_{13}$ and R$_{14}$ are taken together with the adjacent N to form a cycle selected from the group of:

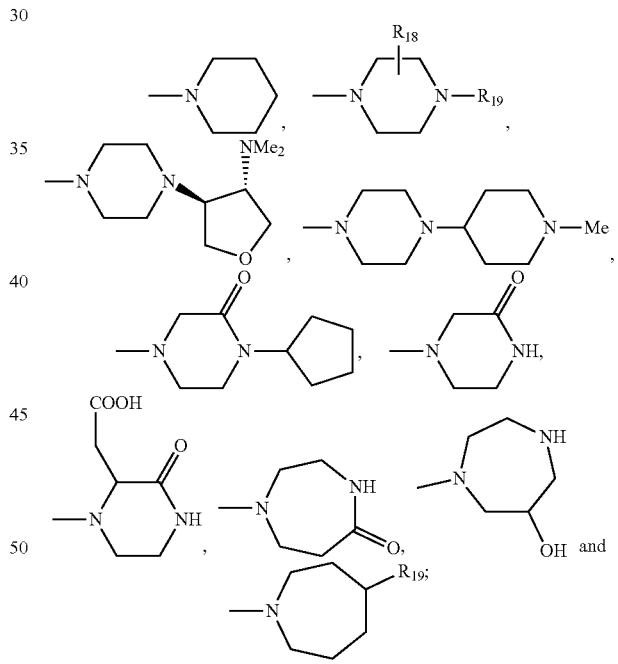

Q$_3$ is selected from the group of heteroaryl, substituted heteroaryl, —NR$_{20}$R$_{21}$, ⁻CONR$_2$R$_2$, —COOR$_2$, —OR$_2$, and —SO$_2$R$_3$;

R$_{15}$ is selected from the group of —C$_{1-6}$ alkyl, —C$_{3-6}$ cycloalkyl, —C$_{1-6}$ substituted alkyl, —C$_{1-6}$ alkyl-Q$_3$, —C$_{1-6}$ alkyl-C$_{3-6}$ cycloalkyl-Q$_3$ and —C$_{1-6}$ substituted alkyl-Q$_3$, R$_{16}$ is selected from the group of —H, —C$_{1-6}$ alkyl, —NR$_2$R$_2$, and —COOR$_3$;

R$_{17}$ is selected from the group of —H, —C$_{1-6}$ alkyl, —COOR$_3$, and aryl;

R$_{18}$ is selected from the group of —COOR$_2$ and —C$_{1-6}$ alkyl-COOR$_2$;

R$_{19}$ is selected from the group of —H, —C$_{1-6}$ alkyl, —C$_{1-6}$ alkyl-Q$_4$, —COR$_3$, —COOR$_3$, wherein Q$_4$ is selected from the group of —NR$_2$R$_2$ and —OR$_2$;

R$_{20}$ and R$_{21}$ are independently selected from the group of —H, —C$_{1-6}$ alkyl, —C$_{1-6}$ substituted alkyl, —C$_{1-6}$ substituted alkyl-OR$_2$, and —COR$_3$, or R$_{20}$ and R$_{21}$ are taken together with the adjacent N to form a cycle selected from the group of

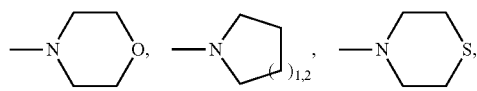

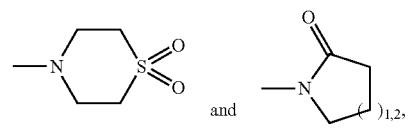

with the proviso that only one of R$_{20}$ or R$_{21}$ is —COR$_3$;

R$_{22}$ and R$_{23}$ are independently selected from the group of H, —C$_{1-6}$ alkyl, —C$_{1-6}$ substituted alkyl, and —C$_{1-6}$ cycloalkyl, or R$_{22}$ and R$_{23}$ are taken together with the adjacent N to form a cycle selected from the group of

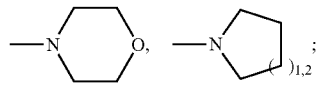

R$_{24}$ and R$_{25}$ are independently from the group of H, —C$_{1-6}$ alkyl, —C$_{1-6}$ substituted alkyl, —C$_{1-6}$ alkyl-Q$_5$, —C$_{1-6}$ cycloalkyl, aryl, substituted aryl, heteroaryl, and substituted heteroaryl, and Q$_5$ is selected from the group of halogen and SO$_2$R$_3$;

and pharmaceutically acceptable salts thereof.

2. The compound as claimed in claim 1, wherein said compound is a compound of Formula I.

3. The compound as claimed in claim 1, wherein said compound is a compound of Formula II.

4. The compound as claimed in claim 1, wherein said compound is a compound of Formula III.

5. The compound as claimed in claim 1, wherein said compound is a compound of Formula IV.

6. The compound as claimed in claim 2, wherein R$_1$ is isopropenyl.

7. The compound as claimed in claim 6, wherein X is selected from the group of C$_{4-8}$ cycloalkenyl, C$_{4-9}$ spirocycloalkyl, and C$_{4-9}$ spirocycloalkenyl.

8. The compound as claimed in claim 7, wherein Y is —COOR$_2$.

9. The compound as claimed in claim 8, wherein Y is —COOH.

10. The compound as claimed in claim 7, wherein A is —H.

11. The compound as claimed in claim 1, wherein W is absent.

12. The compound as claimed in claim 2, wherein said compound is a compound with the following general structure selected from the group of:

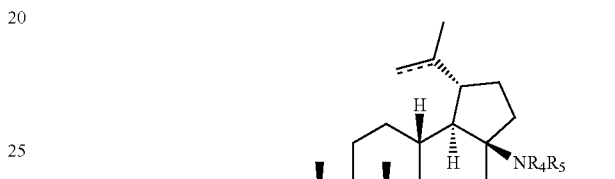

and

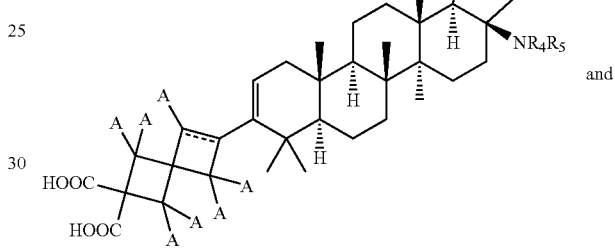

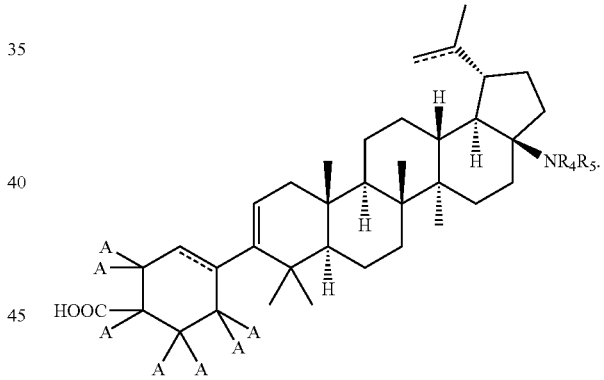

13. A compound which is selected from the group consisting of:

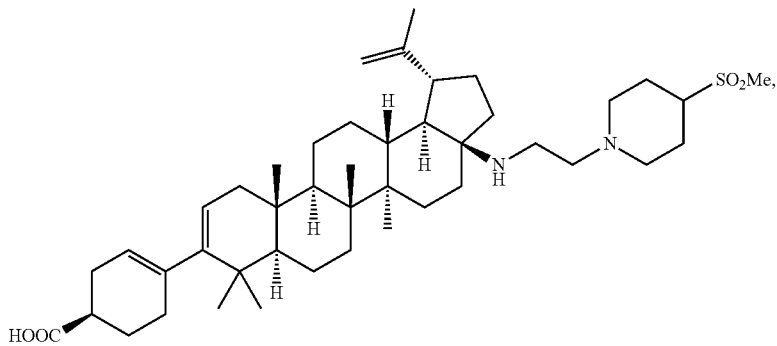

-continued
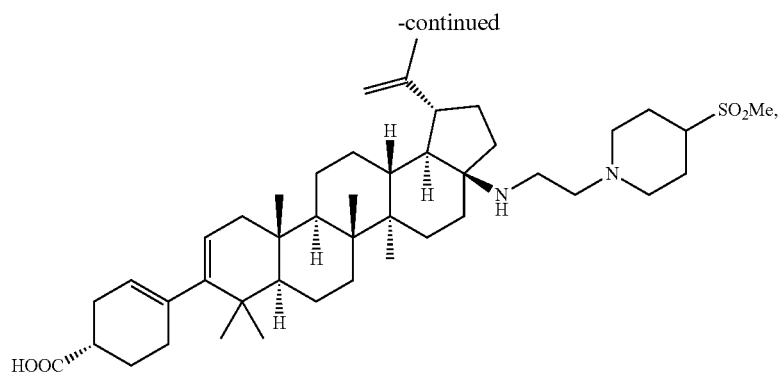
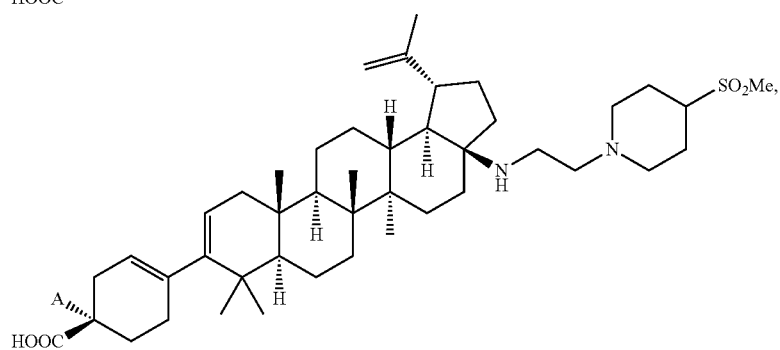
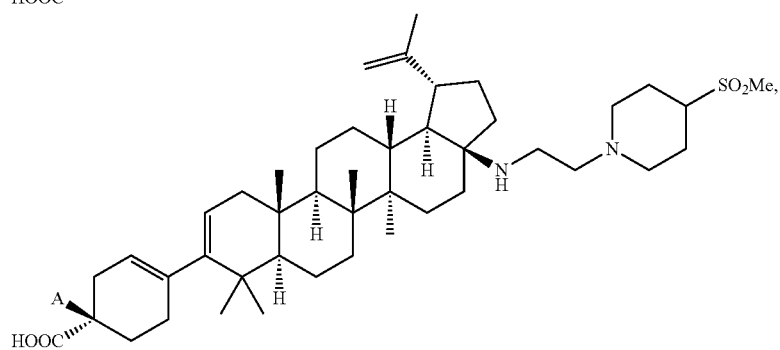
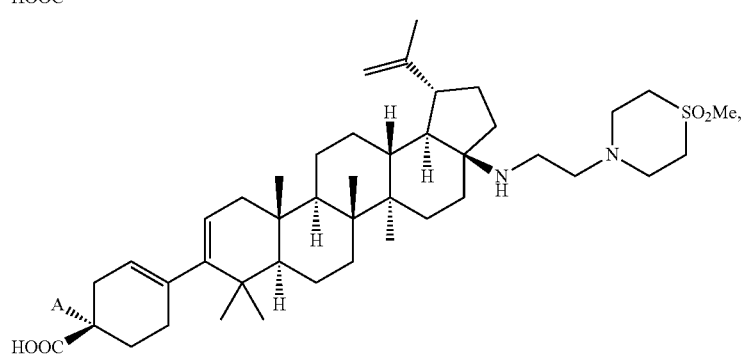
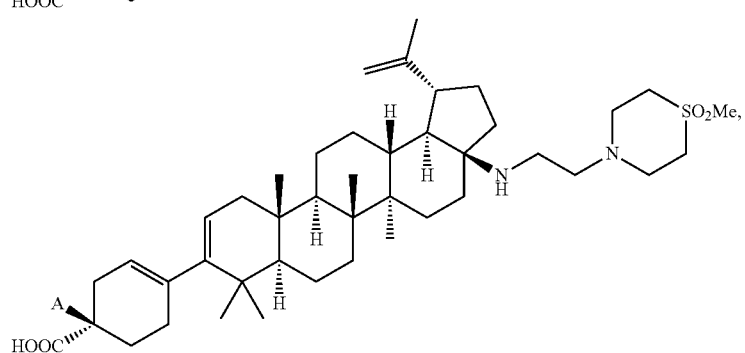

-continued
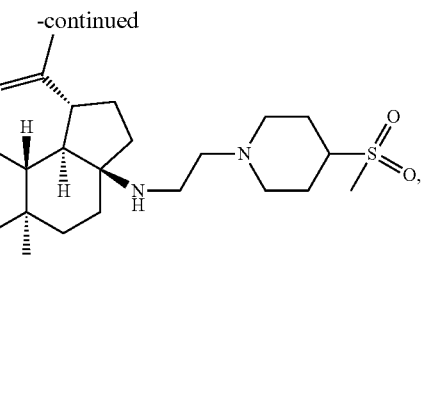
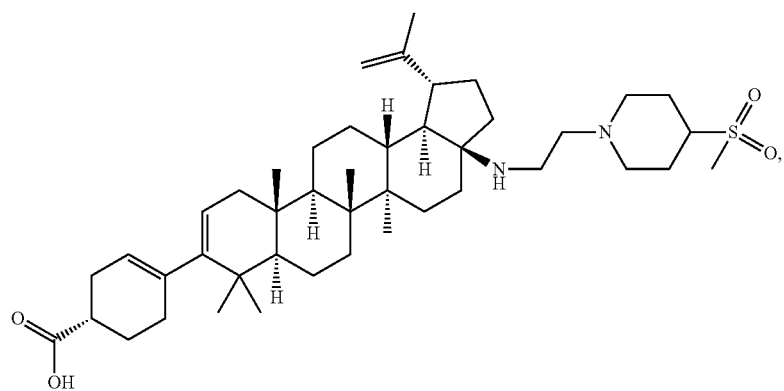
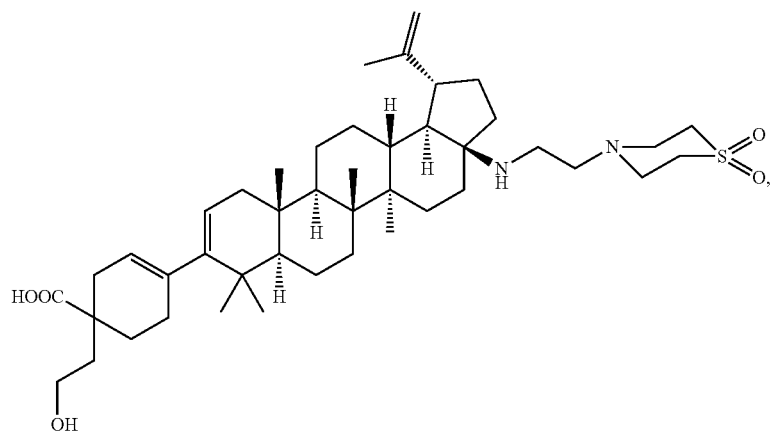
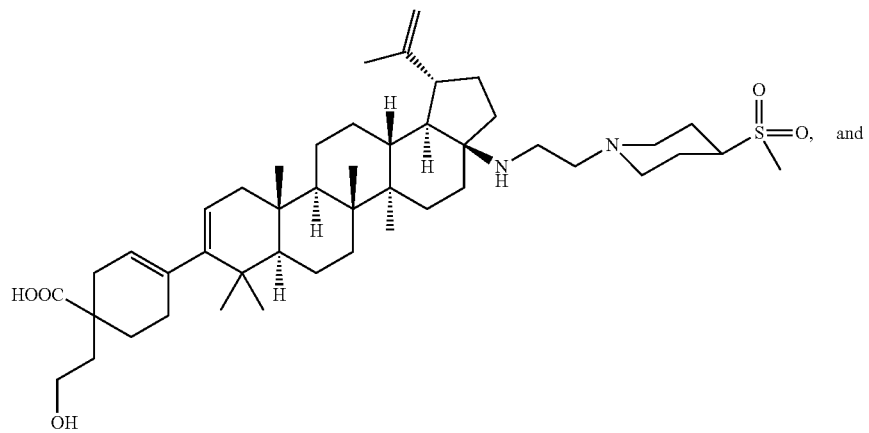
and

-continued

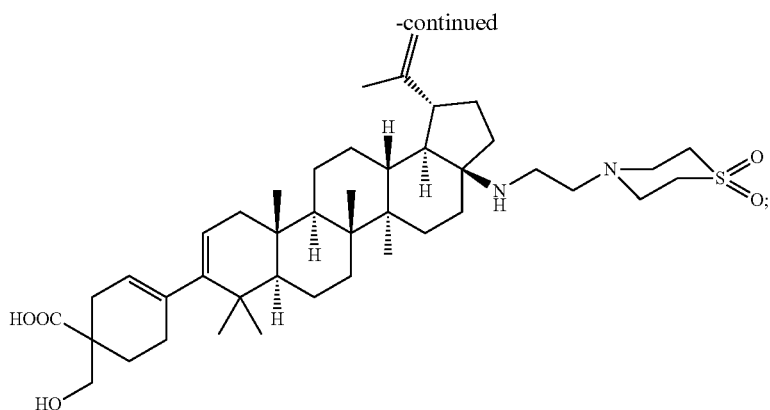

and pharmaceutically acceptable salts thereof.

14. A pharmaceutical composition which comprises an HIV ameliorating amount of one or more of the compounds as claimed in claim 1, together with one or more pharmaceutically acceptable carriers, excipients or diluents.

15. A pharmaceutical composition which comprises an HIV ameliorating amount of one or more of the compounds as claimed in claim 12, together with one or more pharmaceutically acceptable carriers, excipients or diluents.

16. A pharmaceutical composition which comprises an HIV ameliorating amount of one or more of the compounds as claimed in claim 13, together with one or more pharmaceutically acceptable carriers, excipients or diluents.

17. The pharmaceutical composition of claim 14, useful for treating infection by HIV, which additionally comprises an HIV ameliorating amount of an AIDS treatment agent selected from the group consisting of: (a) an AIDS antiviral agent; (b) an anti-infective agent; (c) an immunomodulator; and (d) another HIV entry inhibitor.

18. A method for treating a mammal infected with the HIV virus comprising administering to said mammal an HIV ameliorating amount of a compound as claimed in claim 1, and one or more pharmaceutically acceptable carriers, excipients or diluents.

19. The intermediate compound which is selected from the group of

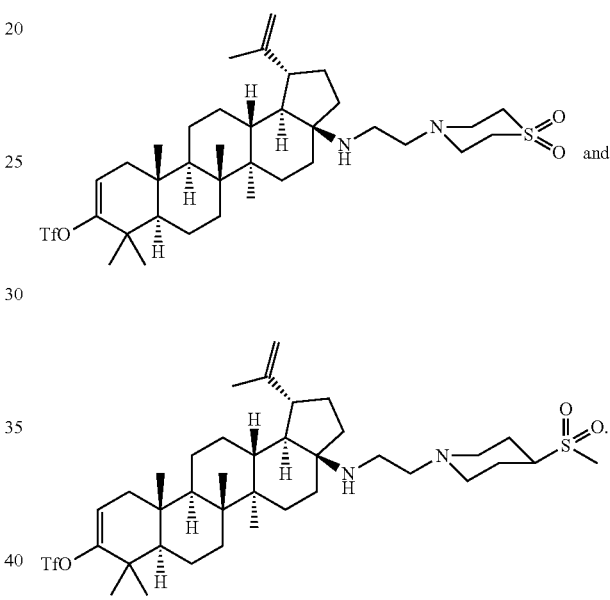

* * * * *